US007790404B2

(12) United States Patent
Lipton et al.

(10) Patent No.: US 7,790,404 B2
(45) Date of Patent: Sep. 7, 2010

(54) EXCITATORY GLYCINE RECEPTORS AND METHODS

(75) Inventors: Stuart A. Lipton, Rancho Santa Fe, CA (US); Dongxian Zhang, San Diego, CA (US); Jon E. Chatterton, San Diego, CA (US); Kevin A Sevarino, Cheshire, CT (US); Marc Awobuluyi, San Francisco, CA (US)

(73) Assignees: Sanford-Burnham Medical Research Institute, La Jolla, CA (US); Yale University, New Haven, CT (US); The Brigham and Women's Hospital, Inc., Boston, MA (US)

( * ) Notice: Subject to any disclaimer, the term of this patent is extended or adjusted under 35 U.S.C. 154(b) by 1313 days.

(21) Appl. No.: 10/222,772

(22) Filed: Aug. 16, 2002

(65) Prior Publication Data

US 2004/0033500 A1  Feb. 19, 2004

Related U.S. Application Data

(60) Provisional application No. 60/453,707, filed on Aug. 20, 2001.

(51) Int. Cl.
*G01N 33/566* (2006.01)
*C07K 14/705* (2006.01)
(52) U.S. Cl. .................. 435/7.2; 435/7.21; 436/501
(58) Field of Classification Search ....................... None
See application file for complete search history.

(56) References Cited

U.S. PATENT DOCUMENTS 6,083,941 A    7/2000 Farb

FOREIGN PATENT DOCUMENTS

WO    WO 02/40538    5/2002

OTHER PUBLICATIONS

Ehrlich-I. et al., Journal of Physiology (1999)520.1.pp. 121-137.*
Bowie et al., 1990, Science 247:1306-1310.*
Guo-HH et al. PNAS 101(25)9205-9210, 2004.*
Alexander et al., Proc. Natl. Acad. Sci. 89(3352-3356)1992.*
Reichling DB et al., Journal of Physiology (1994),476.*
Wang-J, et al., European Journal of Neuroscience vol. 6, polypeptide 1275-1280, 1994.*
Matsuda-K et al., J. Neuroscience 23(1)10064-10073)2003.*
Bendel-O et al, Neuroscience Letters 377(31-36)2005.*
Barth-A. et al., Exp Brain Res. 161(351-357)2005.*
Abdrachmanova et al., "Molecular and functional properties of synaptically activated NMDA receptors in neonatal motoneurons in rat spinal cord slices," *European J. of Neurosci.* 12:955-963 (2000).
Ciaberra et al., "Cloning and characterization of $\chi$-1: A developmentally regulated member of a novel class of the ionotropic glutamate receptor family," *J. Neuroscience* 15:6498-6508 (1995).
Cull-Candy et al., "NMDA receptor subunits: diversity, development and disease," *Curr. Opin. Neurobiol*, 11:327-335 (2001).
Das et al., "Increased NMDA current and spine density in mice lacking the NMDA receptor subunit NR3A," *Nature* 393:377-381 (1998).
Goebel and Poosch, "NMDA receptor subunit gene expression in the rat brain: a quantitative analysis of endogenous mRNA levels of NR1 com, NR2A, NR2B, NR2C, NR2D, and DR3A," *Mol. Bran Res.* 69:164-170 (1999).
Leuscluier and Hoch, "Subtype-specific assembly of α-amino-3-hydroxy-5-methyl-4-isoxazole propionic acid receptor subunits is mediated by their N-terminal domains," *J. of Biol. Chem.* 274:16907-16916 (1999).
Li et al., "In vitro selection of peptides acting at a new site of NMDA_glutamate receptors," *Nature Biotech.* 14:986-991 (1996).
Lipton and Rosenburg, "Excitatory amino acids as a final common pathway for neurologic disorders," *New Eng. J. of Med.* 330(9):613-622 (1994).
Meddows et al., "Identification of molecular determinants that are important in the assembly of N-Methyl-Daspartate receptors," *J. Biol. Chem.* 276 (22):18795-18803 (2001).
Nakanishi et al., "Glutamate receptors: brain function and signal transduction," *Brain Res. Reviews* 26:230-235 (1998).
Ozawa et al., "Glutamate receptors in the mammalian central nervous system," *Progress in Neurobiology* 54:581-618 (1998).
Perez-Otano et al., "Assembly with the NR1 subunit is required for surface expression of NR3A-containing NMDA receptors," *J. Neurosceince* 21(4):1228-1237 (2001).
Planells-Cases et al., "Molecular cloning, functional expressio, and pharmacological characterization of an N-methyl-D-aspartate receptor subunit from human brain," *Proc. Natl. Acad. Sci. USA* 90:5057-5061 (1993).
Rajendra et al., "The glycine receptor," *Pharmacol. Ther.* 73(2):121-146 (1997).
Reggiani et al., "The neuroprotective activity of the glycine receptor antagonist GV150526: an in vivo study by magnetic resonance imaging," *European J. Pharmacology* 419:147-153 (2001).
Seeburg et al, "RNA editing of brain glutamate receptor channels: mechanism and physiology," *Brain Research Reviews* 26:217-229 (1998).
Sheng et al, "Ligand-gated ion channel interactions with cytoskeletal and signaling proteins," *Annu. Rev. Physiol.* 62:755-778 (2000).
Souverbie et al, "Pharmacological characterization of [3H]MK-801 binding in the rat spinal cord," *Eur. J. Pharmacology* 307:347-353 (1996).
Sucher et al., "NMDA receptors: from genes to channels," *TIPS* 17:348-355 (1996).
Sucher et al., "Developmental and regional expression pattern of a novel NMDA receptor-like subunit (NMDAR-L) in the rodent brain," *J. Neuroscience* 15:6509-3520 (1995).

(Continued)

*Primary Examiner*—John D Ulm
(74) *Attorney, Agent, or Firm*—McDermott Will & Emery LLP

(57) ABSTRACT

The invention provides isolated N-methyl-D-aspartate type 3B (NR3B) polypeptides, functional fragments and peptides, encoding nucleic acid molecules and polynucleotides, and specific antibodies. Also provided are excitatory glycine receptors, containing either NR3B or NR3A polypeptides. Further provided are methods for detecting excitatory glycine receptor ligands, agonists and antagonists. The invention also provides related diagnostic and therapeutic methods.

20 Claims, 11 Drawing Sheets

OTHER PUBLICATIONS

Villmann et al., "Investigation by ion channel domain transplantation of rat glutamate receptor subunits, orphan receptors and a putative NMDA receptor," *Eur. J. Neurosci.* 11:1765-1778 (1999).

Wei et al., "Pharmacological characterization of N-methyl-D-aspartate receptors in spinal cord of rats with a chronic peripheral mononeuropathy," *Neuropharmacology* 36: 1561-1569 (1997).

Yamakura and Shimoji,"Subunit- and site-specific pharmacology of the NMDA receptor channel," *Prog. in Neurobiology* 59:279-298 (1999).

Zimmer et al., "Cloning and structure of the gene encoding the human N-methyl-D-aspartate receptor (NMDAR1)," *Gene* 159:219-223 (1995).

GenBank Accession No. NM000833.
GenBank Accession No. U09002.
GenBank Accession No. U90277.
GenBank Accession No. XM030214.
GenBank Accession No. XM030215.
GenBank Accession No. XM007911.
GenBank Accession No. XM016282.
GenBank Accession No. AC007218.
GenBank Accession No. AC006531.
GenBank Accession No. NM012573.
GenBank Accession No. M91561.
GenBank Accession No. AF001423.
GenBank Accession No:: D13211.
GenBank Accession No. NM008170.
GenBank Accession No. D10217.
GenBank Accession No. XM006636.
GenBank Accession No. XM042404.
GenBank Accession No. XM042405.
GenBank Accession No. XM042406.
GenBank Accession No. NM000834.
GenBank Accession No. U88963.
GenBank Accession No. U11287.
GenBank Accession No. U90278.
GenBank Accession No. AC007535.
GenBank Accession No. NM012574.
GenBank Accession No. U11419.
GenBank Accession No. M91562.
GenBank Accession No. NM008171.
GenBank Accession No. D10651.
GenBank Accession No. NM000835.
GenBank Accession No. U77782.
GenBank Accession No. XM046949.
GenBank Accession No. L76224.
GenBank Accession No. XM012596.
GenBank Accession No. NM012575.
GenBank Accession No. D13212.
GenBank Accession No. M91563.
GenBank Accession No. U08259.
GenBank Accession No. NM010350.
GenBank Accession No. D10694.
GenBanlc Accession No. XM009108.
GenBank Accession No. NM000836.
GenBanIc Accession No. U77783.
GenBank Accession No. AC011527.
GenBank Accession No. AC008403.
GenBank Accession No. U08260.
GenBank Accession No. NM022797.
GenBank Accession No. L31612.
GenBank Accession No. L31611.
GenBank Accession No. D13213.
GenBank Accession No. NM008172.
GenBank Accession No. D12822.
GenBank Accession No. U29873.
GenBank Accession No. L34938.
GenBank Accession No. AF061945.
GenBank Accession No. AF073379.
GenBank Accession No. NT025809.
GenBank Accession No. XM042803.
GenBank Accession No. AL359651.
GenBank Accession No:: AL359933.
GenBank Accession No. AC004528.
GenBank Accession No. AAC12680.
GenBank Accession No. BC005494.
GenBank Accession No. AAH05494.
GenBank Accession No. AC087114.

Andersson et al. "Nucleotide sequence, genomic organization, and chromosomal localization of genes encoding the human NMDA receptor subunits NR3A and NR3B," *Genomics* 78:178-184 (2001).

Chatterton et al., "Excitatory glycine receptors containing the NR3 family of NMDA receptor subunits," *Nature* 415:793-798 (2002).

Nishi et al., "Motoneuron-specific expression of NR3B, a novel NMDA-type glutamate receptor subunit that works in a dominant-negative manner," *J. Neurosci.* 21:1-6 (2001).

Genbank Accession No. AAB42494, Feb. 8, 2001.

\* cited by examiner

```
                S1                                              S2
         ∧  ∧              ∧         ∧∧                  ∧      ∧
...... A D G K F G ...... A P L T I N N E R A Q  ......A T V K Q S S V D ——NR1
...... T N G K H G ...... G S L T I N E E R S E  ......G T V P N G S T E ——NR2A
...... T N G K H G ...... G S L T I N E E R S E  ......G T V P N G S T E ——NR2B
...... T N G K H G ...... G S L T I N E E R S E  ......G T V P N G S T E ——NR2C
...... T N G K H G ...... G S L T I N E E R S E  ......G T V P N G S T E ——NR2D
...... G D G K Y G ...... T S F S I N T A R S Q  ......G T V R E S S A E ——NR3A
...... G D G K Y G ...... T S F S I N S A R S Q  ......G T V W E S S A E ——NR3B
...... G D G K Y G ...... A P L T I T L V R E E  ......G T L D S G S T K ——GluR2
       *   * *              *          * *                * *    *  *

Note: A=Acc65I; Ap=Apa; B=BamHI; E=EcoRI; K=KPN I; RV=EcoRV; H=HindIII; S=SacI; Sp=SpeI; X=XbaI; Xh=XhoI

FIGURE 11

EXCITATORY GLYCINE RECEPTORS AND METHODS

This application is based on, and claims the benefit of, U.S. Provisional Application No. 60/453,707, filed Aug. 20, 2001, which was converted from U.S. Ser. No. 09/934,070, and which is incorporated herein by reference.

This invention was made with United States Government support under grant numbers PO1 HD29587 and RO1 EY05477 awarded by the National Institutes of Health. The U.S. Government has certain rights in this invention.

BACKGROUND OF THE INVENTION

1. Field of the Invention

This invention relates generally to the fields of neurobiology and medicine and, more specifically, to the field of ionotropic receptors.

2. Background Information

Ionotropic glutamate receptors activate ligand-gated cation channels that mediate the predominant component of excitatory neurotransmission in the central nervous system (CNS). These receptors have been classified based on their preference for the glutamate-like agonists (RS)-2-amino-3-(3-hydroxy-5-methyl-4-isoxazolyl)propionic acid (AMPA), kainate (KA), and N-methyl-D-aspartate (NMDA). All three glutamate receptor subtypes are heteromultimeric complexes, and many of the subunits that comprise them have been identified and characterized. To date, four AMPA receptor subunits (GluR1-4), five KA receptor subunits (GluR5-7, KA1, and KA2), and six NMDA receptor subunits (NR1, NR2A-2D and NR3A) have been reported.

The NMDA receptor (NMDAR) has unique properties that distinguish it from the other glutamate receptor subtypes. First, the activation of NMDAR requires the presence of dual agonists, glutamate (or NMDA) and glycine. In addition, activation of these receptors is regulated by $Mg^{2+}$ in a voltage-dependent manner (i.e., the NMDAR is blocked at resting membrane potential and activated when depolarized). Most importantly, the NMDAR is extremely permeable to $Ca^{2+}$, a key regulator of cell function. These unique properties allow NMDARs to play a critical role in development of the nervous system, synaptic plasticity, memory, and other physiological processes in the CNS. However, excessive stimulation of NMDARs has also been implicated in many pathological conditions including stroke, ischemia, head and spinal trauma, headache, epilepsy, neuropathic pain syndromes including diabetic neuropathy, glaucoma, depression and anxiety, drug addiction/withdrawal/tolerance, and in chronic neurodegenerative states, such as Alzheimer's disease, Huntington's disease, HIV-associated dementia, Parkinson's disease, multiple sclerosis, and amyotrophic lateral sclerosis (ALS).

The molecular cloning and functional analysis of expressed NR1, NR2A-D, and NR3A subunits, coupled with the examination of their temporal and spatial expression patterns in vivo, has led to significant advances in our understanding of NMDAR function at the molecular level. However, the identification of these six subunits alone has failed to explain the observed diversity in NMDAR function, particularly in motor neurons.

Thus, there exists a need to identify and characterize additional NMDAR subunits, and to characterize the function of additional NMDA receptors. There also exists a need to provide screening assays that identify compounds that modulate the function of additional NMDA receptors. Such compounds can be used to treat pathological conditions in which inappropriate NMDA receptor activation, or inappropriate responses to glycine or glutamate, are involved. The present invention satisfies these needs and provides related advantages as well.

SUMMARY OF THE INVENTION

The invention provides isolated nucleic acid molecules encoding N-methyl-D-aspartate (NMDA) receptor type 3B (NR3B) polypeptides, including human, rat and mouse NR3B polypeptides.

Also provided are vectors and cells containing isolated nucleic acid molecules encoding NR3B polypeptides.

The invention also provides a method of producing an NR3B polypeptide by expressing a nucleic acid molecule encoding an NR3B polypeptide in vitro or in a cell under conditions suitable for expression of the polypeptide.

Further provided are isolated NR3B nucleic acid molecules encoding functional fragments of an NR3B polypeptide, including functional fragments that bind glycine.

The invention also provides an isolated NR3B polynucleotide containing at least 17 contiguous nucleotides from a human, rat or mouse NR3B nucleic acid molecule.

Also provided is a method for detecting a nucleic acid molecule encoding a NR3B polypeptide in a sample, by contacting the sample with one or more NR3B polynucleotides, and detecting specific hybridization to the polynucleotide, thereby detecting a nucleic acid molecule encoding an NR3B polypeptide in said sample.

The invention further provides isolated NR3B polypeptides, including human, rat and mouse NR3B polypeptides.

Also provided are functional fragments of NR3B polypeptides, including functional fragments that bind glycine.

The invention also provides isolated NR3B peptides, containing at least 8 contiguous residues of an NR3B polypeptide.

Further provided is an isolated antibody or antigen binding fragment thereof, which specifically binds an isolated NR3B polypeptide.

Also provided is a method of detecting an NR3B polypeptide in a sample, by contacting the sample with an antibody which specifically binds an NR3B polypeptide, and detecting the presence of specific binding of the antibody to the sample, thereby detecting an NR3B polypeptide in the sample.

The invention also provides methods of detecting an NR3B ligand, by contacting an NR3B polypeptide or functional fragment with one or more candidate compounds under conditions suitable for detecting binding to the polypeptide, and detecting a candidate compound that binds the polypeptide, wherein such a compound is characterized as an NR3B ligand.

Further provided is a composition containing an isolated excitatory glycine receptor. In one embodiment, the excitatory glycine receptor contains and NR3B polypeptide and an NR1 polypeptide. In another embodiment, the excitatory glycine receptor contains and NR3A polypeptide and an NR1 polypeptide. Optionally, the receptor further contains an NR2A, NR2B, NR2C or NR2D polypeptide.

The invention also provides a method of detecting an excitatory glycine receptor ligand, by contacting an excitatory glycine receptor with one or more candidate compounds under conditions suitable for detecting binding to said receptor, and detecting a candidate compound that binds said receptor, wherein such a compound is characterized as an excitatory glycine receptor ligand.

Also provided is a method of detecting an excitatory glycine receptor agonist or antagonist, by contacting an excitatory glycine receptor with one or more candidate compounds under conditions suitable for detecting receptor activation, and detecting a candidate compound that alters receptor activation, wherein such a compound is characterized as an excitatory glycine receptor agonist or antagonist.

Further provided is a method of modulating a cellular response to glycine or glutamate, by introducing a nucleic acid molecule encoding an NR3B polypeptide or functional fragment into a cell, and expressing the NR3B polypeptide or functional fragment encoded by said nucleic acid molecule in said cell, whereby expression of the polypeptide or functional fragment modulates a cellular response to glycine or glutamate.

The invention further provides a method of modulating a cellular response to glycine or glutamate, by introducing an antisense nucleic acid molecule, a ribozyme molecule or a small interfering RNA (siRNA) molecule into the cell, wherein the molecule hybridizes to an NR3B nucleic acid molecule and prevents translation of the encoded NR3B polypeptide.

BRIEF DESCRIPTION OF THE DRAWINGS

FIG. 1 shows an alignment of the deduced amino acid sequence of ionotropic glutamate receptor subunits from rat, designated NR1 (SEQ ID NO:14), NR2A (SEQ ID NO:15), NR3B B4 (SEQ ID NO:4) and NR3A (SEQ ID NO:16). Sequences were aligned using ClustalW and the BLOSUM series protein scoring matrix. Exact matches are boxed and shaded; conservative substitutions are boxed (no shading). Predicted signal peptide cleavage sites are indicated by vertical lines. Membrane regions (M1-M4) are indicated by horizontal lines. Asterisks indicate the positions of amino acid residues in NR1 and NR2A which have been shown to be required for glycine and glutamate binding, respectively. An arrow marks the position of the conserved asparagine residue in NR1 and NR2A-D.

FIGS. 2a and 2b show that positive signals (arrows) were detected only by probes derived from antisense (AS) sequences, but not with sense (S) probes in adult rat tissue. Strong NR3B signals were observed in facial and trigeminal nuclei of the brainstem and in the ventral horn of the spinal cord.

FIG. 2c shows NR3B-positive cells viewed under high magnification (400×, top panel). These cells resemble motor neurons retrogradely labeled by injection of a fluorescent dye (granular blue) into leg muscles (bottom panel).

FIG. 2d shows the distribution of the NR3B subunit in the lumbar spinal cord of rats at different ages. NR3B signals developed postnatally, appearing as early as P2, reached a peak around P14, and remained elevated in the adult. The positive cells are large and are located in layer VIII and IX, suggesting that they are motor neurons. Arrows pointing to the labeled motor neurons are placed only on the right side of the spinal cord.

FIG. 3a shows a dose-response of glycine-evoked NR1/NR3B currents.

FIG. 3b shows that NMDA and L-glutamate did not potentiate glycine-evoked currents, and did not evoke a glycine-independent response.

FIG. 3c1 shows that D-serine evoked small currents alone but inhibited the glycine response.

FIG. 3c2 shows inhibition (mean±SEM) of glycine-evoked currents by D-serine, D-alanine (30 μM), D-cycloserine (30 μM), or ACPC (1 μM).

FIGS. 3d1 and d2 show inhibition by AP5, strychnine (10 μM), and 5,7-DCKA (100 μM).

FIGS. 3e1 and 3e2 show inhibition by $Mg^{2+}$, MK-801 (10 μM), and memantine (12 μM). Data are representative of recordings from 3-9 oocytes in each case.

FIG. 4a shows inhibition of glycine (10 μM)-evoked NR1/NR3B currents by addition of $Mg^{2+}$ (0.5 mM) or replacement of cations in the bath solution with 90 mM NMDG.

FIG. 4b shows glycine-evoked NR1/NR3B currents during voltage ramps (20 mV/s) in normal bath solution containing 0.5 mM $Mg^{2+}$ (thin solid line) or no added $Mg^{2+}$ (dashed line), and in isosmotic solution containing 90 mM NMDG (with 1 mM $Ba^{2+}$; thick solid line) or 10 mM $Mg^{2+}$ (with 2 mM $Na^+$, balance NMDG; dotted line)

FIGS. 4c and 4d show glycine-evoked NR1/NR3B currents (c) and NMDA (100 μM)/glycine-evoked NR1/NR2A currents (d) during voltage ramps in 1 mM $Ba^{2+}$ (with 20 mM $Na^+$, balance NMDG; dashed line) versus 10 mM $Ba^{2+}$ (with 2 mM $Na^+$, balance NMDG; solid line).

FIG. 5a shows current recordings at a holding potential of −60 mV. Application of glycine (10 μM) activated single-channel currents, and $Mg^{2+}$ (0.5 mM) had no significant effect on these currents. Single-channel currents are shown at higher time resolution below. The single-channel currents display a main conductance state (2.3 pA) and a sub conductance state (0.7 pA) in the presence of 2 mM $Ba^{2+}$ (the zero current level is shown as a dotted line).

FIG. 5b shows all point amplitude histograms of single channel currents of NR1/NR3B receptors activated by glycine.

FIG. 5c shows single-channel currents recorded at different membrane potentials.

FIG. 5d shows single channel current-voltage relationship of the main conductance (squares) and sub conductance (circle) states.

FIG. 6a shows dose-response of glycine-evoked NR1/NR3A currents.

FIG. 6b shows that NMDA and L-glutamate did not potentiate glycine-evoked currents.

FIG. 6c shows inhibition of glycine (2 μM)-evoked currents by D-serine (10 μM), AP5 (100 μM), $Mg^{2+}$ (1 mM), MK-801 (10 μM), and memantine (12 μM).

FIG. 8 shows the deduced amino acid sequences of a rat NR3B B4 (SEQ ID NO:4) and a rat NR3B A2 (SEQ ID NO:2) and their alignment with the predicted sequences of a mouse NR3B (SEQ ID NO:8) and a human NR3B (SEQ ID NO:6). Sequences were aligned using ClustalW and the BLOSUM series protein scoring matrix. Exact matches are boxed and shaded; conservative substitutions are boxed (no shading). Gaps (−) were inserted to maximize homology. Thick horizontal lines indicate the positions of the predicted signal peptide and membrane regions (M1-M4). Dotted horizontal lines indicate the positions of the S1 and S2 ligand binding domains.

FIG. 9 shows an alignment of regions of ionotropic glutamate receptor subunits NR1, NR2A, NR2B, NR2C, NR2D, NR3A, NR3B and GluR2. Top: Residues of the S1 (SEQ ID NOS:21-28 and 29-36, respectively) and S2 (SEQ ID NOS:37-44, respectively) regions considered to be important for glutamate binding are indicated by *. Residues of the S1 and S2 regions considered to be important for glycine binding are indicated by ^. Bottom: Residues of the channel lumen that are accessible from either one or both sides of the channel are boxed. (SEQ ID NOS:45-51, respectively).

FIG. 11 shows the deduced amino acid sequences of a rat NR3B B4 (SEQ ID NO:58) and a rat NR3B A2 (SEQ ID NO:60) and their alignment with the predicted sequences of a mouse NR3B (SEQ ID NO:8) and a human NR3B (SEQ ID NO:62). Sequences were aligned using ClustalW and the BLOSUM series protein scoring matrix. Exact matches to NR3B B4 are boxed and shaded. Gaps (−) were inserted to maximize homology. Thick horizontal lines indicate the positions of the predicted signal peptide and membrane regions (M1-M4). Dotted horizontal lines indicate the positions of the S1 and S2 ligand binding domains.

DETAILED DESCRIPTION OF THE INVENTION

Figure 2:
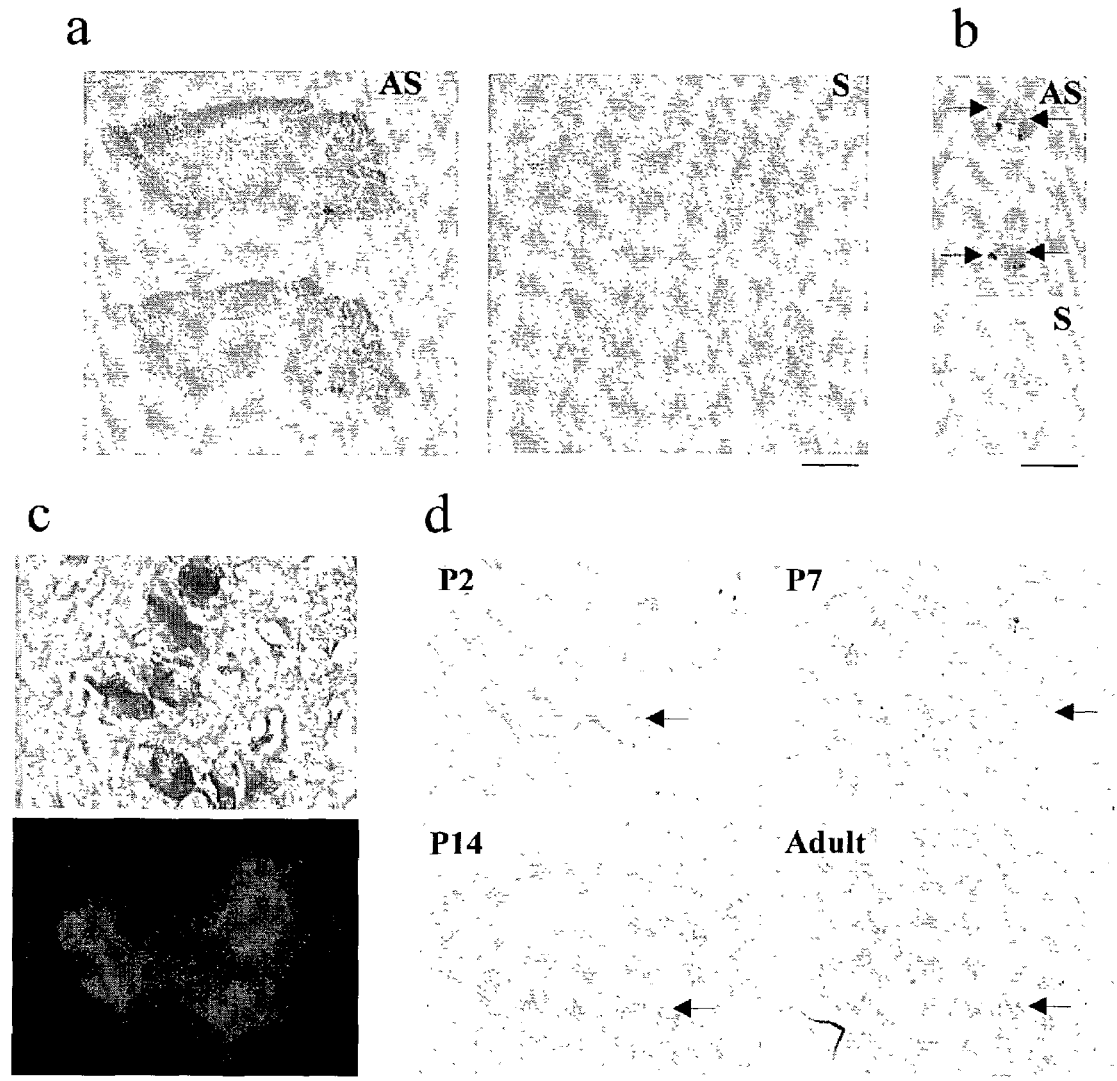
FIGS. 2(a-d) shows the distribution of the NR3B subunit in the CNS by in situ hybridization. NR3B probes were labeled using isotopic ($^{33}$P)-(a, b) and non-isotopic (digoxigenin) (c, d) methods. Bar represents 6 mm for panel a, 3 mm for b, 50 mm for c, and 1 mm for d.

The present invention relates to the cloning and characterization of a seventh NMDAR subunit, designated herein NR3B. The present invention also relates to the determination that receptors containing NR3B, or receptors containing the previously identified NMDAR subunit NR3A, display strikingly distinctive properties from all previously characterized NMDARs. The invention provides molecules and methods that can be used to prevent or ameliorate conditions in which inappropriate NMDA receptor activation, or inappropriate responses to glycine or glutamate, are involved.

The invention provides an isolated nucleic acid molecule encoding a NR3B polypeptide. As used herein, the term "NR3B polypeptide" refers to a polypeptide that retains at least one biological activity characteristic of the naturally occurring mammalian NR3B polypeptides designated herein SEQ ID NOS:2, 4, 58, 60, 6, 62 or 8. As disclosed herein, an exemplary biological activity characteristic of NR3B is the ability to form a subunit of an excitatory glycine receptor. An "excitatory glycine receptor" can be characterized as a receptor that responds to micromolar concentrations of glycine with a cation current. An excitatory glycine receptor can further be characterized by exhibiting any or all of the following properties: little or no response to NMDA or glutamate; little or no response to certain NR1 glycine site agonists, such as D-alanine, ACPC or D-cycloserine; inhibition of current in response to D-serine; inhibition of current in response to 5,7-dichlorokynuric acid; lack of inhibition of current in response to L-strychnine; lack of substantial inhibitory response to $Mg^{2+}$, MK801 or memantine; enhancement of glycine-invoked current by ≧40 μM APV; relatively $Ca^{2+}$-impermeable.

A further exemplary biological activity characteristic of NR3B is the ability to oligomerize with an NR1 subunit, and possibly further with both an NR1 and an NR2 subunit.

Yet another exemplary biological activity characteristic of NR3B is the ability to bind glycine with high affinity. The skilled person can determine other biological activities characteristic of an NR3B polypeptide designated herein SEQ ID NOS:2, 4, 58, 60, 6, 62 or 8.

Isolated nucleic acid molecules encoding NR3B polypeptides can be used, for example, as templates for the recombinant expression of NR3B subunits (the uses of which are described in more detail below); as probes to detect NR3B-encoding nucleic acid molecules in samples; in in vivo and ex vivo gene therapy applications in which modulation of NR3B expression is desired; and in other therapeutic, diagnostic, screening and research applications known to those skilled in the art.

The term "isolated," in reference to an invention nucleic acid molecule or polypeptide is intended to mean that the molecule is substantially removed or separated from components with which it is naturally associated, or is otherwise modified by the hand of man, thereby excluding nucleic acid and polypeptide molecules as they exist in nature. An isolated molecule can be in any form, such as in a buffered solution, a suspension, a lyophilized powder, attached to a solid support (e.g. as a component of an array, or on a filter or column), or in a cell or cell extract.

The term "nucleic acid molecule," as used herein, refers to a polynucleotide of natural or synthetic origin. A nucleic acid molecule can be single- or double-stranded genomic DNA, cDNA or RNA, and can represent a sense strand, an antisense strand, or both. Accordingly, a designated sequence identifier, unless specified otherwise, is intended to refer to the single-stranded molecule having the recited sequence, the single-stranded complement of the recited sequence, or a double stranded (or partially double-stranded) molecule in which one strand has the recited sequence.

A nucleic acid molecule can optionally include one or more non-native nucleotides, having, for example, modifications to the base, the sugar, or the phosphate portion, or having a modified phosphodiester linkage. Such modifications can be advantageous in increasing the stability of the nucleic acid molecule. Furthermore, a nucleic acid molecule can include, for example, a detectable moiety, such as a radiolabel, a fluorochrome, a ferromagnetic substance, a luminescent tag or a detectable binding agent such as biotin. Such modifications can be advantageous in applications where detection of a hybridizing nucleic acid molecule is desired.

An isolated nucleic acid molecule encoding a NR3B polypeptide can encode SEQ ID NO:6, or encode a polypeptide having at least 60% identity to SEQ ID NO:6, such as at least 70%, 80%, 85%, 90%, 95%, 97%, 99% or greater identity to SEQ ID NO:6. Identity of any two nucleic acid or amino acid sequences can be determined by those skilled in the art based, for example, on known computer alignments such as BLAST 2.0, ClustalW and the like, which can be adjusted manually, if appropriate, to insert gaps to optimize the alignment according to standard practice in the art.

An isolated nucleic acid molecule encoding a NR3B polypeptide with at least 60% identity to SEQ ID NO:6 can encode a naturally occurring or a non-naturally occurring amino acid sequence. SEQ ID NO:6 represents the predicted amino acid sequence of a naturally occurring human NR3B polypeptide.

The skilled person will appreciate from the alignment shown in FIG. 8 that the C-terminus of SEQ ID NO:6 differs somewhat from the rat and mouse orthologs. Based on these observed differences, it is contemplated that a naturally occurring human NR3B polypeptide can contain additional sequence corresponding to one or more of the gaps where SEQ ID NO:6 does not apparently align with SEQ ID NOS:2, 4 and 8, or no sequence in these positions.

For example, it is contemplated that a naturally occurring human NR3B polypeptide can contain several additional amino acids (e.g. 1-20 additional amino acids, such as 11 additional amino acids), or no amino acids, between the sequence "PPEGS" and "KEETA" of SEQ ID NO:6. Such additional sequence can be identical to, substantially similar to, or different from, the sequence QQERAEQERSGP (portion of SEQ ID NO:4) or the sequence QQERAEQECRGP (portion of SEQ ID NO:8). Likewise, it is contemplated that a naturally occurring human NR3B polypeptide can contain several additional amino acids (e.g. 1-20 additional amino acids, such as 8 additional amino acids), or no amino acids, between the sequence "FLLEP" and "WLCS" of SEQ ID NO:6. Such additional sequence can be identical to, substantially similar to, or different from, the sequence GEAGGDRP (portion of SEQ ID NO:4) or the sequence GEAGGDHP (portion of SEQ ID NO:8).

Likewise, it is contemplated that a naturally occurring human NR3B polypeptide can contain several additional amino acids (e.g. 1-20 additional amino acids, such as 7 additional amino acids), or no amino acids, between the sequence "WLCS" and "ELQEL" of SEQ ID NO:6. Such additional sequence can be identical to, substantially similar to, or different from, the sequence NGPGLQA (portion of SEQ ID NO:4) or the sequence NGPGVQA (portion of SEQ ID NO:8). Furthermore, it is contemplated that a naturally occurring human NR3B polypeptide does not contain the residues in SEQ ID NO:6 that extend beyond the corresponding residues from the C-terminus of SEQ ID NO:4 and 8, such as the sequence PPHSGRPGSQE (portion of SEQ ID NO:6).

A human NR3B polypeptide can contain C-terminal amino acid sequences that are not present in a sequence submitted to GenBank and annotated as a hypothetical protein most similar to rat Ionotropic gluatmate receptor (L34938) with an ill-defined C-terminus (GenBank entry AC004528 and AAC12680; SEQ ID NOS:9 and 10). In particular, a human NR3B polypeptide can contain any or all of the C-terminal portion of SEQ ID NO:6 not also present in SEQ ID NO:10, such as the sequence XXXXXXXXXXXXXWKRAR-RAVDKERRVRFLLEPXXXXXXXXWLCSXXXXXXX-ELQELERRIEVARERLRQALVRRGQLLAQLGDSAR-HRPRRLLQARAAPAEAPPHSGRPGSQE (SEQ ID NO:63) where X can be any amino acid.

By further sequence analysis of nucleic acid molecules encoding human NR3B, the nucleotide sequence set forth as SEQ ID NO:61 was identified, which encodes SEQ ID NO:62. SEQ ID NO:62 contains identified amino acid residues in place of certain of the C-terminal residues designated by an "X" in SEQ ID NO:6, and several additional modifications relative to SEQ ID NO:6. This further amino acid sequence is an example of a sequence containing "minor modifications," as described herein, relative to SEQ ID NO:6.

The skilled person will appreciate from the alignment shown in FIG. 11 that the C-terminus of SEQ ID NO:62 differs somewhat from the rat and mouse orthologs. Based on these observed differences, it is contemplated that a naturally occurring human NR3B polypeptide, or an NR3B polypeptide with minor modifications, can contain alternative sequences at one or more of the positions where SEQ ID NO:62 does not contain exact matches with residues of SEQ ID NOS:60, 58 and 8, such as any or all of the amino acids between 890 and 1008 of SEQ ID NO:62 that are unboxed in FIG. 11. Such alternative sequences can be additions, deletions or substitutions of amino acids. It is contemplated that substitutions at these positions can be identical to the corresponding residues in SEQ ID NOS:60, 58 or 8, or can be conservative or non-conservative substitutions of these residues.

SEQ ID NOS:4 and 2 represent the predicted amino acid sequences of two naturally occurring rat NR3B polypeptides, NR3B B4 and NR3B A2, respectively.

By further sequence analysis of nucleic acid molecules encoding rat NR3B, the nucleotide sequences set forth as SEQ ID NO:57, which encodes SEQ ID NO:58 (B4 form) and SEQ ID NO:59, which encodes SEQ ID NO:60 (A2 form), were identified. SEQ ID NO:58 differs from SEQ ID NO:4 by virtue of having an "Arg" at residue 968 instead of a "Gln" and, likewise, SEQ ID NO:60 differs from SEQ ID NO:2 by virtue of having an "Arg" at residue 953 instead of a "Gln." These further amino acid sequences are examples of sequences containing "minor modifications," as described herein, relative to SEQ ID NOS:2 and 4.

SEQ ID NO:8 represents the predicted amino acid sequence of a naturally occurring mouse NR3B polypeptide.

An isolated nucleic acid molecule encoding SEQ ID NO:6 can have the nucleotide sequence designated SEQ ID NO:5, which represents a naturally occurring human NR3B cDNA sequence. The skilled person understands, however, that due to the degeneracy of the genetic code, SEQ ID NO:6 can also be encoded by a nucleotide sequence that differs from SEQ ID NO:5 at one or more codons.

Likewise, isolated nucleic acid molecules encoding SEQ ID NOS:4, 2 or 8 can have the nucleotide sequences designated SEQ ID NOS:3, 1 or 7, or be degenerate variants thereof, and isolated nucleic acid molecules encoding SEQ ID NOS:58, 60 and 62 can have the nucleotide sequences designated SEQ ID NOS:57, 59 and 61, or be degenerate variants thereof.

As shown in the alignments in FIG. 8 and FIG. 11, SEQ ID NOS:2, 4, 6 and 8, and likewise SEQ ID NOS:58, 60, 8 and 62, are highly homologous over their entire lengths. Because of this high degree of identity of NR3B polypeptides across these three mammalian species, it is expected that other naturally occurring mammalian NR3B polypeptides, such as NR3B polypeptides from non-human primates, mouse, rat, rabbit, bovine, porcine, ovine, canine or feline species, as well as naturally occurring NR3B polypeptides from other vertebrates, including fish, birds, reptiles and amphibians (e.g. Xenopus) will also exhibit a high degree of identity across their lengths with SEQ ID NO:6 or 62.

Using knowledge of the human, rat or mouse NR3B-encoding nucleic acid sequences and polypeptides disclosed herein, those skilled in the art can readily clone NR3B-encoding nucleic acids from other mammalian or vertebrate species using conventional cDNA or expression library screening methods, or using the polymerase chain reaction (PCR). Additionally, using knowledge of the human, rat or mouse NR3B-encoding nucleic acid sequences and polypeptides disclosed herein, those skilled in the art can readily determine cDNA and coding sequences form other species from an analysis of ESTs and genomic sequences present in available databases.

In contrast, SEQ ID NO:4 exhibits about 47% identity to rat NR3A, with much lower identity to other NMDA receptor subunits (i.e. 19.7% identity to rat NR1; 18.6% identity to rat NR2A). Therefore, the skilled person can readily distinguish an NR3B polypeptide from related receptor subunits based on sequence similarity.

For certain applications, an isolated nucleic acid molecule encoding an NR3B polypeptide need not encode the naturally occurring signal peptide sequence, which is cleaved in the mature polypeptide. The predicted signal peptide sequences of rat (SEQ ID NOS:2 and 4; also SEQ ID NOS:58 and 60), human (SEQ ID NO:6; also SEQ ID NO:62) and mouse (SEQ ID NO:8) NR3B polypeptides are shown by overlining and the designation "SP" in FIG. 8 and FIG. 11. Accordingly, in one embodiment, an isolated nucleic acid molecule can encode an NR3B polypeptide in which some or all or of amino acids 1-51 or 1-53 of SEQ ID NOS:2, 4, 58, 60, 6, 62 or 8 are not present. The skilled person can readily determine the boundaries of the signal peptide sequence from NR3B polypeptides and, if desired, replace these residues with another signal or sorting sequence.

An isolated nucleic acid molecule encoding an NR3B polypeptide can also be a splice variant form that differs from another form by one or more exons, thereby encoding a NR3B polypeptide that differs from another NR3B polypeptide by an insertion or deletion of one or more residues at one or more places in the polypeptide. NR3B splice variants can be expressed in a tissue or developmental stage-specific manner. Rat NR3B A2 (SEQ ID NOS:2 and 60) and rat NR3B B4 (SEQ ID NOS:4 and 58) are examples of splice variant forms that differ by containing (SEQ ID NOS:4 and 58) or not containing (SEQ ID NOS:2 and 60) the sequence VSVLR-REVRTALGAP (portion of SEQ ID NO:4). An exemplary splice variant of a human NR3B differs from SEQ ID NOS:6 or 62 by not containing the sequence LSLLRREARAPLGAP (portion of SEQ ID NO:6) or by not containing the sequence LSLLRREARAPLGAPN (portion of SEQ ID NO:6). An exemplary splice variant of a mouse NR3B differs from SEQ ID NO:8 by not containing the sequence LSVLRREVRAPL-GAR (portion of SEQ ID NO:8) or by not containing the sequence LSVLRREVRAPLGARR (portion of SEQ ID NO:8). The skilled person can readily determine additional splice variants of these and other NR3B polypeptides.

An isolated nucleic acid molecule encoding an NR3B polypeptide can also have one or more minor modifications to the naturally occurring sequence, such as one or more substitutions additions or deletions. Such modifications can be advantageous, for example, in enhancing the stability, bioavailability, bioactivity or immunogenicity of the polypeptide, or to facilitate its purification.

Substitutions to an NR3B amino acid sequence can either be conservative or non-conservative. Conservative amino acid substitutions include, but are not limited to, substitution of an apolar amino acid with another apolar amino acid (such as replacement of leucine with an isoleucine, valine, alanine, proline, tryptophan, phenylalanine or methionine); substitution of a charged amino acid with a similarly charged amino acid (such as replacement of a glutamic acid with an aspartic acid, or replacement of an arginine with a lysine or histidine); substitution of an uncharged polar amino acid with another uncharged polar amino acid (such as replacement of a serine with a glycine, threonine, tyrosine, cysteine, asparagine or glutamine); or substitution of a residue with a different functional group with a residue of similar size and shape (such as replacement of a serine with an alanine; an arginine with a methionine; or a tyrosine with a phenylalanine).

Additions to an NR3B amino acid sequence include, but are not limited to, the addition of "tag" sequences, which are conveniently added at the N- or C-termini, after the signal peptide, or within extracellular or intracellular loops. Such tag sequence include, for example, epitope tags, histidine tags, glutathione-S-transferase (GST), fluorescent proteins (e.g. Enhanced Green Fluorescent Protein (EGFP)) and the like. Such additional sequences can be used, for example, to facilitate expression, purification or characterization of an NR3B polypeptide.

Deletions to an NR3B amino acid sequence include, but are not limited to, deletion of signal peptide residues, and deletion of residues at the N- or C-termini that are not critical for function. Deleted sequences can optionally be replaced by tag sequences or fusion sequences, as described previously.

Modifications to an encoded NR3B amino acid sequence, such as modifications to any of SEQ ID NOS:2, 4, 58, 60, 6, 62 or 8, can be randomly generated, such as by random insertions, deletions or substitutions of nucleotides in a nucleic acid molecule encoding the polypeptide. Alternatively, modifications can be directed, such as by site-directed mutagenesis of a nucleic acid molecule encoding the polypeptide.

Guidance in modifying the sequence of an NR3B polypeptide while retaining biological activity can be provided by the alignment of the sequence of the NR3B orthologs from human, rat and mouse shown in FIG. 8 and FIG. 11. It is well known in the art that evolutionarily conserved amino acid residues are more likely to be important for maintaining biological activity than less well-conserved residues. Thus, it would be expected that substituting a residue that is highly conserved among NR3B polypeptides across species with a non-conserved residue may be deleterious, whereas making the same substitution at a residue which varies among species would likely not have a significant effect on biological activity.

Additionally, guidance in modifying amino acid residues of an NR3B polypeptide while retaining a desired biological activity can be provided by structure-function studies of known NMDA receptor subunits, which share an overall transmembrane topology and domain structure with NR3B. By analogy to other subunits, the ligand binding domain of NR3B is predicted to be formed by the extracellular S1 domain before the first membrane spanning region (M1) and by the extracellular S2 domain between membrane spanning regions M3 and M4 (FIG. 8 and FIG. 11). The second membrane domain (M2, or P-loop) is predicted to line the ion channel pore (see FIG. 8 and FIG. 11). Meddows et al., *J. Biol. Chem.* 276:18795-18803 (2001) have also determined that retention of the N-terminal residues of the NMDA receptor subunit NR1 (i.e. amino acids 1-380 of NR1) is important for subunit oligomerization, whereas the M4 domain and C-terminal residues (i.e. amino acids 811-938 of NR1) are dispensible for oligomerization but required for functional channel formation. The skilled person could apply this knowledge to predict the effect of various modifications within the above-described structural and functional domains on NR3B biological activity.

Computer programs well known in the art can also provide guidance in predicting which amino acid residues can be modified without abolishing a topological or functional feature of an NR3B polypeptide.

The invention also provides an isolated nucleic acid molecule that encodes a functional fragment of an NR3B polypeptide. As used herein, the term "functional fragment" refers to a portion of a full-length NR3B polypeptide that retains at least one biological activity characteristic of the full-length polypeptide. A functional fragment can contain, for example, at least about 6, 8, 10, 12, 15, 20, 25, 30, 35, 40, 50, 60, 70, 80, 90, 100, 110, 125, 150, 200, 250, 300, 400, 500, 600, 700, 800, 900, 950 or more amino acids of an NR3B polypeptide.

For example, a functional fragment of an NR3B polypeptide can retain the ability to bind glycine. As shown in FIGS. 1 and 9, the residues of the S1 and S2 regions considered to be important in binding glycine are known. Thus, a functional fragment can contain all or part of the S1 and/or S2 domains of rat, human or mouse NR3B (see FIG. 8 and FIG. 11), and optionally further contain the naturally occurring NR3B intervening sequence, such as membrane regions M1-M3.

An exemplary NR3B functional fragment that binds glycine can contain SEQ ID NO:27 and/or SEQ ID NO:35 and/or SEQ ID NO:43. Advantageously, a chimeric polypeptide containing all or a portion of a different NMDA receptor subunit (e.g. NR1, NR2A-D or NR3A), with the glycine binding domain (e.g. the S1 and/or S2 regions; or SEQ ID NO:27 and/or SEQ ID NO:35 and/or SEQ ID NO:43) of NR3B replacing the corresponding region of the NMDA receptor subunit, can be constructed. Likewise, a chimeric polypeptide containing all or a portion of an NMDA receptor subunit (e.g. NR1, NR2A-D or NR3B), with the glycine binding domain (e.g. the S1 and/or S2 regions; or SEQ ID NO:26 and/or SEQ ID NO:34 and/or SEQ ID NO:42) of NR3A replacing the corresponding region of the NMDA receptor subunit, can be constructed. Such a functional fragment, or a chimeric polypeptide containing such a fragment, can be used, for example, in screening applications described further below to detect excitatory glycine receptor ligands, agonists and antagonists. Additionally, such a functional fragment can be used in therapeutic applications in which it is desirable to compete with an endogenous receptor for binding to agonist. Methods for making and testing chimeric glutamate receptor polypeptides are described, for example, in Villmann et al., *Eur. J. Neurosci.* 11:1765-1778 (1999).

A functional fragment of NR3B can also retain the ability to oligomerize with other NMDA receptor subunits, such as NR1, and optionally NR2. By analogy to NR1, such a fragment can retain all or most of the N-terminal region before the S1 domain, which is predicted to be important for oligomerization (see Meddows et al., supra (2001)).

A further exemplary functional fragment of NR3B can retain the ability to insert into the membrane or form a channel pore by retaining some or all of the membrane regions (M1-M4). Such fragments can be used, for example, to compete with or disrupt the structure of the naturally occurring NR3B.

Another exemplary functional fragment of NR3B can retain the ability to interact with intracellular proteins, such as effector proteins, by retaining some or all of the intracellular region C-terminal to M4. Such fragments can be used, for example, in binding assays to identify polypeptides that interact with NR3B, which can then themselves be used as targets in screening assays; and also can be used to compete with naturally occurring NR3B for binding to effector polypeptides.

Accordingly, the invention provides an isolated nucleic acid molecule that encodes an NR3B functional fragment that contains the extracellular domain of an NR3B polyepeptide N-terminal to the S1 domain (with or without the signal peptide), and/or the S1 domain, and/or the M1 domain, and/or the M2 domain, and/or the and/or the M3 domain, and/or the S2 domain, and/or the M4 domain, and/or the intracellular domain C-terminal to the M4 domain. The boundaries of these domains for several mammalian NR3B polypeptides are shown in FIG. 8 and FIG. 11. The skilled person can determine appropriate functional fragments of an NR3B polypeptide for use in a particular application.

The biological activities of NR3B polypeptides and functional fragments can be determined or confirmed by methods known in the art and described further in the Examples. For example, the ability of an NR3B polypeptide or functional fragment to act as a subunit of an excitatory glycine receptor can be tested by recombinantly expressing an NR3B polypeptide in an appropriate cell (e.g. a Xenopus oocyte or mammalian cell) in the presence of a suitable amount of another endogenous or exogenous NMDAR subunit (e.g. an NR1 subunit, an NR2 subunit, or an NR3A subunit, or any combination thereof that includes an NR1 subunit), and detecting currents evoked in a dose-dependent fashion by addition of glycine. Other suitable methods for detecting the ability of an NR3B polypeptide to act as a subunit of an excitatory glycine receptor are known in the art and described further below with respect to screening assays.

The ability of an NR3B polypeptide or functional fragment to oligomerize with an NR1 and/or an NR2 and/or an NR3A polypeptide can be assayed, for example, by a functional assay to measure excitatory ionic responses of an NR3B/NR1 receptor to glycine, as described above, or alternatively by co-expressing the polypeptides and detecting NR3B/NR1 polypeptide association. Various assays for detecting polypeptide associations are well known in the art and include, for example, co-immunoprecipitation assays (see, for example, Meddows et al., supra (2001)), two-hybrid assays, GST pull-down assays, protein chip proteomic array analysis (e.g. ProteinChip™ System from Ciphergen Biosystems, which can be used in tandem with mass spectrometry analysis for sequence or structure determination) and the like, using an NR3B polypeptide or functional fragment.

The ability of an NR3B poiypeptide or functional fragment to bind glycine can be also detected by a functional assay to measure excitatory ionic responses of an NR3B/NR1 receptor to glycine, as described above, or alternatively by a ligand binding assay. Various direct and competitive ligand binding assays, such as those described above with respect to oligomerization, and assays described below with respect to screening, are well known in the art and can be used to determine the ability of an NR3B polypeptide or functional fragment to bind glycine.

Further provided are isolated polynucleotides containing at least 17 contiguous nucleotides of an invention NR3B nucleic acid molecule or of its complement. An isolated polynucleotide can thus contain at least 18, 19, 20, 22, or at least 25 contiguous nucleotides, such as at least 30, 40, 50, 60, 70, 80, 90, 100, 125, 150, 175, 200, 225, 250, 275, 300, 350, 400, 500, 600, 700, 800, 1000, 1500, 2000, 2500, 3000, 3500 or more contiguous nucleotides from the reference nucleotide sequence, up to the full length sequence. An invention polynucleotide can be single or double stranded, represent the sense or antisense strand, and contain either coding or noncoding sequence or both. An invention polynucleotide can, but need not, encode a biologically active polypeptide and can, but need not, be inserted into a vector.

In one embodiment, the isolated polynucleotide comprises at least 17 contiguous nucleotides of any of SEQ ID NOS:1, 59, 3, 57, 5, 61 or 7 or the complement thereof. Such polynucleotides are of sufficient length and complexity to be able to specifically hybridize to an NR3B-encoding nucleic acid molecule under highly stringent hybridization conditions. Therefore, the invention polynucleotides can advantageously be used, for example, as probes to detect, the presence, abundance or fidelity of NR3B-encoding nucleic acid molecules in a sample; as NR3B-specific sequencing or PCR primers; as antisense, RNA interference or ribozyme reagents for use in ex vivo or in vivo gene therapy applications to block expression of NR3B in a cell, as described in more detail below; or in other applications known to those skilled in the art in which hybridization to an NR3B-encoding nucleic acid molecule is desirable. In certain applications, polynucleotides that distinguish a splice variant form of an NR3B receptor are useful, such as polynucleotides containing the region of the rat NR3B B4 form not present in the NR3B A2 form.

Specific hybridization refers to the ability of a nucleic acid molecule to hybridize to the reference nucleic acid molecule without hybridization under the same conditions with nucleic acid molecules that are not the reference molecule, such as a nucleic acid molecule encoding another NMDA receptor subunit. Moderately stringent hybridization conditions are conditions equivalent to hybridization of filter-bound nucleic acid in 50% formamide, 5×Denhart's solution, 5×SSPE, 0.2% SDS at 42° C., followed by washing in 0.2×SSPE, 0.2% SDS, at 50°. Highly stringent conditions are conditions equivalent to hybridization of filter-bound nucleic acid in 50% formamide, 5×Denhart's solution, 5×SSPE, 0.2% SDS at 42° C., followed by washing in 0.2×SSPE, 0.2% SDS, at 65° C. Other suitable moderately stringent and highly stringent hybridization buffers and conditions are well known to those of skill in the art and are described, for example, in Sambrook et al., *Molecular Cloning: A Laboratory Manual*, 3rd ed., Cold Spring Harbor Press, Plainview, N.Y. (2001) and in Ausubel et al. (*Current Protocols in Molecular Biology* (Supplement 47), John Wiley & Sons, New York (1999)).

In one embodiment, the invention provides a primer pair containing two isolated polynucleotides as set forth above. The primer pair can be used, for example, to amplify an NR3B-encoding nucleic acid molecule by the polymerase chain reaction (PCR). A suitable primer pair can contain an isolated polynucleotide containing at least 17 contiguous nucleotides of the sense strand of an invention NR3B nucleic acid molecule, and an isolated polynucleotide containing at least 17 contiguous nucleotides of the antisense strand of an invention NR3B nucleic acid molecule. The skilled person can determine an appropriate primer length and sequence composition for the intended application.

NR3B nucleic acid molecules (including nucleic acid molecules encoding NR3B polypeptides, functional fragments thereof and polynucleotides, as described above) can optionally contain exogenous nucleotide sequences including, for example, sequences that facilitate identification or purification of the molecule, and sequences that facilitate cloning, such as restriction endonuclease recognition sites.

NR3B nucleic acid molecules can be produced or isolated by methods known in the art. The method chosen will depend on the type of nucleic acid molecule one intends to isolate. Those skilled in the art, based on knowledge of the nucleotide sequences disclosed herein, can readily isolate NR3B nucleic acid molecules as genomic DNA, as full-length cDNA or desired fragments therefrom, or as full-length mRNA or cRNA or desired fragments therefrom, by methods known in the art.

It will be appreciated that an invention NR3B polypeptide, functional fragment or peptide does not consist of the exact sequence of an amino acid sequence set forth in a publically available database, or of the exact amino acid sequence of a translated product of a nucleic acid molecule set forth in a publically available database. Likewise, an invention nucleic acid molecule encoding a NR3B polypeptide or functional fragment, or an NR3B polynucleotide, does not consist of the exact sequence of a nucleotide sequence set forth in publically available databases, including but not limited to Expressed Sequence Tags (ESTs), Sequence Tagged Sites (STSs) and genomic fragments deposited in public databases such as the GenBank nr, dbest, dbsts and gss databases.

Specifically excluded from the invention polypeptides and nucleic acid molecules are molecules having the exact sequence of any of the following: the human EST sequence designated SEQ ID NO:13 (GenBank Accession No. AL359933); fragments of human chromosome 19 genomic sequences (e.g. GenBank Accession No. AC004528), such as the predicted cDNA sequence designated SEQ ID NO:9 which encodes a protein designated as a hypothetical human protein most similar to rat ionotropic gluatmate receptor, and the encoded polypeptide, SEQ ID NO:10 (GenBank Accession No. AAC12680); the mouse EST sequence designated SEQ ID NO:11 (GenBank Accession No. BC005494) and its predicted encoded polypeptide designated SEQ ID NO:12 (GenBank Accession No. AAH05494.1); and deposited fragments of mouse chromosome 10 genomic sequences (e.g. GenBank Accession No. AC087114).

Since one of skill in the art will realize that the above-recited excluded sequences may be revised in the database at a later date, it is intended that the above-recited sequences are excluded as they stand on the priority date of this application.

Isolated NR3B nucleic acid molecules can be prepared or isolated by methods well known in the art. The method chosen will depend on factors such as the type and size of the nucleic acid molecule; whether or not it encodes a biologically active polypeptide; and the source of the nucleic acid molecule. Such methods are described, for example, in Sambrook et al., supra (2001) and in Ausubel et al., supra (1999).

One useful method for producing an isolated NR3B nucleic acid molecule involves amplification of the nucleic acid molecule using the polymerase chain reaction (PCR) and specific primers and, optionally, purification of the resulting product by gel electrophoresis. Either PCR or reverse-transcription PCR (RT-PCR) can be used to produce a nucleic acid molecule having any desired nucleotide boundaries. Desired modifications to the nucleic acid sequence can also be conveniently introduced by choosing an appropriate primer with one or more additions, deletions or substitutions. Such nucleic acid molecules can be amplified exponentially starting from as little as a single gene or mRNA copy, from any cell, tissue or species of interest.

An isolated NR3B nucleic acid molecule can also be prepared by screening a library, such as a genomic library, cDNA library or expression library, with a detectable NR3B nucleic acid molecule or antibody. Human libraries, and libraries from a large variety of other species, are commercially available or can be produced from species or cells of interest. The library clones identified as containing NR3B nucleic acid molecules can be isolated, subcloned or sequenced by routine methods. From an initially identified fragment, nucleic acid molecules encoding full-length polypeptides can be obtained, if desired, by a variety of methods well-known in the art, such as 5' or 3' RACE.

Furthermore, an isolated NR3B nucleic acid molecule can be produced by synthetic means. For example, a single strand of a nucleic acid molecule can be chemically synthesized in one piece, or in several pieces, by automated synthesis methods known in the art. The complementary strand can likewise be synthesized in one or more pieces, and a double-stranded molecule made by annealing the complementary strands. Direct synthesis is particularly advantageous for producing relatively short molecules, such as probes and primers, and nucleic acid molecules containing modified nucleotides or linkages.

The invention also provides a vector containing an isolated NR3B nucleic acid molecule. The vectors of the invention are useful, for example, for subcloning and amplifying NR3B nucleic acid molecules, and for recombinantly expressing NR3B polypeptides and functional fragments thereof. A vector of the invention can include a variety of elements useful for cloning and/or expression of the encoded nucleic acid molecule in the desired host cell, such as promoter and/or enhancer sequences, which can provide for constitutive, inducible or cell-specific RNA transcription; transcription termination and RNA processing signals, including polyadenylation signals, which provide for stability of a transcribed mRNA sequence; an origin of replication, which allows for proper episomal replication; selectable marker genes, such as a neomycin or hygromycin resistance gene, useful for selecting stable or transient transfectants in mammalian cells, or an ampicillin resistance gene, useful for selecting transformants in prokaryotic cells; and versatile multiple cloning sites for inserting nucleic acid molecules of interest.

Cloning vectors of the invention include, for example, viral vectors such as a bacteriophage, a baculovirus or a retrovirus; cosmids or plasmids; and, particularly for cloning large nucleic acid molecules, bacterial artificial chromosome vectors (BACs) and yeast artificial chromosome vectors (YACs). Such vectors are commercially available, and their uses are well known in the art.

If it is desired to express NR3B RNA transcripts or polypeptides, an invention nucleic acid molecule can be operatively linked to a promoter of RNA transcription. The term "operatively linked," as used herein, is intended to mean that the nucleic acid molecule is positioned with respect to the endogenous promoter, or heterologous promoter, in such a manner that the promoter will direct the transcription of RNA using the nucleic acid molecule as a template. Methods for operatively linking a nucleic acid to a desired promoter are well known in the art and include, for example, cloning the nucleic acid into a vector containing the desired promoter, or appending the promoter to a nucleic acid sequence using PCR.

Thus, an invention nucleic acid molecule operatively linked to a promoter of RNA transcription can be used to express NR3B transcripts and polypeptides in a desired host cell, or in an in vitro system, such as an extract or lysate that supports transcription and translation.

Contemplated promoters and expression vectors provide for expression in bacterial cells, yeast cells, insect cells, amphibian cells, mammalian cells (including human, non-human primate and rodent cells) and other vertebrate cells. A variety of promoters and expression vectors suitable for such purposes are commercially available, and can be further modified, if desired, to include appropriate regulatory elements to provide for the desired level of expression or replication in the host cell.

For use in the gene therapy applications described further below, an invention nucleic acid molecule can be incorporated into suitable gene therapy vector, such as a viral vector or plasmid. Viral based vectors are advantageous in being able to introduce relatively high levels of a heterologous nucleic acid into a variety of cells, including nondividing cells.

Suitable viral vectors for gene therapy applications are well known in the art, and include, for example, Herpes simplex virus vectors (U.S. Pat. No. 5,501,979), Vaccinia virus vectors (U.S. Pat. No. 5,506,138), Cytomegalovirus vectors (U.S. Pat. No. 5,561,063), Modified Moloney murine leukemia virus vectors (U.S. Pat. No. 5,693,508), adenovirus vectors (U.S. Pat. Nos. 5,700,470 and 5,731,172), adeno-associated virus vectors (U.S. Pat. No. 5,604,090), constitutive and regulatable retrovirus vectors (U.S. Pat. Nos. 4,405,712; 4,650,764 and 5,739,018, 5,646,013, 5,624,820, 5,693,508 and 5,674,703), papilloma virus vectors (U.S. Pat. Nos. 5,674,703 and 5,719,054), lentiviral vectors (Kafri et al., Mol. Ther. 1:516-521 (2000), and the like. For targeting neural cells in the treatment of neuronal diseases, adenoviral vectors, Herpes simplex virus vectors and lentiviral vectors are particularly useful.

The invention also provides a cell containing an isolated NR3B nucleic acid molecule. Such a cell need not express a recombinant NR3B polypeptide or fragment for use in cloning procedures. However, a cell can optionally express an NR3B polypeptide or functional fragment encoded by the nucleic acid molecule. Such cells can be used in a variety of applications including, for example, screening for agonists, antagonists and ligands of excitatory glycine receptors, as described further below; as a source to isolate recombinantly expressed NR3B polypeptides; for identifying additional cellular molecules, such as additional receptor subunits or intracellular proteins that associate with NR3B; and in other applications known to those skilled in the art.

Optionally, a cell that recombinantly expresses an NR3B polypeptide can further endogenously or recombinantly express at least one other NMDA subunit, such as an NR1 subunit. As disclosed herein, co-expression of an NR3B and an NR1 polypeptide results in the formation of excitatory glycine receptors. NR1 polypeptides and encoding nucleic acid molecules from various species are known in the art, and include the naturally occurring NR1 polypeptides from human, rat, mouse, duck, fish and Xenopus having the nucleotide and predicted amino acid sequences set forth in Table 1:

TABLE 1

| SUBUNIT | ACCESSION NUMBER |
| --- | --- |
| Human NR1 | D13515 |
| Human NR1-1 | L13266 |
| Human NR1-2 | L13267 |
| Human NR1-3 | L13268 |
| Human NR1-3b | AF015730 |
| Human NR1-4b | AF015731 |
| Rat NR1 | U11418 |
| Rat NR1 | X63255 |
| Rat NR1-2b | U08264 |
| Rat NR1-3a | U08265 |
| Rat NR1-3b | U08266 |
| Rat NR1-4a | U08267 |
| Rat NR1-4b | U08268 |
| Mouse NR1 | D10028 |
| Duck NR1 | D83352 |
| Fish NR1 | AF060557 |
| Rat NR1-1a | U08261 |
| Rat NR1-2a | U08262 |
| Rat NR1-1b | U08263 |
| Xenopus NR1 | X94081 |

The skilled person will appreciate that for use in the methods described herein, a co-expressed NR1 polypeptide can have modifications to the naturally occurring sequence, or be a functional fragment of the naturally occurring sequence, so long as the desired NR1 biological activity is retained. An exemplary modification of a naturally occurring NR1 polypeptide that does not affect biological activity is the addition of an epitope tag to facilitate identification in procedures such as immunolocalization and immunoprecipitation. NR1 biological activities include, for example, the ability to oligomerize with other NMDA subunits, including NR2A-D, NR3B and NR3A; the ability to bind glycine; the ability to form excitatory glycine receptors in association with either NR3B or NR3A; and the ability to form NMDA- and glycine-responsive receptors in association with NR2 subunits. As described above with respect to NR3B polypeptides and functional fragments, the skilled person can readily make NR1 molecules with sequences that differ from the naturally occurring sequence and test such molecules to confirm that a desired NR1 biological activity is retained.

Exemplary host cells that can be used to recombinantly express receptor polypeptides and fragments include mammalian primary cells; established mammalian cell lines, such as COS, CHO, HeLa, NIH3T3, HEK 293-T and PC12 cells; amphibian cells, such as Xenopus embryos and oocytes; and other vertebrate cells. Exemplary host cells also include insect cells (e.g. *Drosophila*), yeast cells (e.g. *S. cerevisiae, S. pombe*, or *Pichia pastoris*) and prokaryotic cells (e.g. *E. coli*).

Also provided are extracts of recombinant cells that express NR3B at the cell membrane, wherein the extract contains the cell membrane. Advantageously, NR3B is expected to retain a biologically active conformation in a membrane extract, but is partially purified away from other cellular components that may be undesirable for certain applications. Cell membrane extracts can be prepared by methods known in the art (see, for example Das et al., *Nature* 393:377-381 (1998)) and can be used in many of the screening assays described herein.

Methods for introducing a recombinant nucleic acid molecule into a host cell are well known in the art. The choice of method will depend on the host cell, the type of nucleic acid molecule, and the intended application of the host cell. Suitable methods include, for example, various methods of transfection such as calcium phosphate, DEAE-dextran and lipofection methods; viral transduction; electroporation; and microinjection.

Animal model systems can be useful for elucidating normal and pathological functions of NR3B polypeptides, and for determining the efficacy and safety of potential therapeutic compounds that target excitatory glycine receptors. Accordingly, the invention also provides a transgenic non-human animal that contains an NR3B nucleic acid molecule. Such transgenic animals can express a nucleic acid molecule encoding an invention NR3B polypeptide or functional fragment, including a functional fragment that competes with or inhibits the function of the naturally occurring NR3B, as described previously. Alternatively, transgenic animals can express an invention NR3B polynucleotide that prevents effective translation of the naturally occurring NR3B polypeptide, such as an antisense, ribozyme, RNAi or similar construct. By employing suitable inducible and/or tissue specific regulatory elements, NR3B expression or activity in the transgenic animal can be restricted to specific cell types, developmental stages, or induction conditions.

Any of a variety of methods known in the art can be used to introduce a desired transgene into animals to produce the founder lines of transgenic animals (see, for example, Hogan et al., *Manipulating the Mouse Embryo: A Laboratory Manual*, second ed., Cold Spring Harbor Laboratory (1994), U.S. Pat. Nos. 5,602,299; 5,175,384; 6,066,778; and 6,037,521). Such techniques include, but are not limited to, pronuclear microinjection (U.S. Pat. No. 4,873,191); retrovirus mediated gene transfer into germ lines (Van der Putten et al., *Proc. Natl. Acad. Sci. USA* 82:6148-6152 (1985)); gene targeting in embryonic stem cells (Thompson et al., *Cell* 56:313-321 (1989)); electroporation of embryos (Lo, *Mol Cell. Biol.* 3:1803-1814 (1983)); and sperm-mediated gene transfer (Lavitrano et al., *Cell* 57:717-723 (1989)). Once the founder animals are produced, they can be bred to produce colonies of the particular animal by methods known in the art.

Figure 10:
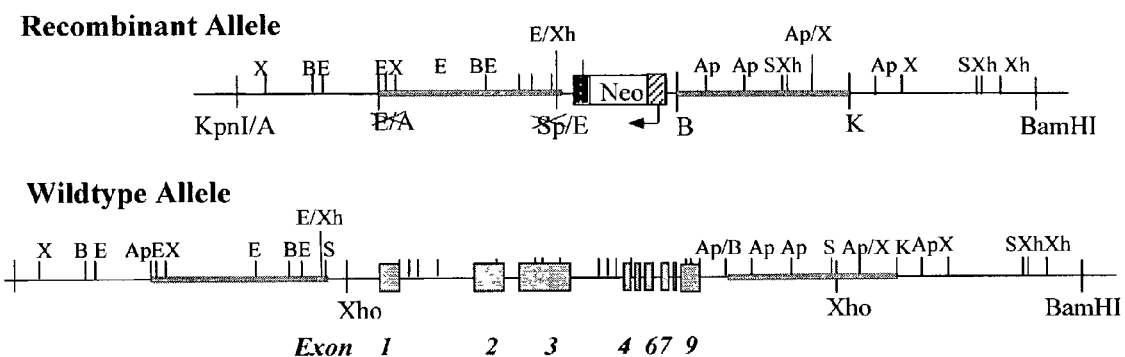
FIG. 10 shows the design of an NR3B targeting vector. The DNA fragment containing mouse NR3B exons 2-10 (~7.6 kb) was replaced by a fragment containing the neomycin resistant (Neo$^r$) gene-(~2 kb). The 5'-(~3.6 kb) and 3'-(~3.2 kb) arms used for homologous recombination are indicated by the thicker lines. The targeting DNA fragment was inserted into a pGTN29 vector.

In another embodiment, the invention provides NR3B-deficient non-human animals, or NR3B "knock-out" animals. Methods of deleting all or a portion of a gene so as to alter or prevent expression of the naturally occurring polypeptide are well known in the art. Gene knockout by homologous recombination is described, for example, in Capecchi et al., *Science* 244:1288 (1989), and in U.S. Pat. Nos. 5,616,491, 5,750,826, and 5,981,830. Methods of making and using an NR3A knockout mouse are described in Das et al., *Nature* 393:377-381 (1998). Analogous targeting vectors and methods are expected to be useful in generating NR3B knockout animals. FIG. 10 describes a targeting construct suitable for use in generating an NR3B knockout mouse.

The invention also provides a method for detecting a nucleic acid molecule encoding an NR3B polypeptide in a sample. Because of the critical role NMDA receptors play in neurologic disorders, the method can be used, for example, to diagnose or prognose a pathological condition mediated, in part, by altered expression, abundance or integrity of an NR3B nucleic acid molecule. Such conditions include, for example, acute neurologic conditions and chronic neurodegenerative diseases described further below. The detection method can also be used to identify additional regions of the nervous system in which NR3B is normally or pathologically expressed. Such information can be valuable in determining additional diagnostic and therapeutic applications for the invention molecules and methods described herein. Furthermore, the detection method can also be used to identify additional naturally occurring splice variants of NR3B receptors, and NR3B-encoding nucleic acid molecules from other species of interest, such as veterinary and laboratory animals.

In one embodiment, the detection method is practiced by contacting a sample with one or more NR3B polynucleotides and detecting specific hybridization to the polynucleotide. Suitable hybridization conditions for detecting specific hybridization will depend on the detection format, and are well known in the art. Exemplary conditions useful for filter-based assays have been described previously. Example II provides exemplary conditions suitable for in situ hybridization assays. Suitable conditions for PCR-based detection methods are also well known in the art and described, for example, in Sambrook et al., supra (2001) and in Ausubel et al., supra (1999).

As used herein, the term "sample" is intended to mean any biological fluid, cell, tissue, organ or portion thereof that contains or potentially contains an NR3B nucleic acid molecule or polypeptide. For example, a sample can be a histologic section of a specimen obtained by biopsy, or cells that are placed in or adapted to tissue culture. A sample further can be a subcellular fraction or extract, or a crude or substantially pure nucleic acid or protein preparation. A sample can be prepared by methods known in the art suitable for the particular format of the detection method employed.

The methods of detecting an NR3B nucleic acid molecule in a sample can be either qualitative or quantitative, and can detect the presence, abundance, integrity or structure of the nucleic acid molecule, as desired for a particular application. Suitable hybridization-based assay methods include, for example, in situ hybridization, which can be used to detect altered chromosomal location of the nucleic acid molecule, altered gene copy number, and RNA abundance, depending on the assay format used. Other hybridization methods include, for example, Northern blots and RNase protection assays, which can be used to determine the abundance and integrity of different RNA splice variants, and Southern blots, which can be used to determine the copy number and integrity of DNA. A hybridization probe can be labeled with any suitable detectable moiety, such as a radioisotope, fluorochrome, chemiluminescent marker, biotin, or other detectable moiety known in the art that is detectable by analytical methods.

Suitable amplification-based detection methods are also well known in the art, and include, for example, qualitative or quantitative polymerase chain reaction (PCR); reverse-transcription PCR (RT-PCR); single strand conformational polymorphism (SSCP) analysis, which can readily identify a single point mutation in DNA based on differences in the secondary structure of single-strand DNA that produce an altered electrophoretic mobility upon non-denaturing gel electrophoresis; and coupled PCR, transcription and translation assays, such as a protein truncation test, in which a mutation in DNA is determined by an altered protein product on an electrophoresis gel. The amplified nucleic acid molecule can be sequenced to detect mutations and mutational hot-spots, and specific PCR-based assays for large-scale screening of samples to identify such mutations can be developed.

The invention also provides isolated NR3B polypeptides and functional fragments therefrom, having amino acid sequences as described above with respect to polypeptides encoded by invention nucleic acid molecules. NR3B polypeptides and functional fragments can be used, for example, in therapeutic applications in which such polypeptides and fragments are administered onto or into cells; in screening assays to identify ligands, agonists and antagonists of excitatory glycine receptors; in research applications to identify additional NR3B-associating polypeptides; to raise antibodies for use in diagnostic and prognostic methods; to affinity purify antibodies and ligands; and in other applications known to those skilled in the art.

An isolated NR3B polypeptide of the invention can optionally contain amino acids with various chemical or enzymatic modifications with respect to naturally occurring amino acids. Such modifications can enhance the stability, bioactivity, immunogenicity or other advantageous property of an invention polypeptide. Thus, a polypeptide can contain an amino acid modified by replacement of hydrogen by an alkyl, acyl, or amino group; by esterification of a carboxyl group with a suitable alkyl or aryl moiety; by alkylation of a hydroxyl group to form an ether derivative; by phosphorylation or dephosphorylation of a serine, threonine or tyrosine residue; by N- or O-linked glycosylation; by iodination; by radiolabeling; or the like. A polypeptide can also include a modified amino acids such as hydroxyproline or carboxyglutamate, or a D-amino acid in place of its corresponding L-amino acid. Those skilled in the art can determine an appropriate amino acid modification for a given application.

In another embodiment, the invention provides an isolated NR3B peptide. An exemplary NR3B peptide contains at least 8 contiguous amino acids of a naturally occurring NR3B polypeptide, such as at least 8 contiguous amino acids of SEQ ID NOS:2, 4, 58, 60, 6, 62 or 8. Such a peptide can contain, for example, at least about 10, 12, 15, 20, 25, 30, 35, 40, 50, 60, 70, 80, 90, 100, 110, 125, 150, 200, 250, 300, 400, 500, 600, 700, 800, 900, 950 or more amino acids, up to the full length of the reference polypeptide. A peptide of at least about 8 amino acids can be used, for example, as an immunogen to raise antibodies specific for an NR3B polypeptide, or as an antigen to purify antibodies specific for an NR3B polypeptide. When used as an antigen, an invention peptide can be attached to a carrier molecule such as bovine serum albumin (BSA) or keyhole limpet hemocyanin (KLH).

Peptides that are likely to be antigenic or immunogenic can be predicted using methods and algorithms known in the art and described, for example, by Irnaten et al., *Protein Eng.* 11:949-955 (1998), and Savoie et al., *Pac. Symp. Biocomput.* 1999:182-189 (1999). Immunogenicity of the peptides of the invention can be determined by methods known in the art, such as assay of a delayed-type hypersensitivity response in an animal sensitized to a NR3B polypeptide, or by elicitation of antibodies specific for NR3B polypeptides. Likewise, antigenicity of the peptides of the invention can be determined by methods known in the art, such as by ELISA analysis, as described, for example, in Harlow and Lane, *Antibodies: A Laboratory Manual*, Cold Spring Harbor Laboratory Press (1988).

The isolated NR3B polypeptides, functional fragments and peptides of the invention can be prepared by methods known in the art, including biochemical, recombinant and synthetic methods. For example, polypeptides can be purified by routine biochemical methods from cells or tissues that express the polypeptide. The detection methods disclosed herein can be adapted for determining which cells or tissues are appropriate starting materials. Biochemical purification can include, for example, steps such as solubilization of the appropriate cells, size or affinity chromatography, electrophoresis, and immunoaffinity procedures. The methods and conditions for biochemical purification of a polypeptide of the invention can be chosen by those skilled in the art, and purification monitored, for example, by an ELISA assay or a functional assay.

An NR3B polypeptide, functional fragment or peptide having any desired boundaries can also be produced by recombinant methods. Recombinant methods involve expressing a nucleic acid molecule encoding the desired polypeptide or fragment in a host cell or cell extract, and isolating the recombinant polypeptide or fragment, such as by routine biochemical purification methods described above. To facilitate identification and purification of the recombinant polypeptide, it is often desirable to insert or add, in-frame with the coding sequence, nucleic acid sequences that encode epitope tags, polyhistidine tags, glutathione-S-transferase (GST) domains, fluorescent proteins (e.g. EGFP) and the like. Methods for producing and expressing recombinant polypeptides in vitro and in prokaryotic and eukaryotic host cells are well known in the art.

Thus, the invention provides a method of producing an NR3B polypeptide or functional fragment either in vitro or in a cell, by expressing a nucleic acid molecule encoding the polypeptide or fragment under appropriate conditions. Optionally, the polypeptide or fragment so produced can be partially purified, such as obtained as a membrane extract.

The invention NR3B polypeptide fragments and peptides can also be produced, for example, by enzymatic or chemical cleavage of the full-length polypeptide. Methods for enzymatic and chemical cleavage and for purification of the resultant peptide fragments are well known in the art (see, for example, Deutscher, *Methods in Enzymology*, Vol. 182, "Guide to Protein Purification," San Diego: Academic Press, Inc. (1990)).

Depending on the intended application, the isolated NR3B polypeptide or functional fragment can optionally be isolated in, or reconstituted into, a natural or artificial lipid bilayer, such as a cell membrane or liposome, with or without other cellular components. Thus, in one embodiment, the invention provides an isolated NR3B polypeptide, further comprising a membrane, and optionally further comprising an NMDA receptor subunit, such as an NR1 subunit. Membrane-associated NR3B polypeptides and functional fragments are useful in applications in which structural integrity of the subunit and/or excitatory glycine receptor are important, such as in the screening assays described herein.

The invention also provides an antibody or antigen binding fragment thereof which specifically binds an NR3B polypeptide. Such antibodies, which include polyclonal, monoclonal, chimeric, bifunctional, and humanized antibodies, can be used, for example, to affinity purify an NR3B polypeptide or functional fragment; to detect cellular polypeptides, including NMDA receptor subunits, that associate with NR3B; and in therapeutic, diagnostic and research applications known to those skilled in the art and described further below. An antibody that "specifically binds" and NR3B polypeptide binds with high affinity to a NR3B polypeptide in a binding assay, such as an immunoblot or ELISA assay, without substantial cross-reactivity with other polypeptides such as other NMDA receptor subunits.

An "antigen binding fragment" of an antibody of the invention includes, for example, individual heavy or light chains and fragments thereof, such as VL, VH and Fd; monovalent fragments, such as Fv, Fab, and Fab'; bivalent fragments such as $F(ab')_2$; single chain Fv (scFv); and Fc fragments. Antigen binding fragments include, for example, fragments produced by protease digestion or reduction of an antibody, as well as fragments produced by recombinant DNA methods known to those skilled in the art.

In one embodiment, the invention provides antibodies and antigen binding fragments thereof that specifically bind an NR3B polypeptide containing an amino acid sequence designated SEQ ID NO:2, 4, 6 or 8. For certain applications, such as to antagonize receptor activity, antibodies that bind an extracellular portion of NR3B are desirable, including antibodies that bind the region N-terminal to the S1 domain, the S1 domain, the S2 domain, or the region between the M3 and M4 domains. For other applications, antibodies that distinguish a splice variant form of an NR3B receptor are useful, such as antibodies that bind the 15 amino acid portion of rat NR3B B4 not present in the NR3B A2 form.

The antibodies of the invention can be produced by any suitable method known in the art. For example, a NR3B polypeptide or immunogenic peptide of the invention, or a nucleic acid expressing such a polypeptide or peptide, can be administered to an animal, using standard methods, and polyclonal antibodies isolated therefrom. Such polypeptides or peptides, if desired, can be conjugated to a carrier, such as KLH, serum albumin, tetanus toxoid and the like, using standard linking techniques, to increase their immunogenicity. Additionally, such peptides can be formulated together with an adjuvant known in the art, such as Freund's complete or incomplete adjuvant. The antibodies so generated can be used in the form of serum isolated from an immunized animal, or the antibody can be affinity purified from the serum using the invention peptides or polypeptides.

Additionally, the antibodies of the invention can be monoclonal antibodies produced by a hybridoma cell line, by chemical synthesis, or by recombinant methods. Modified antibodies, such as chimeric antibodies, single chain antibodies, humanized antibodies and CDR-grafted or bifunctional antibodies, can also be produced by methods well known to those skilled in the art.

Methods of preparing and using antibodies and antigen-binding fragments, including detectably labeled antibodies, are described, for example, in Harlow and Lane, *Antibodies: A Laboratory Manual*, Cold Spring Harbor Laboratory, New York (1989); in Day, E. D., *Advanced Immunochemistry*, Second Ed., Wiley-Liss, Inc., New York, N.Y. (1990); and in Borrebaeck (Ed.), *Antibody Engineering*, Second Ed., Oxford University Press, New York (1995). Example V describes a method for producing NR3B-specific antibodies.

The invention also provides a method for detecting an NR3B polypeptide in a sample. The method is practiced by contacting a sample with an antibody specific for an NR3B polypeptide and detecting specific binding of the antibody to the sample. As described above with respect to encoding nucleic acid molecules, altered expression, abundance or integrity of an NR3B polypeptide in a sample can thus be indicative of a pathological condition, including any of the acute or chronic neurological and neurodegenerative conditions described herein.

The methods of detecting an NR3B polypeptide in a sample can be either qualitative or quantitative, and can detect the presence, abundance, integrity or localization of the polypeptide, as desired for a particular application. Contemplated assays to detect a polypeptide in a sample include in situ histochemistry, immunoblotting, immunoprecipitation, FACS analysis, radioligand binding, and ELISA analysis. Such assays can be direct, using a detectably labeled ligand, or indirect, using a labeled secondary reagent, such as an anti-ligand antibody. Exemplary labels include fluorescent labels, enzymes, radioisotopes, and biotin. Detection can be by any convenient analytical means, including by spectrophotometric, radiographic or chemiluminescent means, depending on the assay.

The invention also provides a method of detecting an NR3B ligand. In one embodiment, the method is practiced by contacting an NR3B polypeptide with one or more compounds under conditions suitable for detecting binding to the polypeptide, and detecting a candidate compound that binds the polypeptide. In another embodiment, the invention is practiced by contacting an NR3B functional fragment with one or more compounds under conditions suitable for detecting binding to the fragment, and detecting a candidate compound that binds the fragment. For use in such an application, the NR3B functional fragment desirably contains at least one extracellular domain of the NR3B polypeptide, such as the region N-terminal to the S1 domain, the S1 domain, the S2 domain, or the region between the M3 and M4 domains (see FIG. 8 and FIG. 11).

The invention further provides a method of detecting an excitatory glycine receptor ligand. The method is practiced by contacting an excitatory glycine receptor with one or more compounds under conditions suitable for detecting binding to the receptor, and detecting a candidate compound that binds the receptor.

In one embodiment, the excitatory glycine receptor contains an NR3B polypeptide and an NR1 polypeptide. In another embodiment, the excitatory glycine receptor contains an NR3A polypeptide and an NR1 polypeptide. In a further embodiment, the excitatory glycine receptor contains an NR3B polypeptide, an NR3A polypeptide and an NR1 polypeptide. In yet another embodiment, the excitatory glycine receptor contains an NR3B and/or an NR3A polypeptide, an NR1 polypeptide and an NR2 polypeptide (ie. an NR2A, 2B, 2C or 2D polypeptide).

As disclosed herein, co-expression of an NR3A and an NR1 polypeptide also results in the formation of excitatory glycine receptors. Rat NR3A polypeptides and encoding nucleic acid molecules are known in the art, and exemplary molecules have the nucleotide and predicted amino acid sequences set forth in Table 2:

TABLE 2

| SUBUNIT | ACCESSION NUMBER |
| --- | --- |
| Rat NR3A (NMDAR-L) | U29873 |
| Rat NR3A (x-1) | L34938 |
| Rat NR3A (splicing variant) | AF061945 |
| Rat NR3A (splicing variant) | AF073379 |

Disclosed herein as SEQ ID NO:55 is the predicted human NR3A cDNA sequence and its encoding amino acid sequence (SEQ ID NO:56). These sequence were predicted from the human NR3A genomic sequences in the database (GenBank Accession Nos. NT_025809, AL35616, XM042803.1 and AL359651.1) based on the rat NR3A cDNA and amino acid sequences. The skilled person can likewise determine additional NR3A sequences from other species.

NR2 polypeptides and encoding nucleic acid molecules are also known in the art, and exemplary molecules have the nucleotide and predicted amino acid sequences set forth in Table 3:

TABLE 3

| SUBUNIT | ACCESSION NUMBER |
| --- | --- |
| Human NR2A cDNA | NM_000833, U09002, U90277, XM_030214, XM_030215, XM_007911, XM_016282 |
| Human NR2A genomic | AC007218, AC006531 |
| Rat NR2A cDNA | NM_012573, M91561, AF001423, D13211 |
| Mouse NR2A (epsilon 1) | NM_008170, D10217 |
| Human NR2B cDNA | XM_006636, XM_042404, XM_042405, XM_042406, NM_000834, U88963, U11287, U90278 |
| Human NR2B genomic | AC007535 |
| Rat NR2B cDNA | NM_012574, U11419, M91562 |
| Mouse NR2B (epsilon 2) | NM_008171, D10651 |
| Human NR2C CDNA | NM_000835, U77782, XM_046949, L76224, XM_012596 |
| Rat NR2C | NM_012575, D13212, M91563, U08259 |
| Mouse NR2C (epsilon 3) | NM_010350, D10694 |
| Human NR2D cDNA | XM_009108, NM_000836, U77783 |
| Human NR2D genomic | AC011527, AC008403 |
| Rat NR2D | U08260, NM_022797, L31612, L31611, D13213 |
| Mouse NR2D (epsilon 4) | NM_008172, D12822 |

The skilled person will appreciate that for use in the methods described herein, an NR3A or NR2 polypeptide can have modifications to a naturally occurring sequence, or be a functional fragment of the naturally occurring sequence, so long as the desired biological activity is retained. An exemplary modification of a naturally occurring NR3A or NR2 polypeptide that does not affect biological activity is the addition of an epitope tag to facilitate identification in procedures such as immunolocalization and immunoprecipitation.

NR3A biological activities include, for example, the ability to oligomerize with other NMDA subunits, including NR1; the ability to bind glycine; and the ability to form excitatory glycine receptors in association with NR1. NR2 biological activities include, for example, the ability to oligomerize with other NMDA subunits, including NR1; the ability to bind glutamate; and the ability to form excitatory glutamate receptors in association with NR1.

As described above with respect to NR3B and NR1 polypeptides and functional fragments, the skilled person can readily make NR3A and NR2 molecules with sequences that differ from the naturally occurring sequence and test such molecules to confirm that a desired NR3A or NR2 biological activity is retained.

As used herein, the term "ligand" refers to any biological or chemical compound that binds the recited polypeptide, fragment or receptor with high affinity. High affinity binding refers to binding with a Kd of less than about $10^{-3}$ M, such as less than $10^{-5}$ M, and often less than $10^{-7}$ M. Glycine and NR3B antibodies are examples of ligands of NR3B.

An "NR3B ligand" or "excitatory glycine receptor ligand" can further be an agonist or antagonist of an excitatory glycine receptor, as described below, or can be a compound having little or no effect on excitatory glycine receptor biological activity. For example, a ligand without agonistic or antagonistic activity can be used to specifically target a diagnostic or therapeutic moiety to cells and tissues that express an excitatory glycine receptor. Thus, an identified ligand can be labeled with a detectable moiety, such as a radiolabel, fluorochrome, ferromagnetic substance, or luminescent substance, and used to detect normal or abnormal expression of an excitatory glycine receptor in an isolated sample or in in vivo diagnostic imaging procedures. Likewise, an identified ligand can be labeled with a therapeutic moiety, such as a cytotoxic or cytostatic agent or radioisotope, and administered in an effective amount to arrest proliferation or kill a cell or tissue that aberrantly expresses an excitatory glycine receptor for use in therapeutic applications described further below.

Binding assays, including high-throughput automated binding assays, are well known in the art and can be used in the invention methods. The assay format can employ a cell, cell membrane, artificial membrane system, or purified polypeptide, fragment or receptor, either in solution or attached to a solid phase. If desired, the binding assay can be performed in the presence of a known ligand of NR3B or of an excitatory glycine receptor, such as glycine.

Suitable assays that can be used for detecting ligand binding include, for example, scintillation proximity assays (SPA) (Alouani, *Methods Mol. Biol.* 138:135-41 (2000)), UV or chemical cross-linking (Fancy, *Curr. Opin. Chem. Biol.* 4:28-33 (2000)), competition binding assays (Yamamura et al., *Methods in Neurotransmitter Receptor Analysis*, Raven Press, New York, 1990), biomolecular interaction analysis (BIA) (Weinberger et al., *Pharmacogenomics* 1:395-416 (2000)), mass spectrometry (MS) (McLafferty et al., *Science* 284:1289-1290 (1999) and Degterev, et al., *Nature Cell Biology* 3:173-182 (2001)), nuclear magnetic resonance (NMR) (Shuker et al., *Science* 274:1531-1534 (1996), Hajduk et al.,*J. Med. Chem.* 42:2315-2317 (1999), and Chen and Shapiro, *Anal. Chem.* 71:669A-675A (1999)), fluorescence polarization assays (FPA) (Degterev et al., supra, 2001); surface plasmon resonance (SPR) (Liparoto et al., *J. Mol Recognit.* 12:316-321 (1999)); and protein chip proteomic array analysis (e.g. ProteinChip™ System from Ciphergen Biosystems, which can be used in tandem with mass spectrometry analysis for sequence or structure determination).

An exemplary assay that has been used successfully to identify ligands of an NMDA receptor is phage display (see Li et al., *Nature Biotech.* 14:986-991 (1996), which describes contacting an N-terminal fragment of an NR1 polypeptide with a phage display library). A similar phage display approach can be applied to determine NR3B ligands and excitatory glycine receptor ligands.

Exemplary high-throughput receptor binding assays are described, for example, in Mellentin-Micelotti et al., *Anal. Biochem.* 272:P182-190 (1999); Zuck et al., *Proc. Natl. Acad. Sci. USA* 96:11122-11127 (1999); and Zhang et al., *Anal. Biochem.* 268;134-142 (1999). Other suitable methods are known in the art.

The invention also provides methods of detecting an excitatory glycine receptor agonist or antagonist The method is practiced by contacting an excitatory glycine receptor under conditions suitable for detecting excitatory glycine receptor activation, and detecting a candidate compound that alters excitatory glycine receptor activation. As described herein, excitatory glycine receptor activation can be evidenced by elicitation of a monovalent cation current, with little or no channel permeability to $Ca^{2+}$ and little or no inhibition by $Mg^{2+}$.

In one embodiment, the excitatory glycine receptor contains an NR3B polypeptide and an NR1 polypeptide. In another embodiment, the excitatory glycine receptor contains an NR3A polypeptide and an NR1 polypeptide. In a further embodiment, the excitatory glycine receptor contains an NR3B polypeptide, an NR3A polypeptide and an NR1 polypeptide. In yet another embodiment, the excitatory glycine receptor contains an NR3B polypeptide, an NR1 polypeptide and an NR2 polypeptide (ie. an NR2A, 2B, 2C or 2D polypeptide). In another embodiment, the excitatory glycine receptor contains an NR3A polypeptide, an NR1 polypeptide and an NR2 polypeptide (ie. an NR2A, 2B, 2C or 2D polypeptide).

The agonists and antagonists identified by the methods of the invention are useful in therapeutic applications, described further below, in which it is desirable to increase or decrease ion flow through the excitatory glycine receptor.

As used herein, the term "excitatory glycine receptor agonist" refers to a compound that increases or activates excitatory glycine receptor cation currents. An agonist can act by any mechanism, such as by binding the receptor at the normal glycine binding site, thereby mimicking glycine and promoting receptor activation. An agonist can also act, for example, by potentiating the activity of glycine, or by favorably altering the conformation of the receptor. The methods of the invention can be used to detect agonists that act through any agonistic mechanism.

As used herein, the term "excitatory glycine receptor antagonist" refers to a compound that decreases or inhibits excitatory glycine receptor cation currents. Typically, the effect of an antagonist is observed as a blocking of activation by an agonist. For example, 5, 7-di-Cl-Kynurenate blocks glycine activated currents through the NR3B/NR1 receptor.

Figure 3:
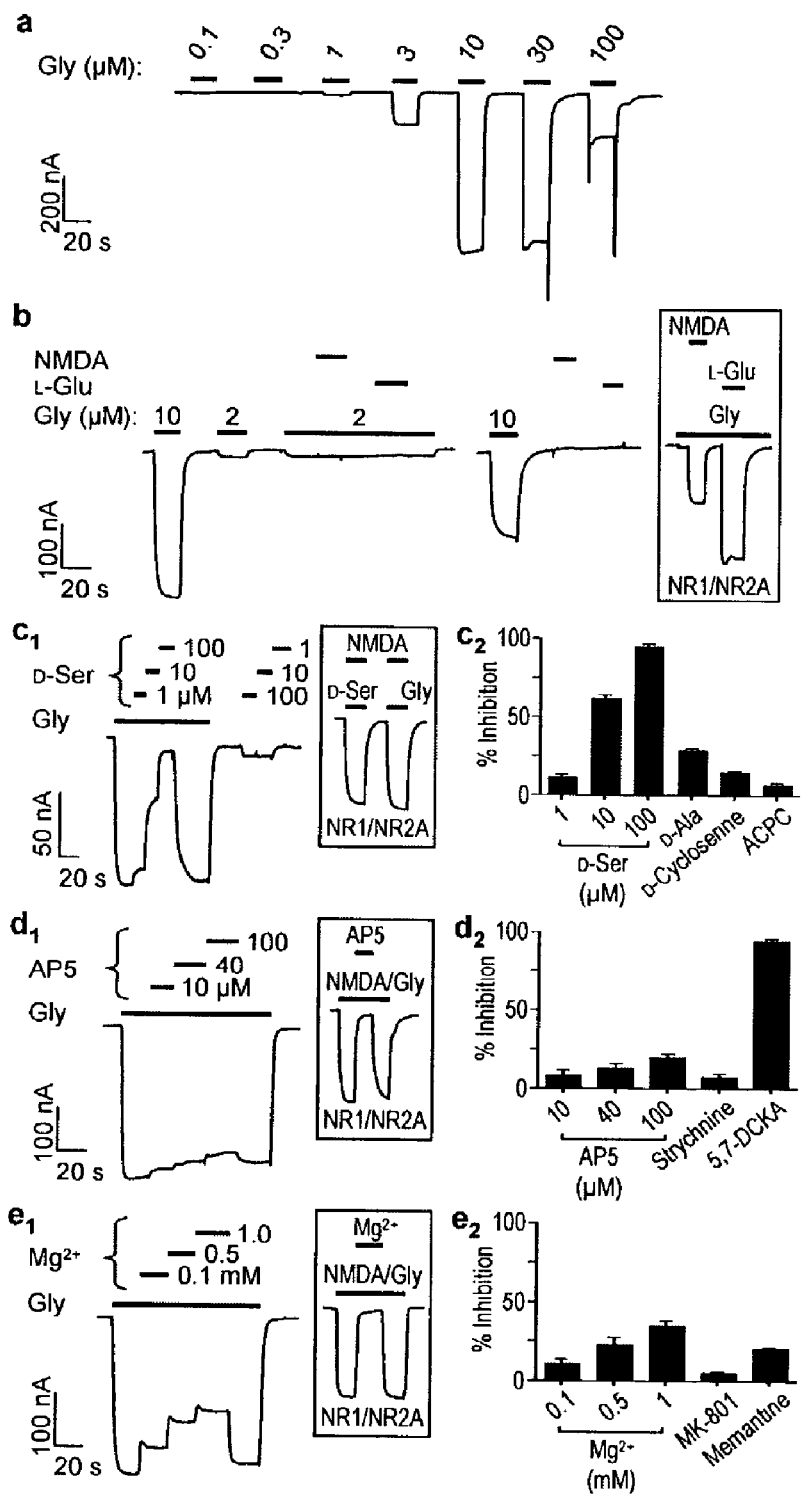
FIG. 3(a-e) shows pharmacological characterization of NR1/NR3B receptors in Xenopus oocytes. Glycine-evoked currents were recorded from oocytes injected with NR1/NR3B. The insets show NMDA/glycine-evoked NR1/NR2A currents for comparison. Glycine and NMDA (or L-glutamate) concentrations were 10 and 100 μM, respectively, unless otherwise indicated. Data are representative of recordings from 3-9 oocytes in each case.

Antagonists include, for example, partial antagonists, partial agonists, competitive antagonists, non-competitive antagonists and uncompetitive antagonists. A competitive antagonist interacts with or near the site specific for the agonist. A non-competitive antagonist inactivates the function of the receptor by interacting with a site other than the site that interacts with the agonist. Partial agonists have both agonistic and antagonistic activity. For example, as shown in FIG. 3, D-serine evokes small NR1/NR3B currents alone, but dose-dependently inhibits currents in the presence of glycine. The methods of the invention can be used to detect antagonists that act through any antagonistic mechanism.

Methods of detecting excitatory glycine receptor agonists and antagonists can advantageously be performed either in the presence or absence of a physiologically relevant excitatory glycine receptor agonist such as glycine. Compounds that demonstrate agonistic and antagonistic effects in the presence of glycine are particularly useful for use in therapeutic applications, in which physiological concentrations of circulatory glycine are present. In such methods, concentrations of glycine of about 1 to about 100 µM, such as about 5-10 µM, are suitable.

Electrophysiological methods for detecting monovalent cation currents through an excitatory glycine receptor are well known in the art. Exemplary methods for recording whole-cell and single-channel currents in Xenopus oocytes, brain slices, mammalian cells and cell-free membrane patches are described in Das et al., *Nature* 393:377-381 (1998); Sakmann and Neherand, in *Single-Channel Recording*, 2nd ed., Ch. 15, pp. 341-355, (1995), edited by Bert Sakmann and Erwin Neher, Plenum Press, New York; Penner, in *Single-Channel Recording*, 2nd ed., Ch. 1, pp. 3-28; Hamill et al., Pflugers Arch. 391:85-100 (1981); Ilers et al., in *Single-Channel Recording*, 2nd ed., Ch. 9, pp. 213-229, (1995), edited by Bert Sakmann and Erwin Neher, Plenum Press, New York; and in the Examples, below.

Ionic currents can also be detected using suitable detectably labeled ion indicators. Ion indicators and methods for their use are known in the art. For example, monovalent cation currents through the excitatory glycine receptor can be detected using $Na^+$ or $K^1$ ion indicators, which can be fluorescently labeled or radiolabeled (see, for example, Moore et al., *Proc. Natl. Acad. Sci. USA* 90:8058-8062 (1993); Paucek et al., *J. Biol. Chem.* 267:26062-26069 (1992); Xu et al., *J. Biol. Chem.* 270: 19606-19612 (1995)). Exemplary ion indicators include: SBFI sodium indicator, Sodium Green sodium indicator; CoroNa Red sodium indicator; PBFI potassium indicator; 6-Methoxy-N-(3-sulfopropyl)quinolinium (SPQ) chloride indicator; N-(Ethoxycarbonylmethyl)-6-methoxyquinolinium bromide (MQAE) chloride indicator; 6-Methoxy-N-ethylquinolinium iodide (MEQ) chloride indicator; Lucigenin chloride indicator, which are available from Molecular Probes, Inc.

Subsequent to excitatory glycine receptor activation and membrane depolarization, an influx of $Ca^{2+}$ ions occurs if voltage-dependent $Ca^{2+}$ channels are present in the cell being studied. If the cell of interest does not endogenously express voltage-dependent $Ca^{2+}$ channels, the cell can be recombinantly engineered to express such channels, using voltage-dependent $Ca^{2+}$ channel subunit gene sequences and molecular biology methods known in the art. Accordingly, ionic currents through the excitatory glycine receptor can also be detected, indirectly, using detectably labeled $Ca^{2+}$ ion indicators, which can be fluorescently labeled or radiolabeled. Exemplary $Ca^{2+}$ ion indicators include FLUO-3 AM, FLUO-4 AM, FURA-2, INDO-1, FURA RED, CALCIUM GREEN, CALCIUM ORANGE, CALCIUM CRIMSON, BTC, and OREGON GREEN BAPTA (see, for example, Grynkiewitz et al., *J. Biol. Chem.* 260:3440-3450 (1985); Sullivan et al., in *Calcium Signal Protocol, Methods in Molecular Biology* 114: 125-133, Edited by David G. Lambert, Human Press, Totowa, N.J. (1999); Miyawaki et al., *Proc. Natl. Acad. Sci. USA* 96:2135-2140 (1999); and Coward et al., *Analyt. Biochem.* 270:242-248 (1999)).

Assay methods for identifying compounds that bind to or modulate excitatory glycine receptor activity (e.g. ligands, agonists and antagonists) generally involve comparison to a control. One type of a "control" is a NR3B polypeptide or excitatory glycine receptor that is treated substantially the same as the polypeptide or receptor exposed to the candidate compound, except the control is not exposed to the candidate compound. For example, the same recombinant cell can be tested in the presence and absence of candidate compound, by merely changing the solution contacting the cell. Another type of "control" is a cell that is essentially identical to the NR3B polypeptide- or excitatory glycine receptor-expressing recombinant cell, except the control cell does not express the polypeptide or receptor. In this situation, the response of the test cell to a candidate compound is compared to the response (or lack of response) of the control cell to the same compound under substantially the same reaction conditions.

The term "candidate compound" refers to any molecule that potentially acts as a ligand, agonist or antagonist or ligand in the screening methods disclosed herein. A candidate compound can be a naturally occurring macromolecule, such as a polypeptide, amino acid, nucleic acid, carbohydrate, lipid, or any combination thereof. A candidate compound also can be a partially or completely synthetic derivative, analog or mimetic of such a macromolecule, or a small organic molecule prepared by combinatorial chemistry methods. If desired in a particular assay format, a candidate compound can be detectably labeled or attached to a solid support.

Methods for preparing large libraries of compounds, including simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., Curr. Opin. Chem. Biol. 2:422-428 (1998); Tietze et al., Curr. Biol., 2:363-371 (1998); Sofia, Mol. Divers. 3:75-94 (1998); Eichler et al., Med. Res. Rev. 15:481-496 (1995); and the like. Libraries containing large numbers of natural and synthetic compounds also can be obtained from commercial sources.

The number of different candidate compounds to test in the methods of the invention will depend on the application of the method. For example, one or a small number of candidate compounds can be advantageous in manual screening procedures, or when it is desired to compare efficacy among several predicted ligands, agonists or antagonists. However, it is generally understood that the larger the number of candidate compounds, the greater the likelihood of identifying a compound having the desired activity in a screening assay. Additionally, large numbers of compounds can be processed in high-throughput automated screening assays. Therefore, "one or more candidate compounds" can be, for example, 2 or more, such as 5, 10, 15, 20, 50 or 100 or more different compounds, such as greater than about $10^3$, $10^5$ or $10^7$ different compounds, which can be assayed simultaneously or sequentially.

The function of the NR3A polypeptide has remained elusive, despite years of investigation (see Ciaberra et al., J. Neuroscience 15:6498-6508 (1995); Sucher et al., J. Neuroscience 15:6509-6520 (1995); Das et al. supra (1998); Perez-Otano et al., J. Neuroscience 21:1228-1237 (2001)). As disclosed herein, when expressed in combination with NR1 and optionally also NR2 subunits, the NR3A polypeptide, like the NR3B polypeptide, forms an excitatory glycine receptor (see Example IV). The invention thus provides isolated excitatory glycine receptors containing either an NR3A polypeptide or an NR3B polypeptide, or both. Such receptors are suitable use in the methods described herein of detecting excitatory glycine receptors agonists, antagonists and ligands. As described previously, depending on the particular assay, the isolated receptors can optionally be present at the surface of an intact cell, present in a cell membrane with or without other cellular components, or reconstituted into a natural or artificial lipid bilayer.

In one embodiment, the excitatory glycine receptor contains an NR3B polypeptide and an NR1 polypeptide. In another embodiment, the excitatory glycine receptor contains an NR3A polypeptide and an NR1 polypeptide. In a further embodiment, the excitatory glycine receptor contains an NR3B polypeptide, an NR3A polypeptide and an NR1 polypeptide. In yet another embodiment, the excitatory glycine receptor contains an NR3B polypeptide, an NR1 polypeptide and an NR2 polypeptide (ie. an NR2A, 2B, 2C or 2D polypeptide). In another embodiment, the excitatory glycine receptor contains an NR3A polypeptide, an NR1 polypeptide and an NR2 polypeptide (ie. an NR2A, 2B, 2C or 2D polypeptide).

Suitable NR3B, NR3A, NR2A-D and NR1 polypeptides that can be used as subunits of excitatory glycine receptors, including both naturally occurring polypeptides, and modifications and functional fragments of such polypeptides, have been described previously.

The invention also provides therapeutic methods for the prevention and amelioration of conditions in which inappropriate NMDA receptor activation, or inappropriate responses to glycine or glutamate, are implicated. Such conditions include, for example, acute neurologic condition, such as cerebral ischemia; stroke; hypoxia; anoxia; poisoning by carbon monoxide, manganese, cyanide or domoic acid; hypoglycemia; mechanical trauma to the nervous system such as trauma to the head or spinal cord; or epileptic seizure. Other conditions include, for example, chronic neurodegenerative disease, such as Huntington's disease; a disorder of photoreceptor degeneration such as retinitis pigmentosa; acquired immunodeficiency syndrome (AIDS) dementia complex (HIV-associated dementia); a neuropathic pain syndrome such as causalgia or a painful peripheral neuropathy; olivopontocerebellar atrophy; Parkinsonism; amyotrophic lateral sclerosis; a mitochondrial abnormality or other biochemical disorder such as MELAS syndrome, MERRF, Leber's disease, Wernicke's encephalopathy, Rett syndrome, homocysteinuria, hyperhomocysteinemia, hyperprolinemia, nonketotic hyperglycinemia, hydroxybutyric aminoaciduria, sulfite oxidase deficiency, combined systems disease, lead encephalopathy, Alzheimer's disease, hepatic encephalopathy, Tourette's syndrome, drug addiction/tolerance/dependency, glaucoma, depression, anxiety, multiple sclerosis and other demyelinating disorders. Other conditions are known in the art and reviewed, for example, in Lipton et al., New Engl. J. Med. 330:613-622 (1994) and Cull-Candy et al., Curr. Opin. Neurobiol. 11:327-335 (2001).

Thus, the invention provides methods for increasing or decreasing signaling through an excitatory glycine receptor by administering an excitatory glycine receptor agonist, antagonist or ligand, or an NR3B ligand, to an individual. Methods of identifying such agonist, antagonist and ligands have been described previously.

The invention also provides gene therapy methods for modulating a cellular response to glycine or glutamate. By overexpressing a full-length NR3B polypeptide, the NR1 subunit can form NR1/NR3B receptors, which are insensitive to glutamate, rather than NR1/NR2 receptors. Therefore, detrimental glutamate responses can be reduced. In contrast, by expressing a dominant negative NR3B polypeptide, or a construct that prevents translation of endogenous NR3B, fewer functional NR1/NR3B receptors will be formed. Therefore, detrimental glycine responses can be reduced. Therapeutic applications in which it is desirable to modulate cellular responses to glutamate and glycine are described above.

In one embodiment, the invention provides a method of modulating a cellular response to glycine or glutamate by introducing a nucleic acid molecule encoding an NR3B polypeptide or functional fragment into a cell, and expressing the NR3B functional fragment encoded by the nucleic acid molecule in the cell. In another embodiment, the invention provides a method of modulating a cellular response to glycine or glutamate by introducing an antisense nucleic acid molecule, a ribozyme molecule or a small interfering RNA (siRNA) molecule into the cell, wherein the molecule hybridizes to an NR3B nucleic acid molecule and prevents translation of the encoded NR3B polypeptide.

Suitable gene therapy vectors have been described previously. For gene therapy applications, the nucleic acid molecule can be administered to a subject by various routes. For example, local administration at the site of a pathology can be advantageous because there is no dilution effect and, therefore, the likelihood that a majority of the targeted cells will be contacted with the nucleic acid molecule is increased. This is particularly true in the eye, where either intravitreal or intraretinal administration is possible. In addition, administration can be systemic, such as via intravenous or subcutaneous injection into the subject. For example, following injection, viral vectors will circulate until they recognize host cells with the appropriate target specificity for infection.

Receptor-mediated DNA delivery approaches also can be used to deliver a nucleic acid molecule into cells in a tissue-specific manner using a tissue-specific ligand or an antibody that is non-covalently complexed with the nucleic acid molecule via a bridging molecule. Direct injection of a naked nucleic acid molecule or a nucleic acid molecule encapsulated, for example, in cationic liposomes also can be used for stable gene transfer into non-dividing or dividing cells. In addition, a nucleic acid molecule can be transferred into a variety of tissues using the particle bombardment method.

Antisense nucleotide sequences that are complementary to a nucleic acid molecule encoding an NR3B polypeptide can be used to prevent or reduce NR3B expression. Therefore, the method can be practiced with an antisense nucleic acid molecule complementary to at least a portion of the nucleotide sequence of SEQ ID NOS:1, 59, 3, 57, 5, 61 or 7 For example, the antisense nucleic acid molecule can be complementary to a region within the N-terminus of SEQ ID NOS:1, 59, 3, 57, 5, 61 or 7, such as within nucleotides 1-1000, 1-500, 1-100 or 1-18, and can optionally include sequences 5' to the start codon. Methods of preparing antisense nucleic acids molecules and using them therapeutically are known in the art and described, for example, in Galderisi et al., *J. Cell Physiol.* 181:251-257 (1999).

Likewise, ribozymes that bind to and cleave SEQ ID NOS: 1, 59, 3, 57, 5, 61 or 7 can also be effective in preventing or reducing NR3B expression. Methods of preparing ribozymes and DNA encoding ribozymes, including hairpin and hammerhead ribozymes, and using them therapeutically are known in the art and described, for example, in Lewin et al., *Trends Mol. Med.* 7:221-228 (2001).

Additionally, small interfering RNAs (siRNAs), which are short duplex RNAs with overhanging 3' ends, directed against SEQ ID NOS:1, 59, 3, 57, 5, 61 or 7, can also be effective in preventing or reducing NR3B expression. Methods of preparing and using siRNAs are known in the art and described, for example, in Elbashir et al., *Nature* 411:494-498 (2001).

The therapeutic compounds of the invention, including agonists, antagonists, ligands and nucleic acid molecules, can be formulated and administered in a manner and in an amount appropriate for the condition to be treated; the weight, gender, age and health of the individual; the biochemical nature, bioactivity, bioavailability and side effects of the particular compound; and in a manner compatible with concurrent treatment regimens. An appropriate amount and formulation for a particular therapeutic application in humans can be extrapolated based on the activity of the compound in the in vitro binding and signaling assays described herein, or from recognized animal models of the particular disorder.

The total amount of therapeutic compound can be administered as a single dose or by infusion over a relatively short period of time, or can be administered in multiple doses administered over a more prolonged period of time. Additionally, the compound can be administered in a slow-release matrice, which can be implanted for systemic delivery at or near the site of the target tissue. Contemplated matrices useful for controlled release of therapeutic compounds are well known in the art, and include materials such as DepoFoam™, biopolymers, micropumps, and the like.

The therapeutic compounds can be administered to an individual by routes known in the art including, for example, intravenously, intramuscularly, subcutaneously, intraorbitally, intracapsularly, intraperitoneally, intracisternally, intraarticularly, intracerebrally, orally, intravaginally, rectally, topically, intranasally, transdermally or intravitreally.

Preferably, the therapeutic compounds are administered to a subject as a pharmaceutical composition comprising the compound and a pharmaceutically acceptable carrier. The choice of pharmaceutically acceptable carrier depends on the route of administration of the compound and on its particular physical and chemical characteristics. Pharmaceutically acceptable carriers are well known in the art and include sterile aqueous solvents such as physiologically buffered saline, and other solvents or vehicles such as glycols, glycerol, oils such as olive oil and injectable organic esters. A pharmaceutically acceptable carrier can further contain physiologically acceptable compounds that stabilize the compound, increase its solubility, or increase its absorption. Such physiologically acceptable compounds include carbohydrates such as glucose, sucrose or dextrans; antioxidants, such as ascorbic acid or glutathione; chelating agents; and low molecular weight proteins.

For applications that require the compounds and compositions to cross the blood-brain barrier, or to cross the cell membrane, formulations that increase the lipophilicity of the compound are particularly desirable. For example, the compounds of the invention can be incorporated into liposomes (Gregoriadis, *Liposome Technology*, Vols. I to III, 2nd ed. (CRC Press, Boca Raton Fla. (1993)). Liposomes, which consist of phospholipids or other lipids, are nontoxic, physiologically acceptable and metabolizable carriers that are relatively simple to make and administer. Additionally, the therapeutic compound can be conjugated to a peptide that facilitates cell entry, such as penetratin (also known as Antennapedia peptide), other homeodomain sequences, or the HIV protein Tat.

It is contemplated that administration of the therapeutic compounds and compositions of the invention will result in some beneficial effect to the individual, such as improved overall neurological function or a specific neurological function; an improvement in the quality of life; a reduction in the severity of the symptoms of the disease; a reduction in the number of diseased cells; prolonged survival, and the like. Indicators of beneficial effect are well known in the art, and an appropriate indicator for a particular application can be determined by the skilled person.

The following examples are intended to illustrate but not limit the present invention.

EXAMPLE I

This example shows cloning and sequence analysis of NR3B.

Degenerate primers were designed based on the sequences of NR3A and other NMDAR family members. Using degenerate PCR in concert with homology screening of a rat brain cDNA library, two novel cDNA fragments (called 5-2 clone 1 and 5-2 clone 2) were obtained which exhibited significant sequence identity with NR3A, but clearly corresponded to a distinct and previously unidentified gene. The novel gene was therefore designated NR3B.

Based on the sequences of 5-2 clone 1 and 5-2 clone 2, two pairs of more specific, nested primers (f4, TGCTGCTATGGCTACTGCATC (SEQ ID NO:17); r4, ATGACAGCAGCCAGGTTGGCCGT (SEQ ID NO:18); f5, CACACATGGCTGTGACCAGC (SEQ ID NO:19); and r5, AGAATGGCATAGCACAGGTTG (SEQ ID NO:20)) were designed and used to PCR screen a Rapid-Screen rat brain cDNA library panel (OriGene Technologies, Inc., Rockville, Md.). Four independent partial NR3B cDNA clones were thus obtained. The coding regions of three of the clones were identical (one of these was designated clone B4), but the fourth clone (clone A2) had a 45-nucleotide deletion in the 5' coding region, which may, therefore, represent a splice variant of NR3B. A comparison of the sequences of clones B4, A2, 5-2 clone 1, and 5-2 clone 2 revealed that all overlap, e.g., 5-2 clone 2 spans 49% of the $_5$' end, and clones B4 and A2 span 92% of the 3' end of the full-length NR3B cDNA. Full-length NR3B cDNAs were assembled by ligating the EcoRI-XhoI fragment of 5-2 clone 2 (345 bp) to the XhoI-XbaI fragment of either clone B4 (2847 bp) or clone A2 (2802 bp).

The NR3B (B4 form) cDNA has an open reading frame encoding a peptide of 1002 amino acid (aa) residues. Multiple alignments of the predicted amino acid sequence of NR3B with other glutamate receptor subunits indicated that NR3B is closely related to NR3A (47% identity), but shares less identity with the NR1 and NR2 subfamilies (17 to 21%) (FIG. 1). To a lesser degree, NR3B also shares sequence identity (13 to 16%) with other GluR subunits representing non-NMDAR subunits.

The major structural features of NR3A are highly conserved in NR3B, including the S1 and S2 agonist binding domains, and the membrane spanning regions (FIG. 1). A detailed comparison of the critical residues involved in ligand binding to the NR1 and NR2 subunits revealed that NR3B could potentially share ligand specificity with either or both of these classes of NMDA receptor subunits. Five of the seven amino acid residues required for glycine binding to NR1 and six of the ten amino acid residues required for glutamate binding to NR2A are conserved in NR3B. Furthermore, the M2 region of NR3B is similar to that of NR3A, but strikingly different from those of the NR1 and NR2 subunits. The M2 region forms the re-entrant P-loop which lines the ion channel pore of fully assembled NMDA receptors. These molecular features suggest that the NR3B subunit may confer novel ligand binding and channel gating properties to the NMDA receptor complexes into which it is assembled.

The first ~500 aa residues in the extracellular N-terminus and intracellular C-terminus are the most divergent regions between NR3B and other NMDA receptor subunits, including the NR3A subunit. These regions are important for intra-subunit assembly of glutamate receptors and for interaction of the receptor complex with associated proteins. Thus, these differences may uniquely specify the selection of partner subunits, subcellular localization and CNS distribution of the NR3B subunit.

A rat NR3B nucleotide sequence (SEQ ID NO:57) with a single nucleotide difference with respect to SEQ ID NO:3 was identified by further sequence analysis. SEQ ID NO:57 has a "G" at position 2978, whereas SEQ ID NO:3 has an "A" at the corresponding position. The rat NR3B amino acid sequence encoded by SEQ ID NO:57 (designated SEQ ID NO:58) differs from SEQ ID NO:4 by virtue of having an "Arg" at amino acid 968 instead of a "Gln."

Based on the rat NR3B sequence, the corresponding mouse (SEQ ID NOS:7 and 8) and human (SEQ ID NOS:5 and 6; SEQ ID NOS:61 and 62) NR3B sequences were identified from an analysis of homologous genomic sequences in the database (Accession numbers AC087114 and AC004528, respectively).

EXAMPLE II

This example shows analysis of the expression and localization of the NR3B subunit.

Initially, in situ hybridization was used to detect NR3B mRNA in adult rat brain. Three probes of approximately 400 bp were generated from different N-terminal and C-terminal regions of NR3B. These regions shared little sequence identity with other NMDAR subunits, including NR3A. All three probes detected NR3B signals in the initial experiment. The probe in the N-terminal region giving the strongest signal was chosen for subsequent experiments. $^{33}$P-labeled antisense probes detected "hot spots" in the facial and trigeminal nuclei of the brainstem, and in the ventral horn of the spinal cord (FIGS. 2a, b). Subsequent use of non-isotopic (digoxigenin) labeled probes yielded signals of much higher resolution at the cellular level. NR3B was not detectable in most brain areas, including the cerebrocortex, thalamus, basal ganglia, and hippocampus. In contrast, the spinal cord and the brainstem displayed very strong NR3B signals. In the spinal cord, the NR3B signal was found in motor neurons of the anterior horn at all levels in both layers VIII and IX, which innervate proximal and distal muscle groups, respectively (FIGS. 2c, d). However, an NR3B signal was detected only in specific motor nuclei of the brainstem, specifically the facial and trigeminal nuclei. In addition, some large cells in the vestibular nucleus and reticular formation were also positive for NR3B mRNA.

Further analysis using rats at different ages (P2, P7, P14 and adult) confirmed that NR3B mRNA expression begins at an early postnatal stage (FIG. 2d). A weak NR3B signal was detectable at P2 but increased substantially by P7. The level of NR3B mRNA expression increased postnatally, reaching a peak at P14, and remained elevated into adulthood, consistent with a specific role of NR3B in developing and maintaining motor neuron functions. Based upon these data, it was concluded that NR3B mRNA is localized mainly in motor neurons of the spinal cord and in some motor nuclei of the brainstem. Expression of NR3B protein in these regions has been confirmed by immunocytochemistry.

EXAMPLE III

This example shows characterization of biological activities of NR3B-containing and NR3A-containing excitatory glycine receptors.

NR3B cRNA for oocyte expression was produced as follows. The full-length NR3B cDNA was constructed in the pCMV6-XL4 vector (OriGene Technologies, Inc., Rockville, Md.), which contains a T7 promoter upstream of the cDNA insert. Initial attempts to generate an NR3B cRNA using T7 RNA polymerase resulted in the formation of both full-length and truncated species. The truncated cRNA could potentially encode a dominant negative form of NR3B. Therefore, a new vector was constructed to facilitate production of exclusively full-length NR3B cRNA. Construction of this vector proceeded as follows. NR1 cDNA was excised from the pGEM-HE/NR1 vector (a gift from S. F. Heinemann) by digestion with EcoRI and the two ends of the truncated pGEM-HE vector were re-ligated. The truncated pGEM-HE vector retained the 5' and 3' UTRs of the *X. laevis* β-globin gene for high level protein expression in frog oocytes. The SfoI-KpnI fragment of truncated PGEM-HE, which contains the T7 promoter, was replaced with the PvuII-KpnI fragment of pBluescript II KS, which contains the T3 promoter, to generate pJC32. The abbreviated multiple cloning site of pJC32 was then replaced with the multiple cloning site from pcDNA3.1(+) (Invitrogen, Carlsbad, Calif.) by ligating the 102 bp PmeI fragment of pcDNA3.1(+) into the 3 kb SmaI-EcoRV fragment of pJC32 to generate pJC34. Oligos encoding restriction sites for AscI, PacI, and PmeI (ctagcG-GCGCGCCTTAATTAAGTTTAAACg (SEQ ID NO:52) and ctagcGTTTAAACTTAATTAAGGCGCGCCg (SEQ ID NO:53)) were annealed and ligated into the NheJ site of pJC34. The resulting vector, pJC39, contains three rare restriction sites downstream of the multiple cloning site to facilitate linearization prior to in vitro transcription using T3 RNA polymerase.

The full-length NR3B (B4 form) cDNA was then excised from pCMV6-XL4 by digestion with EcoRI and XbaI, and the 3.2 kb fragment was ligated into EcoRI/XbaI-digested pJC39. The resulting vector, pJC42, was linearized with PmeI, and in vitro transcription was performed using the mMessage mMachine T3 kit (Ambion, Inc., Austin, Tex.) according to the manufacturer's instructions. The cRNA product consisted of a single species with a molecular weight of approximately 1.5 kb.

Microinjection of oocytes and electrophysiological recordings were performed as follows. Physiological and pharmacological properties of NMDA receptor subunits were characterized in the *X. laevis* oocyte expression system. Full-length cDNAs encoding NMDA receptor subunits were linearized and used as templates for synthesis of cRNA by in vitro transcription using T3 or T7 RNA polymerase (Ambion, Inc., Austin, Tex.). The DNA template was removed by DNase I digestion, and the RNA was purified by phenol/chloroform extraction and ethanol precipitation. The RNA was resuspended in water at 1 μg/μl and stored in −80° C. freezer until use. *X. laevis* oocytes were harvested and defolliculated by digestion with collagenase (2 mg/ml) for 2 hrs. Twenty to 40 ng of cRNA were injected into each oocyte using glass pipettes with a tip size of 20-40 μm in diameter. Electrophysiological recordings were performed from whole oocytes 2-7 days after injection using a dual-electrode voltage-clamp amplifier (Model OC-725A, Warner Instrument, Hamden, Conn.). Micropipettes were filled with 3 M KCl. The bath solution contained 115 mM NaCl, 2.5 mM KCl, 1.5 mM $BaCl_2$, and 10 mM Hepes at pH 7.4. Drugs were applied to oocytes via a rapid perfusion system. Data were collected at 2.2 to 11.1 Hz at room temperature using the MacLab/4e A/D converter (AD Instruments, Mountain View, Calif.). Data analysis was performed using the programs Chart (AD Instruments, Mountain View, Calif.) and Microsoft Excel.

Additionally, using the patch-clamp technique, outside-out patches were pulled from oocytes previously injected with NMDAR cRNAs. This method allowed the recording of NMDA-evoked or glycine-evoked single-channel currents, as described previously (Das et al., *supra* (1998)).

Several novel properties of the NR3B subunit were identified by functional expression of the B4 form in Xenopus oocytes. First, functional receptors (defined by the presence of glycine-evoked current) were assembled in oocytes after co-injection of cRNAs for the NR3B and NR1 subunits. Functional receptors were also observed after co-injection of NR3B cRNA with both NR1 and NR2A subunit cRNAs. However, oocytes expressing NR1/NR2A/NR3B receptors exhibited ligand-evoked currents that were 5 to 10 times larger than those expressing NR1/NR3B receptors. In contrast, no functional receptors were detected when NR3B cRNA was co-injected with either NR2A or NR3A alone in the absence of NR1. These results suggest that assembly of the NR3B subunit into a functional receptor complex requires association with the NR1 subunit.

Unlike conventional (that is, NR1/NR2) NMDARs, it was found that the NR1/NR3B receptor was activated by glycine alone, in the absence of glutamate or NMDA (FIG. 3a). NMDA and L-glutamate, agonists that activate conventional NMDARs through NR2 subunits, displayed little or no effect on the glycine-induced current of NR1/NR3B receptors and did not evoke glycine-independent responses (FIG. 3b).

Figure 6:
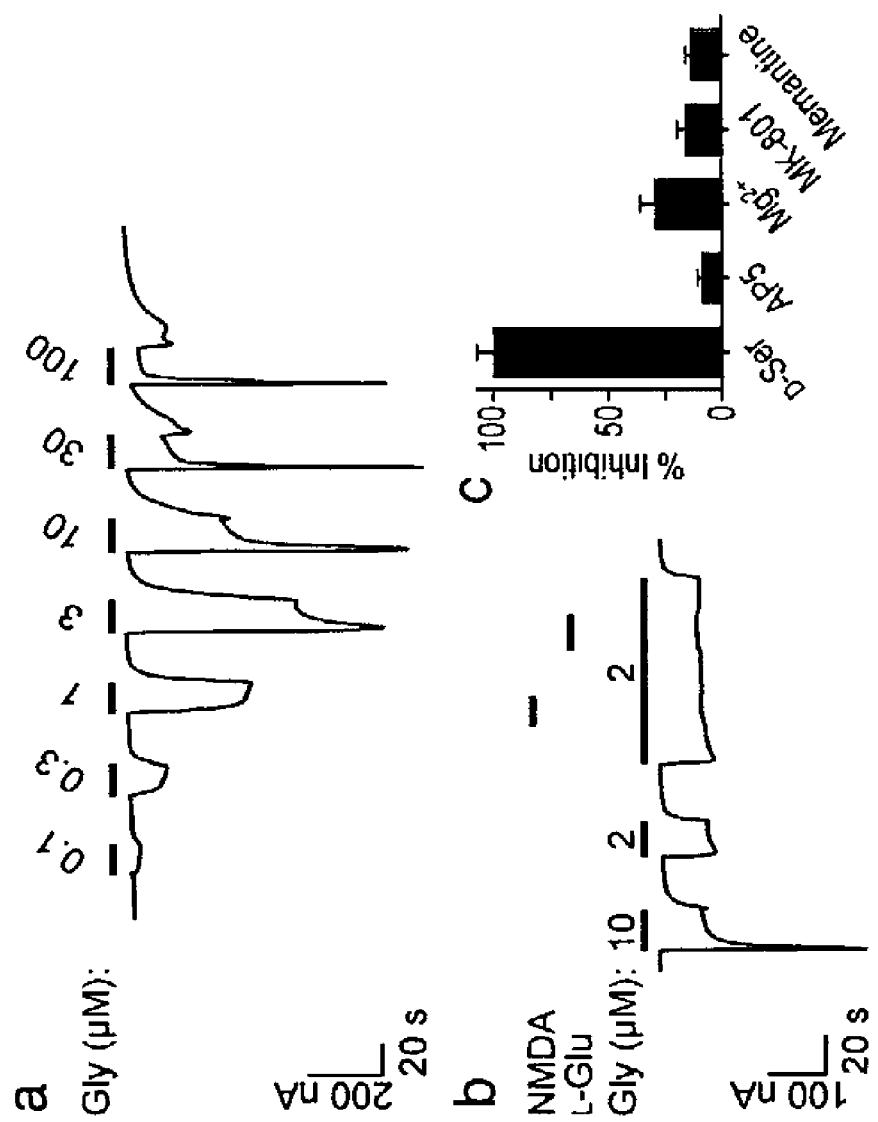
FIGS. 6(a-c) shows pharmacological characterization of NR1/NR3A receptors in Xenopus oocytes. Glycine-evoked currents were recorded from oocytes injected with NR1/NR3A. Glycine and NMDA (or L-glutamate) concentrations were 10 and 100 μM, respectively, unless otherwise indicated. Data are representative of recordings from 3-9 oocytes in each case.

Because of the high degree of sequence similarity between NR3B and NR3A subunits, the ability of the NR3A subunit to form functional receptors when co-expressed with NR1 was re-examined. Reminiscent of NR1/NR3B receptors, it was found that under specific conditions during two-electrode voltage recordings from oocytes, NR1/NR3A receptors could be activated by glycine alone (FIG. 6a). However, rapid desensitization of the current from NR1/NR3A receptors at micromolar concentrations of ligand rendered the observation of glycine-evoked currents extremely difficult (FIG. 6a), which may explain why they had not been reported previously (Ciabarra et al., *J. Neurosci.* 15:6498-6508 (1995); Sucher et al., *J. Neuroscience* 15:6509-6520 (1995); Das et al., *Nature* 393:377-381 (1998).

Of note, glycine alone activated NR1/NR3B receptors with high efficacy despite the fact that by itself glycine fails to excite the previously studied NMDARs or any other type of glutamate receptors. For NR1/NR3B receptors, the $EC_{50}$ for glycine was estimated to be approximately 5 μM. A more precise calculation of $EC_{50}$ was precluded by the desensitization that occurs at high glycine concentrations (FIG. 3a). For NR1/NR3A receptors the $EC_{50}$ was even lower (about 1 μM glycine), with detectable responses at 0.1 μM, and rapid desensitization at 3 μM and above (FIG. 6a).

D-serine, D-alanine, D-cycloserine and 1-aminocyclopropanecarboxylic acid (ACPC), all co-agonists of traditional NMDARs via activation of the glycine site on the NR1 subunit, each inhibited glycine-induced currents of NR1/NR3B receptors (FIG. 3c). Among these, only D-serine activated NR1/NR3B receptors in the absence of glycine (FIG. 3c). At NR1/NR3A receptors, D-serine was an even more potent antagonist (FIG. 6c) and did not independently manifest any agonist activity.

The effect of traditional NMDAR antagonists and channel blockers further demonstrated the altered pharmacological properties conferred by the NR3 family of subunits. A competitive antagonist at the glutamate site of NR2 subunits, D-(−)-2-amino-5-phosphonopentanoate (AP5), had little or no effect at 10 μM on glycine-evoked currents of NR1/NR3B receptors (FIG. 3d) or NR1/NR3A receptors (FIG. 6c). In contrast, 5,7-dichlorokynurenate (5,7-DCKA), a noncompetitive antagonist of the NR1 subunit glycine binding site, virtually abolished glycine-evoked currents of NR1/NR3B receptors (FIG. 3d). Strychnine, an antagonist of the inhibitory, chloride permeable glycine receptors, had minimal effect (FIG. 3d).

Properties linked to the channel region were also altered by the presence of an NR3 subunit. Compared to NR1/NR2A receptors, NR1/NR3B receptors (FIG. 3e) and NR1/NR3A receptors (FIG. 6c) were drastically less sensitive to the open-channel blockers $Mg^{2+}$, MK-801, and memantine.

Figure 4:
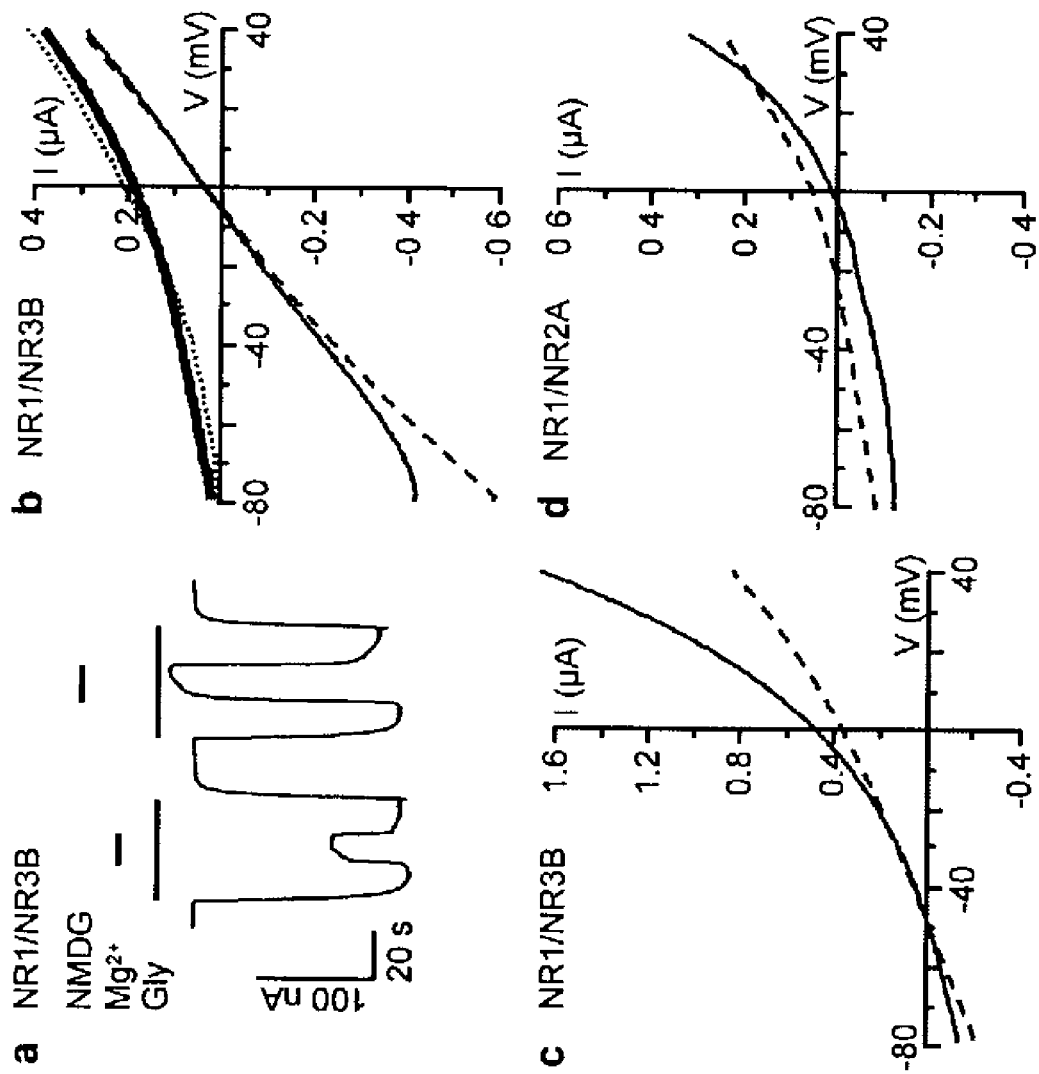
FIGS. 4(a-d) shows ion-selectivity of NR1/NR3B receptors in Xenopus oocytes.

The voltage dependence and permeation of channels operated by NR1/NR3B receptors was examined. I-V curves remained nearly linear between −80 and +40 mV in the presence of 0.5 mM $Mg^{2+}$ (FIGS. 4a, b), reflecting relative $Mg^{2+}$ insensitivity at physiologically relevant voltages and further distinguishing NR1/NR3B receptors from conventional NMDARs. However, between −80 and −120 mV, the channel became outwardly rectifying, indicating a shift in the voltage-dependent $Mg^{2+}$ block towards more negative potentials compared with NR1/NR2 receptors (data not shown). Replacement of cations in the external bath with the large cation N-methyl-D-glutamine (NMDG) completely abolished the glycine-induced inward current (FIGS. 4a, b), suggesting that NR1/NR3B channels are impermeable to large cations and anions ($Cl^-$) but permeable to small cations such as $Na^+$. Similarly, $Mg^{2+}$ did not permeate NR1/NR3B channels at potentials positive to −80 mV (FIG. 4b). Increasing the $Ba^{2+}$ concentration from 1 to 10 mM caused virtually no change in reversal potential for NR1/NR3B receptors, whereas NR1/NR2A receptors underwent a rightward shift of about 20 mV (FIGS. 4c, d). Furthermore, with $Ca^{2+}$ in the external bath, activation of NR1/NR3B receptors evoked far less $Ca^{2+}$-triggered $Cl^-$ current than NR1/NR2 receptors. These results suggest that NR1/NR3B channels are less permeable to divalent cations such as $Ca^{2+}$ and $Ba^{2+}$ than are conventional NMDARs. Similar results were obtained for channels containing NR3A instead of NR3B.

Figure 5:
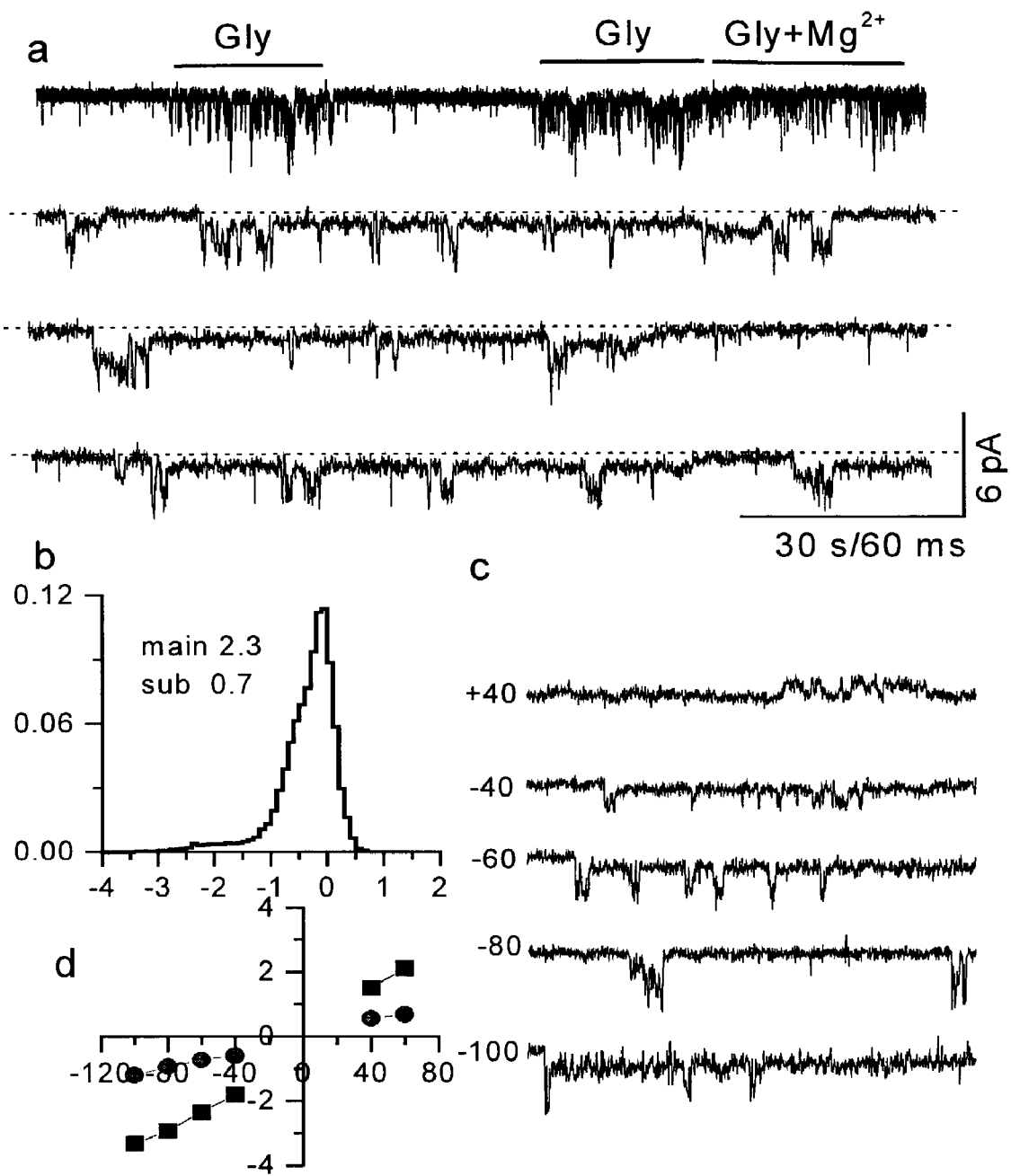
FIGS. 5(a-d) shows single-channel recordings from outside-out patches obtained from oocytes injected with NR1/NR3B (1:12) cRNA.

Single-channel recording of NR1/NR3B receptors confirmed many of the aforementioned unique properties of these receptors, including activation by glycine alone and reduced sensitivity to $Mg^{2+}$ (FIG. 5a). Recorded from outside-out patches of oocyte membrane, NR1/NR3B receptor-operated channels manifest a unitary conductance of ~38 pS and a subconductance of 12 pS in the presence of 2 mM external $Ba^{2+}$ (FIGS. 5a, c). When all anions in the patch electrode were replaced by impermeant gluconate, the conductance states remained unaffected at both positive and negative holding potentials (FIG. 5c), confirming that the channels were permeable to cations.

EXAMPLE IV

This example shows the production of NR3B-specific antibodies using NR3B peptides.

In order to produce NR3B-specific antibodies, the XhoI-AvrII and MluI-XbaI fragments of rat NR3B cDNA (B4 form), which encode amino acids 89-238 and 927-1002, respectively, were subcloned into pET28 to facilitate expression of 6×His-tagged NR3B fragments in bacteria. These regions of NR3B exhibit relatively poor homology with NR3A and other NMDA receptor subunits. The 6×His-tagged proteins were expressed in BL21(DE3) cells and purified by metal affinity chromatography (Talon Purification Kit, Clontech, Palo Alto, Calif.). The purified proteins are used to immunize chickens (Aves Labs, Tigard, Oreg.) and rabbits (Covance, Princton, N.J.) for the production of anti-NR3B polyclonal antibodies.

EXAMPLE V

This example shows physiological effects of glycine in cerebrocortical neurons containing NR3 family members.

To investigate the physiological relevance of the NR3 family, whole-cell and single-channel recordings were performed as described in Das et al., Nature 393:377-381 (1998) and Chen et al., J. Neurosci. 12:4427-4436 (1992), except that 5-10 µM strychnine was generally added to the bathing medium.

Figure 7:
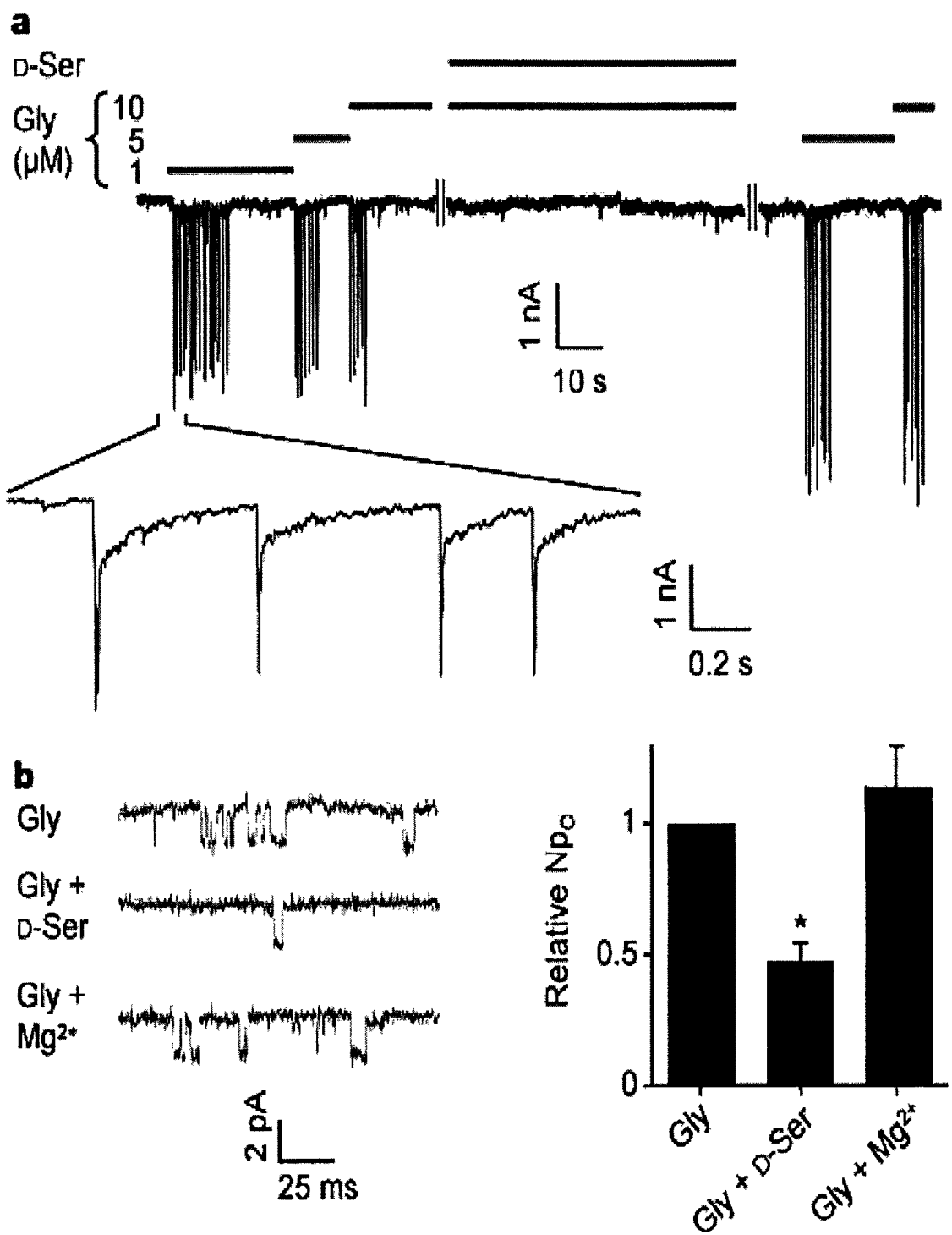
FIG. 7a shows whole-cell recording from cultured neurons in the presence of strychnine (10 μM), which revealed glycine-evoked bursts of action currents. The glycine-evoked response was inhibited by D-serine (10 μM).
FIG. 7b shows that single-channel currents from outside-out patches of cerebrocortical neurons in response to 2.5 μM glycine at −60 mV manifested a main conductance state of 38±1.0 pS (in n=3 of 12 patches recorded for 5-30 min). Channel activity was decreased by D-serine (100 μM) (asterisk, P<0.01, Student's t-test), but 1 mM $Mg^{2+}$ had little effect. $NP_o$ represents the product of the number (N) of channels in the patch and the single-channel open probability ($P_o$).

Whole-cell currents were monitored from cultured cerebrocortical neurons dissociated on P0 (recorded at days 8-13 in vitro) or E16 (recorded at day 19 in vitro), at which times NR3A is maximally expressed and NR3B may also be present (Das et al., supra (1998)). In 22 of 26 recordings performed in the presence of strychnine, glycine (1-10 µM) triggered neuronal bursting, accompanied by little inward current monitored at the cell body; D-serine inhibited this effect in 5 of 22 glycine-responsive cells (FIG. 7a). Thus, the pharmacological profile matched that of NR1/NR3A or -3B receptors in about one-quarter of the recordings. If conventional NMDARs had been involved (for example, if submaximal glycine were present in conjunction with endogenous glutamate), then D-serine would have enhanced the responses rather than inhibiting them, as observed in other recordings. This glycine-triggered bursting phenomenon was ascribed to a presynaptic or network effect, as it was inhibited by tetrodotoxin. Whatever the mechanism, these glycine-mediated responses seem to affect the threshold for bursts of action potentials within a network, and a substantial number of these responses displayed the pharmacology of NR1/NR3A or -3B receptors. Additionally, application of glycine to outside-out patches formed from the cell body of cerebrocortical neneurons evoked single channels of appropriate size (38 pS) and with appropriate pharmacology for the described receptors: in the presence of strychnine, D-serine inhibited the glycine-activated channels and $Mg^{2+}$ had little effect (FIG. 7b). The easily desensitized nature of these extrasynaptic currents, similar to those of recombinant NR1/NR3A channels, may have obscured them from previous workers.

In vivo, co-assembly of NR3A or NR3B with NR1 and possibly NR2 subunits may impart to heteromeric NMDARs some or all of the unique properties described here, and may account for the observed diversity in NMDAR function (von Euler et al., J. Neurotrauma 14:53-61 (1997); Palecek et al., Eur. J. Neurosci 11:827-836 (1999); and Souverbie et al., Eur. J. Pharmacol 307:347-353 (1996)). NR3 may also be physiologically important during synapse formation and long-term potentiation when NMDARs are thought to be functionally silent in the absence of AMPA (α-amino-3-hydroxy-5-methyl-4-isoxazole propionic acid) receptors. In this case, insensitivity of NR3-containing channels to $Mg^{2+}$ may obviate the need for AMPAR-mediated depolarization. Rather, NR1/NR3-mediated depolarization may activate conventional NMDARs at the synapse. For these reasons, standard pharmacological methods that have been used to study NMDAR activity in culture and in vivo must be re-evaluated in light of NR3A or NR3B expression.

All journal article, reference, sequence and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention.

```

What is claimed is:

1. A method of detecting an excitatory glycine receptor agonist or antagonist, comprising:
   (a) contacting an excitatory glycine receptor comprising an NR3B polypeptide, wherein said NR3B polypeptide comprises the amino acid sequence designated SEQ ID NO:2, 60, 4, 58, 6, 62, or 8, with one or more candidate compounds under conditions suitable for detecting receptor activation; and
   (b) detecting a candidate compound that alters said receptor activation,
   wherein said compound altering receptor activation is characterized as an excitatory glycine receptor agonist or antagonist.

2. The method of claim 1, wherein said excitatory glycine receptor comprises said NR3B polypeptide and an NR1 polypeptide.

3. The method of claim 2, wherein said excitatory glycine receptor further comprises an NR2 polypeptide.

4. The method of claim 2, wherein said NR1 polypeptide comprises a naturally-occurring human, rat or mouse NR1 amino acid sequence.

5. The method of claim 1, wherein said excitatory glycine receptor comprises an NR3A polypeptide and an NR1 polypeptide.

6. The method of claim 5, wherein said excitatory glycine receptor further comprises an NR2 polypeptide.

7. The method of claim 5, wherein said NR3A polypeptide comprises a naturally-occurring human or rat NR3A amino acid sequence.

8. The method of claim 5, wherein said NR1 polypeptide comprises a naturally-occurring human, rat or mouse NR1 amino acid sequence.

9. The method of claim 1, wherein said receptor activation is detected by assaying whole-cell currents.

10. The method of claim 1, wherein said receptor activation is detected by assaying single-channel currents.

11. The method of claim 1, wherein said receptor activation is detected by assaying ion fluxes using ion indicators.

12. The method of claim 9, wherein said cell is a *Xenopus* oocyte or mammalian cell that expresses said excitatory glycine receptor.

13. The method of claim 1, wherein said contacting occurs in the presence of glycine.

14. The method of claim 1, wherein said NR3B polypeptide comprises the amino acid sequence designated SEQ ID NO:2.

15. The method of claim 1, wherein said NR3B polypeptide comprises the amino acid sequence designated SEQ ID NO:60.

16. The method of claim 1, wherein said NR3B polypeptide comprises the amino acid sequence designated SEQ ID NO:4.

17. The method of claim 1, wherein said NR3B polypeptide comprises the amino acid sequence designated SEQ ID NO:58.

18. The method of claim 1, wherein said NR3B polypeptide comprises the amino acid sequence designated SEQ ID NO:6.

19. The method of claim 1, wherein said NR3B polypeptide comprises the amino acid sequence designated SEQ ID NO:62.

20. The method of claim 1, wherein said NR3B polypeptide comprises the amino acid sequence designated SEQ ID NO:8.

* * * * *

                              SEQUENCE LISTING

<160> NUMBER OF SEQ ID NOS: 63

<210> SEQ ID NO 1
<211> LENGTH: 3133
<212> TYPE: DNA
<213> ORGANISM: Rattus sp.
<220> FEATURE:
<221> NAME/KEY: CDS
<222> LOCATION: (76)...(3036)

<400> SEQUENCE: 1
gcacgagggg acaagagcgg gtctggctgg ggtgtctcct tcccttcgca cagcacagtg      60
gtaacttctt tcggg atg gag agt gtg cgg acg ctg tgg ctc agc gtg gcc     111
                Met Glu Ser Val Arg Thr Leu Trp Leu Ser Val Ala
                  1               5                  10 ctg gcg ctg gcg gtg ggg tcc cga gtg gtg cgc ggt cac cct cag ccc      159
Leu Ala Leu Ala Val Gly Ser Arg Val Val Arg Gly His Pro Gln Pro
         15                  20                  25 tgc cgg gtt ccc acg cgc gct ggg gcc tcc gtg cgc ctg gcg gcg ctc      207
Cys Arg Val Pro Thr Arg Ala Gly Ala Ser Val Arg Leu Ala Ala Leu
 30                  35                  40 ctg ccc cgg gcg ccc gcc gcc cgc gcc cgc gtc cta gct gcc ctg gcc      255
Leu Pro Arg Ala Pro Ala Ala Arg Ala Arg Val Leu Ala Ala Leu Ala
 45                  50                  55                  60 acc cct gcg ccg cgg ctg ccg cac aac ctg agt ctg gaa ctg gtg gcc      303
Thr Pro Ala Pro Arg Leu Pro His Asn Leu Ser Leu Glu Leu Val Ala
                 65                  70                  75 gtc gcg tcc ccg acc cgg gac ccc gcg tcg cta gct cga ggt ctg tgc      351
Val Ala Ser Pro Thr Arg Asp Pro Ala Ser Leu Ala Arg Gly Leu Cys
             80                  85                  90 cag gtt ctg gca ccg cct ggc gtg gtg gcc tct ata gcc ttt ccc gag      399
Gln Val Leu Ala Pro Pro Gly Val Val Ala Ser Ile Ala Phe Pro Glu
         95                 100                 105 gcg cgg ccc gag ctg cgg cta ctg cag ttc ctg gca gcc gcc aca gag      447
Ala Arg Pro Glu Leu Arg Leu Leu Gln Phe Leu Ala Ala Ala Thr Glu
 110                 115                 120 acc cca gtg act ccg ttc cat ctg cag ctg gac tgg gct agt ccc ctg      495
Thr Pro Val Thr Pro Phe His Leu Gln Leu Asp Trp Ala Ser Pro Leu
125                 130                 135                 140 gag acc ata ctg gat gtg ctg gtg tcc ctg gta cgg gca cat gcc tgg      543
Glu Thr Ile Leu Asp Val Leu Val Ser Leu Val Arg Ala His Ala Trp
                 145                 150                 155 gag gac att gct cta gta ctc tgc cgt gtc cgg gac cct ggc agc ctg      591
Glu Asp Ile Ala Leu Val Leu Cys Arg Val Arg Asp Pro Gly Ser Leu
             160                 165                 170 gtg aca ctc tgg act aac cat gct agc cag gct cca aag ttt gtg ctg      639
Val Thr Leu Trp Thr Asn His Ala Ser Gln Ala Pro Lys Phe Val Leu
         175                 180                 185 gac ctg agc cgg ctg gac agc agg aat gac agc ctt cgg gct gga ctg      687
Asp Leu Ser Arg Leu Asp Ser Arg Asn Asp Ser Leu Arg Ala Gly Leu
     190                 195                 200 gcc ctg ttg ggg gcg ctg gaa gga ggg gga acc cca gtg cct gca gca      735
Ala Leu Leu Gly Ala Leu Glu Gly Gly Gly Thr Pro Val Pro Ala Ala
205                 210                 215                 220
```

| | | |
|---|---|---|
| gtc ctc cta ggc tgc agc act gcc cgt gca cat gag gtc cta gag gct<br>Val Leu Leu Gly Cys Ser Thr Ala Arg Ala His Glu Val Leu Glu Ala<br>225 230 235 | | 783 |
| gca cca ccg ggt ccc cag tgg ttg ctg ggc aca cca ttg ccc gct gag<br>Ala Pro Pro Gly Pro Gln Trp Leu Leu Gly Thr Pro Leu Pro Ala Glu<br>240 245 250 | | 831 |
| gca ctg ccc acg act ggt ctg cca cct ggc gtg ctg gcg ctg ggg gaa<br>Ala Leu Pro Thr Thr Gly Leu Pro Pro Gly Val Leu Ala Leu Gly Glu<br>255 260 265 | | 879 |
| acc gaa caa cac tct ctg gaa gct gtc gtc cac gac atg gtg gag ctt<br>Thr Glu Gln His Ser Leu Glu Ala Val Val His Asp Met Val Glu Leu<br>270 275 280 | | 927 |
| gtg gct cag gca ctc agt agc atg gcc ctt gta cac cca gag cgg gca<br>Val Ala Gln Ala Leu Ser Ser Met Ala Leu Val His Pro Glu Arg Ala<br>285 290 295 300 | | 975 |
| ctg ctt cca gct gtg gtg aac tgt gat gac ctg aaa aca ggc gga tct<br>Leu Leu Pro Ala Val Val Asn Cys Asp Asp Leu Lys Thr Gly Gly Ser<br>305 310 315 | | 1023 |
| gag gca aca ggg cgc acc ttg gct cgg ttt ctc ggc aac acc tca ttt<br>Glu Ala Thr Gly Arg Thr Leu Ala Arg Phe Leu Gly Asn Thr Ser Phe<br>320 325 330 | | 1071 |
| cag ggc cga aca ggg gcc gtg tgg gtg aca ggc tcc tct cag gtg cat<br>Gln Gly Arg Thr Gly Ala Val Trp Val Thr Gly Ser Ser Gln Val His<br>335 340 345 | | 1119 |
| gtg tct cgg cat ttc aag gta tgg agc ctg cgc cgg gat ccg ctg ggt<br>Val Ser Arg His Phe Lys Val Trp Ser Leu Arg Arg Asp Pro Leu Gly<br>350 355 360 | | 1167 |
| gcc cca gcc tgg gca acc gtg ggc agc tgg cag gat gga cag ctg gac<br>Ala Pro Ala Trp Ala Thr Val Gly Ser Trp Gln Asp Gly Gln Leu Asp<br>365 370 375 380 | | 1215 |
| ttc cag cca ggg gca gcc gct ctc cga gtc cca tct ccg tct ggc acc<br>Phe Gln Pro Gly Ala Ala Ala Leu Arg Val Pro Ser Pro Ser Gly Thr<br>385 390 395 | | 1263 |
| cag gcc cga cca aag ctg cgt gtg gta acc ctg gtg gaa cac ccg ttt<br>Gln Ala Arg Pro Lys Leu Arg Val Val Thr Leu Val Glu His Pro Phe<br>400 405 410 | | 1311 |
| gtg ttc acc agg gaa tct gat gaa gac gga cag tgc cca gct ggg cag<br>Val Phe Thr Arg Glu Ser Asp Glu Asp Gly Gln Cys Pro Ala Gly Gln<br>415 420 425 | | 1359 |
| ctg tgt ctg gac cca ggc acc aat gac tca gcc agg ctg gat gcc ctc<br>Leu Cys Leu Asp Pro Gly Thr Asn Asp Ser Ala Arg Leu Asp Ala Leu<br>430 435 440 | | 1407 |
| ttt gct gca ctg gtg aat ggc tca gta cct cga acg ctg aga aga tgc<br>Phe Ala Ala Leu Val Asn Gly Ser Val Pro Arg Thr Leu Arg Arg Cys<br>445 450 455 460 | | 1455 |
| tgc tat ggc tac tgc atc gac ctg ctg gag cgg ctg gcc gag gac ctg<br>Cys Tyr Gly Tyr Cys Ile Asp Leu Leu Glu Arg Leu Ala Glu Asp Leu<br>465 470 475 | | 1503 |
| gcc ttt gac ttt gag ctc tat att gtg ggg gat ggc aag tac ggg gcc<br>Ala Phe Asp Phe Glu Leu Tyr Ile Val Gly Asp Gly Lys Tyr Gly Ala<br>480 485 490 | | 1551 |
| ctg cgt gat ggg cgc tgg acg ggc ctg gtg ggt gac ctg ctg gct ggc<br>Leu Arg Asp Gly Arg Trp Thr Gly Leu Val Gly Asp Leu Leu Ala Gly<br>495 500 505 | | 1599 |
| cgg gca cac atg gct gtg acc agc ttc agc atc aac tca gct cgc tct<br>Arg Ala His Met Ala Val Thr Ser Phe Ser Ile Asn Ser Ala Arg Ser<br>510 515 520 | | 1647 |
| cag gtg gtg gat ttc acc agc cct ttc ttc tcc acc agc ctg ggg att<br>Gln Val Val Asp Phe Thr Ser Pro Phe Phe Ser Thr Ser Leu Gly Ile<br>525 530 535 540 | | 1695 |

| | | | | | | | | | | | | | | | |
|---|---|---|---|---|---|---|---|---|---|---|---|---|---|---|---|
| atg | gtg | cgc | acg | aga | gac | acg | gcc | tcg | ccc | atc | ggg | gct | ttc | atg | tgg | 1743 |
| Met | Val | Arg | Thr | Arg | Asp | Thr | Ala | Ser | Pro | Ile | Gly | Ala | Phe | Met | Trp |
| | | | 545 | | | | 550 | | | | 555 | | | |

```
atg gtg cgc acg aga gac acg gcc tcg ccc atc ggg gct ttc atg tgg      1743
Met Val Arg Thr Arg Asp Thr Ala Ser Pro Ile Gly Ala Phe Met Trp
            545             550             555 ccc ctg cac tgg tcc atg tgg gtg ggc gtg ttt gct gct ctg cac ctc      1791
Pro Leu His Trp Ser Met Trp Val Gly Val Phe Ala Ala Leu His Leu
            560             565             570 aca gcg ctc ttt ctc acc ctg tac gaa tgg cga agt ccc tac ggg ctc      1839
Thr Ala Leu Phe Leu Thr Leu Tyr Glu Trp Arg Ser Pro Tyr Gly Leu
            575             580             585 acg ccg cgc ggc cgc aac cgt ggc act gtc ttc tct tac tcc tcc gcg      1887
Thr Pro Arg Gly Arg Asn Arg Gly Thr Val Phe Ser Tyr Ser Ser Ala
        590             595             600 ctc aac ctg tgc tat gcc att ctc ttt gga cgc act gtc tcc agt aag      1935
Leu Asn Leu Cys Tyr Ala Ile Leu Phe Gly Arg Thr Val Ser Ser Lys
605             610             615             620 acg ccc aag tgc cct act gga cgc ttc ctc atg aac ctc tgg gca atc      1983
Thr Pro Lys Cys Pro Thr Gly Arg Phe Leu Met Asn Leu Trp Ala Ile
            625             630             635 ttc tgc ctg ctg gtg ctt tcc agt tac acg gcc aac ctg gct gct gtc      2031
Phe Cys Leu Leu Val Leu Ser Ser Tyr Thr Ala Asn Leu Ala Ala Val
            640             645             650 atg gtt ggg gac aaa acc ttt gag gag ctg tct gga atc cat gat ccc      2079
Met Val Gly Asp Lys Thr Phe Glu Glu Leu Ser Gly Ile His Asp Pro
            655             660             665 aag ctg cac cac cct tcc caa ggc ttt cgc ttt ggc acc gta tgg gag      2127
Lys Leu His His Pro Ser Gln Gly Phe Arg Phe Gly Thr Val Trp Glu
            670             675             680 agc agc gcg gag gcc tac atc aag gca agc ttc cct gag atg cac gca      2175
Ser Ser Ala Glu Ala Tyr Ile Lys Ala Ser Phe Pro Glu Met His Ala
685             690             695             700 cac atg cgt cgg cac agc gca ccc acc act cca cat ggg gtg gcc atg      2223
His Met Arg Arg His Ser Ala Pro Thr Thr Pro His Gly Val Ala Met
            705             710             715 ctc acg agc gac ccg ccc aag ctc aac gcc ttc atc atg gat aaa tca      2271
Leu Thr Ser Asp Pro Pro Lys Leu Asn Ala Phe Ile Met Asp Lys Ser
            720             725             730 cta ctg gac tat gag gtg tcc ata gat gcg gac tgc aag ctg ctc acc      2319
Leu Leu Asp Tyr Glu Val Ser Ile Asp Ala Asp Cys Lys Leu Leu Thr
            735             740             745 gtt ggc aaa ccc ttt gct atc gag ggc tac ggc ata ggg cta ccc caa      2367
Val Gly Lys Pro Phe Ala Ile Glu Gly Tyr Gly Ile Gly Leu Pro Gln
            750             755             760 aac tcg ccg ctc acc tcc aac ctg tcg gag ttc atc agt agg tac aag      2415
Asn Ser Pro Leu Thr Ser Asn Leu Ser Glu Phe Ile Ser Arg Tyr Lys
765             770             775             780 tct tca ggc ttc att gat ctg ctc cat gac aag tgg tac aag atg gtg      2463
Ser Ser Gly Phe Ile Asp Leu Leu His Asp Lys Trp Tyr Lys Met Val
            785             790             795 cct tgc ggg aag cgg gtg ttc gcc gtg acg gag acg ctg cag atg ggg      2511
Pro Cys Gly Lys Arg Val Phe Ala Val Thr Glu Thr Leu Gln Met Gly
            800             805             810 gtc tac cac ttc tca gga ttg ttt gtc ctg ctg tgc ctc ggg ctg ggc      2559
Val Tyr His Phe Ser Gly Leu Phe Val Leu Leu Cys Leu Gly Leu Gly
            815             820             825 agc gcg ctt ctc acc tct ctg ggt gag cat gtc ttc tac cgc ctg gtg      2607
Ser Ala Leu Leu Thr Ser Leu Gly Glu His Val Phe Tyr Arg Leu Val
            830             835             840 ctg ccg cgc atc cgc agg ggt aat aag ctg cag tat tgg ctt cac acg      2655
Leu Pro Arg Ile Arg Arg Gly Asn Lys Leu Gln Tyr Trp Leu His Thr
```

-continued

```
                845                 850                 855                 860 agc cag aag atc cac cga gcc ctc aat aca gga cca ccc gag ggg caa       2703
Ser Gln Lys Ile His Arg Ala Leu Asn Thr Gly Pro Pro Glu Gly Gln
            865                 870                 875 cag gag agg gca gag cag gag cgc agc ggc ccc aag gac gag ctg cct       2751
Gln Glu Arg Ala Glu Gln Glu Arg Ser Gly Pro Lys Asp Glu Leu Pro
        880                 885                 890 gcc acc gat ggt gca ggg cgc tgg agg cgg gtg cgc cgg gct gtg gaa       2799
Ala Thr Asp Gly Ala Gly Arg Trp Arg Arg Val Arg Arg Ala Val Glu
    895                 900                 905 cgg gag cga cgc gtg cgt ttc ctg ctg gaa cct ggg gag gct ggc gga       2847
Arg Glu Arg Arg Val Arg Phe Leu Leu Glu Pro Gly Glu Ala Gly Gly
910                 915                 920 gac cgc ccg tgg ctc tgc tcc aac ggg ccc ggg ctg caa gcg gag ctg       2895
Asp Arg Pro Trp Leu Cys Ser Asn Gly Pro Gly Leu Gln Ala Glu Leu
925                 930                 935                 940 cgg gag ctg gag ctg cgc att gag gct gca cgg gag cag ctg cgc agt       2943
Arg Glu Leu Glu Leu Arg Ile Glu Ala Ala Arg Glu Gln Leu Arg Ser
                945                 950                 955 gcg ctg ttg cgg cgc ggg gag ctg cgg gcc ctg ctt ggg gat ggc acc       2991
Ala Leu Leu Arg Arg Gly Glu Leu Arg Ala Leu Leu Gly Asp Gly Thr
            960                 965                 970 cgg ctc agg cca ctg cgc ctg ttg cat gcg gcg cct gct gag agc           3036
Arg Leu Arg Pro Leu Arg Leu Leu His Ala Ala Pro Ala Glu Ser
        975                 980                 985 tgaggaacca caaggccgca ctgtccacga cagtttattc tatatacaaa cacgactctg    3096
tacactgcaa ttaaatagcg tggaacgtga aaaaaaa                              3133

<210> SEQ ID NO 2
<211> LENGTH: 987
<212> TYPE: PRT
<213> ORGANISM: Rattus sp.

<400> SEQUENCE: 2

Met Glu Ser Val Arg Thr Leu Trp Leu Ser Val Ala Leu Ala Leu Ala
1               5                   10                  15

Val Gly Ser Arg Val Val Arg Gly His Pro Gln Pro Cys Arg Val Pro
            20                  25                  30

Thr Arg Ala Gly Ala Ser Val Arg Leu Ala Ala Leu Leu Pro Arg Ala
        35                  40                  45

Pro Ala Ala Arg Ala Arg Val Leu Ala Ala Leu Ala Thr Pro Ala Pro
    50                  55                  60

Arg Leu Pro His Asn Leu Ser Leu Glu Leu Val Ala Val Ala Ser Pro
65                  70                  75                  80

Thr Arg Asp Pro Ala Ser Leu Ala Arg Gly Leu Cys Gln Val Leu Ala
                85                  90                  95

Pro Pro Gly Val Val Ala Ser Ile Ala Phe Pro Glu Ala Arg Pro Glu
            100                 105                 110

Leu Arg Leu Leu Gln Phe Leu Ala Ala Ala Thr Glu Thr Pro Val Thr
        115                 120                 125

Pro Phe His Leu Gln Leu Asp Trp Ala Ser Pro Leu Glu Thr Ile Leu
    130                 135                 140

Asp Val Leu Val Ser Leu Val Arg Ala His Ala Trp Glu Asp Ile Ala
145                 150                 155                 160

Leu Val Leu Cys Arg Val Arg Asp Pro Gly Ser Leu Val Thr Leu Trp
                165                 170                 175
```

```
Thr Asn His Ala Ser Gln Ala Pro Lys Phe Val Leu Asp Leu Ser Arg
            180                 185                 190

Leu Asp Ser Arg Asn Asp Ser Leu Arg Ala Gly Leu Ala Leu Leu Gly
        195                 200                 205

Ala Leu Glu Gly Gly Gly Thr Pro Val Pro Ala Val Leu Leu Gly
    210                 215                 220

Cys Ser Thr Ala Arg Ala His Glu Val Leu Glu Ala Ala Pro Pro Gly
225                 230                 235                 240

Pro Gln Trp Leu Leu Gly Thr Pro Leu Pro Ala Glu Ala Leu Pro Thr
                245                 250                 255

Thr Gly Leu Pro Pro Gly Val Leu Ala Leu Gly Glu Thr Glu Gln His
                260                 265                 270

Ser Leu Glu Ala Val His Asp Met Val Glu Leu Val Ala Gln Ala
        275                 280                 285

Leu Ser Ser Met Ala Leu Val His Pro Glu Arg Ala Leu Leu Pro Ala
    290                 295                 300

Val Val Asn Cys Asp Asp Leu Lys Thr Gly Gly Ser Glu Ala Thr Gly
305                 310                 315                 320

Arg Thr Leu Ala Arg Phe Leu Gly Asn Thr Ser Phe Gln Gly Arg Thr
                325                 330                 335

Gly Ala Val Trp Val Thr Gly Ser Ser Gln Val His Val Ser Arg His
                340                 345                 350

Phe Lys Val Trp Ser Leu Arg Arg Asp Pro Leu Gly Ala Pro Ala Trp
        355                 360                 365

Ala Thr Val Gly Ser Trp Gln Asp Gly Gln Leu Asp Phe Gln Pro Gly
    370                 375                 380

Ala Ala Ala Leu Arg Val Pro Ser Pro Ser Gly Thr Gln Ala Arg Pro
385                 390                 395                 400

Lys Leu Arg Val Val Thr Leu Val Glu His Pro Phe Val Phe Thr Arg
                405                 410                 415

Glu Ser Asp Glu Asp Gly Gln Cys Pro Ala Gly Gln Leu Cys Leu Asp
                420                 425                 430

Pro Gly Thr Asn Asp Ser Ala Arg Leu Asp Ala Leu Phe Ala Ala Leu
            435                 440                 445

Val Asn Gly Ser Val Pro Arg Thr Leu Arg Arg Cys Cys Tyr Gly Tyr
    450                 455                 460

Cys Ile Asp Leu Leu Glu Arg Leu Ala Glu Asp Leu Ala Phe Asp Phe
465                 470                 475                 480

Glu Leu Tyr Ile Val Gly Asp Gly Lys Tyr Gly Ala Leu Arg Asp Gly
                485                 490                 495

Arg Trp Thr Gly Leu Val Gly Asp Leu Leu Ala Gly Arg Ala His Met
            500                 505                 510

Ala Val Thr Ser Phe Ser Ile Asn Ser Ala Arg Ser Gln Val Val Asp
    515                 520                 525

Phe Thr Ser Pro Phe Phe Ser Thr Ser Leu Gly Ile Met Val Arg Thr
530                 535                 540

Arg Asp Thr Ala Ser Pro Ile Gly Ala Phe Met Trp Pro Leu His Trp
545                 550                 555                 560

Ser Met Trp Val Gly Val Phe Ala Ala Leu His Leu Thr Ala Leu Phe
                565                 570                 575

Leu Thr Leu Tyr Glu Trp Arg Ser Pro Tyr Gly Leu Thr Pro Arg Gly
                580                 585                 590

Arg Asn Arg Gly Thr Val Phe Ser Tyr Ser Ser Ala Leu Asn Leu Cys
```

```
                    595                 600                 605
Tyr Ala Ile Leu Phe Gly Arg Thr Val Ser Ser Lys Thr Pro Lys Cys
    610                 615                 620

Pro Thr Gly Arg Phe Leu Met Asn Leu Trp Ala Ile Phe Cys Leu Leu
625                 630                 635                 640

Val Leu Ser Ser Tyr Thr Ala Asn Leu Ala Ala Val Met Val Gly Asp
                645                 650                 655

Lys Thr Phe Glu Glu Leu Ser Gly Ile His Asp Pro Lys Leu His His
            660                 665                 670

Pro Ser Gln Gly Phe Arg Phe Gly Thr Val Trp Glu Ser Ser Ala Glu
        675                 680                 685

Ala Tyr Ile Lys Ala Ser Phe Pro Glu Met His Ala His Met Arg Arg
    690                 695                 700

His Ser Ala Pro Thr Thr Pro His Gly Val Ala Met Leu Thr Ser Asp
705                 710                 715                 720

Pro Pro Lys Leu Asn Ala Phe Ile Met Asp Lys Ser Leu Leu Asp Tyr
                725                 730                 735

Glu Val Ser Ile Asp Ala Asp Cys Lys Leu Leu Thr Val Gly Lys Pro
            740                 745                 750

Phe Ala Ile Glu Gly Tyr Gly Ile Gly Leu Pro Gln Asn Ser Pro Leu
        755                 760                 765

Thr Ser Asn Leu Ser Glu Phe Ile Ser Arg Tyr Lys Ser Ser Gly Phe
    770                 775                 780

Ile Asp Leu Leu His Asp Lys Trp Tyr Lys Met Val Pro Cys Gly Lys
785                 790                 795                 800

Arg Val Phe Ala Val Thr Glu Thr Leu Gln Met Gly Val Tyr His Phe
                805                 810                 815

Ser Gly Leu Phe Val Leu Leu Cys Leu Gly Leu Gly Ser Ala Leu Leu
            820                 825                 830

Thr Ser Leu Gly Glu His Val Phe Tyr Arg Leu Val Leu Pro Arg Ile
        835                 840                 845

Arg Arg Gly Asn Lys Leu Gln Tyr Trp Leu His Thr Ser Gln Lys Ile
    850                 855                 860

His Arg Ala Leu Asn Thr Gly Pro Pro Glu Gly Gln Gln Glu Arg Ala
865                 870                 875                 880

Glu Gln Glu Arg Ser Gly Pro Lys Asp Glu Leu Pro Ala Thr Asp Gly
                885                 890                 895

Ala Gly Arg Trp Arg Arg Val Arg Ala Val Glu Arg Glu Arg Arg
            900                 905                 910

Val Arg Phe Leu Leu Glu Pro Gly Glu Ala Gly Gly Asp Arg Pro Trp
        915                 920                 925

Leu Cys Ser Asn Gly Pro Gly Leu Gln Ala Glu Leu Arg Glu Leu Glu
    930                 935                 940

Leu Arg Ile Glu Ala Ala Arg Glu Gln Leu Arg Ser Ala Leu Leu Arg
945                 950                 955                 960

Arg Gly Glu Leu Arg Ala Leu Leu Gly Asp Gly Thr Arg Leu Arg Pro
                965                 970                 975

Leu Arg Leu Leu His Ala Ala Pro Ala Glu Ser
            980                 985

<210> SEQ ID NO 3
<211> LENGTH: 3178
<212> TYPE: DNA
<213> ORGANISM: Rattus sp.
```

-continued

```
<220> FEATURE:
<221> NAME/KEY: CDS
<222> LOCATION: (76)...(3081)

<400> SEQUENCE: 3
gcacgagggg acaagagcgg gtctggctgg ggtgtctcct tcccttcgca cagcacagtg         60
gtaacttctt tcggg atg gag agt gtg cgg acg ctg tgg ctc agc gtg gcc        111
              Met Glu Ser Val Arg Thr Leu Trp Leu Ser Val Ala
                1               5                  10 ctg gcg ctg gcg gtg ggg tcc cga gtg gtg cgc ggt cac cct cag ccc         159
Leu Ala Leu Ala Val Gly Ser Arg Val Val Arg Gly His Pro Gln Pro
             15                  20                  25 tgc cgg gtt ccc acg cgc gct ggg gcc tcc gtg cgc ctg gcg gcg ctc         207
Cys Arg Val Pro Thr Arg Ala Gly Ala Ser Val Arg Leu Ala Ala Leu
 30                  35                  40 ctg ccc cgg gcg ccc gcc gcc cgc gcc cgc gtc cta gct gcc ctg gcc         255
Leu Pro Arg Ala Pro Ala Ala Arg Ala Arg Val Leu Ala Ala Leu Ala
 45                  50                  55                  60 acc cct gcg ccg cgg ctg ccg cac aac ctg agt ctg gaa ctg gtg gcc         303
Thr Pro Ala Pro Arg Leu Pro His Asn Leu Ser Leu Glu Leu Val Ala
                 65                  70                  75 gtc gcg tcc ccg acc cgg gac ccc gcg tcg cta gct cga ggt ctg tgc         351
Val Ala Ser Pro Thr Arg Asp Pro Ala Ser Leu Ala Arg Gly Leu Cys
             80                  85                  90 cag gtt ctg gca ccg cct ggc gtg gtg gcc tct ata gcc ttt ccc gag         399
Gln Val Leu Ala Pro Pro Gly Val Val Ala Ser Ile Ala Phe Pro Glu
         95                 100                 105 gcg cgg ccc gag ctg cgg cta ctg cag ttc ctg gca gcc gcc aca gag         447
Ala Arg Pro Glu Leu Arg Leu Leu Gln Phe Leu Ala Ala Ala Thr Glu
110                 115                 120 acc cca gtg gtg agc gtc ctg cgg agg gag gtg cgc acg gcc ctc gga         495
Thr Pro Val Val Ser Val Leu Arg Arg Glu Val Arg Thr Ala Leu Gly
125                 130                 135                 140 gcc ccg act ccg ttc cat ctg cag ctg gac tgg gct agt ccc ctg gag         543
Ala Pro Thr Pro Phe His Leu Gln Leu Asp Trp Ala Ser Pro Leu Glu
                145                 150                 155 acc ata ctg gat gtg ctg gtg tcc ctg gta cgg gca cat gcc tgg gag         591
Thr Ile Leu Asp Val Leu Val Ser Leu Val Arg Ala His Ala Trp Glu
            160                 165                 170 gac att gct cta gta ctc tgc cgt gtc cgg gac cct ggc agc ctg gtg         639
Asp Ile Ala Leu Val Leu Cys Arg Val Arg Asp Pro Gly Ser Leu Val
        175                 180                 185 aca ctc tgg act aac cat gct agc cag gct cca aag ttt gtg ctg gac         687
Thr Leu Trp Thr Asn His Ala Ser Gln Ala Pro Lys Phe Val Leu Asp
    190                 195                 200 ctg agc cgg ctg gac agc agg aat gac agc ctt cgg gct gga ctg gcc         735
Leu Ser Arg Leu Asp Ser Arg Asn Asp Ser Leu Arg Ala Gly Leu Ala
205                 210                 215                 220 ctg ttg ggg gcg ctg gaa gga ggg gga acc cca gtg cct gca gca gtc         783
Leu Leu Gly Ala Leu Glu Gly Gly Gly Thr Pro Val Pro Ala Ala Val
                225                 230                 235 ctc cta ggc tgc agc act gcc cgt gca cat gag gtc cta gag gct gca         831
Leu Leu Gly Cys Ser Thr Ala Arg Ala His Glu Val Leu Glu Ala Ala
            240                 245                 250 cca ccg ggt ccc cag tgg ttg ctg ggc aca cca ttg ccc gct gag gca         879
Pro Pro Gly Pro Gln Trp Leu Leu Gly Thr Pro Leu Pro Ala Glu Ala
        255                 260                 265 ctg ccc acg act ggt ctg cca cct ggc gtg ctg gcg ctg ggg gaa acc         927
Leu Pro Thr Thr Gly Leu Pro Pro Gly Val Leu Ala Leu Gly Glu Thr
    270                 275                 280
```

-continued

| | |
|---|---|
| gaa caa cac tct ctg gaa gct gtc gtc cac gac atg gtg gag ctt gtg<br>Glu Gln His Ser Leu Glu Ala Val Val His Asp Met Val Glu Leu Val<br>285                         290                        295                        300 | 975 |
| gct cag gca ctc agt agc atg gcc ctt gta cac cca gag cgg gca ctg<br>Ala Gln Ala Leu Ser Ser Met Ala Leu Val His Pro Glu Arg Ala Leu<br>                      305                        310                        315 | 1023 |
| ctt cca gct gtg gtg aac tgt gat gac ctg aaa aca ggc gga tct gag<br>Leu Pro Ala Val Val Asn Cys Asp Asp Leu Lys Thr Gly Gly Ser Glu<br>            320                        325                        330 | 1071 |
| gca aca ggg cgc acc ttg gct cgg ttt ctc ggc aac acc tca ttt cag<br>Ala Thr Gly Arg Thr Leu Ala Arg Phe Leu Gly Asn Thr Ser Phe Gln<br>335                         340                        345 | 1119 |
| ggc cga aca ggg gcc gtg tgg gtg aca ggc tcc tct cag gtg cat gtg<br>Gly Arg Thr Gly Ala Val Trp Val Thr Gly Ser Ser Gln Val His Val<br>            350                        355                        360 | 1167 |
| tct cgg cat ttc aag gta tgg agc ctg cgc cgg gat ccg ctg ggt gcc<br>Ser Arg His Phe Lys Val Trp Ser Leu Arg Arg Asp Pro Leu Gly Ala<br>365                         370                        375                        380 | 1215 |
| cca gcc tgg gca acc gtg ggc agc tgg cag gat gga cag ctg gac ttc<br>Pro Ala Trp Ala Thr Val Gly Ser Trp Gln Asp Gly Gln Leu Asp Phe<br>                      385                        390                        395 | 1263 |
| cag cca ggg gca gcc gct ctc cga gtc cca tct ccg tct ggc acc cag<br>Gln Pro Gly Ala Ala Ala Leu Arg Val Pro Ser Pro Ser Gly Thr Gln<br>            400                        405                        410 | 1311 |
| gcc cga cca aag ctg cgt gtg gta acc ctg gtg gaa cac ccg ttt gtg<br>Ala Arg Pro Lys Leu Arg Val Val Thr Leu Val Glu His Pro Phe Val<br>415                         420                        425 | 1359 |
| ttc acc agg gaa tct gat gaa gac gga cag tgc cca gct ggg cag ctg<br>Phe Thr Arg Glu Ser Asp Glu Asp Gly Gln Cys Pro Ala Gly Gln Leu<br>            430                        435                        440 | 1407 |
| tgt ctg gac cca ggc acc aat gac tca gcc agg ctg gat gcc ctc ttt<br>Cys Leu Asp Pro Gly Thr Asn Asp Ser Ala Arg Leu Asp Ala Leu Phe<br>445                         450                        455                        460 | 1455 |
| gct gca ctg gtg aat ggc tca gta cct cga acg ctg aga aga tgc tgc<br>Ala Ala Leu Val Asn Gly Ser Val Pro Arg Thr Leu Arg Arg Cys Cys<br>                      465                        470                        475 | 1503 |
| tat ggc tac tgc atc gac ctg ctg gag cgg ctg gcc gag gac ctg gcc<br>Tyr Gly Tyr Cys Ile Asp Leu Leu Glu Arg Leu Ala Glu Asp Leu Ala<br>            480                        485                        490 | 1551 |
| ttt gac ttt gag ctc tat att gtg ggg gat ggc aag tac ggg gcc ctg<br>Phe Asp Phe Glu Leu Tyr Ile Val Gly Asp Gly Lys Tyr Gly Ala Leu<br>                      495                        500                        505 | 1599 |
| cgt gat ggg cgc tgg acg ggc ctg gtg ggt gac ctg ctg gct ggc cgg<br>Arg Asp Gly Arg Trp Thr Gly Leu Val Gly Asp Leu Leu Ala Gly Arg<br>            510                        515                        520 | 1647 |
| gca cac atg gct gtg acc agc ttc agc atc aac tca gct cgc tct cag<br>Ala His Met Ala Val Thr Ser Phe Ser Ile Asn Ser Ala Arg Ser Gln<br>525                         530                        535                        540 | 1695 |
| gtg gtg gat ttc acc agc cct ttc ttc tcc acc agc ctg ggg att atg<br>Val Val Asp Phe Thr Ser Pro Phe Phe Ser Thr Ser Leu Gly Ile Met<br>                      545                        550                        555 | 1743 |
| gtg cgc acg aga gac acg gcc tcg ccc atc ggg gct ttc atg tgg ccc<br>Val Arg Thr Arg Asp Thr Ala Ser Pro Ile Gly Ala Phe Met Trp Pro<br>            560                        565                        570 | 1791 |
| ctg cac tgg tcc atg tgg gtg ggc gtg ttt gct gct ctg cac ctc aca<br>Leu His Trp Ser Met Trp Val Gly Val Phe Ala Ala Leu His Leu Thr<br>575                         580                        585 | 1839 |
| gcg ctc ttt ctc acc ctg tac gaa tgg cga agt ccc tac ggg ctc acg<br>Ala Leu Phe Leu Thr Leu Tyr Glu Trp Arg Ser Pro Tyr Gly Leu Thr | 1887 |

-continued

```
              590                 595                 600
ccg cgc ggc cgc aac cgt ggc act gtc ttc tct tac tcc tcc gcg ctc    1935
Pro Arg Gly Arg Asn Arg Gly Thr Val Phe Ser Tyr Ser Ser Ala Leu
605                 610                 615                 620 aac ctg tgc tat gcc att ctc ttt gga cgc act gtc tcc agt aag acg    1983
Asn Leu Cys Tyr Ala Ile Leu Phe Gly Arg Thr Val Ser Ser Lys Thr
                625                 630                 635 ccc aag tgc cct act gga cgc ttc ctc atg aac ctc tgg gca atc ttc    2031
Pro Lys Cys Pro Thr Gly Arg Phe Leu Met Asn Leu Trp Ala Ile Phe
            640                 645                 650 tgc ctg ctg gtg ctt tcc agt tac acg gcc aac ctg gct gct gtc atg    2079
Cys Leu Leu Val Leu Ser Ser Tyr Thr Ala Asn Leu Ala Ala Val Met
        655                 660                 665 gtt ggg gac aaa acc ttt gag gag ctg tct gga atc cat gat ccc aag    2127
Val Gly Asp Lys Thr Phe Glu Glu Leu Ser Gly Ile His Asp Pro Lys
    670                 675                 680 ctg cac cac cct tcc caa ggc ttt cgc ttt ggc acc gta tgg gag agc    2175
Leu His His Pro Ser Gln Gly Phe Arg Phe Gly Thr Val Trp Glu Ser
685                 690                 695                 700 agc gcg gag gcc tac atc aag gca agc ttc cct gag atg cac gca cac    2223
Ser Ala Glu Ala Tyr Ile Lys Ala Ser Phe Pro Glu Met His Ala His
                705                 710                 715 atg cgt cgg cac agc gca ccc acc act cca cat ggg gtg gcc atg ctc    2271
Met Arg Arg His Ser Ala Pro Thr Thr Pro His Gly Val Ala Met Leu
            720                 725                 730 acg agc gac ccg ccc aag ctc aac gcc ttc atc atg gat aaa tca cta    2319
Thr Ser Asp Pro Pro Lys Leu Asn Ala Phe Ile Met Asp Lys Ser Leu
        735                 740                 745 ctg gac tat gag gtg tcc ata gat gcg gac tgc aag ctg ctc acc gtt    2367
Leu Asp Tyr Glu Val Ser Ile Asp Ala Asp Cys Lys Leu Leu Thr Val
    750                 755                 760 ggc aaa ccc ttt gct atc gag ggc tac ggc ata ggg cta ccc caa aac    2415
Gly Lys Pro Phe Ala Ile Glu Gly Tyr Gly Ile Gly Leu Pro Gln Asn
765                 770                 775                 780 tcg ccg ctc acc tcc aac ctg tcg gag ttc atc agt agg tac aag tct    2463
Ser Pro Leu Thr Ser Asn Leu Ser Glu Phe Ile Ser Arg Tyr Lys Ser
                785                 790                 795 tca ggc ttc att gat ctg ctc cat gac aag tgg tac aag atg gtg cct    2511
Ser Gly Phe Ile Asp Leu Leu His Asp Lys Trp Tyr Lys Met Val Pro
            800                 805                 810 tgc ggg aag cgg gtg ttc gcc gtg acg gag acg ctg cag atg ggg gtc    2559
Cys Gly Lys Arg Val Phe Ala Val Thr Glu Thr Leu Gln Met Gly Val
        815                 820                 825 tac cac ttc tca gga ttg ttt gtc ctg ctg tgc ctc ggg ctg ggc agc    2607
Tyr His Phe Ser Gly Leu Phe Val Leu Leu Cys Leu Gly Leu Gly Ser
    830                 835                 840 gcg ctt ctc acc tct ctg ggt gag cat gtc ttc tac cgc ctg gtg ctg    2655
Ala Leu Leu Thr Ser Leu Gly Glu His Val Phe Tyr Arg Leu Val Leu
845                 850                 855                 860 ccg cgc atc cgc agg ggt aat aag ctg cag tat tgg ctt cac acg agc    2703
Pro Arg Ile Arg Arg Gly Asn Lys Leu Gln Tyr Trp Leu His Thr Ser
                865                 870                 875 cag aag atc cac cga gcc ctc aat aca gga cca ccc gag ggg caa cag    2751
Gln Lys Ile His Arg Ala Leu Asn Thr Gly Pro Pro Glu Gly Gln Gln
            880                 885                 890 gag agg gca gag cag gag cgc agc ggc ccc aag gac gag ctg cct gcc    2799
Glu Arg Ala Glu Gln Glu Arg Ser Gly Pro Lys Asp Glu Leu Pro Ala
        895                 900                 905 acc gat ggt gca ggg cgc tgg agg cgg gtg cgc cgg gct gtg gaa cgg    2847
```

```
Thr Asp Gly Ala Gly Arg Trp Arg Arg Val Arg Arg Ala Val Glu Arg
    910                 915                 920 gag cga cgc gtg cgt ttc ctg ctg gaa cct ggg gag gct ggc gga gac    2895
Glu Arg Arg Val Arg Phe Leu Leu Glu Pro Gly Glu Ala Gly Gly Asp
925                 930                 935                 940 cgc ccg tgg ctc tgc tcc aac ggg ccc ggg ctg caa gcg gag ctg cgg    2943
Arg Pro Trp Leu Cys Ser Asn Gly Pro Gly Leu Gln Ala Glu Leu Arg
                945                 950                 955 gag ctg gag ctg cgc att gag gct gca cgg gag cag ctg cgc agt gcg    2991
Glu Leu Glu Leu Arg Ile Glu Ala Ala Arg Glu Gln Leu Arg Ser Ala
            960                 965                 970 ctg ttg cgg cgc ggg gag ctg cgg gcc ctg ctt ggg gat ggc acc cgg    3039
Leu Leu Arg Arg Gly Glu Leu Arg Ala Leu Leu Gly Asp Gly Thr Arg
        975                 980                 985 ctc agg cca ctg cgc ctg ttg cat gcg gcg cct gct gag agc            3081
Leu Arg Pro Leu Arg Leu Leu His Ala Ala Pro Ala Glu Ser
    990                 995                 1000 tgaggaacca caaggccgca ctgtccacga cagtttattc tatatacaaa cacgactctg    3141
tacactgcaa ttaaatagcg tggaacgtga aaaaaaa                             3178

<210> SEQ ID NO 4
<211> LENGTH: 1002
<212> TYPE: PRT
<213> ORGANISM: Rattus sp.

<400> SEQUENCE: 4

Met Glu Ser Val Arg Thr Leu Trp Leu Ser Val Ala Leu Ala Leu Ala
1               5                   10                  15

Val Gly Ser Arg Val Val Arg Gly His Pro Gln Pro Cys Arg Val Pro
            20                  25                  30

Thr Arg Ala Gly Ala Ser Val Arg Leu Ala Ala Leu Leu Pro Arg Ala
        35                  40                  45

Pro Ala Arg Ala Arg Val Leu Ala Ala Leu Ala Thr Pro Ala Pro
    50                  55                  60

Arg Leu Pro His Asn Leu Ser Leu Glu Leu Val Ala Val Ala Ser Pro
65              70                  75                  80

Thr Arg Asp Pro Ala Ser Leu Ala Arg Gly Leu Cys Gln Val Leu Ala
            85                  90                  95

Pro Pro Gly Val Val Ala Ser Ile Ala Phe Pro Glu Ala Arg Pro Glu
        100                 105                 110

Leu Arg Leu Leu Gln Phe Leu Ala Ala Ala Thr Glu Thr Pro Val Val
    115                 120                 125

Ser Val Leu Arg Arg Glu Val Arg Thr Ala Leu Gly Ala Pro Thr Pro
    130                 135                 140

Phe His Leu Gln Leu Asp Trp Ala Ser Pro Leu Glu Thr Ile Leu Asp
145                 150                 155                 160

Val Leu Val Ser Leu Val Arg Ala His Ala Trp Glu Asp Ile Ala Leu
            165                 170                 175

Val Leu Cys Arg Val Arg Asp Pro Gly Ser Leu Val Thr Leu Trp Thr
        180                 185                 190

Asn His Ala Ser Gln Ala Pro Lys Phe Val Leu Asp Leu Ser Arg Leu
    195                 200                 205

Asp Ser Arg Asn Asp Ser Leu Arg Ala Gly Leu Ala Leu Leu Gly Ala
    210                 215                 220

Leu Glu Gly Gly Gly Thr Pro Val Pro Ala Ala Val Leu Leu Gly Cys
225                 230                 235                 240
```

-continued

```
Ser Thr Ala Arg Ala His Glu Val Leu Glu Ala Pro Pro Gly Pro
                245                 250                 255

Gln Trp Leu Leu Gly Thr Pro Leu Pro Ala Glu Ala Leu Pro Thr Thr
            260                 265                 270

Gly Leu Pro Pro Gly Val Leu Ala Leu Gly Glu Thr Glu Gln His Ser
        275                 280                 285

Leu Glu Ala Val Val His Asp Met Val Glu Leu Val Ala Gln Ala Leu
    290                 295                 300

Ser Ser Met Ala Leu Val His Pro Glu Arg Ala Leu Leu Pro Ala Val
305                 310                 315                 320

Val Asn Cys Asp Asp Leu Lys Thr Gly Gly Ser Glu Ala Thr Gly Arg
                325                 330                 335

Thr Leu Ala Arg Phe Leu Gly Asn Thr Ser Phe Gln Gly Arg Thr Gly
            340                 345                 350

Ala Val Trp Val Thr Gly Ser Ser Gln Val His Val Ser Arg His Phe
        355                 360                 365

Lys Val Trp Ser Leu Arg Arg Asp Pro Leu Gly Ala Pro Ala Trp Ala
    370                 375                 380

Thr Val Gly Ser Trp Gln Asp Gly Gln Leu Asp Phe Gln Pro Gly Ala
385                 390                 395                 400

Ala Ala Leu Arg Val Pro Ser Pro Ser Gly Thr Gln Ala Arg Pro Lys
                405                 410                 415

Leu Arg Val Val Thr Leu Val Glu His Pro Phe Val Phe Thr Arg Glu
            420                 425                 430

Ser Asp Glu Asp Gly Gln Cys Pro Ala Gly Gln Leu Cys Leu Asp Pro
        435                 440                 445

Gly Thr Asn Asp Ser Ala Arg Leu Asp Ala Leu Phe Ala Ala Leu Val
    450                 455                 460

Asn Gly Ser Val Pro Arg Thr Leu Arg Arg Cys Cys Tyr Gly Tyr Cys
465                 470                 475                 480

Ile Asp Leu Leu Glu Arg Leu Ala Glu Asp Leu Ala Phe Asp Phe Glu
                485                 490                 495

Leu Tyr Ile Val Gly Asp Gly Lys Tyr Gly Ala Leu Arg Asp Gly Arg
            500                 505                 510

Trp Thr Gly Leu Val Gly Asp Leu Leu Ala Gly Arg Ala His Met Ala
        515                 520                 525

Val Thr Ser Phe Ser Ile Asn Ser Ala Arg Ser Gln Val Val Asp Phe
    530                 535                 540

Thr Ser Pro Phe Phe Ser Thr Ser Leu Gly Ile Met Val Arg Thr Arg
545                 550                 555                 560

Asp Thr Ala Ser Pro Ile Gly Ala Phe Met Trp Pro Leu His Trp Ser
                565                 570                 575

Met Trp Val Gly Val Phe Ala Ala Leu His Leu Thr Ala Leu Phe Leu
            580                 585                 590

Thr Leu Tyr Glu Trp Arg Ser Pro Tyr Gly Leu Thr Pro Arg Gly Arg
        595                 600                 605

Asn Arg Gly Thr Val Phe Ser Tyr Ser Ser Ala Leu Asn Leu Cys Tyr
    610                 615                 620

Ala Ile Leu Phe Gly Arg Thr Val Ser Ser Lys Thr Pro Lys Cys Pro
625                 630                 635                 640

Thr Gly Arg Phe Leu Met Asn Leu Trp Ala Ile Phe Cys Leu Leu Val
                645                 650                 655
```

```
Leu Ser Ser Tyr Thr Ala Asn Leu Ala Ala Val Met Val Gly Asp Lys
            660                 665                 670

Thr Phe Glu Glu Leu Ser Gly Ile His Asp Pro Lys Leu His His Pro
        675                 680                 685

Ser Gln Gly Phe Arg Phe Gly Thr Val Trp Ser Ser Ala Glu Ala
    690                 695                 700

Tyr Ile Lys Ala Ser Phe Pro Glu Met His Ala His Met Arg Arg His
705                 710                 715                 720

Ser Ala Pro Thr Thr Pro His Gly Val Ala Met Leu Thr Ser Asp Pro
                725                 730                 735

Pro Lys Leu Asn Ala Phe Ile Met Asp Lys Ser Leu Leu Asp Tyr Glu
                740                 745                 750

Val Ser Ile Asp Ala Asp Cys Lys Leu Leu Thr Val Gly Lys Pro Phe
            755                 760                 765

Ala Ile Glu Gly Tyr Gly Ile Gly Leu Pro Gln Asn Ser Pro Leu Thr
    770                 775                 780

Ser Asn Leu Ser Glu Phe Ile Ser Arg Tyr Lys Ser Ser Gly Phe Ile
785                 790                 795                 800

Asp Leu Leu His Asp Lys Trp Tyr Lys Met Val Pro Cys Gly Lys Arg
                805                 810                 815

Val Phe Ala Val Thr Glu Thr Leu Gln Met Gly Val Tyr His Phe Ser
                820                 825                 830

Gly Leu Phe Val Leu Leu Cys Leu Gly Leu Gly Ser Ala Leu Leu Thr
            835                 840                 845

Ser Leu Gly Glu His Val Phe Tyr Arg Leu Val Leu Pro Arg Ile Arg
    850                 855                 860

Arg Gly Asn Lys Leu Gln Tyr Trp Leu His Thr Ser Gln Lys Ile His
865                 870                 875                 880

Arg Ala Leu Asn Thr Gly Pro Pro Glu Gly Gln Gln Glu Arg Ala Glu
                885                 890                 895

Gln Glu Arg Ser Gly Pro Lys Asp Glu Leu Pro Ala Thr Asp Gly Ala
                900                 905                 910

Gly Arg Trp Arg Arg Val Arg Arg Ala Val Glu Arg Glu Arg Arg Val
            915                 920                 925

Arg Phe Leu Leu Glu Pro Gly Glu Ala Gly Gly Asp Arg Pro Trp Leu
    930                 935                 940

Cys Ser Asn Gly Pro Gly Leu Gln Ala Glu Leu Arg Glu Leu Glu Leu
945                 950                 955                 960

Arg Ile Glu Ala Ala Arg Glu Gln Leu Arg Ser Ala Leu Leu Arg Arg
                965                 970                 975

Gly Glu Leu Arg Ala Leu Leu Gly Asp Gly Thr Arg Leu Arg Pro Leu
            980                 985                 990

Arg Leu Leu His Ala Ala Pro Ala Glu Ser
        995                 1000

<210> SEQ ID NO 5
<211> LENGTH: 3096
<212> TYPE: DNA
<213> ORGANISM: Homo sapiens
<220> FEATURE:
<221> NAME/KEY: CDS
<222> LOCATION: (1)...(3033)
<220> FEATURE:
<221> NAME/KEY: misc_feature
<222> LOCATION: 2692, 2693, 2694, 2695, 2696, 2697, 2698, 2699, 2700,
    2701, 2702, 2703, 2704, 2705, 2706, 2707, 2708, 2709, 2710, 2711,
    2712, 2713, 2714, 2715, 2716, 2717, 2718, 2719, 2720, 2721,
```

-continued 2722, 2723, 2724, 2725, 2726, 2727, 2728, 2729, 2730
<223> OTHER INFORMATION: n = A,T,C or G
<220> FEATURE:
<221> NAME/KEY: misc_feature
<222> LOCATION: 2791, 2792, 2793, 2794, 2795, 2796, 2797, 2798, 2799,
      2800, 2801, 2802, 2803, 2804, 2805, 2806, 2807, 2808, 2809, 2810,
      2811, 2812, 2813, 2814, 2827, 2828, 2829, 2830, 2831, 2832, 2833,
      2834, 2835, 2836, 2837, 2838, 2839, 2840, 2841
<223> OTHER INFORMATION: n = A,T,C or G
<220> FEATURE:
<221> NAME/KEY: misc_feature
<222> LOCATION: 2842, 2843, 2844, 2845, 2846, 2847, 3037, 3038, 3039
<223> OTHER INFORMATION: n = A,T,C or G

<400> SEQUENCE: 5

| | | | | | | | | | | | | | | | | |
|---|---|---|---|---|---|---|---|---|---|---|---|---|---|---|---|---|
| atg | gag | ttt | gtg | cgg | gcg | ctg | tgg | ctg | ggc | ctg | gcg | ctg | gcg | ctg | ggg | 48 |
| Met | Glu | Phe | Val | Arg | Ala | Leu | Trp | Leu | Gly | Leu | Ala | Leu | Ala | Leu | Gly | |
| 1 | | | | 5 | | | | | 10 | | | | | 15 | | |

| ccg | ggg | tcc | gcg | ggg | ggc | cac | cct | cag | ccg | tgc | ggg | gtc | ctg | gcg | cgc | 96 |
|---|---|---|---|---|---|---|---|---|---|---|---|---|---|---|---|---|
| Pro | Gly | Ser | Ala | Gly | Gly | His | Pro | Gln | Pro | Cys | Gly | Val | Leu | Ala | Arg | |
| | | | 20 | | | | | 25 | | | | | 30 | | | |

| ctc | ggg | ggc | tcc | gtg | cgc | ctg | ggc | gcc | ctg | ccc | cgc | gcg | cct | ctc | | 144 |
|---|---|---|---|---|---|---|---|---|---|---|---|---|---|---|---|---|
| Leu | Gly | Gly | Ser | Val | Arg | Leu | Gly | Ala | Leu | Pro | Arg | Ala | Pro | Leu | | |
| | 35 | | | | | 40 | | | | | 45 | | | | | |

| gcc | cgc | gcc | cgc | gcc | cgc | gcc | gcc | ctg | gcc | cgg | gcc | gcc | ctg | gcg | ccg | 192 |
|---|---|---|---|---|---|---|---|---|---|---|---|---|---|---|---|---|
| Ala | Arg | Ala | Arg | Ala | Arg | Ala | Ala | Leu | Ala | Arg | Ala | Ala | Leu | Ala | Pro | |
| 50 | | | | | 55 | | | | | 60 | | | | | | |

| cgg | ctg | ccg | cac | aac | ctg | agc | ttg | gag | ctg | gtg | gtc | gcc | gcg | ccc | ccc | 240 |
|---|---|---|---|---|---|---|---|---|---|---|---|---|---|---|---|---|
| Arg | Leu | Pro | His | Asn | Leu | Ser | Leu | Glu | Leu | Val | Val | Ala | Ala | Pro | Pro | |
| 65 | | | | | 70 | | | | | 75 | | | | | 80 | |

| gcc | cgc | gac | ccc | gcc | tcg | ctg | acc | cgc | ggc | ctg | tgc | cag | gcg | ctg | gtg | 288 |
|---|---|---|---|---|---|---|---|---|---|---|---|---|---|---|---|---|
| Ala | Arg | Asp | Pro | Ala | Ser | Leu | Thr | Arg | Gly | Leu | Cys | Gln | Ala | Leu | Val | |
| | | | | 85 | | | | | 90 | | | | | 95 | | |

| cct | ccg | ggc | gtg | gcg | gcc | ctg | ctc | gcc | ttt | ccc | gag | gct | cgg | ccc | gag | 336 |
|---|---|---|---|---|---|---|---|---|---|---|---|---|---|---|---|---|
| Pro | Pro | Gly | Val | Ala | Ala | Leu | Leu | Ala | Phe | Pro | Glu | Ala | Arg | Pro | Glu | |
| | | | 100 | | | | | 105 | | | | | 110 | | | |

| ctg | ctg | cag | ctg | cac | ttc | ctg | gcg | gcg | gcc | acc | gag | acc | ccc | gtg | ctc | 384 |
|---|---|---|---|---|---|---|---|---|---|---|---|---|---|---|---|---|
| Leu | Leu | Gln | Leu | His | Phe | Leu | Ala | Ala | Ala | Thr | Glu | Thr | Pro | Val | Leu | |
| | | 115 | | | | | 120 | | | | | 125 | | | | |

| agc | ctg | ctg | cgg | cgg | gag | gcg | cgc | gcg | ccc | ctc | gga | gcc | ccg | aac | cca | 432 |
|---|---|---|---|---|---|---|---|---|---|---|---|---|---|---|---|---|
| Ser | Leu | Leu | Arg | Arg | Glu | Ala | Arg | Ala | Pro | Leu | Gly | Ala | Pro | Asn | Pro | |
| | 130 | | | | | 135 | | | | | 140 | | | | | |

| ttc | cac | ctg | cag | ctg | cac | tgg | gcc | agc | ccc | ctg | gag | acg | ctg | ctg | gat | 480 |
|---|---|---|---|---|---|---|---|---|---|---|---|---|---|---|---|---|
| Phe | His | Leu | Gln | Leu | His | Trp | Ala | Ser | Pro | Leu | Glu | Thr | Leu | Leu | Asp | |
| 145 | | | | | 150 | | | | | 155 | | | | | 160 | |

| gtg | ctg | gtg | gcg | gtg | ctg | cag | gcg | cac | gcc | tgg | gaa | gac | gtc | ggc | ctg | 528 |
|---|---|---|---|---|---|---|---|---|---|---|---|---|---|---|---|---|
| Val | Leu | Val | Ala | Val | Leu | Gln | Ala | His | Ala | Trp | Glu | Asp | Val | Gly | Leu | |
| | | | | 165 | | | | | 170 | | | | | 175 | | |

| gcc | ctg | tgc | cgc | act | cag | gac | ccc | ggc | ggc | ctg | gtg | gcc | ctc | tgg | aca | 576 |
|---|---|---|---|---|---|---|---|---|---|---|---|---|---|---|---|---|
| Ala | Leu | Cys | Arg | Thr | Gln | Asp | Pro | Gly | Gly | Leu | Val | Ala | Leu | Trp | Thr | |
| | | | 180 | | | | | 185 | | | | | 190 | | | |

| agc | cgg | gct | ggc | cgg | ccc | cca | cag | ctg | gtc | ctg | gac | cta | agc | cgg | cgg | 624 |
|---|---|---|---|---|---|---|---|---|---|---|---|---|---|---|---|---|
| Ser | Arg | Ala | Gly | Arg | Pro | Pro | Gln | Leu | Val | Leu | Asp | Leu | Ser | Arg | Arg | |
| | 195 | | | | | 200 | | | | | 205 | | | | | |

| gac | acg | gga | gat | gca | gga | ctg | cgg | gca | cgc | ctg | gcc | ccg | atg | gcg | gcg | 672 |
|---|---|---|---|---|---|---|---|---|---|---|---|---|---|---|---|---|
| Asp | Thr | Gly | Asp | Ala | Gly | Leu | Arg | Ala | Arg | Leu | Ala | Pro | Met | Ala | Ala | |
| | 210 | | | | | 215 | | | | | 220 | | | | | |

| cca | gtg | ggg | ggt | gaa | gca | ccg | gta | ccc | gcg | gcg | gtc | ctc | ctc | ggc | tgt | 720 |
|---|---|---|---|---|---|---|---|---|---|---|---|---|---|---|---|---|
| Pro | Val | Gly | Gly | Glu | Ala | Pro | Val | Pro | Ala | Ala | Val | Leu | Leu | Gly | Cys | |
| 225 | | | | | 230 | | | | | 235 | | | | | 240 | |

| gac | atc | gcc | cgt | gcc | cgt | cgg | gtg | ctg | gag | gcc | gta | cct | ccc | ggc | ccc | 768 |
|---|---|---|---|---|---|---|---|---|---|---|---|---|---|---|---|---|
| Asp | Ile | Ala | Arg | Ala | Arg | Arg | Val | Leu | Glu | Ala | Val | Pro | Pro | Gly | Pro | |
| | | | | 245 | | | | | 250 | | | | | 255 | | |

```
cac tgg ctg ttg ggg aca cca ctg ccg ccc aag gcc ctg ccc acc gcg      816
His Trp Leu Leu Gly Thr Pro Leu Pro Pro Lys Ala Leu Pro Thr Ala
            260                 265                 270 ggg ctg cca cca ggg ctg ctg gcg ctg ggc gag gtg gca cga ccc ccg      864
Gly Leu Pro Pro Gly Leu Leu Ala Leu Gly Glu Val Ala Arg Pro Pro
        275                 280                 285 ctg gag gcc gcc atc cat gac att gtg caa ctg gtg gcc cgg gcg ctg      912
Leu Glu Ala Ala Ile His Asp Ile Val Gln Leu Val Ala Arg Ala Leu
    290                 295                 300 ggc agt gcg gcc cag gtg cag ccg aag cga gcc ctc ctc ccc gcc ccg      960
Gly Ser Ala Ala Gln Val Gln Pro Lys Arg Ala Leu Leu Pro Ala Pro
305                 310                 315                 320 gtc aac tgc ggg gac ctg cag ccg gcc ggg ccc gag tcc ccg ggg cgc     1008
Val Asn Cys Gly Asp Leu Gln Pro Ala Gly Pro Glu Ser Pro Gly Arg
                325                 330                 335 ttc ttg gcc aac acg tcc ttc cag ggc cgc acg ggc ccc gtg tgg gtg     1056
Phe Leu Ala Asn Thr Ser Phe Gln Gly Arg Thr Gly Pro Val Trp Val
            340                 345                 350 aca ggc agc tcc cag gta cac atg tct cgg cac ttt aag gtg tgg agc     1104
Thr Gly Ser Ser Gln Val His Met Ser Arg His Phe Lys Val Trp Ser
        355                 360                 365 ctt cgc cgg gac cca cgg ggc gcc ccg gcc tgg gcc acg gtg ggc agc     1152
Leu Arg Arg Asp Pro Arg Gly Ala Pro Ala Trp Ala Thr Val Gly Ser
    370                 375                 380 tgg cgg gac ggc cag ctg gac ttg gaa ccg gga ggt gcc tct gca cgg     1200
Trp Arg Asp Gly Gln Leu Asp Leu Glu Pro Gly Gly Ala Ser Ala Arg
385                 390                 395                 400 ccc ccg ccc cca cag ggt gcc cag gtc tgg ccc aag ctg cgt gtg gta     1248
Pro Pro Pro Pro Gln Gly Ala Gln Val Trp Pro Lys Leu Arg Val Val
                405                 410                 415 acg ctg ttg gaa cac cca ttt gtg ttt gcc cgt gat cca gac gaa gac     1296
Thr Leu Leu Glu His Pro Phe Val Phe Ala Arg Asp Pro Asp Glu Asp
            420                 425                 430 ggg cag tgc cca gcg ggg cag ctg tgc ctg gac cct ggc acc aac gac     1344
Gly Gln Cys Pro Ala Gly Gln Leu Cys Leu Asp Pro Gly Thr Asn Asp
        435                 440                 445 tcg gcc acc ctg gac gca ctg ttc gcc gcg ctg gcc aac ggc tca gcg     1392
Ser Ala Thr Leu Asp Ala Leu Phe Ala Ala Leu Ala Asn Gly Ser Ala
    450                 455                 460 ccc cgt gcc ctg cgc aag tgc tgc tac ggc tac tgc att gac ctg ctg     1440
Pro Arg Ala Leu Arg Lys Cys Cys Tyr Gly Tyr Cys Ile Asp Leu Leu
465                 470                 475                 480 gag cgg ctg gcg gag gac acg ccc ttc gac ttc gag ctg tac ctc gtg     1488
Glu Arg Leu Ala Glu Asp Thr Pro Phe Asp Phe Glu Leu Tyr Leu Val
                485                 490                 495 ggt gac ggc aag tac ggc gcc ctg cgg gac ggc cgc tgg acc ggc ctg     1536
Gly Asp Gly Lys Tyr Gly Ala Leu Arg Asp Gly Arg Trp Thr Gly Leu
            500                 505                 510 gtc ggg gac ctg ctg gcc ggc cgg gcc cac atg gcg gtc acc agc ttc     1584
Val Gly Asp Leu Leu Ala Gly Arg Ala His Met Ala Val Thr Ser Phe
        515                 520                 525 agt atc aac tcc gcc cgc tca cag gtg gtg gac ttc acc agc ccc ttc     1632
Ser Ile Asn Ser Ala Arg Ser Gln Val Val Asp Phe Thr Ser Pro Phe
    530                 535                 540 ttc tcc acc agc ctg ggc atc atg gtg cgg gca cgg gac acg gcc tca     1680
Phe Ser Thr Ser Leu Gly Ile Met Val Arg Ala Arg Asp Thr Ala Ser
545                 550                 555                 560 ccc atc ggt gcc ttt atg tgg ccc ctg cac tgg tcc acg tgg ctg ggc     1728
Pro Ile Gly Ala Phe Met Trp Pro Leu His Trp Ser Thr Trp Leu Gly
```

-continued

```
            565                 570                 575
gtc ttt gcg gcc ctg cac ctc acc gcg ctc ttc ctc acc gtg tac gag     1776
Val Phe Ala Ala Leu His Leu Thr Ala Leu Phe Leu Thr Val Tyr Glu
            580                 585                 590 tgg cgt agc ccc tac ggc ctc acg cca cgt ggc cgc aac cga agc acc     1824
Trp Arg Ser Pro Tyr Gly Leu Thr Pro Arg Gly Arg Asn Arg Ser Thr
            595                 600                 605 gtc ttc tcc tac tcc tca gcc ctc aac ctg tgc tac gcc atc ctc ttc     1872
Val Phe Ser Tyr Ser Ser Ala Leu Asn Leu Cys Tyr Ala Ile Leu Phe
            610                 615                 620 aga cgc acc gtg tcc agc aag acg ccc aag tgc ccc acg ggc cgc ctg     1920
Arg Arg Thr Val Ser Ser Lys Thr Pro Lys Cys Pro Thr Gly Arg Leu
625                 630                 635                 640 ctc atg aac ctc tgg gcc atc ttc tgc ctg ctg gtg ctg tcc agc tac     1968
Leu Met Asn Leu Trp Ala Ile Phe Cys Leu Leu Val Leu Ser Ser Tyr
                645                 650                 655 acg gcc aac ctg gct gcc gtc atg gtc ggg gac aag acc ttc gag gag     2016
Thr Ala Asn Leu Ala Ala Val Met Val Gly Asp Lys Thr Phe Glu Glu
                660                 665                 670 ctg tcg ggg atc cac gac ccc aag ctg cac cac ccg gcg cag ggc ttc     2064
Leu Ser Gly Ile His Asp Pro Lys Leu His His Pro Ala Gln Gly Phe
            675                 680                 685 cgc ttc ggc acc gtg tgg gag agc agc gcc gag gcg tac atc aag aag     2112
Arg Phe Gly Thr Val Trp Glu Ser Ser Ala Glu Ala Tyr Ile Lys Lys
            690                 695                 700 agc ttc ccc gac atg cac gca cac atg cgg cgc cac agc gcg ccc acc     2160
Ser Phe Pro Asp Met His Ala His Met Arg Arg His Ser Ala Pro Thr
705                 710                 715                 720 acg ccc cgc ggc gtc gcc atg ctc acg agc gac ccc ccc aag ctc aac     2208
Thr Pro Arg Gly Val Ala Met Leu Thr Ser Asp Pro Pro Lys Leu Asn
                725                 730                 735 gcc ttc atc atg gac aag tcg ctc ctg gac tac gag gtc tcc atc gac     2256
Ala Phe Ile Met Asp Lys Ser Leu Leu Asp Tyr Glu Val Ser Ile Asp
                740                 745                 750 gcc gac tgc aaa ctg ctg acc gtg gga aag ccc ttc gcc att gag ggc     2304
Ala Asp Cys Lys Leu Leu Thr Val Gly Lys Pro Phe Ala Ile Glu Gly
            755                 760                 765 tat ggg atc gga ctg ccc cag aac tcg ccg ctc acc tcc aac ctg tcc     2352
Tyr Gly Ile Gly Leu Pro Gln Asn Ser Pro Leu Thr Ser Asn Leu Ser
            770                 775                 780 gag ttc atc agc cgc tac aag tcc tcc ggc ttc atc gac ctg ctc cac     2400
Glu Phe Ile Ser Arg Tyr Lys Ser Ser Gly Phe Ile Asp Leu Leu His
785                 790                 795                 800 gac aag tgg tac aag atg gtg cct tgc ggc aag cgg gtc ttt gcg gtt     2448
Asp Lys Trp Tyr Lys Met Val Pro Cys Gly Lys Arg Val Phe Ala Val
                805                 810                 815 aca gag acc ctg cag atg agc atc tac cac ttc gcg ggc ctc ttc gtg     2496
Thr Glu Thr Leu Gln Met Ser Ile Tyr His Phe Ala Gly Leu Phe Val
                820                 825                 830 ttg ctg tgc ctg ggc ctg ggc agc gct ctg ctc agc tcg ctg ggc gag     2544
Leu Leu Cys Leu Gly Leu Gly Ser Ala Leu Leu Ser Ser Leu Gly Glu
            835                 840                 845 cac gcc ttc ttc cgc ctg gcg ctg ccg cgc atc cgc aag ggg agc agg     2592
His Ala Phe Phe Arg Leu Ala Leu Pro Arg Ile Arg Lys Gly Ser Arg
            850                 855                 860 ctg cag tac tgg ctg cac acc agc cag aaa atc cac cgc gcc ctc aac     2640
Leu Gln Tyr Trp Leu His Thr Ser Gln Lys Ile His Arg Ala Leu Asn
865                 870                 875                 880 acg gag cca cca gag ggg tcg aag gag gag acg gca gag gcg gag ccc     2688
```

-continued

```
                    Thr Glu Pro Pro Glu Gly Ser Lys Glu Glu Thr Ala Glu Ala Glu Pro
                                    885                 890                 895 agg nnn nnn nnn nnn nnn nnn nnn nnn nnn nnn nnn nnn tgg aaa            2736
Arg Xaa Xaa Xaa Xaa Xaa Xaa Xaa Xaa Xaa Xaa Xaa Xaa Trp Lys
        900                 905                 910 cgg gcg cgc cgg gcc gtg gac aag gag cgc cgc gtg cgc ttc ctg ctg        2784
Arg Ala Arg Arg Ala Val Asp Lys Glu Arg Arg Val Arg Phe Leu Leu
            915                 920                 925 gag ccc nnn nnn nnn nnn nnn nnn nnn tgg ctg tgc tcc nnn nnn            2832
Glu Pro Xaa Xaa Xaa Xaa Xaa Xaa Xaa Trp Leu Cys Ser Xaa Xaa
930                 935                 940 nnn nnn nnn nnn nnn gag ctg cag gag ctg gag cgc cgc atc gaa gtc        2880
Xaa Xaa Xaa Xaa Xaa Glu Leu Gln Glu Leu Glu Arg Arg Ile Glu Val
945                 950                 955                 960 gcg cgt gag cgg ctc cgc cag gcc ctg gtg cgg cgc ggc cag ctc ctg        2928
Ala Arg Glu Arg Leu Arg Gln Ala Leu Val Arg Arg Gly Gln Leu Leu
                965                 970                 975 gca cag ctc ggg gac agc gca cgt cac cgg cct cgg cgc ttg ctt cag        2976
Ala Gln Leu Gly Asp Ser Ala Arg His Arg Pro Arg Arg Leu Leu Gln
            980                 985                 990 gcc aga gcg gcc ccc gcg gag gcc cca cca cac tct ggc cga ccg ggg        3024
Ala Arg Ala Ala Pro Ala Glu Ala Pro Pro His Ser Gly Arg Pro Gly
        995                 1000                1005 agc cag gaa tgannngaca gtttattcta tatacaaaca caattttgta                3073
Ser Gln Glu
      1010 cactgcaatt aaatagaatg gaa                                              3096

<210> SEQ ID NO 6
<211> LENGTH: 1011
<212> TYPE: PRT
<213> ORGANISM: Homo sapiens
<220> FEATURE:
<221> NAME/KEY: VARIANT
<222> LOCATION: 898, 899, 900, 901, 902, 903, 904, 905, 906, 907, 908,
      909, 910, 931, 932, 933, 934, 935, 936, 937, 938, 943, 944, 945,
      946, 947, 948, 949
<223> OTHER INFORMATION: Xaa = Any Amino Acid

<400> SEQUENCE: 6

Met Glu Phe Val Arg Ala Leu Trp Leu Gly Leu Ala Leu Ala Leu Gly
1               5                   10                  15

Pro Gly Ser Ala Gly Gly His Pro Gln Pro Cys Gly Val Leu Ala Arg
            20                  25                  30

Leu Gly Gly Ser Val Arg Leu Gly Ala Leu Leu Pro Arg Ala Pro Leu
        35                  40                  45

Ala Arg Ala Arg Ala Arg Ala Ala Leu Ala Arg Ala Ala Leu Ala Pro
    50                  55                  60

Arg Leu Pro His Asn Leu Ser Leu Glu Leu Val Val Ala Ala Pro Pro
65                  70                  75                  80

Ala Arg Asp Pro Ala Ser Leu Thr Arg Gly Leu Cys Gln Ala Leu Val
                85                  90                  95

Pro Pro Gly Val Ala Ala Leu Leu Phe Pro Glu Ala Arg Pro Glu
            100                 105                 110

Leu Leu Gln Leu His Phe Leu Ala Ala Ala Thr Glu Thr Pro Val Leu
        115                 120                 125

Ser Leu Leu Arg Arg Glu Ala Arg Ala Pro Leu Gly Ala Pro Asn Pro
    130                 135                 140

Phe His Leu Gln Leu His Trp Ala Ser Pro Leu Glu Thr Leu Leu Asp
```

```
            145                 150                 155                 160
Val Leu Val Ala Val Leu Gln Ala His Ala Trp Glu Asp Val Gly Leu
                165                 170                 175
Ala Leu Cys Arg Thr Gln Asp Pro Gly Gly Leu Val Ala Leu Trp Thr
            180                 185                 190
Ser Arg Ala Gly Arg Pro Pro Gln Leu Val Leu Asp Leu Ser Arg Arg
        195                 200                 205
Asp Thr Gly Asp Ala Gly Leu Arg Ala Arg Leu Ala Pro Met Ala Ala
    210                 215                 220
Pro Val Gly Gly Glu Ala Pro Val Pro Ala Ala Val Leu Leu Gly Cys
225                 230                 235                 240
Asp Ile Ala Arg Ala Arg Arg Val Leu Glu Ala Val Pro Pro Gly Pro
                245                 250                 255
His Trp Leu Leu Gly Thr Pro Leu Pro Pro Lys Ala Leu Pro Thr Ala
            260                 265                 270
Gly Leu Pro Pro Gly Leu Leu Ala Leu Gly Glu Val Ala Arg Pro Pro
        275                 280                 285
Leu Glu Ala Ala Ile His Asp Ile Val Gln Leu Val Ala Arg Ala Leu
    290                 295                 300
Gly Ser Ala Ala Gln Val Gln Pro Lys Arg Ala Leu Leu Pro Ala Pro
305                 310                 315                 320
Val Asn Cys Gly Asp Leu Gln Pro Ala Gly Pro Glu Ser Pro Gly Arg
                325                 330                 335
Phe Leu Ala Asn Thr Ser Phe Gln Gly Arg Thr Gly Pro Val Trp Val
            340                 345                 350
Thr Gly Ser Ser Gln Val His Met Ser Arg His Phe Lys Val Trp Ser
        355                 360                 365
Leu Arg Arg Asp Pro Arg Gly Ala Pro Ala Trp Ala Thr Val Gly Ser
    370                 375                 380
Trp Arg Asp Gly Gln Leu Asp Leu Glu Pro Gly Gly Ala Ser Ala Arg
385                 390                 395                 400
Pro Pro Pro Pro Gln Gly Ala Gln Val Trp Pro Lys Leu Arg Val Val
                405                 410                 415
Thr Leu Leu Glu His Pro Phe Val Phe Ala Arg Asp Pro Asp Glu Asp
            420                 425                 430
Gly Gln Cys Pro Ala Gly Gln Leu Cys Leu Asp Pro Gly Thr Asn Asp
        435                 440                 445
Ser Ala Thr Leu Asp Ala Leu Phe Ala Ala Leu Ala Asn Gly Ser Ala
    450                 455                 460
Pro Arg Ala Leu Arg Lys Cys Cys Tyr Gly Tyr Cys Ile Asp Leu Leu
465                 470                 475                 480
Glu Arg Leu Ala Glu Asp Thr Pro Phe Asp Phe Glu Leu Tyr Leu Val
                485                 490                 495
Gly Asp Gly Lys Tyr Gly Ala Leu Arg Asp Gly Arg Trp Thr Gly Leu
            500                 505                 510
Val Gly Asp Leu Leu Ala Gly Arg Ala His Met Ala Val Thr Ser Phe
        515                 520                 525
Ser Ile Asn Ser Ala Arg Ser Gln Val Val Asp Phe Thr Ser Pro Phe
    530                 535                 540
Phe Ser Thr Ser Leu Gly Ile Met Val Arg Ala Arg Asp Thr Ala Ser
545                 550                 555                 560
Pro Ile Gly Ala Phe Met Trp Pro Leu His Trp Ser Thr Trp Leu Gly
                565                 570                 575
```

-continued

```
Val Phe Ala Ala Leu His Leu Thr Ala Leu Phe Leu Thr Val Tyr Glu
            580                 585                 590

Trp Arg Ser Pro Tyr Gly Leu Thr Pro Arg Gly Arg Asn Arg Ser Thr
            595                 600                 605

Val Phe Ser Tyr Ser Ser Ala Leu Asn Leu Cys Tyr Ala Ile Leu Phe
            610                 615                 620

Arg Arg Thr Val Ser Ser Lys Thr Pro Lys Cys Pro Thr Gly Arg Leu
625                 630                 635                 640

Leu Met Asn Leu Trp Ala Ile Phe Cys Leu Leu Val Leu Ser Ser Tyr
                    645                 650                 655

Thr Ala Asn Leu Ala Ala Val Met Val Gly Asp Lys Thr Phe Glu Glu
                660                 665                 670

Leu Ser Gly Ile His Asp Pro Lys Leu His His Pro Ala Gln Gly Phe
            675                 680                 685

Arg Phe Gly Thr Val Trp Glu Ser Ser Ala Glu Ala Tyr Ile Lys Lys
        690                 695                 700

Ser Phe Pro Asp Met His Ala His Met Arg Arg His Ser Ala Pro Thr
705                 710                 715                 720

Thr Pro Arg Gly Val Ala Met Leu Thr Ser Asp Pro Pro Lys Leu Asn
                    725                 730                 735

Ala Phe Ile Met Asp Lys Ser Leu Leu Asp Tyr Glu Val Ser Ile Asp
                740                 745                 750

Ala Asp Cys Lys Leu Leu Thr Val Gly Lys Pro Phe Ala Ile Glu Gly
            755                 760                 765

Tyr Gly Ile Gly Leu Pro Gln Asn Ser Pro Leu Thr Ser Asn Leu Ser
        770                 775                 780

Glu Phe Ile Ser Arg Tyr Lys Ser Ser Gly Phe Ile Asp Leu Leu His
785                 790                 795                 800

Asp Lys Trp Tyr Lys Met Val Pro Cys Gly Lys Arg Val Phe Ala Val
                    805                 810                 815

Thr Glu Thr Leu Gln Met Ser Ile Tyr His Phe Ala Gly Leu Phe Val
                820                 825                 830

Leu Leu Cys Leu Gly Leu Gly Ser Ala Leu Leu Ser Ser Leu Gly Glu
            835                 840                 845

His Ala Phe Phe Arg Leu Ala Leu Pro Arg Ile Arg Lys Gly Ser Arg
        850                 855                 860

Leu Gln Tyr Trp Leu His Thr Ser Gln Lys Ile His Arg Ala Leu Asn
865                 870                 875                 880

Thr Glu Pro Pro Glu Gly Ser Lys Glu Glu Thr Ala Glu Ala Glu Pro
                    885                 890                 895

Arg Xaa Xaa Xaa Xaa Xaa Xaa Xaa Xaa Xaa Xaa Xaa Trp Lys
                900                 905                 910

Arg Ala Arg Arg Ala Val Asp Lys Glu Arg Arg Val Arg Phe Leu Leu
            915                 920                 925

Glu Pro Xaa Xaa Xaa Xaa Xaa Xaa Xaa Trp Leu Cys Ser Xaa Xaa
        930                 935                 940

Xaa Xaa Xaa Xaa Xaa Glu Leu Gln Glu Leu Glu Arg Arg Ile Glu Val
945                 950                 955                 960

Ala Arg Glu Arg Leu Arg Gln Ala Leu Val Arg Gly Gln Leu Leu
                    965                 970                 975

Ala Gln Leu Gly Asp Ser Ala Arg His Arg Pro Arg Arg Leu Leu Gln
                980                 985                 990
```

Ala Arg Ala Ala Pro Ala Glu Ala Pro Pro His Ser Gly Arg Pro Gly
        995                 1000                1005

Ser Gln Glu
    1010

<210> SEQ ID NO 7
<211> LENGTH: 3166
<212> TYPE: DNA
<213> ORGANISM: Mus musculus
<220> FEATURE:
<221> NAME/KEY: CDS
<222> LOCATION: (63)...(3077)

<400> SEQUENCE: 7
agagcggggc tggctgggat gtctccttac cctcgcacag cacagtggta acttccatcg      60 gg atg gag tgt gtg cag acg ctg tgg ctc agc ctg gcc ctg gcg ctg       107
   Met Glu Cys Val Gln Thr Leu Trp Leu Ser Leu Ala Leu Ala Leu
   1               5                   10                  15 gcg cga ggg tcc tgg gtg gtg cgc ggt cac cct cag ccc tgc ggg gtt     155
Ala Arg Gly Ser Trp Val Val Arg Gly His Pro Gln Pro Cys Gly Val
                20                  25                  30 ccc acg cgc gcc ggg gcc tcc gtg cgc ctg gct gcg ctc cta ccc cgg     203
Pro Thr Arg Ala Gly Ala Ser Val Arg Leu Ala Ala Leu Leu Pro Arg
            35                  40                  45 gcg ccc gcc gcc cgc gcc cgc gtc cta gcc gcc ctg gcc acc cct tcc     251
Ala Pro Ala Ala Arg Ala Arg Val Leu Ala Ala Leu Ala Thr Pro Ser
        50                  55                  60 ccg cgg ctg ccg cac aac ctg agt ctg gag cta gtg gcc gtc gcg tcc     299
Pro Arg Leu Pro His Asn Leu Ser Leu Glu Leu Val Ala Val Ala Ser
    65                  70                  75 cca acc cgg gac ccc gcg tcg ctg gcc cga ggt ctg tgc cag gtt ctg     347
Pro Thr Arg Asp Pro Ala Ser Leu Ala Arg Gly Leu Cys Gln Val Leu
80                  85                  90                  95 gca ccg ccc ggc gtg gtg gcc tct ata acc ttt ccc gag gcg cgg cct     395
Ala Pro Pro Gly Val Val Ala Ser Ile Thr Phe Pro Glu Ala Arg Pro
                100                 105                 110 gag cta cgg cta ttg cag ttc ctg gca gct gcc aca gag acc ccg gtg     443
Glu Leu Arg Leu Leu Gln Phe Leu Ala Ala Ala Thr Glu Thr Pro Val
            115                 120                 125 ctg agc gtc cta cgg agg gag gtg cgc gcg ccc ctc gga gct cgg cgg     491
Leu Ser Val Leu Arg Arg Glu Val Arg Ala Pro Leu Gly Ala Arg Arg
        130                 135                 140 acc ccg ttc cac ctg cag ctg gac tgg gct agt ccc ctg gag acc atc     539
Thr Pro Phe His Leu Gln Leu Asp Trp Ala Ser Pro Leu Glu Thr Ile
    145                 150                 155 ctg gat gtg ctg gtg tcc ctg gta cgg gca cac gcc tgg gag gac att     587
Leu Asp Val Leu Val Ser Leu Val Arg Ala His Ala Trp Glu Asp Ile
160                 165                 170                 175 gct cta gtg ctc tgt cgt gtc cgg gac ccc agt ggc ctg gtg aca ctc     635
Ala Leu Val Leu Cys Arg Val Arg Asp Pro Ser Gly Leu Val Thr Leu
                180                 185                 190 tgg acc agc cgt gct agc cag gct cca aag ttt gtg ctg gac ctg agc     683
Trp Thr Ser Arg Ala Ser Gln Ala Pro Lys Phe Val Leu Asp Leu Ser
            195                 200                 205 cag ttg gac agc ggg aat gac agc ctt cgg gct aca ctg gcc ctg ctg     731
Gln Leu Asp Ser Gly Asn Asp Ser Leu Arg Ala Thr Leu Ala Leu Leu
        210                 215                 220 ggg acg ctg gaa gga ggg gga acc ccc gtg tct gca gcc gtc ctc ctg     779
Gly Thr Leu Glu Gly Gly Gly Thr Pro Val Ser Ala Ala Val Leu Leu
    225                 230                 235

-continued

| | |
|---|---|
| ggc tgc agc act gcc cat gca cat gag gtc cta gag gca gca cca ccg<br>Gly Cys Ser Thr Ala His Ala His Glu Val Leu Glu Ala Ala Pro Pro<br>240               245                   250                  255 | 827 |
| ggt ccc cag tgg ctg ctg ggc aca cca ctg ccc gcc gag gca ctg ccc<br>Gly Pro Gln Trp Leu Leu Gly Thr Pro Leu Pro Ala Glu Ala Leu Pro<br>                 260                   265                   270 | 875 |
| aaa acc ggt ctg ccc cct ggg gtg ttg gtg ctg ggg gaa acc ggg cag<br>Lys Thr Gly Leu Pro Pro Gly Val Leu Val Leu Gly Glu Thr Gly Gln<br>           275                      280                  285 | 923 |
| cct tcc ctg gaa gct gcc gtc cac gac atg gtg gag ctt gtg gct cgg<br>Pro Ser Leu Glu Ala Ala Val His Asp Met Val Glu Leu Val Ala Arg<br>290                     295                   300 | 971 |
| gca ctc agc agc atg gcc ctc atg cac cca gag cgg gcc ctg ctt cca<br>Ala Leu Ser Ser Met Ala Leu Met His Pro Glu Arg Ala Leu Leu Pro<br>305               310                   315 | 1019 |
| gcg gca gta aat tgt gag gac ctg aaa acg ggc ggc tct gag tca aca<br>Ala Ala Val Asn Cys Glu Asp Leu Lys Thr Gly Gly Ser Glu Ser Thr<br>320                     325                   330                  335 | 1067 |
| gca cgc acc ttg gct agg tgg ttt ctg agc aac acc tca ttt cag ggc<br>Ala Arg Thr Leu Ala Arg Trp Phe Leu Ser Asn Thr Ser Phe Gln Gly<br>                 340                   345                   350 | 1115 |
| cgc aca ggg gct gtg tgg gtg gca ggc tcc tct cag gtg cat gtg tct<br>Arg Thr Gly Ala Val Trp Val Ala Gly Ser Ser Gln Val His Val Ser<br>           355                      360                  365 | 1163 |
| cgg cat ttc aag gta tgg agc tta cgc agg gac ccg ctg ggt gcc cca<br>Arg His Phe Lys Val Trp Ser Leu Arg Arg Asp Pro Leu Gly Ala Pro<br>370                     375                   380 | 1211 |
| gcc tgg gca aca gta ggc agc tgg cag gat gga cag ctg gac ttc cag<br>Ala Trp Ala Thr Val Gly Ser Trp Gln Asp Gly Gln Leu Asp Phe Gln<br>385                     390                   395 | 1259 |
| cca ggg gcg gct gct ctc cga gtt cca tct cca tct ggc acc cag gcc<br>Pro Gly Ala Ala Ala Leu Arg Val Pro Ser Pro Ser Gly Thr Gln Ala<br>400                     405                   410                  415 | 1307 |
| cgg cca aag ctg cga gtg gta act ctg gtg gaa cac cca ttt gtg ttc<br>Arg Pro Lys Leu Arg Val Val Thr Leu Val Glu His Pro Phe Val Phe<br>                 420                   425                   430 | 1355 |
| acc agg gaa tct gat gaa gat ggg cag tgc ccg gct ggg cag ctg tgt<br>Thr Arg Glu Ser Asp Glu Asp Gly Gln Cys Pro Ala Gly Gln Leu Cys<br>           435                      440                  445 | 1403 |
| cta gac cca ggc acc aat gac tcg gcc agg ctg gat gcg ctc ttc act<br>Leu Asp Pro Gly Thr Asn Asp Ser Ala Arg Leu Asp Ala Leu Phe Thr<br>450                     455                   460 | 1451 |
| gca ttg gag aat ggc tcc gtg cct cgc acc ctg aga aga tgc tgt tat<br>Ala Leu Glu Asn Gly Ser Val Pro Arg Thr Leu Arg Arg Cys Cys Tyr<br>465                     470                   475 | 1499 |
| ggc tac tgc att gac ctg ctg gag cgg ctg gcc gag gac ctg gcc ttt<br>Gly Tyr Cys Ile Asp Leu Leu Glu Arg Leu Ala Glu Asp Leu Ala Phe<br>480                     485                   490                  495 | 1547 |
| gac ttt gag ctc tat att gtg ggg gat ggc aag tac ggg gcc ctg cgt<br>Asp Phe Glu Leu Tyr Ile Val Gly Asp Gly Lys Tyr Gly Ala Leu Arg<br>                 500                   505                   510 | 1595 |
| gat gga cgc tgg aca ggc ctg gtg ggt gac ctg ctg gcc ggt cgg gca<br>Asp Gly Arg Trp Thr Gly Leu Val Gly Asp Leu Leu Ala Gly Arg Ala<br>           515                      520                  525 | 1643 |
| cac atg gcc gtg acc agc ttc agt atc aac tcg gct cgc tcc cag gtg<br>His Met Ala Val Thr Ser Phe Ser Ile Asn Ser Ala Arg Ser Gln Val<br>530                     535                   540 | 1691 |
| gtg gat ttc acc agc cct ttc ttc tcc acc agc ctg ggc atc atg gtg<br>Val Asp Phe Thr Ser Pro Phe Phe Ser Thr Ser Leu Gly Ile Met Val<br>545                     550                   555 | 1739 |

-continued

```
cgc acg cga gat aca gcc tca ccc att ggg gct ttc atg tgg ccc ctg    1787
Arg Thr Arg Asp Thr Ala Ser Pro Ile Gly Ala Phe Met Trp Pro Leu
560             565                 570                 575 cac tgg tcc atg tgg gtg ggt gtg ttt gct gcc ctg cac ctc aca gcg    1835
His Trp Ser Met Trp Val Gly Val Phe Ala Ala Leu His Leu Thr Ala
                580                 585                 590 ctc ttc ctt act ctg tac gaa tgg cgg agt ccc tac ggg ctc acg cca    1883
Leu Phe Leu Thr Leu Tyr Glu Trp Arg Ser Pro Tyr Gly Leu Thr Pro
            595                 600                 605 cgc ggc cgc aac cgt ggt acc gtc ttc tcc tac tcc tcc gct ctc aac    1931
Arg Gly Arg Asn Arg Gly Thr Val Phe Ser Tyr Ser Ser Ala Leu Asn
        610                 615                 620 ctc tgc tac gcc att ctc ttc gga cgc act gtc tcc agt aag aca ccc    1979
Leu Cys Tyr Ala Ile Leu Phe Gly Arg Thr Val Ser Ser Lys Thr Pro
    625                 630                 635 aag tgt cct acc gga cgc ttc ctc atg aat ctc tgg gca atc ttc tgc    2027
Lys Cys Pro Thr Gly Arg Phe Leu Met Asn Leu Trp Ala Ile Phe Cys
640                 645                 650                 655 ctg ctg gtg cta tcc agt tac aca gcc aac ctg gca gct gtc atg gtc    2075
Leu Leu Val Leu Ser Ser Tyr Thr Ala Asn Leu Ala Ala Val Met Val
                660                 665                 670 ggg gac aag aca ttt gag gag ctg tct gga atc cat gat ccc aag ctg    2123
Gly Asp Lys Thr Phe Glu Glu Leu Ser Gly Ile His Asp Pro Lys Leu
            675                 680                 685 cac cac cct tcc caa ggc ttc cgc ttt ggc acc gtg tgg gag agc agc    2171
His His Pro Ser Gln Gly Phe Arg Phe Gly Thr Val Trp Glu Ser Ser
        690                 695                 700 gcg gag gcc tac atc aag gcg agc ttc ccc gag atg cac gca cac atg    2219
Ala Glu Ala Tyr Ile Lys Ala Ser Phe Pro Glu Met His Ala His Met
    705                 710                 715 cgt cgc cac agc gca cct acc act cca cac gga gtg gcc atg ctc acg    2267
Arg Arg His Ser Ala Pro Thr Thr Pro His Gly Val Ala Met Leu Thr
720                 725                 730                 735 agc gac ccg ccc aag ctc aac gcc ttc atc atg gat aaa tca cta ctg    2315
Ser Asp Pro Pro Lys Leu Asn Ala Phe Ile Met Asp Lys Ser Leu Leu
                740                 745                 750 gat tat gag gtg tcc ata gat gcg gac tgc aag ctg ctc acc gtg ggc    2363
Asp Tyr Glu Val Ser Ile Asp Ala Asp Cys Lys Leu Leu Thr Val Gly
            755                 760                 765 aaa ccc ttt gcg atc gag ggc tac ggc ata ggg ctg ccc caa aat tcg    2411
Lys Pro Phe Ala Ile Glu Gly Tyr Gly Ile Gly Leu Pro Gln Asn Ser
        770                 775                 780 ccg ctc acc tcc aac ctg tca gag ttc atc agt agg tac aag tcc tca    2459
Pro Leu Thr Ser Asn Leu Ser Glu Phe Ile Ser Arg Tyr Lys Ser Ser
    785                 790                 795 ggc ttc att gat ctg ctc cat gac aag tgg tac aag atg gtg cct tgc    2507
Gly Phe Ile Asp Leu Leu His Asp Lys Trp Tyr Lys Met Val Pro Cys
800                 805                 810                 815 ggg aag cgg gtg ttc gcc gtg acg gag acg ctg cag atg ggg gtc tac    2555
Gly Lys Arg Val Phe Ala Val Thr Glu Thr Leu Gln Met Gly Val Tyr
                820                 825                 830 cac ttg tca ggg ttg ttt gtc ctg ctg tgc ctc ggg ctg ggc agt gca    2603
His Leu Ser Gly Leu Phe Val Leu Leu Cys Leu Gly Leu Gly Ser Ala
            835                 840                 845 ctt ctc acc tcg ctg ggt gag cac gtc ttc tac cgc ctg gtg ctg ccg    2651
Leu Leu Thr Ser Leu Gly Glu His Val Phe Tyr Arg Leu Val Leu Pro
        850                 855                 860 cgc atc cgc agg ggc aat aag ctg cag tat tgg ctt cac acg agc cag    2699
Arg Ile Arg Arg Gly Asn Lys Leu Gln Tyr Trp Leu His Thr Ser Gln
```

-continued

```
                    865                 870                 875
gaa gat cca ccg agc cct caa cac agg gcc acc aga ggg gca aca gga          2747
Glu Asp Pro Pro Ser Pro Gln His Arg Ala Thr Arg Gly Ala Thr Gly
880                 885                 890                 895 gag ggc aga gca gga gtg cag ggc ccc aag gag gag caa cct gca gcc          2795
Glu Gly Arg Ala Gly Val Gln Gly Pro Lys Glu Glu Gln Pro Ala Ala
                900                 905                 910 gac ggt gcg ggg cgc tgg agg cgg gtg cgc cgg gcc gtg gtg gaa cgg          2843
Asp Gly Ala Gly Arg Trp Arg Arg Val Arg Arg Ala Val Val Glu Arg
            915                 920                 925 gaa cgg cgc gtg cgt ttc ctg ctg gaa cct ggg gag gct ggc ggg gac          2891
Glu Arg Arg Val Arg Phe Leu Leu Glu Pro Gly Glu Ala Gly Gly Asp
        930                 935                 940 cat ccg tgg ctc tgc tcc aat ggg ccc ggg gtg caa gca gaa ctg cgg          2939
His Pro Trp Leu Cys Ser Asn Gly Pro Gly Val Gln Ala Glu Leu Arg
    945                 950                 955 gag ctg gag ctg cgc att gag gct gca cgg gag cgg ctg cgt agt gcg          2987
Glu Leu Glu Leu Arg Ile Glu Ala Ala Arg Glu Arg Leu Arg Ser Ala
960                 965                 970                 975 ctg ctg cgg cga ggg gaa ctg cgg gcc cag ctt ggg gat ggc acc cgg          3035
Leu Leu Arg Arg Gly Glu Leu Arg Ala Gln Leu Gly Asp Gly Thr Arg
                980                 985                 990 ctc agg cca ctg cgc ctg ctg cat gcg gcg ccc gcc gag agc                  3077
Leu Arg Pro Leu Arg Leu Leu His Ala Ala Pro Ala Glu Ser
            995                 1000                1005 tgaggaacta cacggccaca ctgtccacga cagtttattc tatatacaaa cacgactctg        3137
tacactgcaa ttaaatagcg tggaacgtg                                          3166

<210> SEQ ID NO 8
<211> LENGTH: 1005
<212> TYPE: PRT
<213> ORGANISM: Mus musculus

<400> SEQUENCE: 8

Met Glu Cys Val Gln Thr Leu Trp Leu Ser Leu Ala Leu Ala Leu Ala
1               5                   10                  15

Arg Gly Ser Trp Val Val Arg Gly His Pro Gln Pro Cys Gly Val Pro
            20                  25                  30

Thr Arg Ala Gly Ala Ser Val Arg Leu Ala Ala Leu Leu Pro Arg Ala
        35                  40                  45

Pro Ala Ala Arg Ala Arg Val Leu Ala Ala Leu Ala Thr Pro Ser Pro
    50                  55                  60

Arg Leu Pro His Asn Leu Ser Leu Glu Leu Val Ala Val Ala Ser Pro
65                  70                  75                  80

Thr Arg Asp Pro Ala Ser Leu Ala Arg Gly Leu Cys Gln Val Leu Ala
                85                  90                  95

Pro Pro Gly Val Val Ala Ser Ile Thr Phe Pro Glu Ala Arg Pro Glu
            100                 105                 110

Leu Arg Leu Leu Gln Phe Leu Ala Ala Ala Thr Glu Thr Pro Val Leu
        115                 120                 125

Ser Val Leu Arg Arg Glu Val Arg Ala Pro Leu Gly Ala Arg Arg Thr
    130                 135                 140

Pro Phe His Leu Gln Leu Asp Trp Ala Ser Pro Leu Glu Thr Ile Leu
145                 150                 155                 160

Asp Val Leu Val Ser Leu Val Arg Ala His Ala Trp Glu Asp Ile Ala
                165                 170                 175
```

```
Leu Val Leu Cys Arg Val Arg Asp Pro Ser Gly Leu Val Thr Leu Trp
            180                 185                 190

Thr Ser Arg Ala Ser Gln Ala Pro Lys Phe Val Leu Asp Leu Ser Gln
        195                 200                 205

Leu Asp Ser Gly Asn Asp Ser Leu Arg Ala Thr Leu Ala Leu Leu Gly
    210                 215                 220

Thr Leu Glu Gly Gly Gly Thr Pro Val Ser Ala Ala Val Leu Leu Gly
225                 230                 235                 240

Cys Ser Thr Ala His Ala His Glu Val Leu Glu Ala Ala Pro Pro Gly
                245                 250                 255

Pro Gln Trp Leu Leu Gly Thr Pro Leu Pro Ala Glu Ala Leu Pro Lys
            260                 265                 270

Thr Gly Leu Pro Pro Gly Val Leu Val Leu Gly Glu Thr Gly Gln Pro
        275                 280                 285

Ser Leu Glu Ala Ala Val His Asp Met Val Glu Leu Val Ala Arg Ala
    290                 295                 300

Leu Ser Ser Met Ala Leu Met His Pro Glu Arg Ala Leu Leu Pro Ala
305                 310                 315                 320

Ala Val Asn Cys Glu Asp Leu Lys Thr Gly Gly Ser Glu Ser Thr Ala
                325                 330                 335

Arg Thr Leu Ala Arg Trp Phe Leu Ser Asn Thr Ser Phe Gln Gly Arg
            340                 345                 350

Thr Gly Ala Val Trp Val Ala Gly Ser Ser Gln Val His Val Ser Arg
        355                 360                 365

His Phe Lys Val Trp Ser Leu Arg Arg Asp Pro Leu Gly Ala Pro Ala
    370                 375                 380

Trp Ala Thr Val Gly Ser Trp Gln Asp Gly Gln Leu Asp Phe Gln Pro
385                 390                 395                 400

Gly Ala Ala Ala Leu Arg Val Pro Ser Pro Ser Gly Thr Gln Ala Arg
                405                 410                 415

Pro Lys Leu Arg Val Val Thr Leu Val Glu His Pro Phe Val Phe Thr
            420                 425                 430

Arg Glu Ser Asp Glu Asp Gly Gln Cys Pro Ala Gly Gln Leu Cys Leu
        435                 440                 445

Asp Pro Gly Thr Asn Asp Ser Ala Arg Leu Asp Ala Leu Phe Thr Ala
    450                 455                 460

Leu Glu Asn Gly Ser Val Pro Arg Thr Leu Arg Arg Cys Cys Tyr Gly
465                 470                 475                 480

Tyr Cys Ile Asp Leu Leu Glu Arg Leu Ala Glu Asp Leu Ala Phe Asp
                485                 490                 495

Phe Glu Leu Tyr Ile Val Gly Asp Gly Lys Tyr Gly Ala Leu Arg Asp
            500                 505                 510

Gly Arg Trp Thr Gly Leu Val Gly Asp Leu Leu Ala Gly Arg Ala His
        515                 520                 525

Met Ala Val Thr Ser Phe Ser Ile Asn Ser Ala Arg Ser Gln Val Val
    530                 535                 540

Asp Phe Thr Ser Pro Phe Ser Thr Ser Leu Gly Ile Met Val Arg
545                 550                 555                 560

Thr Arg Asp Thr Ala Ser Pro Ile Gly Ala Phe Met Trp Pro Leu His
                565                 570                 575

Trp Ser Met Trp Val Gly Val Phe Ala Ala Leu His Leu Thr Ala Leu
            580                 585                 590

Phe Leu Thr Leu Tyr Glu Trp Arg Ser Pro Tyr Gly Leu Thr Pro Arg
```

```
                   595                 600                 605
Gly Arg Asn Arg Gly Thr Val Phe Ser Tyr Ser Ala Leu Asn Leu
            610                 615                 620
Cys Tyr Ala Ile Leu Phe Gly Arg Thr Val Ser Ser Lys Thr Pro Lys
625                 630                 635                 640
Cys Pro Thr Gly Arg Phe Leu Met Asn Leu Trp Ala Ile Phe Cys Leu
                645                 650                 655
Leu Val Leu Ser Ser Tyr Thr Ala Asn Leu Ala Ala Val Met Val Gly
                660                 665                 670
Asp Lys Thr Phe Glu Glu Leu Ser Gly Ile His Asp Pro Lys Leu His
            675                 680                 685
His Pro Ser Gln Gly Phe Arg Phe Gly Thr Val Trp Glu Ser Ser Ala
        690                 695                 700
Glu Ala Tyr Ile Lys Ala Ser Phe Pro Glu Met His Ala His Met Arg
705                 710                 715                 720
Arg His Ser Ala Pro Thr Thr Pro His Gly Val Ala Met Leu Thr Ser
                725                 730                 735
Asp Pro Pro Lys Leu Asn Ala Phe Ile Met Asp Lys Ser Leu Leu Asp
                740                 745                 750
Tyr Glu Val Ser Ile Asp Ala Asp Cys Lys Leu Leu Thr Val Gly Lys
            755                 760                 765
Pro Phe Ala Ile Glu Gly Tyr Gly Ile Gly Leu Pro Gln Asn Ser Pro
        770                 775                 780
Leu Thr Ser Asn Leu Ser Glu Phe Ile Ser Arg Tyr Lys Ser Ser Gly
785                 790                 795                 800
Phe Ile Asp Leu Leu His Asp Lys Trp Tyr Lys Met Val Pro Cys Gly
                805                 810                 815
Lys Arg Val Phe Ala Val Thr Glu Thr Leu Gln Met Gly Val Tyr His
            820                 825                 830
Leu Ser Gly Leu Phe Val Leu Leu Cys Leu Gly Leu Gly Ser Ala Leu
            835                 840                 845
Leu Thr Ser Leu Gly Glu His Val Phe Tyr Arg Leu Val Leu Pro Arg
        850                 855                 860
Ile Arg Arg Gly Asn Lys Leu Gln Tyr Trp Leu His Thr Ser Gln Glu
865                 870                 875                 880
Asp Pro Pro Ser Pro Gln His Arg Ala Thr Arg Gly Ala Thr Gly Glu
                885                 890                 895
Gly Arg Ala Gly Val Gln Gly Pro Lys Glu Gln Pro Ala Ala Asp
            900                 905                 910
Gly Ala Gly Arg Trp Arg Arg Val Arg Arg Ala Val Val Glu Arg Glu
        915                 920                 925
Arg Arg Val Arg Phe Leu Leu Glu Pro Gly Glu Ala Gly Gly Asp His
            930                 935                 940
Pro Trp Leu Cys Ser Asn Gly Pro Gly Val Gln Ala Glu Leu Arg Glu
945                 950                 955                 960
Leu Glu Leu Arg Ile Glu Ala Ala Arg Glu Arg Leu Arg Ser Ala Leu
                965                 970                 975
Leu Arg Arg Gly Glu Leu Arg Ala Gln Leu Gly Asp Gly Thr Arg Leu
            980                 985                 990
Arg Pro Leu Arg Leu Leu His Ala Ala Pro Ala Glu Ser
        995                 1000                1005

<210> SEQ ID NO 9
```

```
<211> LENGTH: 2691
<212> TYPE: DNA
<213> ORGANISM: Homo sapiens
<220> FEATURE:
<221> NAME/KEY: CDS
<222> LOCATION: (1)...(2691)

<400> SEQUENCE: 9 atg gag ttt gtg cgg gcg ctg tgg ctg ggc ctg gcg ctg gcg ctg ggg      48
Met Glu Phe Val Arg Ala Leu Trp Leu Gly Leu Ala Leu Ala Leu Gly
 1               5                  10                  15 ccg ggg tcc gcg ggg ggc cac cct cag ccg tgc ggc gtc ctg gcg cgc      96
Pro Gly Ser Ala Gly Gly His Pro Gln Pro Cys Gly Val Leu Ala Arg
             20                  25                  30 ctc ggg ggc tcc gtg cgc ctg ggc gcc ctg ctg ccc cgc gcg cct ctc     144
Leu Gly Gly Ser Val Arg Leu Gly Ala Leu Leu Pro Arg Ala Pro Leu
         35                  40                  45 gcc cgc gcc cgc gcc cgc gcc gcc ctg gcc cgg gcc gcc ctg gcg ccg     192
Ala Arg Ala Arg Ala Arg Ala Ala Leu Ala Arg Ala Ala Leu Ala Pro
     50                  55                  60 cgg ctg ccg cac aac ctg agc ttg gag ctg gtg gtc gcc gcg ccc ccc     240
Arg Leu Pro His Asn Leu Ser Leu Glu Leu Val Val Ala Ala Pro Pro
 65                  70                  75                  80 gcc cgc gac ccc gcc tcg ctg acc cgc ggc ctg tgc cag gcg ctg gtg     288
Ala Arg Asp Pro Ala Ser Leu Thr Arg Gly Leu Cys Gln Ala Leu Val
                 85                  90                  95 cct ccg ggc gtg gcg gcc ctg ctc gcc ttt ccc gag gct cgg ccc gag     336
Pro Pro Gly Val Ala Ala Leu Leu Ala Phe Pro Glu Ala Arg Pro Glu
            100                 105                 110 ctg ctg cag ctg cac ttc ctg gcg gcg gcc acc gag acc ccc gtg ctc     384
Leu Leu Gln Leu His Phe Leu Ala Ala Ala Thr Glu Thr Pro Val Leu
        115                 120                 125 agc ctg ctg cgg cgg gag gcg cgc gcg ccc ctc gga gcc ccg aac cca     432
Ser Leu Leu Arg Arg Glu Ala Arg Ala Pro Leu Gly Ala Pro Asn Pro
    130                 135                 140 ttc cac ctg cag ctg cac tgg gcc agc ccc ctg gag acg ctg ctg gat     480
Phe His Leu Gln Leu His Trp Ala Ser Pro Leu Glu Thr Leu Leu Asp
145                 150                 155                 160 gtg ctg gtg gcg gtg ctg cag gcg cac gcc tgg gaa gac gtc ggc ctg     528
Val Leu Val Ala Val Leu Gln Ala His Ala Trp Glu Asp Val Gly Leu
                165                 170                 175 gcc ctg tgc cgc act cag gac ccc ggc ggc ctg gtg gcc ctc tgg aca     576
Ala Leu Cys Arg Thr Gln Asp Pro Gly Gly Leu Val Ala Leu Trp Thr
            180                 185                 190 agc cgg gct ggc cgg ccc cca cag ctg gtc ctg gac cta agc cgg cgg     624
Ser Arg Ala Gly Arg Pro Pro Gln Leu Val Leu Asp Leu Ser Arg Arg
        195                 200                 205 gac acg gga gat gca gga ctg cgg gca cgc ctg gcc ccg atg gcg gcg     672
Asp Thr Gly Asp Ala Gly Leu Arg Ala Arg Leu Ala Pro Met Ala Ala
    210                 215                 220 cca gtg ggg ggt gaa gca ccg gta ccc gcg gcg gtc ctc ctc ggc tgt     720
Pro Val Gly Gly Glu Ala Pro Val Pro Ala Ala Val Leu Leu Gly Cys
225                 230                 235                 240 gac atc gcc cgt gcc cgt cgg gtg ctg gag gcc gta cct ccc ggc ccc     768
Asp Ile Ala Arg Ala Arg Arg Val Leu Glu Ala Val Pro Pro Gly Pro
                245                 250                 255 cac tgg ctg ttg ggg aca cca ctg ccg ccc aag gcc ctg ccc acc gcg     816
His Trp Leu Leu Gly Thr Pro Leu Pro Pro Lys Ala Leu Pro Thr Ala
            260                 265                 270 ggg ctg cca cca ggg ctg ctg gcg ctg ggc gag gtg gca cga ccc ccg     864
Gly Leu Pro Pro Gly Leu Leu Ala Leu Gly Glu Val Ala Arg Pro Pro
```

```
                  275                 280                 285
ctg gag gcc gcc atc cat gac att gtg caa ctg gtg gcc cgg gcg ctg         912
Leu Glu Ala Ala Ile His Asp Ile Val Gln Leu Val Ala Arg Ala Leu
    290                 295                 300 ggc agt gcg gcc cag gtg cag ccg aag cga gcc ctc ctc ccc gcc ccg         960
Gly Ser Ala Ala Gln Val Gln Pro Lys Arg Ala Leu Leu Pro Ala Pro
305                 310                 315                 320 gtc aac tgc ggg gac ctg cag ccg gcg ggc ccc gag tcc ccg ggg cgc        1008
Val Asn Cys Gly Asp Leu Gln Pro Ala Gly Pro Glu Ser Pro Gly Arg
                325                 330                 335 ttc ttg gcc aac acg tcc ttc cag ggc cgc acg ggc ccc gtg tgg gtg        1056
Phe Leu Ala Asn Thr Ser Phe Gln Gly Arg Thr Gly Pro Val Trp Val
            340                 345                 350 aca ggc agc tcc cag gta cac atg tct cgg cac ttt aag gtg tgg agc        1104
Thr Gly Ser Ser Gln Val His Met Ser Arg His Phe Lys Val Trp Ser
        355                 360                 365 ctt cgc cgg gac cca cgg ggc gcc ccg gcc tgg gcc acg gtg ggc agc        1152
Leu Arg Arg Asp Pro Arg Gly Ala Pro Ala Trp Ala Thr Val Gly Ser
    370                 375                 380 tgg cgg gac ggc cag ctg gac ttg gaa ccg gga ggt gcc tct gca cgg        1200
Trp Arg Asp Gly Gln Leu Asp Leu Glu Pro Gly Gly Ala Ser Ala Arg
385                 390                 395                 400 ccc ccg ccc cca cag ggt gcc cag gtc tgg ccc aag ctg cgt gtg gta        1248
Pro Pro Pro Pro Gln Gly Ala Gln Val Trp Pro Lys Leu Arg Val Val
                405                 410                 415 acg ctg ttg gaa cac cca ttt gtg ttt gcc cgt gat cca gac gaa gac        1296
Thr Leu Leu Glu His Pro Phe Val Phe Ala Arg Asp Pro Asp Glu Asp
            420                 425                 430 ggg cag tgc cca gcg ggg cag ctg tgc ctg gac cct ggc acc aac gac        1344
Gly Gln Cys Pro Ala Gly Gln Leu Cys Leu Asp Pro Gly Thr Asn Asp
        435                 440                 445 tcg gcc acc ctg gac gca ctg ttc gcc gcg ctg gcc aac ggc tca gcg        1392
Ser Ala Thr Leu Asp Ala Leu Phe Ala Ala Leu Ala Asn Gly Ser Ala
    450                 455                 460 ccc cgt gcc ctg cgc aag tgc tgc tac ggc tac tgc att gac ctg ctg        1440
Pro Arg Ala Leu Arg Lys Cys Cys Tyr Gly Tyr Cys Ile Asp Leu Leu
465                 470                 475                 480 gag cgg ctg gcg gag gac acg ccc ttc gac ttc gag ctg tac ctc gtg        1488
Glu Arg Leu Ala Glu Asp Thr Pro Phe Asp Phe Glu Leu Tyr Leu Val
                485                 490                 495 ggt gac ggc aag tac ggc gcc ctg cgg gac ggc cgc tgg acc ggc ctg        1536
Gly Asp Gly Lys Tyr Gly Ala Leu Arg Asp Gly Arg Trp Thr Gly Leu
            500                 505                 510 gtc ggg gac ctg ctg gcc ggc cgg gcc cac atg gcg gtc acc agc ttc        1584
Val Gly Asp Leu Leu Ala Gly Arg Ala His Met Ala Val Thr Ser Phe
        515                 520                 525 agt atc aac tcc gcc cgc tca cag gtg gtg gac ttc acc agc ccc ttc        1632
Ser Ile Asn Ser Ala Arg Ser Gln Val Val Asp Phe Thr Ser Pro Phe
    530                 535                 540 ttc tcc acc agc ctg ggc atc atg gtg cgg gca cgg gac acg gcc tca        1680
Phe Ser Thr Ser Leu Gly Ile Met Val Arg Ala Arg Asp Thr Ala Ser
545                 550                 555                 560 ccc atc ggt gcc ttt atg tgg ccc ctg cac tgg tcc acg tgg ctg ggc        1728
Pro Ile Gly Ala Phe Met Trp Pro Leu His Trp Ser Thr Trp Leu Gly
                565                 570                 575 gtc ttt gcg gcc ctg cac ctc acc gcg ctc ttc ctc acc gtg tac gag        1776
Val Phe Ala Ala Leu His Leu Thr Ala Leu Phe Leu Thr Val Tyr Glu
            580                 585                 590 tgg cgt agc ccc tac ggc ctc acg cca cgt ggc cgc aac cgc agc acc        1824
```

```
                Trp Arg Ser Pro Tyr Gly Leu Thr Pro Arg Gly Arg Asn Arg Ser Thr
                            595                 600                 605 gtc ttc tcc tac tcc tca gcc ctc aac ctg tgc tac gcc atc ctc ttc            1872
Val Phe Ser Tyr Ser Ser Ala Leu Asn Leu Cys Tyr Ala Ile Leu Phe
            610                 615                 620 aga cgc acc gtg tcc agc aag acg ccc aag tgc ccc acg ggc cgc ctg            1920
Arg Arg Thr Val Ser Ser Lys Thr Pro Lys Cys Pro Thr Gly Arg Leu
625                 630                 635                 640 ctc atg aac ctc tgg gcc atc ttc tgc ctg ctg gtg ctg tcc agc tac            1968
Leu Met Asn Leu Trp Ala Ile Phe Cys Leu Leu Val Leu Ser Ser Tyr
            645                 650                 655 acg gcc aac ctg gct gcc gtc atg gtc ggg gac aag acc ttc gag gag            2016
Thr Ala Asn Leu Ala Ala Val Met Val Gly Asp Lys Thr Phe Glu Glu
            660                 665                 670 ctg tcg ggg atc cac gac ccc aag ctg cac cac ccg gcg cag ggc ttc            2064
Leu Ser Gly Ile His Asp Pro Lys Leu His His Pro Ala Gln Gly Phe
            675                 680                 685 cgc ttc ggc acc gtg tgg gag agc agc gcc gag gcg tac atc aag aag            2112
Arg Phe Gly Thr Val Trp Glu Ser Ser Ala Glu Ala Tyr Ile Lys Lys
        690                 695                 700 agc ttc ccc gac atg cac gca cac atg cgg cgc cac agc gcg ccc acc            2160
Ser Phe Pro Asp Met His Ala His Met Arg Arg His Ser Ala Pro Thr
705                 710                 715                 720 acg ccc cgc ggc gtc gcc atg ctc acg agc gac ccc ccc aag ctc aac            2208
Thr Pro Arg Gly Val Ala Met Leu Thr Ser Asp Pro Pro Lys Leu Asn
            725                 730                 735 gcc ttc atc atg gac aag tcg ctc ctg gac tac gag gtc tcc atc gac            2256
Ala Phe Ile Met Asp Lys Ser Leu Leu Asp Tyr Glu Val Ser Ile Asp
            740                 745                 750 gcc gac tgc aaa ctg ctg acc gtg gga aag ccc ttc gcc att gag ggc            2304
Ala Asp Cys Lys Leu Leu Thr Val Gly Lys Pro Phe Ala Ile Glu Gly
            755                 760                 765 tat ggg atc gga ctg ccc cag aac tcg ccg ctc acc tcc aac ctg tcc            2352
Tyr Gly Ile Gly Leu Pro Gln Asn Ser Pro Leu Thr Ser Asn Leu Ser
        770                 775                 780 gag ttc atc agc cgc tac aag tcc tcc ggc ttc atc gac ctg ctc cac            2400
Glu Phe Ile Ser Arg Tyr Lys Ser Ser Gly Phe Ile Asp Leu Leu His
785                 790                 795                 800 gac aag tgg tac aag atg gtg cct tgc ggc aag cgg gtc ttt gcg gtt            2448
Asp Lys Trp Tyr Lys Met Val Pro Cys Gly Lys Arg Val Phe Ala Val
            805                 810                 815 aca gag acc ctg cag atg agc atc tac cac ttc gcg ggc ctc ttc gtg            2496
Thr Glu Thr Leu Gln Met Ser Ile Tyr His Phe Ala Gly Leu Phe Val
            820                 825                 830 ttg ctg tgc ctg ggc ctg ggc agc gct ctg ctc agc tcg ctg ggc gag            2544
Leu Leu Cys Leu Gly Leu Gly Ser Ala Leu Leu Ser Ser Leu Gly Glu
            835                 840                 845 cac gcc ttc ttc cgc ctg gcg ctg ccg cgc atc cgc aag ggg agc agg            2592
His Ala Phe Phe Arg Leu Ala Leu Pro Arg Ile Arg Lys Gly Ser Arg
        850                 855                 860 ctg cag tac tgg ctg cac acc agc cag aaa atc cac cgc gcc ctc aac            2640
Leu Gln Tyr Trp Leu His Thr Ser Gln Lys Ile His Arg Ala Leu Asn
865                 870                 875                 880 acg gag cca cca gag ggg tcg aag gag gag acg gca gag gcg gag ccc            2688
Thr Glu Pro Pro Glu Gly Ser Lys Glu Glu Thr Ala Glu Ala Glu Pro
            885                 890                 895 agg                                                                         2691
Arg
```

<210> SEQ ID NO 10
<211> LENGTH: 897
<212> TYPE: PRT
<213> ORGANISM: Homo sapiens

<400> SEQUENCE: 10

```
Met Glu Phe Val Arg Ala Leu Trp Leu Gly Leu Ala Leu Ala Leu Gly
1               5                   10                  15

Pro Gly Ser Ala Gly Gly His Pro Gln Pro Cys Gly Val Leu Ala Arg
            20                  25                  30

Leu Gly Gly Ser Val Arg Leu Gly Ala Leu Leu Pro Arg Ala Pro Leu
        35                  40                  45

Ala Arg Ala Arg Ala Arg Ala Ala Leu Ala Arg Ala Ala Leu Ala Pro
    50                  55                  60

Arg Leu Pro His Asn Leu Ser Leu Glu Leu Val Val Ala Ala Pro Pro
65                  70                  75                  80

Ala Arg Asp Pro Ala Ser Leu Thr Arg Gly Leu Cys Gln Ala Leu Val
                85                  90                  95

Pro Pro Gly Val Ala Ala Leu Leu Ala Phe Pro Glu Ala Arg Pro Glu
            100                 105                 110

Leu Leu Gln Leu His Phe Leu Ala Ala Ala Thr Glu Thr Pro Val Leu
        115                 120                 125

Ser Leu Leu Arg Arg Glu Ala Arg Ala Pro Leu Gly Ala Pro Asn Pro
    130                 135                 140

Phe His Leu Gln Leu His Trp Ala Ser Pro Leu Glu Thr Leu Leu Asp
145                 150                 155                 160

Val Leu Val Ala Val Leu Gln Ala His Ala Trp Glu Asp Val Gly Leu
                165                 170                 175

Ala Leu Cys Arg Thr Gln Asp Pro Gly Leu Val Ala Leu Trp Thr
            180                 185                 190

Ser Arg Ala Gly Arg Pro Pro Gln Leu Val Leu Asp Leu Ser Arg Arg
        195                 200                 205

Asp Thr Gly Asp Ala Gly Leu Arg Ala Arg Leu Ala Pro Met Ala Ala
    210                 215                 220

Pro Val Gly Gly Glu Ala Pro Val Pro Ala Ala Val Leu Leu Gly Cys
225                 230                 235                 240

Asp Ile Ala Arg Ala Arg Arg Val Leu Glu Ala Val Pro Pro Gly Pro
                245                 250                 255

His Trp Leu Leu Gly Thr Pro Leu Pro Pro Lys Ala Leu Pro Thr Ala
            260                 265                 270

Gly Leu Pro Pro Gly Leu Leu Ala Leu Gly Glu Val Ala Arg Pro Pro
        275                 280                 285

Leu Glu Ala Ala Ile His Asp Ile Val Gln Leu Val Ala Arg Ala Leu
    290                 295                 300

Gly Ser Ala Ala Gln Val Gln Pro Lys Arg Ala Leu Leu Pro Ala Pro
305                 310                 315                 320

Val Asn Cys Gly Asp Leu Gln Pro Ala Gly Pro Glu Ser Pro Gly Arg
                325                 330                 335

Phe Leu Ala Asn Thr Ser Phe Gln Gly Arg Thr Gly Pro Val Trp Val
            340                 345                 350

Thr Gly Ser Ser Gln Val His Met Ser Arg His Phe Lys Val Trp Ser
        355                 360                 365

Leu Arg Arg Asp Pro Arg Gly Ala Pro Ala Trp Ala Thr Val Gly Ser
    370                 375                 380
```

-continued

```
Trp Arg Asp Gly Gln Leu Asp Leu Glu Pro Gly Gly Ala Ser Ala Arg
385                 390                 395                 400

Pro Pro Pro Pro Gln Gly Ala Gln Val Trp Pro Lys Leu Arg Val Val
                405                 410                 415

Thr Leu Leu Glu His Pro Phe Val Phe Ala Arg Asp Pro Asp Glu Asp
            420                 425                 430

Gly Gln Cys Pro Ala Gly Gln Leu Cys Leu Asp Pro Gly Thr Asn Asp
        435                 440                 445

Ser Ala Thr Leu Asp Ala Leu Phe Ala Ala Leu Ala Asn Gly Ser Ala
    450                 455                 460

Pro Arg Ala Leu Arg Lys Cys Cys Tyr Gly Tyr Cys Ile Asp Leu Leu
465                 470                 475                 480

Glu Arg Leu Ala Glu Asp Thr Pro Phe Asp Phe Glu Leu Tyr Leu Val
                485                 490                 495

Gly Asp Gly Lys Tyr Gly Ala Leu Arg Asp Gly Arg Trp Thr Gly Leu
                500                 505                 510

Val Gly Asp Leu Leu Ala Gly Arg Ala His Met Ala Val Thr Ser Phe
            515                 520                 525

Ser Ile Asn Ser Ala Arg Ser Gln Val Val Asp Phe Thr Ser Pro Phe
        530                 535                 540

Phe Ser Thr Ser Leu Gly Ile Met Val Arg Ala Arg Asp Thr Ala Ser
545                 550                 555                 560

Pro Ile Gly Ala Phe Met Trp Pro Leu His Trp Ser Thr Trp Leu Gly
                565                 570                 575

Val Phe Ala Ala Leu His Leu Thr Ala Leu Phe Leu Thr Val Tyr Glu
            580                 585                 590

Trp Arg Ser Pro Tyr Gly Leu Thr Pro Arg Gly Arg Asn Arg Ser Thr
        595                 600                 605

Val Phe Ser Tyr Ser Ser Ala Leu Asn Leu Cys Tyr Ala Ile Leu Phe
    610                 615                 620

Arg Arg Thr Val Ser Ser Lys Thr Pro Lys Cys Pro Thr Gly Arg Leu
625                 630                 635                 640

Leu Met Asn Leu Trp Ala Ile Phe Cys Leu Leu Val Leu Ser Ser Tyr
                645                 650                 655

Thr Ala Asn Leu Ala Ala Val Met Val Gly Asp Lys Thr Phe Glu Glu
            660                 665                 670

Leu Ser Gly Ile His Asp Pro Lys Leu His His Pro Ala Gln Gly Phe
        675                 680                 685

Arg Phe Gly Thr Val Trp Glu Ser Ser Ala Glu Ala Tyr Ile Lys Lys
    690                 695                 700

Ser Phe Pro Asp Met His Ala His Met Arg Arg His Ser Ala Pro Thr
705                 710                 715                 720

Thr Pro Arg Gly Val Ala Met Leu Thr Ser Asp Pro Pro Lys Leu Asn
                725                 730                 735

Ala Phe Ile Met Asp Lys Ser Leu Leu Asp Tyr Glu Val Ser Ile Asp
            740                 745                 750

Ala Asp Cys Lys Leu Leu Thr Val Gly Lys Pro Phe Ala Ile Glu Gly
        755                 760                 765

Tyr Gly Ile Gly Leu Pro Gln Asn Ser Pro Leu Thr Ser Asn Leu Ser
    770                 775                 780

Glu Phe Ile Ser Arg Tyr Lys Ser Ser Gly Phe Ile Asp Leu Leu His
785                 790                 795                 800

Asp Lys Trp Tyr Lys Met Val Pro Cys Gly Lys Arg Val Phe Ala Val
```

```
                     805                 810                 815
Thr Glu Thr Leu Gln Met Ser Ile Tyr His Phe Ala Gly Leu Phe Val
            820                 825                 830

Leu Leu Cys Leu Gly Leu Gly Ser Ala Leu Leu Ser Ser Leu Gly Glu
            835                 840                 845

His Ala Phe Phe Arg Leu Ala Leu Pro Arg Ile Arg Lys Gly Ser Arg
            850                 855                 860

Leu Gln Tyr Trp Leu His Thr Ser Gln Lys Ile His Arg Ala Leu Asn
865                 870                 875                 880

Thr Glu Pro Pro Glu Gly Ser Lys Glu Glu Thr Ala Glu Ala Glu Pro
                885                 890                 895

Arg

<210> SEQ ID NO 11
<211> LENGTH: 1786
<212> TYPE: DNA
<213> ORGANISM: Mus musculus
<220> FEATURE:
<221> NAME/KEY: CDS
<222> LOCATION: (2)...(1444)

<400> SEQUENCE: 11 c atc aac tgc tta gag cat gtt cga gat cga tgg ccg cgg gag ggt gtc     49
  Ile Asn Cys Leu Glu His Val Arg Asp Arg Trp Pro Arg Glu Gly Val
  1               5                  10                  15 ctg cgg gtg gag gtg cgc cac aac tcg agc cgg gca ccg gtg atc ctg       97
Leu Arg Val Glu Val Arg His Asn Ser Ser Arg Ala Pro Val Ile Leu
             20                  25                  30 cag ttc tgt gat ggg ggc ctc ggt ggc ctg gag ctg gaa ccc ggg ggc      145
Gln Phe Cys Asp Gly Gly Leu Gly Gly Leu Glu Leu Glu Pro Gly Gly
         35                  40                  45 ctg gag ctg gag gag gag gag ctc aca gtg gag atg ttc acc aac agc     193
Leu Glu Leu Glu Glu Glu Glu Leu Thr Val Glu Met Phe Thr Asn Ser
     50                  55                  60 tcc atc aag ttt gag ctg gac att gag ccc aag gtg ttc aag cca cag     241
Ser Ile Lys Phe Glu Leu Asp Ile Glu Pro Lys Val Phe Lys Pro Gln
 65                  70                  75                  80 agc ggt gca gat gcc ctg aac gac agc cag gac ttc cct ttt cct gag     289
Ser Gly Ala Asp Ala Leu Asn Asp Ser Gln Asp Phe Pro Phe Pro Glu
                 85                  90                  95 acg cca gca aaa gtg tgg cca cag gat gag tac att gtg gag tac tca     337
Thr Pro Ala Lys Val Trp Pro Gln Asp Glu Tyr Ile Val Glu Tyr Ser
            100                 105                 110 ctg gaa tat ggc ttc ctg cgg cta tcc caa gcc aca cgc cag cgt ctg     385
Leu Glu Tyr Gly Phe Leu Arg Leu Ser Gln Ala Thr Arg Gln Arg Leu
        115                 120                 125 agc att cct gtc atg gtg gtc acc cta gac ccc acg cgg gac cag tgc     433
Ser Ile Pro Val Met Val Val Thr Leu Asp Pro Thr Arg Asp Gln Cys
    130                 135                 140 ttt ggg gac cgc ttc agc cgc cta ttg ctg gat gag ttc ctg ggc tat     481
Phe Gly Asp Arg Phe Ser Arg Leu Leu Leu Asp Glu Phe Leu Gly Tyr
145                 150                 155                 160 gat gac atc ctc atg tcc agt gta aag ggt ctg gca gag aac gag gag     529
Asp Asp Ile Leu Met Ser Ser Val Lys Gly Leu Ala Glu Asn Glu Glu
                165                 170                 175 aac aaa ggc ttc ttg agg aat gtg gtc tct ggg gag cac tac cgc ttt     577
Asn Lys Gly Phe Leu Arg Asn Val Val Ser Gly Glu His Tyr Arg Phe
            180                 185                 190 gtc agc atg tgg atg gcg cgc aca tcc tac ctg gcg gcc ttt gtc atc     625
```

-continued

```
                Val Ser Met Trp Met Ala Arg Thr Ser Tyr Leu Ala Ala Phe Val Ile
                    195                 200                 205 atg gtc atc ttt acc ctc agc gtg tcc atg ctg ttg cga tac tcg cac      673
Met Val Ile Phe Thr Leu Ser Val Ser Met Leu Leu Arg Tyr Ser His
    210                 215                 220 cac cag atc ttc gtc ttc atc gtg gac ctg ctg cag atg ctg gag atg      721
His Gln Ile Phe Val Phe Ile Val Asp Leu Leu Gln Met Leu Glu Met
225                 230                 235                 240 aac atg gcc atc gcc ttc ccc gca gcg ccc ttg ctg acc gtc atc ctg      769
Asn Met Ala Ile Ala Phe Pro Ala Ala Pro Leu Leu Thr Val Ile Leu
                245                 250                 255 gct ctc gtc ggg atg gaa gcc atc atg tct gag ttc ttc aat gat acc      817
Ala Leu Val Gly Met Glu Ala Ile Met Ser Glu Phe Phe Asn Asp Thr
            260                 265                 270 acc acg gcc ttc tac atc atc ctc act gtg tgg ctg gcc gac cag tat      865
Thr Thr Ala Phe Tyr Ile Ile Leu Thr Val Trp Leu Ala Asp Gln Tyr
        275                 280                 285 gat gcc atc tgc tgc cac acc aac acc agc aag cgg cac tgg ctg agg      913
Asp Ala Ile Cys Cys His Thr Asn Thr Ser Lys Arg His Trp Leu Arg
    290                 295                 300 ttc ttc tac ctc tac cac ttc gcc ttc tat gcc tac cac tac cgc ttt      961
Phe Phe Tyr Leu Tyr His Phe Ala Phe Tyr Ala Tyr His Tyr Arg Phe
305                 310                 315                 320 aac ggg cag tac agc agc ctg gcc ctg gtc acc tcc tgg ctc ttc atc     1009
Asn Gly Gln Tyr Ser Ser Leu Ala Leu Val Thr Ser Trp Leu Phe Ile
                325                 330                 335 cag cat tcc atg atc tac ttc ttc cac cac tat gag ttg ccc gcc atc     1057
Gln His Ser Met Ile Tyr Phe Phe His His Tyr Glu Leu Pro Ala Ile
            340                 345                 350 ctg cag cag atc cga atc cag gag atg ctg ctt cag acg cca ccg ctg     1105
Leu Gln Gln Ile Arg Ile Gln Glu Met Leu Leu Gln Thr Pro Pro Leu
        355                 360                 365 ggc ccc ggg acc ccc acg gcg ctg cct gac gac ctc aac aac aac tct     1153
Gly Pro Gly Thr Pro Thr Ala Leu Pro Asp Asp Leu Asn Asn Asn Ser
    370                 375                 380 ggc tcc cct gcc act ccg gat ccc agc cct ccc ctc gcg ctg ggc ccc     1201
Gly Ser Pro Ala Thr Pro Asp Pro Ser Pro Pro Leu Ala Leu Gly Pro
385                 390                 395                 400 agc tcc agc ccc gcg ccc act ggc ggg gca tct ggg cct ggc tca ctg     1249
Ser Ser Ser Pro Ala Pro Thr Gly Gly Ala Ser Gly Pro Gly Ser Leu
                405                 410                 415 ggc gct ggg gcc tca gta tcc ggc agt gac cta ggt tgg gtg gcc gag     1297
Gly Ala Gly Ala Ser Val Ser Gly Ser Asp Leu Gly Trp Val Ala Glu
            420                 425                 430 acc gcc gcc atc atc tct gac gca tcc ttc ctg tcg ggg ctg agc gcc     1345
Thr Ala Ala Ile Ile Ser Asp Ala Ser Phe Leu Ser Gly Leu Ser Ala
        435                 440                 445 tct ctc ctg gag cgg cgg cca aca gcc cct agt acc ccg gac agc tca     1393
Ser Leu Leu Glu Arg Arg Pro Thr Ala Pro Ser Thr Pro Asp Ser Ser
    450                 455                 460 cga cct gac cct ggg gtc cct ctg gag gac gca ccc gcc cct gcc ggg     1441
Arg Pro Asp Pro Gly Val Pro Leu Glu Asp Ala Pro Ala Pro Ala Gly
465                 470                 475                 480 tcc tgagaccggt gtcgtgcccg gctcccagtg agccgcggc ccgagcccaa           1494
Ser gagagctgtg gtctgcaggg agaggggctg gtggcgaagg ttctggaagc ggccgggaca   1554
gggcggcgat gggcacgagg ccatcggccg cctggtgctc cccagtgcct tccacacggc   1614
gcccgcacgg ggccgagcgc ccgggcccgg actagcaggt ggtggctcac gatgcgggc    1674
```

```
acacgttcca cgctatttaa ttgcagtgta cagagtcgtg tttgtatata gaataaactg   1734
tcgtggacag tgaaaaaaaa aaaaaaaaaa aaaaaaaaaa aa                      1786
```

<210> SEQ ID NO 12
<211> LENGTH: 481
<212> TYPE: PRT
<213> ORGANISM: Mus musculus

<400> SEQUENCE: 12

```
Ile Asn Cys Leu Glu His Val Arg Asp Arg Trp Pro Arg Glu Gly Val
 1               5                  10                  15

Leu Arg Val Glu Val Arg His Asn Ser Ser Arg Ala Pro Val Ile Leu
            20                  25                  30

Gln Phe Cys Asp Gly Gly Leu Gly Gly Leu Glu Leu Pro Gly Gly
        35                  40                  45

Leu Glu Leu Glu Glu Glu Leu Thr Val Glu Met Phe Thr Asn Ser
    50                  55                  60

Ser Ile Lys Phe Glu Leu Asp Ile Glu Pro Lys Val Phe Lys Pro Gln
65                  70                  75                  80

Ser Gly Ala Asp Ala Leu Asn Asp Ser Gln Asp Phe Pro Phe Pro Glu
                85                  90                  95

Thr Pro Ala Lys Val Trp Pro Gln Asp Glu Tyr Ile Val Glu Tyr Ser
            100                 105                 110

Leu Glu Tyr Gly Phe Leu Arg Leu Ser Gln Ala Thr Arg Gln Arg Leu
        115                 120                 125

Ser Ile Pro Val Met Val Val Thr Leu Asp Pro Thr Arg Asp Gln Cys
130                 135                 140

Phe Gly Asp Arg Phe Ser Arg Leu Leu Leu Asp Glu Phe Leu Gly Tyr
145                 150                 155                 160

Asp Asp Ile Leu Met Ser Ser Val Lys Gly Leu Ala Glu Asn Glu Glu
                165                 170                 175

Asn Lys Gly Phe Leu Arg Asn Val Val Ser Gly Glu His Tyr Arg Phe
            180                 185                 190

Val Ser Met Trp Met Ala Arg Thr Ser Tyr Leu Ala Ala Phe Val Ile
        195                 200                 205

Met Val Ile Phe Thr Leu Ser Val Ser Met Leu Leu Arg Tyr Ser His
    210                 215                 220

His Gln Ile Phe Val Phe Ile Val Asp Leu Leu Gln Met Leu Glu Met
225                 230                 235                 240

Asn Met Ala Ile Ala Phe Pro Ala Ala Pro Leu Leu Thr Val Ile Leu
                245                 250                 255

Ala Leu Val Gly Met Glu Ala Ile Met Ser Glu Phe Phe Asn Asp Thr
            260                 265                 270

Thr Thr Ala Phe Tyr Ile Ile Leu Thr Val Trp Leu Ala Asp Gln Tyr
        275                 280                 285

Asp Ala Ile Cys Cys His Thr Asn Thr Ser Lys Arg His Trp Leu Arg
    290                 295                 300

Phe Phe Tyr Leu Tyr His Phe Ala Phe Tyr Ala Tyr His Tyr Arg Phe
305                 310                 315                 320

Asn Gly Gln Tyr Ser Ser Leu Ala Leu Val Thr Ser Trp Leu Phe Ile
                325                 330                 335

Gln His Ser Met Ile Tyr Phe Phe His His Tyr Glu Leu Pro Ala Ile
            340                 345                 350
```

-continued

```
Leu Gln Gln Ile Arg Ile Gln Glu Met Leu Leu Gln Thr Pro Pro Leu
        355                 360                 365

Gly Pro Gly Thr Pro Thr Ala Leu Pro Asp Asp Leu Asn Asn Asn Ser
370                 375                 380

Gly Ser Pro Ala Thr Pro Asp Pro Ser Pro Leu Ala Leu Gly Pro
385                 390                 395                 400

Ser Ser Ser Pro Ala Pro Thr Gly Gly Ala Ser Gly Pro Gly Ser Leu
                405                 410                 415

Gly Ala Gly Ala Ser Val Ser Gly Ser Asp Leu Gly Trp Val Ala Glu
                420                 425                 430

Thr Ala Ala Ile Ile Ser Asp Ala Ser Phe Leu Ser Gly Leu Ser Ala
            435                 440                 445

Ser Leu Leu Glu Arg Arg Pro Thr Ala Pro Ser Thr Pro Asp Ser Ser
    450                 455                 460

Arg Pro Asp Pro Gly Val Pro Leu Glu Asp Ala Pro Ala Pro Ala Gly
465                 470                 475                 480

Ser
```

<210> SEQ ID NO 13
<211> LENGTH: 579
<212> TYPE: DNA
<213> ORGANISM: Homo sapiens

<400> SEQUENCE: 13

```
ccacgcgtcc gatcttgtac cacttgtcgt ggagcaggtc gatgaagccg gaggacttgt      60
agcggctgat gaactcggac aggttggagg aggtccccag agaccccggc gccccgcctc     120
gcccaggtgc ctctcaccct caatggcgaa gggctttccc acggtcagca gtttgcagtc     180
ggcgtcgatg gagacctcgt agtccaggag cgacttgtcc atgatgaagg cgttgagctt     240
ggggggggtcg ctcctgctgg gccgggggc ggggtcagc catcgccccg cccaccccac     300
gccccgcccc cgcctcaccc cgcgcccggg ctcacgtgag catggcgacy ccgcggggcg     360
tggtgggcgc gctgtggcgc cgcatgtgtg cgtgcatgtc ggggaagctc ttcttgatgt     420
acgcctcggc gctgttctcc cacacggtgc cgaagcggaa gccctgcgcc gggtggtgca     480
gctgcgcggg ggaccccgtc agcgcctctg ctgcccctca ggaccctga ccattgaggg      540
gcgcgccgtt ctccggggtg gggccgtcct gggcacttg                             579
```

<210> SEQ ID NO 14
<211> LENGTH: 938
<212> TYPE: PRT
<213> ORGANISM: Rattus sp.

<400> SEQUENCE: 14

```
Met Ser Thr Met His Leu Leu Thr Phe Ala Leu Leu Phe Ser Cys Ser
1               5                   10                  15

Phe Ala Arg Ala Ala Cys Asp Pro Lys Ile Val Asn Ile Gly Ala Val
                20                  25                  30

Leu Ser Thr Arg Lys His Glu Gln Met Phe Arg Glu Ala Val Asn Gln
            35                  40                  45

Ala Asn Lys Arg His Gly Ser Trp Lys Ile Gln Leu Asn Ala Thr Ser
        50                  55                  60

Val Thr His Lys Pro Asn Ala Ile Gln Met Ala Leu Ser Val Cys Glu
65                  70                  75                  80

Asp Leu Ile Ser Ser Gln Val Tyr Ala Ile Leu Val Ser His Pro Pro
                85                  90                  95
```

```
Thr Pro Asn Asp His Phe Thr Pro Thr Pro Val Ser Tyr Thr Ala Gly
            100                 105                 110
Phe Tyr Arg Ile Pro Val Leu Gly Leu Thr Thr Arg Met Ser Ile Tyr
            115                 120                 125
Ser Asp Lys Ser Ile His Leu Ser Phe Leu Arg Thr Val Pro Pro Tyr
            130                 135                 140
Ser His Gln Ser Ser Val Trp Phe Glu Met Met Arg Val Tyr Asn Trp
145                 150                 155                 160
Asn His Ile Ile Leu Leu Val Ser Asp His Glu Gly Arg Ala Ala
            165                 170                 175
Gln Lys Arg Leu Glu Thr Leu Leu Glu Glu Arg Glu Ser Lys Ala Glu
            180                 185                 190
Lys Val Leu Gln Phe Asp Pro Gly Thr Lys Asn Val Thr Ala Leu Leu
            195                 200                 205
Met Glu Ala Arg Glu Leu Glu Ala Arg Val Ile Ile Leu Ser Ala Ser
    210                 215                 220
Glu Asp Asp Ala Ala Thr Val Tyr Arg Ala Ala Ala Met Leu Asn Met
225                 230                 235                 240
Thr Gly Ser Gly Tyr Val Trp Leu Val Gly Glu Arg Glu Ile Ser Gly
            245                 250                 255
Asn Ala Leu Arg Tyr Ala Pro Asp Gly Ile Ile Gly Leu Gln Leu Ile
            260                 265                 270
Asn Gly Lys Asn Glu Ser Ala His Ile Ser Asp Ala Val Gly Val Val
            275                 280                 285
Ala Gln Ala Val His Glu Leu Leu Glu Lys Glu Asn Ile Thr Asp Pro
            290                 295                 300
Pro Arg Gly Cys Val Gly Asn Thr Asn Ile Trp Lys Thr Gly Pro Leu
305                 310                 315                 320
Phe Lys Arg Val Leu Met Ser Ser Lys Tyr Ala Asp Gly Val Thr Gly
            325                 330                 335
Arg Val Glu Phe Asn Glu Asp Gly Asp Arg Lys Phe Ala Asn Tyr Ser
            340                 345                 350
Ile Met Asn Leu Gln Asn Arg Lys Leu Val Gln Val Gly Ile Tyr Asn
            355                 360                 365
Gly Thr His Val Ile Pro Asn Asp Arg Lys Ile Ile Trp Pro Gly Gly
            370                 375                 380
Glu Thr Glu Lys Pro Arg Gly Tyr Gln Met Ser Thr Arg Leu Lys Ile
385                 390                 395                 400
Val Thr Ile His Gln Glu Pro Phe Val Tyr Val Lys Pro Thr Met Ser
            405                 410                 415
Asp Gly Thr Cys Lys Glu Glu Phe Thr Val Asn Gly Asp Pro Val Lys
            420                 425                 430
Lys Val Ile Cys Thr Gly Pro Asn Asp Thr Ser Pro Gly Ser Pro Arg
            435                 440                 445
His Thr Val Pro Gln Cys Cys Tyr Gly Phe Cys Ile Asp Leu Leu Ile
            450                 455                 460
Lys Leu Ala Arg Thr Met Asn Phe Thr Tyr Glu Val His Leu Val Ala
465                 470                 475                 480
Asp Gly Lys Phe Gly Thr Gln Glu Arg Val Asn Asn Ser Asn Lys Lys
            485                 490                 495
Glu Trp Asn Gly Met Met Gly Glu Leu Leu Ser Gly Gln Ala Asp Met
            500                 505                 510
```

-continued

```
Ile Val Ala Pro Leu Thr Ile Asn Asn Glu Arg Ala Gln Tyr Ile Glu
            515                 520                 525

Phe Ser Lys Pro Phe Lys Tyr Gln Gly Leu Thr Ile Leu Val Lys Lys
            530                 535                 540

Glu Ile Pro Arg Ser Thr Leu Asp Ser Phe Met Gln Pro Phe Gln Ser
545                 550                 555                 560

Thr Leu Trp Leu Leu Val Gly Leu Ser Val His Val Ala Val Met
                565                 570                 575

Leu Tyr Leu Leu Asp Arg Phe Ser Pro Phe Gly Arg Phe Lys Val Asn
            580                 585                 590

Ser Glu Glu Glu Glu Asp Ala Leu Thr Leu Ser Ser Ala Met Trp
                595                 600                 605

Phe Ser Trp Gly Val Leu Leu Asn Ser Gly Ile Gly Glu Gly Ala Pro
            610                 615                 620

Arg Ser Phe Ser Ala Arg Ile Leu Gly Met Val Trp Ala Gly Phe Ala
625                 630                 635                 640

Met Ile Ile Val Ala Ser Tyr Thr Ala Asn Leu Ala Ala Phe Leu Val
                645                 650                 655

Leu Asp Arg Pro Glu Glu Arg Ile Thr Gly Ile Asn Asp Pro Arg Leu
            660                 665                 670

Arg Asn Pro Ser Asp Lys Phe Ile Tyr Ala Thr Val Lys Gln Ser Ser
            675                 680                 685

Val Asp Ile Tyr Phe Arg Arg Gln Val Glu Leu Ser Thr Met Tyr Arg
            690                 695                 700

His Met Glu Lys His Asn Tyr Glu Ser Ala Ala Glu Ala Ile Gln Ala
705                 710                 715                 720

Val Arg Asp Asn Lys Leu His Ala Phe Ile Trp Asp Ser Ala Val Leu
                725                 730                 735

Glu Phe Glu Ala Ser Gln Lys Cys Asp Leu Val Thr Thr Gly Glu Leu
            740                 745                 750

Phe Phe Arg Ser Gly Phe Gly Ile Gly Met Arg Lys Asp Ser Pro Trp
            755                 760                 765

Lys Gln Asn Val Ser Leu Ser Ile Leu Lys Ser His Glu Asn Gly Phe
            770                 775                 780

Met Glu Asp Leu Asp Lys Thr Trp Val Arg Tyr Gln Glu Cys Asp Ser
785                 790                 795                 800

Arg Ser Asn Ala Pro Ala Thr Leu Thr Phe Glu Asn Met Ala Gly Val
                805                 810                 815

Phe Met Leu Val Ala Gly Gly Ile Val Ala Gly Ile Phe Leu Ile Phe
            820                 825                 830

Ile Glu Ile Ala Tyr Lys Arg His Lys Asp Ala Arg Arg Lys Gln Met
            835                 840                 845

Gln Leu Ala Phe Ala Ala Val Asn Val Trp Arg Lys Asn Leu Gln Asp
850                 855                 860

Arg Lys Ser Gly Arg Ala Glu Pro Asp Pro Lys Lys Lys Ala Thr Phe
865                 870                 875                 880

Arg Ala Ile Thr Ser Thr Leu Ala Ser Ser Phe Lys Arg Arg Arg Ser
                885                 890                 895

Ser Lys Asp Thr Ser Thr Gly Gly Gly Arg Gly Ala Leu Gln Asn Gln
            900                 905                 910

Lys Asp Thr Val Leu Pro Arg Arg Ala Ile Glu Arg Glu Glu Gly Gln
            915                 920                 925

Leu Gln Leu Cys Ser Arg His Arg Glu Ser
```

```
                   930                 935

<210> SEQ ID NO 15
<211> LENGTH: 1464
<212> TYPE: PRT
<213> ORGANISM: Rattus sp.

<400> SEQUENCE: 15

Met Gly Arg Leu Gly Tyr Trp Thr Leu Leu Val Leu Pro Ala Leu Leu
1               5                   10                  15

Val Trp Arg Asp Pro Ala Gln Asn Ala Ala Glu Lys Gly Pro Pro
            20                  25                  30

Ala Leu Asn Ile Ala Val Leu Leu Gly His Ser His Asp Val Thr Glu
            35                  40                  45

Arg Glu Leu Arg Asn Leu Trp Gly Pro Glu Gln Ala Thr Gly Leu Pro
        50                  55                  60

Leu Asp Val Asn Val Val Ala Leu Leu Met Asn Arg Thr Asp Pro Lys
65                  70                  75                  80

Ser Leu Ile Thr His Val Cys Asp Leu Met Ser Gly Ala Arg Ile His
                85                  90                  95

Gly Leu Val Phe Gly Asp Asp Thr Asp Gln Glu Ala Val Ala Gln Met
                100                 105                 110

Leu Asp Phe Ile Ser Ser Gln Thr Phe Ile Pro Ile Leu Gly Ile His
            115                 120                 125

Gly Gly Ala Ser Met Ile Met Ala Asp Lys Asp Pro Thr Ser Thr Phe
130                 135                 140

Phe Gln Phe Gly Ala Ser Ile Gln Gln Gln Ala Thr Val Met Leu Lys
145                 150                 155                 160

Ile Met Gln Asp Tyr Asp Trp His Val Phe Ser Leu Val Thr Thr Ile
                165                 170                 175

Phe Pro Gly Tyr Arg Asp Phe Ile Ser Phe Ile Lys Thr Thr Val Asp
                180                 185                 190

Asn Ser Phe Val Gly Trp Asp Met Gln Asn Val Ile Thr Leu Asp Thr
            195                 200                 205

Ser Phe Glu Asp Ala Lys Thr Gln Val Gln Leu Lys Lys Ile His Ser
    210                 215                 220

Ser Val Ile Leu Leu Tyr Cys Ser Lys Asp Glu Ala Val Leu Ile Leu
225                 230                 235                 240

Ser Glu Ala Arg Ser Leu Gly Leu Thr Gly Tyr Asp Phe Phe Trp Ile
                245                 250                 255

Val Pro Ser Leu Val Ser Gly Asn Thr Glu Leu Ile Pro Lys Glu Phe
            260                 265                 270

Pro Ser Gly Leu Ile Ser Val Ser Tyr Asp Asp Trp Asp Tyr Ser Leu
        275                 280                 285

Glu Ala Arg Val Arg Asp Gly Leu Gly Ile Leu Thr Thr Ala Ala Ser
    290                 295                 300

Ser Met Leu Glu Lys Phe Ser Tyr Ile Pro Glu Ala Lys Ala Ser Cys
305                 310                 315                 320

Tyr Gly Gln Ala Glu Lys Pro Glu Thr Pro Leu His Thr Leu His Gln
                325                 330                 335

Phe Met Val Asn Val Thr Trp Asp Gly Lys Asp Leu Ser Phe Thr Glu
            340                 345                 350

Glu Gly Tyr Gln Val His Pro Arg Leu Val Val Ile Val Leu Asn Lys
        355                 360                 365
```

-continued

```
Asp Arg Glu Trp Glu Lys Val Gly Lys Trp Glu Asn Gln Thr Leu Ser
370                 375                 380
Leu Arg His Ala Val Trp Pro Arg Tyr Lys Ser Phe Ser Asp Cys Glu
385                 390                 395                 400
Pro Asp Asp Asn His Leu Ser Ile Val Thr Leu Glu Glu Ala Pro Phe
                405                 410                 415
Val Ile Val Glu Asp Ile Asp Pro Leu Thr Glu Thr Cys Val Arg Asn
                420                 425                 430
Thr Val Pro Cys Arg Lys Phe Val Lys Ile Asn Asn Ser Thr Asn Glu
            435                 440                 445
Gly Met Asn Val Lys Lys Cys Cys Lys Gly Phe Cys Ile Asp Ile Leu
        450                 455                 460
Lys Lys Leu Ser Arg Thr Val Lys Phe Thr Tyr Asp Leu Tyr Leu Val
465                 470                 475                 480
Thr Asn Gly Lys His Gly Lys Lys Val Asn Asn Val Trp Asn Gly Met
                485                 490                 495
Ile Gly Glu Val Val Tyr Gln Arg Ala Val Met Ala Val Gly Ser Leu
                500                 505                 510
Thr Ile Asn Glu Glu Arg Ser Glu Val Val Asp Phe Ser Val Pro Phe
            515                 520                 525
Val Glu Thr Gly Ile Ser Val Met Val Ser Arg Ser Asn Gly Thr Val
        530                 535                 540
Ser Pro Ser Ala Phe Leu Glu Pro Phe Ser Ala Ser Val Trp Val Met
545                 550                 555                 560
Met Phe Val Met Leu Leu Ile Val Ser Ala Ile Ala Val Phe Val Phe
                565                 570                 575
Glu Tyr Phe Ser Pro Val Gly Tyr Asn Arg Asn Leu Ala Lys Gly Lys
                580                 585                 590
Ala Pro His Gly Pro Ser Phe Thr Ile Gly Lys Ala Ile Trp Leu Leu
            595                 600                 605
Trp Gly Leu Val Phe Asn Asn Ser Val Pro Val Gln Asn Pro Lys Gly
        610                 615                 620
Thr Thr Ser Lys Ile Met Val Ser Val Trp Ala Phe Phe Ala Val Ile
625                 630                 635                 640
Phe Leu Ala Ser Tyr Thr Ala Asn Leu Ala Ala Phe Met Ile Gln Glu
                645                 650                 655
Glu Phe Val Asp Gln Val Thr Gly Leu Ser Asp Lys Lys Phe Gln Arg
                660                 665                 670
Pro His Asp Tyr Ser Pro Pro Phe Arg Phe Gly Thr Val Pro Asn Gly
            675                 680                 685
Ser Thr Glu Arg Asn Ile Arg Asn Asn Tyr Pro Tyr Met His Gln Tyr
        690                 695                 700
Met Thr Arg Phe Asn Gln Arg Gly Val Glu Asp Ala Leu Val Ser Leu
705                 710                 715                 720
Lys Thr Gly Lys Leu Asp Ala Phe Ile Tyr Asp Ala Ala Val Leu Asn
                725                 730                 735
Tyr Lys Ala Gly Arg Asp Glu Gly Cys Lys Leu Val Thr Ile Gly Ser
                740                 745                 750
Gly Tyr Ile Phe Ala Thr Thr Gly Tyr Gly Ile Ala Leu Gln Lys Gly
            755                 760                 765
Ser Pro Trp Lys Arg Gln Ile Asp Leu Ala Leu Leu Gln Phe Val Gly
        770                 775                 780
Asp Gly Glu Met Glu Glu Leu Glu Thr Leu Trp Leu Thr Gly Ile Cys
```

-continued

```
               785                 790                 795                 800

His Asn Glu Lys Asn Glu Val Met Ser Ser Gln Leu Asp Ile Asp Asn
                805                 810                 815

Met Ala Gly Val Phe Tyr Met Leu Ala Ala Met Ala Leu Ser Leu
            820                 825                 830

Ile Thr Phe Ile Trp Glu His Leu Phe Tyr Trp Lys Leu Arg Phe Cys
            835                 840                 845

Phe Thr Gly Val Cys Ser Asp Arg Pro Gly Leu Leu Phe Ser Ile Ser
        850                 855                 860

Arg Gly Ile Tyr Ser Cys Ile His Gly Val His Ile Glu Glu Lys Lys
865                 870                 875                 880

Lys Ser Pro Asp Phe Asn Leu Thr Gly Ser Gln Ser Asn Met Leu Lys
                885                 890                 895

Leu Leu Arg Ser Ala Lys Asn Ile Ser Asn Met Ser Asn Met Asn Ser
            900                 905                 910

Ser Arg Met Asp Ser Pro Lys Arg Ala Thr Asp Phe Ile Gln Arg Gly
            915                 920                 925

Ser Leu Ile Val Asp Met Val Ser Asp Lys Gly Asn Leu Ile Tyr Ser
        930                 935                 940

Asp Asn Arg Ser Phe Gln Gly Lys Asp Ser Ile Phe Gly Asp Asn Met
945                 950                 955                 960

Asn Glu Leu Gln Thr Phe Val Ala Asn Arg His Lys Asp Asn Leu Ser
                965                 970                 975

Asn Tyr Val Phe Gln Gly Gln His Pro Leu Thr Leu Asn Asp Ser Asn
            980                 985                 990

Pro Asn Thr Val Glu Val Ala Val Ser Thr Glu Ser Lys Gly Asn Ser
            995                 1000                1005

Arg Pro Arg Gln Leu Trp Lys Lys Ser Met Glu Ser Leu Arg Gln Asp
        1010                1015                1020

Ser Leu Asn Gln Asn Pro Val Ser Gln Arg Asp Glu Lys Thr Ala Glu
1025                1030                1035                1040

Asn Arg Thr His Ser Leu Lys Ser Pro Arg Tyr Leu Pro Glu Glu Val
                1045                1050                1055

Ala His Ser Asp Ile Ser Glu Thr Ser Ser Arg Ala Thr Cys His Arg
            1060                1065                1070

Glu Pro Asp Asn Asn Lys Asn His Lys Thr Lys Asp Asn Phe Lys Arg
            1075                1080                1085

Ser Met Ala Ser Lys Tyr Pro Lys Asp Cys Ser Asp Val Asp Arg Thr
        1090                1095                1100

Tyr Met Lys Thr Lys Ala Ser Ser Pro Arg Asp Lys Ile Tyr Thr Ile
1105                1110                1115                1120

Asp Gly Glu Lys Glu Pro Ser Phe His Leu Asp Pro Gln Phe Val
                1125                1130                1135

Glu Asn Ile Thr Leu Pro Glu Asn Val Gly Phe Pro Asp Thr Tyr Gln
            1140                1145                1150

Asp His Asn Glu Asn Phe Arg Lys Gly Asp Ser Thr Leu Pro Met Asn
            1155                1160                1165

Arg Asn Pro Leu His Asn Glu Asp Gly Leu Pro Asn Asn Asp Gln Tyr
        1170                1175                1180

Lys Leu Tyr Ala Lys His Phe Thr Leu Lys Asp Lys Gly Ser Pro His
1185                1190                1195                1200

Ser Glu Gly Ser Asp Arg Tyr Arg Gln Asn Ser Thr His Cys Arg Ser
                1205                1210                1215
```

```
Cys Leu Ser Asn Leu Pro Thr Tyr Ser Gly His Phe Thr Met Arg Ser
            1220                1225                1230

Pro Phe Lys Cys Asp Ala Cys Leu Arg Met Gly Asn Leu Tyr Asp Ile
        1235                1240                1245

Asp Glu Asp Gln Met Leu Gln Glu Thr Gly Asn Pro Ala Thr Arg Glu
    1250                1255                1260

Glu Val Tyr Gln Gln Asp Trp Ser Gln Asn Asn Ala Leu Gln Phe Gln
1265                1270                1275                1280

Lys Asn Lys Leu Arg Ile Asn Arg Gln His Ser Tyr Asp Asn Ile Leu
            1285                1290                1295

Asp Lys Pro Arg Glu Ile Asp Leu Ser Arg Pro Ser Arg Ser Ile Ser
        1300                1305                1310

Leu Lys Asp Arg Glu Arg Leu Leu Glu Gly Asn Leu Tyr Gly Ser Leu
    1315                1320                1325

Phe Ser Val Pro Ser Ser Lys Leu Leu Gly Asn Lys Ser Ser Leu Phe
1330                1335                1340

Pro Gln Gly Leu Glu Asp Ser Lys Arg Ser Lys Ser Leu Leu Pro Asp
1345                1350                1355                1360

His Ala Ser Asp Asn Pro Phe Leu His Thr Tyr Gly Asp Asp Gln Arg
            1365                1370                1375

Leu Val Ile Gly Arg Cys Pro Ser Asp Pro Tyr Lys His Ser Leu Pro
        1380                1385                1390

Ser Gln Ala Val Asn Asp Ser Tyr Leu Arg Ser Ser Leu Arg Ser Thr
    1395                1400                1405

Ala Ser Tyr Cys Ser Arg Asp Ser Arg Gly His Ser Asp Val Tyr Ile
    1410                1415                1420

Ser Glu His Val Met Pro Tyr Ala Ala Asn Lys Asn Thr Met Tyr Ser
1425                1430                1435                1440

Thr Pro Arg Val Leu Asn Ser Cys Ser Asn Arg Arg Val Tyr Lys Lys
            1445                1450                1455

Met Pro Ser Ile Glu Ser Asp Val
            1460

<210> SEQ ID NO 16
<211> LENGTH: 1115
<212> TYPE: PRT
<213> ORGANISM: Rattus sp.

<400> SEQUENCE: 16

Met Arg Arg Leu Ser Leu Trp Trp Leu Leu Ser Arg Val Cys Leu Leu
1               5                   10                  15

Leu Pro Pro Cys Ala Leu Val Leu Ala Gly Val Pro Ser Ser Ser
            20                  25                  30

Ser His Pro Gln Pro Cys Gln Ile Leu Lys Arg Ile Gly His Ala Val
        35                  40                  45

Arg Val Gly Ala Val His Leu Gln Pro Trp Thr Thr Ala Pro Arg Ala
    50                  55                  60

Ala Ser Arg Ala Gln Glu Gly Gly Arg Ala Ala Gln Arg Asp Asp
65                  70                  75                  80

Pro Glu Ser Gly Thr Trp Arg Pro Pro Ala Pro Ser Gln Gly Ala Arg
                85                  90                  95

Trp Leu Gly Ser Ala Leu His Gly Arg Gly Pro Pro Gly Ser Arg Lys
            100                 105                 110

Leu Gly Glu Gly Ala Gly Ala Glu Thr Leu Trp Pro Arg Asp Ala Leu
```

-continued

```
            115                 120                 125
Leu Phe Ala Val Glu Asn Leu Asn Arg Val Glu Gly Leu Leu Pro Tyr
    130                 135                 140
Asn Leu Ser Leu Glu Val Val Met Ala Ile Glu Ala Gly Leu Gly Asp
145                 150                 155                 160
Leu Pro Leu Met Pro Phe Ser Ser Pro Ser Pro Trp Ser Ser Asp
                165                 170                 175
Pro Phe Ser Phe Leu Gln Ser Val Cys His Thr Val Val Gln Gly
                180                 185                 190
Val Ser Ala Leu Leu Ala Phe Pro Gln Ser Gln Gly Glu Met Met Glu
        195                 200                 205
Leu Asp Leu Val Ser Ser Val Leu His Ile Pro Val Leu Ser Ile Val
    210                 215                 220
Arg His Glu Phe Pro Arg Glu Ser Gln Asn Pro Leu His Leu Gln Leu
225                 230                 235                 240
Ser Leu Glu Asn Ser Leu Ser Ser Asp Ala Asp Val Thr Val Ser Ile
                245                 250                 255
Leu Thr Met Asn Asn Trp Tyr Asn Phe Ser Leu Leu Leu Cys Gln Glu
                260                 265                 270
Asp Trp Asn Ile Thr Asp Phe Leu Leu Leu Thr Glu Asn Asn Ser Lys
                275                 280                 285
Phe His Leu Glu Ser Val Ile Asn Ile Thr Ala Asn Leu Ser Ser Thr
        290                 295                 300
Lys Asp Leu Leu Ser Phe Leu Gln Val Gln Met Asp Asn Ile Arg Asn
305                 310                 315                 320
Ser Thr Pro Thr Met Val Met Phe Gly Cys Asp Met Asp Ser Ile Arg
                325                 330                 335
Gln Ile Phe Glu Met Ser Thr Gln Phe Gly Leu Ser Pro Pro Glu Leu
                340                 345                 350
His Trp Val Leu Gly Asp Ser Gln Asn Val Glu Glu Leu Arg Thr Glu
        355                 360                 365
Gly Leu Pro Leu Gly Leu Ile Ala His Gly Lys Thr Thr Gln Ser Val
    370                 375                 380
Phe Glu Tyr Tyr Val Gln Asp Ala Met Glu Leu Val Ala Arg Ala Val
385                 390                 395                 400
Ala Thr Ala Thr Met Ile Gln Pro Glu Leu Ala Leu Leu Pro Ser Thr
                405                 410                 415
Met Asn Cys Met Asp Val Lys Thr Thr Asn Leu Thr Ser Gly Gln Tyr
                420                 425                 430
Leu Ser Arg Phe Leu Ala Asn Thr Thr Phe Arg Gly Leu Ser Gly Ser
        435                 440                 445
Ile Lys Val Lys Gly Ser Thr Ile Ile Ser Ser Glu Asn Asn Phe Phe
    450                 455                 460
Ile Trp Asn Leu Gln His Asp Pro Met Gly Lys Pro Met Trp Thr Arg
465                 470                 475                 480
Leu Gly Ser Trp Gln Gly Gly Arg Ile Val Met Asp Ser Gly Ile Trp
                485                 490                 495
Pro Glu Gln Ala Gln Arg His Lys Thr His Phe Gln His Pro Asn Lys
                500                 505                 510
Leu His Leu Arg Val Val Thr Leu Ile Glu His Pro Phe Val Phe Thr
        515                 520                 525
Arg Glu Val Asp Asp Glu Gly Leu Cys Pro Ala Gly Gln Leu Cys Leu
    530                 535                 540
```

```
Asp Pro Met Thr Asn Asp Ser Ser Met Leu Asp Arg Leu Phe Ser Ser
545                 550                 555                 560

Leu His Ser Ser Asn Asp Thr Val Pro Ile Lys Phe Lys Cys Cys
                565                 570                 575

Tyr Gly Tyr Cys Ile Asp Leu Leu Glu Gln Leu Ala Glu Asp Met Asn
                580                 585                 590

Phe Asp Phe Asp Leu Tyr Ile Val Gly Asp Gly Lys Tyr Gly Ala Trp
            595                 600                 605

Lys Asn Gly His Trp Thr Gly Leu Val Gly Asp Leu Leu Ser Gly Thr
        610                 615                 620

Ala Asn Met Ala Val Thr Ser Phe Ser Ile Asn Thr Ala Arg Ser Gln
625                 630                 635                 640

Val Ile Asp Phe Thr Ser Pro Phe Phe Ser Thr Ser Leu Gly Ile Leu
                645                 650                 655

Val Arg Thr Arg Asp Thr Ala Ala Pro Ile Gly Ala Phe Met Trp Pro
                660                 665                 670

Leu His Trp Thr Met Trp Leu Gly Ile Phe Val Ala Leu His Ile Thr
        675                 680                 685

Ala Ile Phe Leu Thr Leu Tyr Glu Trp Lys Ser Pro Phe Gly Met Thr
690                 695                 700

Pro Lys Gly Arg Asn Arg Asn Lys Val Phe Ser Phe Ser Ser Ala Leu
705                 710                 715                 720

Asn Val Cys Tyr Ala Leu Leu Phe Gly Arg Thr Ala Ala Ile Lys Pro
                725                 730                 735

Pro Lys Cys Trp Thr Gly Arg Phe Leu Met Asn Leu Trp Ala Ile Phe
                740                 745                 750

Cys Met Phe Cys Leu Ser Thr Tyr Thr Ala Asn Leu Ala Ala Val Met
            755                 760                 765

Val Gly Glu Lys Ile Tyr Glu Glu Leu Ser Gly Ile His Asp Pro Lys
        770                 775                 780

Leu His His Pro Ser Gln Gly Phe Arg Phe Gly Thr Val Arg Glu Ser
785                 790                 795                 800

Ser Ala Glu Asp Tyr Val Arg Gln Ser Phe Pro Glu Met His Glu Tyr
                805                 810                 815

Met Arg Arg Tyr Asn Val Pro Ala Thr Pro Asp Gly Val Gln Tyr Leu
                820                 825                 830

Lys Asn Asp Pro Glu Lys Leu Asp Ala Phe Ile Met Asp Lys Ala Leu
            835                 840                 845

Leu Asp Tyr Glu Val Ser Ile Asp Ala Asp Cys Lys Leu Leu Thr Val
850                 855                 860

Gly Lys Pro Phe Ala Ile Glu Gly Tyr Gly Ile Gly Leu Pro Pro Asn
865                 870                 875                 880

Ser Pro Leu Thr Ser Asn Ile Ser Glu Leu Ile Ser Gln Tyr Lys Ser
                885                 890                 895

His Gly Phe Met Asp Val Leu His Asp Lys Trp Tyr Lys Val Val Pro
                900                 905                 910

Cys Gly Lys Arg Ser Phe Ala Val Thr Glu Thr Leu Gln Met Gly Ile
            915                 920                 925

Lys His Phe Ser Gly Leu Phe Val Leu Leu Cys Ile Gly Phe Gly Leu
        930                 935                 940

Ser Ile Leu Thr Thr Ile Gly Glu His Ile Val His Arg Leu Leu Leu
945                 950                 955                 960
```

```
Pro Arg Ile Lys Asn Lys Ser Lys Leu Gln Tyr Trp Leu His Thr Ser
            965                 970                 975

Gln Arg Phe His Arg Ala Leu Asn Thr Ser Phe Val Glu Glu Lys Gln
            980                 985                 990

Pro Arg Ser Lys Thr Lys Arg Val Glu Lys Arg Ser Asn Leu Gly Pro
            995                1000                1005

Gln Gln Leu Met Val Trp Asn Thr Ser Asn Leu Ser His Asp Asn Gln
        1010                1015                1020

Arg Lys Tyr Ile Phe Asn Asp Glu Glu Gly Gln Asn Gln Leu Gly Thr
1025                1030                1035                1040

Gln Ala His Gln Asp Ile Pro Leu Pro Gln Arg Arg Glu Leu Pro
                1045                1050                1055

Ala Ser Leu Thr Thr Asn Gly Lys Ala Asp Ser Leu Asn Val Thr Arg
            1060                1065                1070

Ser Ser Val Ile Gln Glu Leu Ser Glu Leu Lys Gln Ile Gln Val
        1075                1080                1085

Ile Arg Gln Glu Leu Gln Leu Ala Val Ser Arg Lys Thr Glu Leu Glu
        1090                1095                1100

Glu Tyr Gln Lys Thr Asn Arg Thr Cys Glu Ser
1105                1110                1115

<210> SEQ ID NO 17
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 17
tgctgctatg gctactgcat c                                         21

<210> SEQ ID NO 18
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 18
atgacagcag ccaggttggc cgt                                       23

<210> SEQ ID NO 19
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 19
cacacatggc tgtgaccagc                                           20

<210> SEQ ID NO 20
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 20
agaatggcat agcacaggtt g                                         21
```

```
<210> SEQ ID NO 21
<211> LENGTH: 6
<212> TYPE: PRT
<213> ORGANISM: Rattus sp.

<400> SEQUENCE: 21

Ala Asp Gly Lys Phe Gly
 1               5

<210> SEQ ID NO 22
<211> LENGTH: 6
<212> TYPE: PRT
<213> ORGANISM: Rattus sp.

<400> SEQUENCE: 22

Thr Asn Gly Lys His Gly
 1               5

<210> SEQ ID NO 23
<211> LENGTH: 6
<212> TYPE: PRT
<213> ORGANISM: Rattus sp.

<400> SEQUENCE: 23

Thr Asn Gly Lys His Gly
 1               5

<210> SEQ ID NO 24
<211> LENGTH: 6
<212> TYPE: PRT
<213> ORGANISM: Rattus sp.

<400> SEQUENCE: 24

Thr Asn Gly Lys His Gly
 1               5

<210> SEQ ID NO 25
<211> LENGTH: 6
<212> TYPE: PRT
<213> ORGANISM: Rattus sp.

<400> SEQUENCE: 25

Thr Asn Gly Lys His Gly
 1               5

<210> SEQ ID NO 26
<211> LENGTH: 6
<212> TYPE: PRT
<213> ORGANISM: Rattus sp.

<400> SEQUENCE: 26

Gly Asp Gly Lys Tyr Gly
 1               5

<210> SEQ ID NO 27
<211> LENGTH: 6
<212> TYPE: PRT
<213> ORGANISM: Rattus sp.

<400> SEQUENCE: 27

Gly Asp Gly Lys Tyr Gly
 1               5

<210> SEQ ID NO 28
<211> LENGTH: 6
```

```
<212> TYPE: PRT
<213> ORGANISM: Rattus sp.

<400> SEQUENCE: 28

Gly Asp Gly Lys Tyr Gly
 1               5

<210> SEQ ID NO 29
<211> LENGTH: 11
<212> TYPE: PRT
<213> ORGANISM: Rattus sp.

<400> SEQUENCE: 29

Ala Pro Leu Thr Ile Asn Asn Glu Arg Ala Gln
 1               5                  10

<210> SEQ ID NO 30
<211> LENGTH: 11
<212> TYPE: PRT
<213> ORGANISM: Rattus sp.

<400> SEQUENCE: 30

Gly Ser Leu Thr Ile Asn Glu Glu Arg Ser Glu
 1               5                  10

<210> SEQ ID NO 31
<211> LENGTH: 11
<212> TYPE: PRT
<213> ORGANISM: Rattus sp.

<400> SEQUENCE: 31

Gly Ser Leu Thr Ile Asn Glu Glu Arg Ser Glu
 1               5                  10

<210> SEQ ID NO 32
<211> LENGTH: 11
<212> TYPE: PRT
<213> ORGANISM: Rattus sp.

<400> SEQUENCE: 32

Gly Ser Leu Thr Ile Asn Glu Glu Arg Ser Glu
 1               5                  10

<210> SEQ ID NO 33
<211> LENGTH: 11
<212> TYPE: PRT
<213> ORGANISM: Rattus sp.

<400> SEQUENCE: 33

Gly Ser Leu Thr Ile Asn Glu Glu Arg Ser Glu
 1               5                  10

<210> SEQ ID NO 34
<211> LENGTH: 11
<212> TYPE: PRT
<213> ORGANISM: Rattus sp.

<400> SEQUENCE: 34

Thr Ser Phe Ser Ile Asn Thr Ala Arg Ser Gln
 1               5                  10

<210> SEQ ID NO 35
<211> LENGTH: 11
<212> TYPE: PRT
<213> ORGANISM: Rattus sp.
```

```
<400> SEQUENCE: 35

Thr Ser Phe Ser Ile Asn Ser Ala Arg Ser Gln
 1               5                  10

<210> SEQ ID NO 36
<211> LENGTH: 11
<212> TYPE: PRT
<213> ORGANISM: Rattus sp.

<400> SEQUENCE: 36

Ala Pro Leu Thr Ile Thr Leu Val Arg Glu Glu
 1               5                  10

<210> SEQ ID NO 37
<211> LENGTH: 9
<212> TYPE: PRT
<213> ORGANISM: Rattus sp.

<400> SEQUENCE: 37

Ala Thr Val Lys Gln Ser Ser Val Asp
 1               5

<210> SEQ ID NO 38
<211> LENGTH: 9
<212> TYPE: PRT
<213> ORGANISM: Rattus sp.

<400> SEQUENCE: 38

Gly Thr Val Pro Asn Gly Ser Thr Glu
 1               5

<210> SEQ ID NO 39
<211> LENGTH: 9
<212> TYPE: PRT
<213> ORGANISM: Rattus sp.

<400> SEQUENCE: 39

Gly Thr Val Pro Asn Gly Ser Thr Glu
 1               5

<210> SEQ ID NO 40
<211> LENGTH: 9
<212> TYPE: PRT
<213> ORGANISM: Rattus sp.

<400> SEQUENCE: 40

Gly Thr Val Pro Asn Gly Ser Thr Glu
 1               5

<210> SEQ ID NO 41
<211> LENGTH: 9
<212> TYPE: PRT
<213> ORGANISM: Rattus sp.

<400> SEQUENCE: 41

Gly Thr Val Pro Asn Gly Ser Thr Glu
 1               5

<210> SEQ ID NO 42
<211> LENGTH: 9
<212> TYPE: PRT
<213> ORGANISM: Rattus sp.

<400> SEQUENCE: 42
```

```
Gly Thr Val Arg Glu Ser Ser Ala Glu
1               5
```

<210> SEQ ID NO 43
<211> LENGTH: 9
<212> TYPE: PRT
<213> ORGANISM: Rattus sp.

<400> SEQUENCE: 43

```
Gly Thr Val Trp Glu Ser Ser Ala Glu
1               5
```

<210> SEQ ID NO 44
<211> LENGTH: 9
<212> TYPE: PRT
<213> ORGANISM: Rattus sp.

<400> SEQUENCE: 44

```
Gly Thr Leu Asp Ser Gly Ser Thr Lys
1               5
```

<210> SEQ ID NO 45
<211> LENGTH: 25
<212> TYPE: PRT
<213> ORGANISM: Rattus sp.

<400> SEQUENCE: 45

```
Asp Ala Leu Thr Leu Ser Ser Ala Met Trp Phe Ser Trp Gly Val Leu
1               5                   10                  15

Leu Asn Ser Gly Ile Gly Glu Gly Ala
            20                  25
```

<210> SEQ ID NO 46
<211> LENGTH: 25
<212> TYPE: PRT
<213> ORGANISM: Rattus sp.

<400> SEQUENCE: 46

```
Pro Ser Phe Thr Ile Gly Lys Ala Ile Trp Leu Leu Trp Gly Leu Val
1               5                   10                  15

Phe Asn Asn Ser Val Pro Val Gln Asn
            20                  25
```

<210> SEQ ID NO 47
<211> LENGTH: 25
<212> TYPE: PRT
<213> ORGANISM: Rattus sp.

<400> SEQUENCE: 47

```
Pro Ser Phe Thr Ile Gly Lys Ala Ile Trp Leu Leu Trp Gly Leu Val
1               5                   10                  15

Phe Asn Asn Ser Val Pro Val Gln Asn
            20                  25
```

<210> SEQ ID NO 48
<211> LENGTH: 25
<212> TYPE: PRT
<213> ORGANISM: Rattus sp.

<400> SEQUENCE: 48

```
Pro Ser Phe Thr Ile Gly Lys Ser Val Trp Leu Leu Trp Ala Leu Val
1               5                   10                  15
```

```
Phe Asn Asn Ser Val Pro Ile Glu Asn
            20                  25

<210> SEQ ID NO 49
<211> LENGTH: 25
<212> TYPE: PRT
<213> ORGANISM: Rattus sp.

<400> SEQUENCE: 49

Ser Thr Phe Thr Ile Gly Lys Ser Ile Trp Leu Leu Trp Ala Leu Val
1               5                   10                  15

Phe Asn Asn Ser Val Pro Val Glu Asn
            20                  25

<210> SEQ ID NO 50
<211> LENGTH: 25
<212> TYPE: PRT
<213> ORGANISM: Rattus sp.

<400> SEQUENCE: 50

Lys Val Phe Ser Phe Ser Ser Ala Leu Asn Val Cys Tyr Ala Leu Leu
1               5                   10                  15

Phe Gly Arg Thr Ala Ala Ile Lys Pro
            20                  25

<210> SEQ ID NO 51
<211> LENGTH: 25
<212> TYPE: PRT
<213> ORGANISM: Rattus sp.

<400> SEQUENCE: 51

Thr Val Phe Ser Tyr Ser Ser Ala Leu Asn Leu Cys Tyr Ala Ile Leu
1               5                   10                  15

Phe Gly Arg Thr Val Ser Ser Lys Thr
            20                  25

<210> SEQ ID NO 52
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 52
ctagcggcgc gccttaatta agtttaaacg                                    30

<210> SEQ ID NO 53
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 53
ctagcgttta aacttaatta aggcgcgccg                                    30

<210> SEQ ID NO 54

<400> SEQUENCE: 54

000

<210> SEQ ID NO 55
<211> LENGTH: 3571
```

```
<212> TYPE: DNA
<213> ORGANISM: Homo sapiens
<220> FEATURE:
<221> NAME/KEY: CDS
<222> LOCATION: (224)...(3568)

<400> SEQUENCE: 55
```

| | | |
|---|---|---|
| cagaggatgc caggcggagg gacctgggag cgggatctga gactgccgga ggcgcgctac | 60 |
| gctccaactt gcatggccta gagaccgctc cagctcctgg gaccgcttca ccagtggag | 120 |
| tgaagctgcg cgcgggacct ggaggcggag acctcaggca gcggctgcag aggggcgagc | 180 |
| cgggcgcagg agggggcgcg ctttctccct gcgggtctca gta atg agg aga ctg | 235 |
|                                                                                           Met Arg Arg Leu |
|                                                                                             1 |
| agt ttg tgg tgg ctg ctg agc agg gtc tgt ctg ctg ttg ccg ccg ccc | 283 |
| Ser Leu Trp Trp Leu Leu Ser Arg Val Cys Leu Leu Leu Pro Pro Pro |
|  5                           10                   15                   20 |
| tgc gca ctg gtg ctg gcc ggg gtg ccc agc tcc tcc tcg cac ccg cag | 331 |
| Cys Ala Leu Val Leu Ala Gly Val Pro Ser Ser Ser Ser His Pro Gln |
|                   25                         30                         35 |
| ccc tgc cag atc ctc aag cgc atc ggg cac gcg gtg agg gtg ggc gcg | 379 |
| Pro Cys Gln Ile Leu Lys Arg Ile Gly His Ala Val Arg Val Gly Ala |
|                   40                         45                         50 |
| gtg cac ttg cag ccc tgg acc acc gcc ccc cgc gcg gcc agc cgc gct | 427 |
| Val His Leu Gln Pro Trp Thr Thr Ala Pro Arg Ala Ala Ser Arg Ala |
|               55                         60                       65 |
| ccg gac gac agc cga gca gga gcc cag agg gat gag ccg gag cca ggg | 475 |
| Pro Asp Asp Ser Arg Ala Gly Ala Gln Arg Asp Glu Pro Glu Pro Gly |
|         70                         75                         80 |
| act agg cgg tcc ccg gcg ccc tcg ccg ggc gca cgc tgg ttg ggg agc | 523 |
| Thr Arg Arg Ser Pro Ala Pro Ser Pro Gly Ala Arg Trp Leu Gly Ser |
| 85                       90                   95                    100 |
| acc ctg cat ggc cgg ggg ccg ccg ggc tcc cgt aag ccc ggg gag ggc | 571 |
| Thr Leu His Gly Arg Gly Pro Pro Gly Ser Arg Lys Pro Gly Glu Gly |
|                  105                         110                      115 |
| gcc agg gcg gag gcc ctg tgg cca cgg gac gcc ctc cta ttt gcc gtg | 619 |
| Ala Arg Ala Glu Ala Leu Trp Pro Arg Asp Ala Leu Leu Phe Ala Val |
|               120                         125                      130 |
| gac aac ctg aac cgc gtg gaa ggg cta cta ccc tac aac ctg tct ttg | 667 |
| Asp Asn Leu Asn Arg Val Glu Gly Leu Leu Pro Tyr Asn Leu Ser Leu |
|         135                         140                      145 |
| gaa gta gtg atg gcc atc gag gca ggc ctg ggc gat ctg cca ctt ttg | 715 |
| Glu Val Val Met Ala Ile Glu Ala Gly Leu Gly Asp Leu Pro Leu Leu |
| 150                       155                         160 |
| ccc ttc tcc tcc cct agt tcg cca tgg agc agt gac cct ttc tcc ttc | 763 |
| Pro Phe Ser Ser Pro Ser Ser Pro Trp Ser Ser Asp Pro Phe Ser Phe |
| 165                       170                   175                  180 |
| ctg caa agt gtg tgc cat acc gtg gtg gtg caa ggg gtg tcg gcg ctg | 811 |
| Leu Gln Ser Val Cys His Thr Val Val Val Gln Gly Val Ser Ala Leu |
|               185                         190                      195 |
| ctc gcc ttc ccc cag agc cag ggc gaa atg atg gag ctc gac ttg gtc | 859 |
| Leu Ala Phe Pro Gln Ser Gln Gly Glu Met Met Glu Leu Asp Leu Val |
|               200                         205                      210 |
| agc tta gtc ctg cac att cca gtg atc agc atc gtg cgc cac gag ttt | 907 |
| Ser Leu Val Leu His Ile Pro Val Ile Ser Ile Val Arg His Glu Phe |
|         215                         220                      225 |
| cca cgg gag agt cag aat ccc ctt cac cta caa ctg agt tta gaa aat | 955 |
| Pro Arg Glu Ser Gln Asn Pro Leu His Leu Gln Leu Ser Leu Glu Asn |
| 230                       235                         240 |
| tca tta agt tct gat gct gat gtc act gtc tca atc ctg acc atg aac | 1003 |

```
Ser Leu Ser Ser Asp Ala Asp Val Thr Val Ser Ile Leu Thr Met Asn
245                 250                 255                 260 aac tgg tac aat ttt agc ttg ttg ctg tgc cag gaa gac tgg aac atc   1051
Asn Trp Tyr Asn Phe Ser Leu Leu Leu Cys Gln Glu Asp Trp Asn Ile
                265                 270                 275 acc gac ttc ctc ctc ctt acc cag aat aat tcc aag ttc cac ctt ggt   1099
Thr Asp Phe Leu Leu Leu Thr Gln Asn Asn Ser Lys Phe His Leu Gly
            280                 285                 290 tct atc atc aac atc acc gct aac ctc ccc tcc acc cag gac ctc ttg   1147
Ser Ile Ile Asn Ile Thr Ala Asn Leu Pro Ser Thr Gln Asp Leu Leu
        295                 300                 305 agc ttc cta cag atc cag ctt gag agt att aag aac agc aca ccc aca   1195
Ser Phe Leu Gln Ile Gln Leu Glu Ser Ile Lys Asn Ser Thr Pro Thr
    310                 315                 320 gtg gtg atg ttt ggc tgc gac atg gaa agt atc cgg cgg att ttc gaa   1243
Val Val Met Phe Gly Cys Asp Met Glu Ser Ile Arg Arg Ile Phe Glu
325                 330                 335                 340 att aca acc cag ttt ggg gtc atg ccc cct gaa ctt cgt tgg gtg ctg   1291
Ile Thr Thr Gln Phe Gly Val Met Pro Pro Glu Leu Arg Trp Val Leu
                345                 350                 355 gga gat tcc cag aat gtg gag gaa ctg agg aca gag ggt ctg ccc tta   1339
Gly Asp Ser Gln Asn Val Glu Glu Leu Arg Thr Glu Gly Leu Pro Leu
            360                 365                 370 ggg ctc att gct cat gga aaa aca aca cag tct gtc ttt gag cac tac   1387
Gly Leu Ile Ala His Gly Lys Thr Thr Gln Ser Val Phe Glu His Tyr
        375                 380                 385 gta caa gat gct atg gag ctg gtc gca aga gct gta gcc aca gcc acc   1435
Val Gln Asp Ala Met Glu Leu Val Ala Arg Ala Val Ala Thr Ala Thr
    390                 395                 400 atg atc caa cca gaa ctt gct ctc att ccc agc acg atg aac tgc atg   1483
Met Ile Gln Pro Glu Leu Ala Leu Ile Pro Ser Thr Met Asn Cys Met
405                 410                 415                 420 gag gtg gaa act aca aat ctc act tca gga caa tat tta tca agg ttt   1531
Glu Val Glu Thr Thr Asn Leu Thr Ser Gly Gln Tyr Leu Ser Arg Phe
                425                 430                 435 cta gcc aat acc act ttc aga ggc ctc agt ggt tcc atc aga gta aaa   1579
Leu Ala Asn Thr Thr Phe Arg Gly Leu Ser Gly Ser Ile Arg Val Lys
            440                 445                 450 ggt tcc acc atc gtc agc tca gaa aac aac ttt ttc atc tgg aat ctt   1627
Gly Ser Thr Ile Val Ser Ser Glu Asn Asn Phe Phe Ile Trp Asn Leu
        455                 460                 465 caa cat gac ccc atg gga aag cca atg tgg acc cgc ttg ggc agc tgg   1675
Gln His Asp Pro Met Gly Lys Pro Met Trp Thr Arg Leu Gly Ser Trp
    470                 475                 480 cag ggg gga aag att gtc atg gac tat gga ata tgg cca gag cag gcc   1723
Gln Gly Gly Lys Ile Val Met Asp Tyr Gly Ile Trp Pro Glu Gln Ala
485                 490                 495                 500 cag aga cac aaa acc cac ttc caa cat cca agt aag cta cac ttg aga   1771
Gln Arg His Lys Thr His Phe Gln His Pro Ser Lys Leu His Leu Arg
                505                 510                 515 gtg gtt acc ctg att gag cat cct ttt gtc ttc aca agg gag gta gat   1819
Val Val Thr Leu Ile Glu His Pro Phe Val Phe Thr Arg Glu Val Asp
            520                 525                 530 gat gaa ggc ttg tgc cct gct ggc caa ctc tgt cta gac ccc atg act   1867
Asp Glu Gly Leu Cys Pro Ala Gly Gln Leu Cys Leu Asp Pro Met Thr
        535                 540                 545 aat gac tct tcc aca ttg gac agc ctt ttt agc agc ctc cat agc agt   1915
Asn Asp Ser Ser Thr Leu Asp Ser Leu Phe Ser Ser Leu His Ser Ser
    550                 555                 560
```

```
aat gat aca gtg ccc att aaa ttc aag aag tgc tgc tat gga tat tgc     1963
Asn Asp Thr Val Pro Ile Lys Phe Lys Lys Cys Cys Tyr Gly Tyr Cys
565                 570                 575                 580 att gat ctg ctg gaa aag ata gca gaa gac atg aac ttt gac ttc gac     2011
Ile Asp Leu Leu Glu Lys Ile Ala Glu Asp Met Asn Phe Asp Phe Asp
                585                 590                 595 ctc tat att gta ggg gat gga aag tat gga gca tgg aaa aat ggg cac     2059
Leu Tyr Ile Val Gly Asp Gly Lys Tyr Gly Ala Trp Lys Asn Gly His
                    600                 605                 610 tgg act ggg cta gtg ggt gat ctc ctg aga ggg act gcc cac atg gca     2107
Trp Thr Gly Leu Val Gly Asp Leu Leu Arg Gly Thr Ala His Met Ala
                615                 620                 625 gtc act tcc ttt agc atc aat act gca cgg agc cag gtg ata gat ttc     2155
Val Thr Ser Phe Ser Ile Asn Thr Ala Arg Ser Gln Val Ile Asp Phe
630                 635                 640 acc agc cct ttc ttc tcc acc agc ttg ggc atc tta gtg agg acc cga     2203
Thr Ser Pro Phe Phe Ser Thr Ser Leu Gly Ile Leu Val Arg Thr Arg
645                 650                 655                 660 gat aca gca gct ccc att gga gcc ttc atg tgg cca ctc cac tgg aca     2251
Asp Thr Ala Ala Pro Ile Gly Ala Phe Met Trp Pro Leu His Trp Thr
                    665                 670                 675 atg tgg ctg ggg att ttt gtg gct ctg cac atc act gcc gtc ttc ctc     2299
Met Trp Leu Gly Ile Phe Val Ala Leu His Ile Thr Ala Val Phe Leu
                680                 685                 690 act ctg tat gaa tgg aag agt cca ttt ggt ttg act ccc aag ggg cga     2347
Thr Leu Tyr Glu Trp Lys Ser Pro Phe Gly Leu Thr Pro Lys Gly Arg
                695                 700                 705 aat aga agt aaa gtc ttc tcc ttt tct tca gcc ttg aac atc tgt tat     2395
Asn Arg Ser Lys Val Phe Ser Phe Ser Ser Ala Leu Asn Ile Cys Tyr
710                 715                 720 gcc ctc ttg ttt ggc aga aca gtg gcc atc aaa cct cca aaa tgt tgg     2443
Ala Leu Leu Phe Gly Arg Thr Val Ala Ile Lys Pro Pro Lys Cys Trp
725                 730                 735                 740 act gga agg ttt cta atg aac ctt tgg gcc att ttc tgt atg ttt tgc     2491
Thr Gly Arg Phe Leu Met Asn Leu Trp Ala Ile Phe Cys Met Phe Cys
                    745                 750                 755 ctt tcc aca tac acg gca aac ttg gct gct gtc atg gta ggt gag aag     2539
Leu Ser Thr Tyr Thr Ala Asn Leu Ala Ala Val Met Val Gly Glu Lys
                760                 765                 770 atc tat gaa gag ctt tct gga ata cat gac ccc aag tta cat cat cct     2587
Ile Tyr Glu Glu Leu Ser Gly Ile His Asp Pro Lys Leu His His Pro
                775                 780                 785 tcc caa gga ttc cgc ttt gga act gtc cga gaa agc agt gct gaa gat     2635
Ser Gln Gly Phe Arg Phe Gly Thr Val Arg Glu Ser Ser Ala Glu Asp
        790                 795                 800 tat gtg aga caa agt ttc cca gag atg cat gaa tat atg aga agg tac     2683
Tyr Val Arg Gln Ser Phe Pro Glu Met His Glu Tyr Met Arg Arg Tyr
805                 810                 815                 820 aat gtt cca gcc acc cct gat gga gtg gag tat ctg aag aat gat cca     2731
Asn Val Pro Ala Thr Pro Asp Gly Val Glu Tyr Leu Lys Asn Asp Pro
                825                 830                 835 gag aaa cta gac gcc ttc atc atg gac aaa gcc ctt ctg gat tat gaa     2779
Glu Lys Leu Asp Ala Phe Ile Met Asp Lys Ala Leu Leu Asp Tyr Glu
            840                 845                 850 gtg tca ata gat gct gac tgc aaa ctt ctc act gtg ggg aag cca ttt     2827
Val Ser Ile Asp Ala Asp Cys Lys Leu Leu Thr Val Gly Lys Pro Phe
                855                 860                 865 gcc ata gaa gga tac ggc att ggc ctc cca ccc aac tct cca ttg acc     2875
Ala Ile Glu Gly Tyr Gly Ile Gly Leu Pro Pro Asn Ser Pro Leu Thr
            870                 875                 880
```

```
gcc aac ata tcc gag cta atc agt caa tac aag tca cat ggg ttt atg      2923
Ala Asn Ile Ser Glu Leu Ile Ser Gln Tyr Lys Ser His Gly Phe Met
885                 890                 895                 900 gat atg ctc cat gac aag tgg tac agg gtg gtt ccc tgt ggc aag aga      2971
Asp Met Leu His Asp Lys Trp Tyr Arg Val Val Pro Cys Gly Lys Arg
                905                 910                 915 agt ttt gct gtc acg gag act ttg caa atg ggc atc aaa cac ttc tct      3019
Ser Phe Ala Val Thr Glu Thr Leu Gln Met Gly Ile Lys His Phe Ser
            920                 925                 930 ggg ctc ttt gtg ctg ctg tgc att gga ttt ggt ctg tcc att ttg acc      3067
Gly Leu Phe Val Leu Leu Cys Ile Gly Phe Gly Leu Ser Ile Leu Thr
        935                 940                 945 acc att ggt gag cac ata gta tac agg ctg ctg cta cca cga atc aaa      3115
Thr Ile Gly Glu His Ile Val Tyr Arg Leu Leu Leu Pro Arg Ile Lys
    950                 955                 960 aac aaa tcc aag ctg caa tac tgg ctc cac acc agc cag aga tta cac      3163
Asn Lys Ser Lys Leu Gln Tyr Trp Leu His Thr Ser Gln Arg Leu His
965                 970                 975                 980 aga gca ata aat aca tca ttt ata gag gaa aag cag cag cat ttc aag      3211
Arg Ala Ile Asn Thr Ser Phe Ile Glu Glu Lys Gln Gln His Phe Lys
                985                 990                 995 acc aaa cgt gtg gaa aag agg tct aat gtg gga ccc gtt cag ctt acc      3259
Thr Lys Arg Val Glu Lys Arg Ser Asn Val Gly Pro Arg Gln Leu Thr
            1000                1005                1010 gta tgg aat act tcc aat ctg agt cat gac aac cga cgg aaa tac atc      3307
Val Trp Asn Thr Ser Asn Leu Ser His Asp Asn Arg Arg Lys Tyr Ile
        1015                1020                1025 ttt agt gat gag gaa gga caa aac cag ctg ggc atc cgg atc cac cag      3355
Phe Ser Asp Glu Glu Gly Gln Asn Gln Leu Gly Ile Arg Ile His Gln
    1030                1035                1040 gac atc ccc ctc cct cca agg aga aga gag ctc cct gcc ttg cgg acc      3403
Asp Ile Pro Leu Pro Pro Arg Arg Arg Glu Leu Pro Ala Leu Arg Thr
1045                1050                1055                1060 acc aat ggg aaa gca gac tcc cta aat gta tct cgg aac tca gtg atg      3451
Thr Asn Gly Lys Ala Asp Ser Leu Asn Val Ser Arg Asn Ser Val Met
                1065                1070                1075 cag gaa ctc tca gag ctc gag aag cag att cag gtg atc cgt cag gag      3499
Gln Glu Leu Ser Glu Leu Glu Lys Gln Ile Gln Val Ile Arg Gln Glu
            1080                1085                1090 ctg cag ctg gct gtg agc agg aaa acg gag ctg gag gag tat caa agg      3547
Leu Gln Leu Ala Val Ser Arg Lys Thr Glu Leu Glu Glu Tyr Gln Arg
        1095                1100                1105 aca agt cgg act tgt gag tcc tag                                      3571
Thr Ser Arg Thr Cys Glu Ser
    1110                1115

<210> SEQ ID NO 56
<211> LENGTH: 1115
<212> TYPE: PRT
<213> ORGANISM: Homo sapiens

<400> SEQUENCE: 56

Met Arg Arg Leu Ser Leu Trp Trp Leu Leu Ser Arg Val Cys Leu Leu
 1               5                  10                  15

Leu Pro Pro Pro Cys Ala Leu Val Leu Ala Gly Val Pro Ser Ser Ser
            20                  25                  30

Ser His Pro Gln Pro Cys Gln Ile Leu Lys Arg Ile Gly His Ala Val
        35                  40                  45

Arg Val Gly Ala Val His Leu Gln Pro Trp Thr Thr Ala Pro Arg Ala
```

```
                50                  55                  60
Ala Ser Arg Ala Pro Asp Asp Ser Arg Ala Gly Ala Gln Arg Asp Glu
 65                  70                  75                  80

Pro Glu Pro Gly Thr Arg Arg Ser Pro Ala Pro Ser Pro Gly Ala Arg
                 85                  90                  95

Trp Leu Gly Ser Thr Leu His Gly Arg Gly Pro Pro Gly Ser Arg Lys
                100                 105                 110

Pro Gly Glu Gly Ala Arg Ala Glu Ala Leu Trp Pro Arg Asp Ala Leu
            115                 120                 125

Leu Phe Ala Val Asp Asn Leu Asn Arg Val Glu Gly Leu Leu Pro Tyr
        130                 135                 140

Asn Leu Ser Leu Glu Val Val Met Ala Ile Glu Ala Gly Leu Gly Asp
145                 150                 155                 160

Leu Pro Leu Leu Pro Phe Ser Ser Pro Ser Ser Pro Trp Ser Ser Asp
                165                 170                 175

Pro Phe Ser Phe Leu Gln Ser Val Cys His Thr Val Val Val Gln Gly
                180                 185                 190

Val Ser Ala Leu Leu Ala Phe Pro Gln Ser Gln Gly Glu Met Met Glu
            195                 200                 205

Leu Asp Leu Val Ser Leu Val Leu His Ile Pro Val Ile Ser Ile Val
        210                 215                 220

Arg His Glu Phe Pro Arg Glu Ser Gln Asn Pro Leu His Leu Gln Leu
225                 230                 235                 240

Ser Leu Glu Asn Ser Leu Ser Ser Asp Ala Asp Val Thr Val Ser Ile
                245                 250                 255

Leu Thr Met Asn Asn Trp Tyr Asn Phe Ser Leu Leu Leu Cys Gln Glu
                260                 265                 270

Asp Trp Asn Ile Thr Asp Phe Leu Leu Leu Thr Gln Asn Asn Ser Lys
            275                 280                 285

Phe His Leu Gly Ser Ile Ile Asn Ile Thr Ala Asn Leu Pro Ser Thr
        290                 295                 300

Gln Asp Leu Leu Ser Phe Leu Gln Ile Gln Leu Glu Ser Ile Lys Asn
305                 310                 315                 320

Ser Thr Pro Thr Val Val Met Phe Gly Cys Asp Met Glu Ser Ile Arg
                325                 330                 335

Arg Ile Phe Glu Ile Thr Thr Gln Phe Gly Val Met Pro Pro Glu Leu
                340                 345                 350

Arg Trp Val Leu Gly Asp Ser Gln Asn Val Glu Glu Leu Arg Thr Glu
            355                 360                 365

Gly Leu Pro Leu Gly Leu Ile Ala His Gly Lys Thr Thr Gln Ser Val
        370                 375                 380

Phe Glu His Tyr Val Gln Asp Ala Met Glu Leu Val Ala Arg Ala Val
385                 390                 395                 400

Ala Thr Ala Thr Met Ile Gln Pro Glu Leu Ala Leu Ile Pro Ser Thr
                405                 410                 415

Met Asn Cys Met Glu Val Glu Thr Thr Asn Leu Thr Ser Gly Gln Tyr
                420                 425                 430

Leu Ser Arg Phe Leu Ala Asn Thr Thr Phe Arg Gly Leu Ser Gly Ser
            435                 440                 445

Ile Arg Val Lys Gly Ser Thr Ile Val Ser Ser Glu Asn Asn Phe Phe
        450                 455                 460

Ile Trp Asn Leu Gln His Asp Pro Met Gly Lys Pro Met Trp Thr Arg
465                 470                 475                 480
```

-continued

```
Leu Gly Ser Trp Gln Gly Gly Lys Ile Val Met Asp Tyr Gly Ile Trp
            485                 490                 495
Pro Glu Gln Ala Gln Arg His Lys Thr His Phe Gln His Pro Ser Lys
        500                 505                 510
Leu His Leu Arg Val Val Thr Leu Ile Glu His Pro Phe Val Phe Thr
        515                 520                 525
Arg Glu Val Asp Glu Gly Leu Cys Pro Ala Gly Gln Leu Cys Leu
    530                 535                 540
Asp Pro Met Thr Asn Asp Ser Ser Thr Leu Asp Ser Leu Phe Ser Ser
545                 550                 555                 560
Leu His Ser Ser Asn Asp Thr Val Pro Ile Lys Phe Lys Cys Cys
            565                 570                 575
Tyr Gly Tyr Cys Ile Asp Leu Leu Glu Lys Ile Ala Glu Asp Met Asn
                580                 585                 590
Phe Asp Phe Asp Leu Tyr Ile Val Gly Asp Gly Lys Tyr Gly Ala Trp
            595                 600                 605
Lys Asn Gly His Trp Thr Gly Leu Val Gly Asp Leu Leu Arg Gly Thr
        610                 615                 620
Ala His Met Ala Val Thr Ser Phe Ser Ile Asn Thr Ala Arg Ser Gln
625                 630                 635                 640
Val Ile Asp Phe Thr Ser Pro Phe Phe Ser Thr Ser Leu Gly Ile Leu
                645                 650                 655
Val Arg Thr Arg Asp Thr Ala Ala Pro Ile Gly Ala Phe Met Trp Pro
            660                 665                 670
Leu His Trp Thr Met Trp Leu Gly Ile Phe Val Ala Leu His Ile Thr
        675                 680                 685
Ala Val Phe Leu Thr Leu Tyr Glu Trp Lys Ser Pro Phe Gly Leu Thr
    690                 695                 700
Pro Lys Gly Arg Asn Arg Ser Lys Val Phe Ser Phe Ser Ser Ala Leu
705                 710                 715                 720
Asn Ile Cys Tyr Ala Leu Leu Phe Gly Arg Thr Val Ala Ile Lys Pro
                725                 730                 735
Pro Lys Cys Trp Thr Gly Arg Phe Leu Met Asn Leu Trp Ala Ile Phe
            740                 745                 750
Cys Met Phe Cys Leu Ser Thr Tyr Thr Ala Asn Leu Ala Ala Val Met
        755                 760                 765
Val Gly Glu Lys Ile Tyr Glu Glu Leu Ser Gly Ile His Asp Pro Lys
    770                 775                 780
Leu His His Pro Ser Gln Gly Phe Arg Phe Gly Thr Val Arg Glu Ser
785                 790                 795                 800
Ser Ala Glu Asp Tyr Val Arg Gln Ser Phe Pro Glu Met His Glu Tyr
                805                 810                 815
Met Arg Arg Tyr Asn Val Pro Ala Thr Pro Asp Gly Val Glu Tyr Leu
            820                 825                 830
Lys Asn Asp Pro Glu Lys Leu Asp Ala Phe Ile Met Asp Lys Ala Leu
        835                 840                 845
Leu Asp Tyr Glu Val Ser Ile Asp Ala Asp Cys Lys Leu Leu Thr Val
    850                 855                 860
Gly Lys Pro Phe Ala Ile Glu Gly Tyr Gly Ile Gly Leu Pro Pro Asn
865                 870                 875                 880
Ser Pro Leu Thr Ala Asn Ile Ser Glu Leu Ile Ser Gln Tyr Lys Ser
                885                 890                 895
```

```
His Gly Phe Met Asp Met Leu His Asp Lys Trp Tyr Arg Val Val Pro
            900                 905                 910

Cys Gly Lys Arg Ser Phe Ala Val Thr Glu Thr Leu Gln Met Gly Ile
            915                 920                 925

Lys His Phe Ser Gly Leu Phe Val Leu Leu Cys Ile Gly Phe Gly Leu
        930                 935                 940

Ser Ile Leu Thr Thr Ile Gly Glu His Ile Val Tyr Arg Leu Leu Leu
945                 950                 955                 960

Pro Arg Ile Lys Asn Lys Ser Lys Leu Gln Tyr Trp Leu His Thr Ser
                965                 970                 975

Gln Arg Leu His Arg Ala Ile Asn Thr Ser Phe Ile Glu Glu Lys Gln
            980                 985                 990

Gln His Phe Lys Thr Lys Arg Val Glu Lys Arg Ser Asn Val Gly Pro
            995                 1000                1005

Arg Gln Leu Thr Val Trp Asn Thr Ser Asn Leu Ser His Asp Asn Arg
    1010                1015                1020

Arg Lys Tyr Ile Phe Ser Asp Glu Glu Gly Gln Asn Gln Leu Gly Ile
1025                1030                1035                1040

Arg Ile His Gln Asp Ile Pro Leu Pro Pro Arg Arg Glu Leu Pro
                1045                1050                1055

Ala Leu Arg Thr Thr Asn Gly Lys Ala Asp Ser Leu Asn Val Ser Arg
            1060                1065                1070

Asn Ser Val Met Gln Glu Leu Ser Glu Leu Lys Gln Ile Gln Val
                1075                1080                1085

Ile Arg Gln Glu Leu Gln Leu Ala Val Ser Arg Lys Thr Glu Leu Glu
    1090                1095                1100

Glu Tyr Gln Arg Thr Ser Arg Thr Cys Glu Ser
1105                1110                1115

<210> SEQ ID NO 57
<211> LENGTH: 3178
<212> TYPE: DNA
<213> ORGANISM: Rattus sp
<220> FEATURE:
<221> NAME/KEY: CDS
<222> LOCATION: (76)...(3084)

<400> SEQUENCE: 57
gcacgagggg acaagagcgg gtctggctgg ggtgtctcct tcccttcgca cagcacagtg      60
gtaacttctt tcggg atg gag agt gtg cgg acg ctg tgg ctc agc gtg gcc     111
             Met Glu Ser Val Arg Thr Leu Trp Leu Ser Val Ala
               1               5                   10 ctg gcg ctg gcg gtg ggg tcc cga gtg gtg cgc ggt cac cct cag ccc     159
Leu Ala Leu Ala Val Gly Ser Arg Val Val Arg Gly His Pro Gln Pro
        15                  20                  25 tgc cgg gtt ccc acg cgc gct ggg gcc tcc gtg cgc ctg gcg gcg ctc     207
Cys Arg Val Pro Thr Arg Ala Gly Ala Ser Val Arg Leu Ala Ala Leu
    30                  35                  40 ctg ccc cgg gcg ccc gcc gcc cgc gcc cgc gtc cta gct gcc ctg gcc     255
Leu Pro Arg Ala Pro Ala Ala Arg Ala Arg Val Leu Ala Ala Leu Ala
45                  50                  55                  60 acc cct gcg ccg cgg ctg ccg cac aac ctg agt ctg gaa ctg gtg gcc     303
Thr Pro Ala Pro Arg Leu Pro His Asn Leu Ser Leu Glu Leu Val Ala
                65                  70                  75 gtc gcg tcc ccg acc cgg gac ccc gcg tcg cta gct cga ggt ctg tgc     351
Val Ala Ser Pro Thr Arg Asp Pro Ala Ser Leu Ala Arg Gly Leu Cys
            80                  85                  90
```

```
cag gtt ctg gca ccg cct ggc gtg gtg gcc tct ata gcc ttt ccc gag      399
Gln Val Leu Ala Pro Pro Gly Val Val Ala Ser Ile Ala Phe Pro Glu
         95                 100                 105 gcg cgg ccc gag ctg cgg cta ctg cag ttc ctg gca gcc gcc aca gag      447
Ala Arg Pro Glu Leu Arg Leu Leu Gln Phe Leu Ala Ala Ala Thr Glu
    110                 115                 120 acc cca gtg gtg agc gtc ctg cgg agg gag gtg cgc acg gcc ctc gga      495
Thr Pro Val Val Ser Val Leu Arg Arg Glu Val Arg Thr Ala Leu Gly
125                 130                 135                 140 gcc ccg act ccg ttc cat ctg cag ctg gac tgg gct agt ccc ctg gag      543
Ala Pro Thr Pro Phe His Leu Gln Leu Asp Trp Ala Ser Pro Leu Glu
                145                 150                 155 acc ata ctg gat gtg ctg gtg tcc ctg gta cgg gca cat gcc tgg gag      591
Thr Ile Leu Asp Val Leu Val Ser Leu Val Arg Ala His Ala Trp Glu
            160                 165                 170 gac att gct cta gta ctc tgc cgt gtc cgg gac cct ggc agc ctg gtg      639
Asp Ile Ala Leu Val Leu Cys Arg Val Arg Asp Pro Gly Ser Leu Val
        175                 180                 185 aca ctc tgg act aac cat gct agc cag gct cca aag ttt gtg ctg gac      687
Thr Leu Trp Thr Asn His Ala Ser Gln Ala Pro Lys Phe Val Leu Asp
    190                 195                 200 ctg agc cgg ctg gac agc agg aat gac agc ctt cgg gct gga ctg gcc      735
Leu Ser Arg Leu Asp Ser Arg Asn Asp Ser Leu Arg Ala Gly Leu Ala
205                 210                 215                 220 ctg ttg ggg gcg ctg gaa gga ggg gga acc cca gtg cct gca gca gtc      783
Leu Leu Gly Ala Leu Glu Gly Gly Gly Thr Pro Val Pro Ala Ala Val
                225                 230                 235 ctc cta ggc tgc agc act gcc cgt gca cat gag gtc cta gag gct gca      831
Leu Leu Gly Cys Ser Thr Ala Arg Ala His Glu Val Leu Glu Ala Ala
            240                 245                 250 cca ccg ggt ccc cag tgg ttg ctg ggc aca cca ttg ccc gct gag gca      879
Pro Pro Gly Pro Gln Trp Leu Leu Gly Thr Pro Leu Pro Ala Glu Ala
        255                 260                 265 ctg ccc acg act ggt ctg cca cct ggc gtg ctg gcg ctg ggg gaa acc      927
Leu Pro Thr Thr Gly Leu Pro Pro Gly Val Leu Ala Leu Gly Glu Thr
    270                 275                 280 gaa caa cac tct ctg gaa gct gtc gtc cac gac atg gtg gag ctt gtg      975
Glu Gln His Ser Leu Glu Ala Val Val His Asp Met Val Glu Leu Val
285                 290                 295                 300 gct cag gca ctc agt agc atg gcc ctt gta cac cca gag cgg gca ctg      1023
Ala Gln Ala Leu Ser Ser Met Ala Leu Val His Pro Glu Arg Ala Leu
                305                 310                 315 ctt cca gct gtg gtg aac tgt gat gac ctg aaa aca ggc gga tct gag      1071
Leu Pro Ala Val Val Asn Cys Asp Asp Leu Lys Thr Gly Gly Ser Glu
            320                 325                 330 gca aca ggg cgc acc ttg gct cgg ttt ctc ggc aac acc tca ttt cag      1119
Ala Thr Gly Arg Thr Leu Ala Arg Phe Leu Gly Asn Thr Ser Phe Gln
        335                 340                 345 ggc cga aca ggg gcc gtg tgg gtg aca ggc tcc tct cag gtg cat gtg      1167
Gly Arg Thr Gly Ala Val Trp Val Thr Gly Ser Ser Gln Val His Val
    350                 355                 360 tct cgg cat ttc aag gta tgg agc ctg cgc cgg gat ccg ctg ggt gcc      1215
Ser Arg His Phe Lys Val Trp Ser Leu Arg Arg Asp Pro Leu Gly Ala
365                 370                 375                 380 cca gcc tgg gca acc gtg ggc agc tgg cag gat gga cag ctg gac ttc      1263
Pro Ala Trp Ala Thr Val Gly Ser Trp Gln Asp Gly Gln Leu Asp Phe
                385                 390                 395 cag cca ggg gca gcc gct ctc cga gtc cca tct ccg tct ggc acc cag      1311
Gln Pro Gly Ala Ala Ala Leu Arg Val Pro Ser Pro Ser Gly Thr Gln
            400                 405                 410
```

```
gcc cga cca aag ctg cgt gtg gta acc ctg gtg gaa cac ccg ttt gtg      1359
Ala Arg Pro Lys Leu Arg Val Val Thr Leu Val Glu His Pro Phe Val
            415                 420                 425 ttc acc agg gaa tct gat gaa gac gga cag tgc cca gct ggg cag ctg      1407
Phe Thr Arg Glu Ser Asp Glu Asp Gly Gln Cys Pro Ala Gly Gln Leu
        430                 435                 440 tgt ctg gac cca ggc acc aat gac tca gcc agg ctg gat gcc ctc ttt      1455
Cys Leu Asp Pro Gly Thr Asn Asp Ser Ala Arg Leu Asp Ala Leu Phe
445                 450                 455                 460 gct gca ctg gtg aat ggc tca gta cct cga acg ctg aga aga tgc tgc      1503
Ala Ala Leu Val Asn Gly Ser Val Pro Arg Thr Leu Arg Arg Cys Cys
                465                 470                 475 tat ggc tac tgc atc gac ctg ctg gag cgg ctg gcc gag gac ctg gcc      1551
Tyr Gly Tyr Cys Ile Asp Leu Leu Glu Arg Leu Ala Glu Asp Leu Ala
            480                 485                 490 ttt gac ttt gag ctc tat att gtg ggg gat ggc aag tac ggg gcc ctg      1599
Phe Asp Phe Glu Leu Tyr Ile Val Gly Asp Gly Lys Tyr Gly Ala Leu
        495                 500                 505 cgt gat ggg cgc tgg acg ggc ctg gtg ggt gac ctg ctg gct ggc cgg      1647
Arg Asp Gly Arg Trp Thr Gly Leu Val Gly Asp Leu Leu Ala Gly Arg
510                 515                 520 gca cac atg gct gtg acc agc ttc agc atc aac tca gct cgc tct cag      1695
Ala His Met Ala Val Thr Ser Phe Ser Ile Asn Ser Ala Arg Ser Gln
525                 530                 535                 540 gtg gtg gat ttc acc agc cct ttc ttc tcc acc agc ctg ggg att atg      1743
Val Val Asp Phe Thr Ser Pro Phe Phe Ser Thr Ser Leu Gly Ile Met
                545                 550                 555 gtg cgc acg aga gac acg gcc tcg ccc atc ggg gct ttc atg tgg ccc      1791
Val Arg Thr Arg Asp Thr Ala Ser Pro Ile Gly Ala Phe Met Trp Pro
            560                 565                 570 ctg cac tgg tcc atg tgg gtg ggc gtg ttt gct gct ctg cac ctc aca      1839
Leu His Trp Ser Met Trp Val Gly Val Phe Ala Ala Leu His Leu Thr
        575                 580                 585 gcg ctc ttt ctc acc ctg tac gaa tgg cga agt ccc tac ggg ctc acg      1887
Ala Leu Phe Leu Thr Leu Tyr Glu Trp Arg Ser Pro Tyr Gly Leu Thr
590                 595                 600 ccg cgc ggc cgc aac cgt ggc act gtc ttc tct tac tcc tcc gcg ctc      1935
Pro Arg Gly Arg Asn Arg Gly Thr Val Phe Ser Tyr Ser Ser Ala Leu
605                 610                 615                 620 aac ctg tgc tat gcc att ctc ttt gga cgc act gtc tcc agt aag acg      1983
Asn Leu Cys Tyr Ala Ile Leu Phe Gly Arg Thr Val Ser Ser Lys Thr
                625                 630                 635 ccc aag tgc cct act gga cgc ttc ctc atg aac ctc tgg gca atc ttc      2031
Pro Lys Cys Pro Thr Gly Arg Phe Leu Met Asn Leu Trp Ala Ile Phe
            640                 645                 650 tgc ctg ctg gtg ctt tcc agt tac acg gcc aac ctg gct gct gtc atg      2079
Cys Leu Leu Val Leu Ser Ser Tyr Thr Ala Asn Leu Ala Ala Val Met
        655                 660                 665 gtt ggg gac aaa acc ttt gag gag ctg tct gga atc cat gat ccc aag      2127
Val Gly Asp Lys Thr Phe Glu Glu Leu Ser Gly Ile His Asp Pro Lys
670                 675                 680 ctg cac cac cct tcc caa ggc ttt cgc ttt ggc acc gta tgg gag agc      2175
Leu His His Pro Ser Gln Gly Phe Arg Phe Gly Thr Val Trp Glu Ser
685                 690                 695                 700 agc gcg gag gcc tac atc aag gca agc ttc cct gag atg cac gca cac      2223
Ser Ala Glu Ala Tyr Ile Lys Ala Ser Phe Pro Glu Met His Ala His
                705                 710                 715 atg cgt cgg cac agc gca ccc acc act cca cat ggg gtg gcc atg ctc      2271
Met Arg Arg His Ser Ala Pro Thr Thr Pro His Gly Val Ala Met Leu
```

```
                720                 725                 730
acg agc gac ccg ccc aag ctc aac gcc ttc atc atg gat aaa tca cta    2319
Thr Ser Asp Pro Pro Lys Leu Asn Ala Phe Ile Met Asp Lys Ser Leu
        735                 740                 745 ctg gac tat gag gtg tcc ata gat gcg gac tgc aag ctg ctc acc gtt    2367
Leu Asp Tyr Glu Val Ser Ile Asp Ala Asp Cys Lys Leu Leu Thr Val
750                 755                 760 ggc aaa ccc ttt gct atc gag ggc tac ggc ata ggg cta ccc caa aac    2415
Gly Lys Pro Phe Ala Ile Glu Gly Tyr Gly Ile Gly Leu Pro Gln Asn
765                 770                 775                 780 tcg ccg ctc acc tcc aac ctg tcg gag ttc atc agt agg tac aag tct    2463
Ser Pro Leu Thr Ser Asn Leu Ser Glu Phe Ile Ser Arg Tyr Lys Ser
                785                 790                 795 tca ggc ttc att gat ctg ctc cat gac aag tgg tac aag atg gtg cct    2511
Ser Gly Phe Ile Asp Leu Leu His Asp Lys Trp Tyr Lys Met Val Pro
            800                 805                 810 tgc ggg aag cgg gtg ttc gcc gtg acg gag acg ctg cag atg ggg gtc    2559
Cys Gly Lys Arg Val Phe Ala Val Thr Glu Thr Leu Gln Met Gly Val
        815                 820                 825 tac cac ttc tca gga ttg ttt gtc ctg ctg tgc ctc ggg ctg ggc agc    2607
Tyr His Phe Ser Gly Leu Phe Val Leu Leu Cys Leu Gly Leu Gly Ser
    830                 835                 840 gcg ctt ctc acc tct ctg ggt gag cat gtc ttc tac cgc ctg gtg ctg    2655
Ala Leu Leu Thr Ser Leu Gly Glu His Val Phe Tyr Arg Leu Val Leu
845                 850                 855                 860 ccg cgc atc cgc agg ggt aat aag ctg cag tat tgg ctt cac acg agc    2703
Pro Arg Ile Arg Arg Gly Asn Lys Leu Gln Tyr Trp Leu His Thr Ser
                865                 870                 875 cag aag atc cac cga gcc ctc aat aca gga cca ccc gag ggg caa cag    2751
Gln Lys Ile His Arg Ala Leu Asn Thr Gly Pro Pro Glu Gly Gln Gln
            880                 885                 890 gag agg gca gag cag gag cgc agc ggc ccc aag gac gag ctg cct gcc    2799
Glu Arg Ala Glu Gln Glu Arg Ser Gly Pro Lys Asp Glu Leu Pro Ala
        895                 900                 905 acc gat ggt gca ggg cgc tgg agg cgg gtg cgc cgg gct gtg gaa cgg    2847
Thr Asp Gly Ala Gly Arg Trp Arg Arg Val Arg Arg Ala Val Glu Arg
    910                 915                 920 gag cga cgc gtg cgt ttc ctg ctg gaa cct ggg gag gct ggc gga gac    2895
Glu Arg Arg Val Arg Phe Leu Leu Glu Pro Gly Glu Ala Gly Gly Asp
925                 930                 935                 940 cgc ccg tgg ctc tgc tcc aac ggg ccc ggg ctg caa gcg gag ctg cgg    2943
Arg Pro Trp Leu Cys Ser Asn Gly Pro Gly Leu Gln Ala Glu Leu Arg
                945                 950                 955 gag ctg gag ctg cgc att gag gct gca cgg gag cgg ctg cgc agt gcg    2991
Glu Leu Glu Leu Arg Ile Glu Ala Ala Arg Glu Arg Leu Arg Ser Ala
            960                 965                 970 ctg ttg cgg cgc ggg gag ctg cgg gcc ctg ctt ggg gat ggc acc cgg    3039
Leu Leu Arg Arg Gly Glu Leu Arg Ala Leu Leu Gly Asp Gly Thr Arg
        975                 980                 985 ctc agg cca ctg cgc ctg ttg cat gcg gcg cct gct gag agc tga        3084
Leu Arg Pro Leu Arg Leu Leu His Ala Ala Pro Ala Glu Ser *
    990                 995                 1000 ggaaccacaa ggccgcactg tccacgacag tttattctat atacaaacac gactctgtac    3144
actgcaatta aatagcgtgg aacgtgaaaa aaaa                                3178

<210> SEQ ID NO 58
<211> LENGTH: 1002
<212> TYPE: PRT
<213> ORGANISM: Rattus sp
```

<400> SEQUENCE: 58

```
Met Glu Ser Val Arg Thr Leu Trp Leu Ser Val Ala Leu Ala Leu Ala
1               5                   10                  15

Val Gly Ser Arg Val Val Arg Gly His Pro Gln Pro Cys Arg Val Pro
            20                  25                  30

Thr Arg Ala Gly Ala Ser Val Arg Leu Ala Ala Leu Leu Pro Arg Ala
        35                  40                  45

Pro Ala Ala Arg Ala Arg Val Leu Ala Ala Leu Ala Thr Pro Ala Pro
    50                  55                  60

Arg Leu Pro His Asn Leu Ser Leu Glu Leu Val Ala Val Ala Ser Pro
65                  70                  75                  80

Thr Arg Asp Pro Ala Ser Leu Ala Arg Gly Leu Cys Gln Val Leu Ala
                85                  90                  95

Pro Pro Gly Val Val Ala Ser Ile Ala Phe Pro Glu Ala Arg Pro Glu
            100                 105                 110

Leu Arg Leu Leu Gln Phe Leu Ala Ala Thr Glu Thr Pro Val Val
        115                 120                 125

Ser Val Leu Arg Arg Glu Val Arg Thr Ala Leu Gly Ala Pro Thr Pro
    130                 135                 140

Phe His Leu Gln Leu Asp Trp Ala Ser Pro Leu Glu Thr Ile Leu Asp
145                 150                 155                 160

Val Leu Val Ser Leu Val Arg Ala His Ala Trp Glu Asp Ile Ala Leu
                165                 170                 175

Val Leu Cys Arg Val Arg Asp Pro Gly Ser Leu Val Thr Leu Trp Thr
            180                 185                 190

Asn His Ala Ser Gln Ala Pro Lys Phe Val Leu Asp Leu Ser Arg Leu
        195                 200                 205

Asp Ser Arg Asn Asp Ser Leu Arg Ala Gly Leu Ala Leu Leu Gly Ala
    210                 215                 220

Leu Glu Gly Gly Gly Thr Pro Val Pro Ala Ala Val Leu Leu Gly Cys
225                 230                 235                 240

Ser Thr Ala Arg Ala His Glu Val Leu Glu Ala Ala Pro Pro Gly Pro
                245                 250                 255

Gln Trp Leu Leu Gly Thr Pro Leu Pro Ala Glu Ala Leu Pro Thr Thr
            260                 265                 270

Gly Leu Pro Pro Gly Val Leu Ala Leu Gly Glu Thr Glu Gln His Ser
        275                 280                 285

Leu Glu Ala Val Val His Asp Met Val Glu Leu Val Ala Gln Ala Leu
    290                 295                 300

Ser Ser Met Ala Leu Val His Pro Glu Arg Ala Leu Leu Pro Ala Val
305                 310                 315                 320

Val Asn Cys Asp Asp Leu Lys Thr Gly Gly Ser Glu Ala Thr Gly Arg
                325                 330                 335

Thr Leu Ala Arg Phe Leu Gly Asn Thr Ser Phe Gln Gly Arg Thr Gly
            340                 345                 350

Ala Val Trp Val Thr Gly Ser Ser Gln Val His Val Ser Arg His Phe
        355                 360                 365

Lys Val Trp Ser Leu Arg Arg Asp Pro Leu Gly Ala Pro Ala Trp Ala
    370                 375                 380

Thr Val Gly Ser Trp Gln Asp Gly Gln Leu Asp Phe Gln Pro Gly Ala
385                 390                 395                 400

Ala Ala Leu Arg Val Pro Ser Pro Ser Gly Thr Gln Ala Arg Pro Lys
```

-continued

```
                405                 410                 415
Leu Arg Val Val Thr Leu Val Glu His Pro Phe Val Phe Thr Arg Glu
            420                 425                 430
Ser Asp Glu Asp Gly Gln Cys Pro Ala Gly Gln Leu Cys Leu Asp Pro
            435                 440                 445
Gly Thr Asn Asp Ser Ala Arg Leu Asp Ala Leu Phe Ala Ala Leu Val
            450                 455                 460
Asn Gly Ser Val Pro Arg Thr Leu Arg Arg Cys Cys Tyr Gly Tyr Cys
465                 470                 475                 480
Ile Asp Leu Leu Glu Arg Leu Ala Glu Asp Leu Ala Phe Asp Phe Glu
            485                 490                 495
Leu Tyr Ile Val Gly Asp Gly Lys Tyr Gly Ala Leu Arg Asp Gly Arg
            500                 505                 510
Trp Thr Gly Leu Val Gly Asp Leu Leu Ala Gly Arg Ala His Met Ala
            515                 520                 525
Val Thr Ser Phe Ser Ile Asn Ser Ala Arg Ser Gln Val Val Asp Phe
            530                 535                 540
Thr Ser Pro Phe Phe Ser Thr Ser Leu Gly Ile Met Val Arg Thr Arg
545                 550                 555                 560
Asp Thr Ala Ser Pro Ile Gly Ala Phe Met Trp Pro Leu His Trp Ser
            565                 570                 575
Met Trp Val Gly Val Phe Ala Ala Leu His Leu Thr Ala Leu Phe Leu
            580                 585                 590
Thr Leu Tyr Glu Trp Arg Ser Pro Tyr Gly Leu Thr Pro Arg Gly Arg
            595                 600                 605
Asn Arg Gly Thr Val Phe Ser Tyr Ser Ser Ala Leu Asn Leu Cys Tyr
            610                 615                 620
Ala Ile Leu Phe Gly Arg Thr Val Ser Ser Lys Thr Pro Lys Cys Pro
625                 630                 635                 640
Thr Gly Arg Phe Leu Met Asn Leu Trp Ala Ile Phe Cys Leu Leu Val
            645                 650                 655
Leu Ser Ser Tyr Thr Ala Asn Leu Ala Ala Val Met Val Gly Asp Lys
            660                 665                 670
Thr Phe Glu Glu Leu Ser Gly Ile His Asp Pro Lys Leu His His Pro
            675                 680                 685
Ser Gln Gly Phe Arg Phe Gly Thr Val Trp Glu Ser Ser Ala Glu Ala
            690                 695                 700
Tyr Ile Lys Ala Ser Phe Pro Glu Met His Ala His Met Arg Arg His
705                 710                 715                 720
Ser Ala Pro Thr Thr Pro His Gly Val Ala Met Leu Thr Ser Asp Pro
            725                 730                 735
Pro Lys Leu Asn Ala Phe Ile Met Asp Lys Ser Leu Leu Asp Tyr Glu
            740                 745                 750
Val Ser Ile Asp Ala Asp Cys Lys Leu Leu Thr Val Gly Lys Pro Phe
            755                 760                 765
Ala Ile Glu Gly Tyr Gly Ile Gly Leu Pro Gln Asn Ser Pro Leu Thr
            770                 775                 780
Ser Asn Leu Ser Glu Phe Ile Ser Arg Tyr Lys Ser Ser Gly Phe Ile
785                 790                 795                 800
Asp Leu Leu His Asp Lys Trp Tyr Lys Met Val Pro Cys Gly Lys Arg
            805                 810                 815
Val Phe Ala Val Thr Glu Thr Leu Gln Met Gly Val Tyr His Phe Ser
            820                 825                 830
```

```
Gly Leu Phe Val Leu Leu Cys Leu Gly Leu Gly Ser Ala Leu Leu Thr
            835                 840                 845

Ser Leu Gly Glu His Val Phe Tyr Arg Leu Val Leu Pro Arg Ile Arg
    850                 855                 860

Arg Gly Asn Lys Leu Gln Tyr Trp Leu His Thr Ser Gln Lys Ile His
865                 870                 875                 880

Arg Ala Leu Asn Thr Gly Pro Pro Glu Gly Gln Gln Glu Arg Ala Glu
                885                 890                 895

Gln Glu Arg Ser Gly Pro Lys Asp Glu Leu Pro Ala Thr Asp Gly Ala
            900                 905                 910

Gly Arg Trp Arg Arg Val Arg Arg Ala Val Glu Arg Glu Arg Val
            915                 920                 925

Arg Phe Leu Leu Glu Pro Gly Glu Ala Gly Gly Asp Arg Pro Trp Leu
    930                 935                 940

Cys Ser Asn Gly Pro Gly Leu Gln Ala Glu Leu Arg Glu Leu Glu Leu
945                 950                 955                 960

Arg Ile Glu Ala Ala Arg Glu Arg Leu Arg Ser Ala Leu Leu Arg Arg
                965                 970                 975

Gly Glu Leu Arg Ala Leu Leu Gly Asp Gly Thr Arg Leu Arg Pro Leu
            980                 985                 990

Arg Leu Leu His Ala Ala Pro Ala Glu Ser
    995                 1000
```

```
<210> SEQ ID NO 59
<211> LENGTH: 3133
<212> TYPE: DNA
<213> ORGANISM: Rattus sp.
<220> FEATURE:
<221> NAME/KEY: CDS
<222> LOCATION: (76)...(3036)

<400> SEQUENCE: 59
```

```
gcacgagggg acaagagcgg gtctggctgg ggtgtctcct tcccttcgca cagcacagtg       60
gtaacttctt tcggg atg gag agt gtg cgg acg ctg tgg ctc agc gtg gcc      111
                Met Glu Ser Val Arg Thr Leu Trp Leu Ser Val Ala
                  1               5                  10 ctg gcg ctg gcg gtg ggg tcc cga gtg gtg cgc ggt cac cct cag ccc       159
Leu Ala Leu Ala Val Gly Ser Arg Val Val Arg Gly His Pro Gln Pro
             15                  20                  25 tgc cgg gtt ccc acg cgc gct ggg gcc tcc gtg cgc ctg gcg gcg ctc       207
Cys Arg Val Pro Thr Arg Ala Gly Ala Ser Val Arg Leu Ala Ala Leu
         30                  35                  40 ctg ccc cgg gcg ccc gcc gcc cgc gcc cgc gtc cta gct gcc ctg gcc       255
Leu Pro Arg Ala Pro Ala Ala Arg Ala Arg Val Leu Ala Ala Leu Ala
 45                  50                  55                  60 acc cct gcg ccg cgg ctg ccg cac aac ctg agt ctg gaa ctg gtg gcc       303
Thr Pro Ala Pro Arg Leu Pro His Asn Leu Ser Leu Glu Leu Val Ala
                 65                  70                  75 gtc gcg tcc ccg acc cgg gac ccc gcg tcg cta gct cga ggt ctg tgc       351
Val Ala Ser Pro Thr Arg Asp Pro Ala Ser Leu Ala Arg Gly Leu Cys
             80                  85                  90 cag gtt ctg gca ccg cct ggc gtg gtg gcc tct ata gcc ttt ccc gag       399
Gln Val Leu Ala Pro Pro Gly Val Val Ala Ser Ile Ala Phe Pro Glu
         95                 100                 105 gcg cgg ccc gag ctg cgg cta ctg cag ttc ctg gca gcc gca aca gag       447
Ala Arg Pro Glu Leu Arg Leu Leu Gln Phe Leu Ala Ala Ala Thr Glu
    110                 115                 120
```

```
acc cca gtg act ccg ttc cat ctg cag ctg gac tgg gct agt ccc ctg    495
Thr Pro Val Thr Pro Phe His Leu Gln Leu Asp Trp Ala Ser Pro Leu
125                 130                 135                 140 gag acc ata ctg gat gtg ctg gtg tcc ctg gta cgg gca cat gcc tgg    543
Glu Thr Ile Leu Asp Val Leu Val Ser Leu Val Arg Ala His Ala Trp
                145                 150                 155 gag gac att gct cta gta ctc tgc cgt gtc cgg gac cct ggc agc ctg    591
Glu Asp Ile Ala Leu Val Leu Cys Arg Val Arg Asp Pro Gly Ser Leu
    160                 165                 170 gtg aca ctc tgg act aac cat gct agc cag gct cca aag ttt gtg ctg    639
Val Thr Leu Trp Thr Asn His Ala Ser Gln Ala Pro Lys Phe Val Leu
        175                 180                 185 gac ctg agc cgg ctg gac agc agg aat gac agc ctt cgg gct gga ctg    687
Asp Leu Ser Arg Leu Asp Ser Arg Asn Asp Ser Leu Arg Ala Gly Leu
            190                 195                 200 gcc ctg ttg ggg gcg ctg gaa gga ggg gga acc cca gtg cct gca gca    735
Ala Leu Leu Gly Ala Leu Glu Gly Gly Gly Thr Pro Val Pro Ala Ala
205                 210                 215                 220 gtc ctc cta ggc tgc agc act gcc cgt gca cat gag gtc cta gag gct    783
Val Leu Leu Gly Cys Ser Thr Ala Arg Ala His Glu Val Leu Glu Ala
                225                 230                 235 gca cca ccg ggt ccc cag tgg ttg ctg ggc aca cca ttg ccc gct gag    831
Ala Pro Pro Gly Pro Gln Trp Leu Leu Gly Thr Pro Leu Pro Ala Glu
    240                 245                 250 gca ctg ccc acg act ggt ctg cca cct ggc gtg ctg gcg ctg ggg gaa    879
Ala Leu Pro Thr Thr Gly Leu Pro Pro Gly Val Leu Ala Leu Gly Glu
        255                 260                 265 acc gaa caa cac tct ctg gaa gct gtc gtc cac gac atg gtg gag ctt    927
Thr Glu Gln His Ser Leu Glu Ala Val Val His Asp Met Val Glu Leu
            270                 275                 280 gtg gct cag gca ctc agt agc atg gcc ctt gta cac cca gag cgg gca    975
Val Ala Gln Ala Leu Ser Ser Met Ala Leu Val His Pro Glu Arg Ala
285                 290                 295                 300 ctg ctt cca gct gtg gtg aac tgt gat gac ctg aaa aca ggc gga tct   1023
Leu Leu Pro Ala Val Val Asn Cys Asp Asp Leu Lys Thr Gly Gly Ser
                305                 310                 315 gag gca aca ggg cgc acc ttg gct cgg ttt ctc ggc aac acc tca ttt   1071
Glu Ala Thr Gly Arg Thr Leu Ala Arg Phe Leu Gly Asn Thr Ser Phe
    320                 325                 330 cag ggc cga aca ggg gcc gtg tgg gtg aca ggc tcc tct cag gtg cat   1119
Gln Gly Arg Thr Gly Ala Val Trp Val Thr Gly Ser Ser Gln Val His
        335                 340                 345 gtg tct cgg cat ttc aag gta tgg agc ctg cgc cgg gat ccg ctg ggt   1167
Val Ser Arg His Phe Lys Val Trp Ser Leu Arg Arg Asp Pro Leu Gly
            350                 355                 360 gcc cca gcc tgg gca acc gtg ggc agc tgg cag gat gga cag ctg gac   1215
Ala Pro Ala Trp Ala Thr Val Gly Ser Trp Gln Asp Gly Gln Leu Asp
365                 370                 375                 380 ttc cag cca ggg gca gcc gct ctc cga gtc cca tct ccg tct ggc acc   1263
Phe Gln Pro Gly Ala Ala Ala Leu Arg Val Pro Ser Pro Ser Gly Thr
                385                 390                 395 cag gcc cga cca aag ctg cgt gtg gta acc ctg gtg gaa cac ccg ttt   1311
Gln Ala Arg Pro Lys Leu Arg Val Val Thr Leu Val Glu His Pro Phe
    400                 405                 410 gtg ttc acc agg gaa tct gat gaa gac gga cag tgc cca gct ggg cag   1359
Val Phe Thr Arg Glu Ser Asp Glu Asp Gly Gln Cys Pro Ala Gly Gln
        415                 420                 425 ctg tgt ctg gac cca ggc acc aat gac tca gcc agg ctg gat gcc ctc   1407
Leu Cys Leu Asp Pro Gly Thr Asn Asp Ser Ala Arg Leu Asp Ala Leu
            430                 435                 440
```

-continued

| | | |
|---|---|---|
| ttt gct gca ctg gtg aat ggc tca gta cct cga acg ctg aga aga tgc<br>Phe Ala Ala Leu Val Asn Gly Ser Val Pro Arg Thr Leu Arg Arg Cys<br>445                                   450                        455                          460 | 1455 |
| tgc tat ggc tac tgc atc gac ctg ctg gag cgg ctg gcc gag gac ctg<br>Cys Tyr Gly Tyr Cys Ile Asp Leu Leu Glu Arg Leu Ala Glu Asp Leu<br>                               465                          470                        475 | 1503 |
| gcc ttt gac ttt gag ctc tat att gtg ggg gat ggc aag tac ggg gcc<br>Ala Phe Asp Phe Glu Leu Tyr Ile Val Gly Asp Gly Lys Tyr Gly Ala<br>                       480                        485                        490 | 1551 |
| ctg cgt gat ggg cgc tgg acg ggc ctg gtg ggt gac ctg ctg gct ggc<br>Leu Arg Asp Gly Arg Trp Thr Gly Leu Val Gly Asp Leu Leu Ala Gly<br>              495                        500                        505 | 1599 |
| cgg gca cac atg gct gtg acc agc ttc agc atc aac tca gct cgc tct<br>Arg Ala His Met Ala Val Thr Ser Phe Ser Ile Asn Ser Ala Arg Ser<br>510                                   515                        520 | 1647 |
| cag gtg gtg gat ttc acc agc cct ttc ttc tcc acc agc ctg ggg att<br>Gln Val Val Asp Phe Thr Ser Pro Phe Phe Ser Thr Ser Leu Gly Ile<br>525                                   530                        535                        540 | 1695 |
| atg gtg cgc acg aga gac acg gcc tcg ccc atc ggg gct ttc atg tgg<br>Met Val Arg Thr Arg Asp Thr Ala Ser Pro Ile Gly Ala Phe Met Trp<br>                       545                        550                        555 | 1743 |
| ccc ctg cac tgg tcc atg tgg gtg ggc gtg ttt gct gct ctg cac ctc<br>Pro Leu His Trp Ser Met Trp Val Gly Val Phe Ala Ala Leu His Leu<br>                       560                        565                        570 | 1791 |
| aca gcg ctc ttt ctc acc ctg tac gaa tgg cga agt ccc tac ggg ctc<br>Thr Ala Leu Phe Leu Thr Leu Tyr Glu Trp Arg Ser Pro Tyr Gly Leu<br>              575                        580                        585 | 1839 |
| acg ccg cgc ggc cgc aac cgt ggc act gtc ttc tct tac tcc tcc gcg<br>Thr Pro Arg Gly Arg Asn Arg Gly Thr Val Phe Ser Tyr Ser Ser Ala<br>590                                   595                        600 | 1887 |
| ctc aac ctg tgc tat gcc att ctc ttt gga cgc act gtc tcc agt aag<br>Leu Asn Leu Cys Tyr Ala Ile Leu Phe Gly Arg Thr Val Ser Ser Lys<br>605                                   610                        615                        620 | 1935 |
| acg ccc aag tgc cct act gga cgc ttc ctc atg aac ctc tgg gca atc<br>Thr Pro Lys Cys Pro Thr Gly Arg Phe Leu Met Asn Leu Trp Ala Ile<br>                       625                        630                        635 | 1983 |
| ttc tgc ctg ctg gtg ctt tcc agt tac acg gcc aac ctg gct gct gtc<br>Phe Cys Leu Leu Val Leu Ser Ser Tyr Thr Ala Asn Leu Ala Ala Val<br>                           640                        645                        650 | 2031 |
| atg gtt ggg gac aaa acc ttt gag gag ctg tct gga atc cat gat ccc<br>Met Val Gly Asp Lys Thr Phe Glu Glu Leu Ser Gly Ile His Asp Pro<br>                       655                        660                        665 | 2079 |
| aag ctg cac cac cct tcc caa ggc ttt cgc ttt ggc acc gta tgg gag<br>Lys Leu His His Pro Ser Gln Gly Phe Arg Phe Gly Thr Val Trp Glu<br>670                                   675                        680 | 2127 |
| agc agc gcg gag gcc tac atc aag gca agc ttc cct gag atg cac gca<br>Ser Ser Ala Glu Ala Tyr Ile Lys Ala Ser Phe Pro Glu Met His Ala<br>685                                   690                        695                        700 | 2175 |
| cac atg cgt cgg cac agc gca ccc acc act cca cat ggg gtg gcc atg<br>His Met Arg Arg His Ser Ala Pro Thr Thr Pro His Gly Val Ala Met<br>                       705                        710                        715 | 2223 |
| ctc acg agc gac ccg ccc aag ctc aac gcc ttc atc atg gat aaa tca<br>Leu Thr Ser Asp Pro Pro Lys Leu Asn Ala Phe Ile Met Asp Lys Ser<br>              720                        725                        730 | 2271 |
| cta ctg gac tat gag gtg tcc ata gat gcg gac tgc aag ctg ctc acc<br>Leu Leu Asp Tyr Glu Val Ser Ile Asp Ala Asp Cys Lys Leu Leu Thr<br>                       735                        740                        745 | 2319 |
| gtt ggc aaa ccc ttt gct atc gag ggc tac ggc ata ggg cta ccc caa<br>Val Gly Lys Pro Phe Ala Ile Glu Gly Tyr Gly Ile Gly Leu Pro Gln | 2367 |

-continued

```
              750                 755                 760
aac tcg ccg ctc acc tcc aac ctg tcg gag ttc atc agt agg tac aag      2415
Asn Ser Pro Leu Thr Ser Asn Leu Ser Glu Phe Ile Ser Arg Tyr Lys
765                 770                 775                 780 tct tca ggc ttc att gat ctg ctc cat gac aag tgg tac aag atg gtg      2463
Ser Ser Gly Phe Ile Asp Leu Leu His Asp Lys Trp Tyr Lys Met Val
                    785                 790                 795 cct tgc ggg aag cgg gtg ttc gcc gtg acg gag acg ctg cag atg ggg      2511
Pro Cys Gly Lys Arg Val Phe Ala Val Thr Glu Thr Leu Gln Met Gly
                800                 805                 810 gtc tac cac ttc tca gga ttg ttt gtc ctg ctg tgc ctc ggg ctg ggc      2559
Val Tyr His Phe Ser Gly Leu Phe Val Leu Leu Cys Leu Gly Leu Gly
            815                 820                 825 agc gcg ctt ctc acc tct ctg ggt gag cat gtc ttc tac cgc ctg gtg      2607
Ser Ala Leu Leu Thr Ser Leu Gly Glu His Val Phe Tyr Arg Leu Val
        830                 835                 840 ctg ccg cgc atc cgc agg ggt aat aag ctg cag tat tgg ctt cac acg      2655
Leu Pro Arg Ile Arg Arg Gly Asn Lys Leu Gln Tyr Trp Leu His Thr
845                 850                 855                 860 agc cag aag atc cac cga gcc ctc aat aca gga cca ccc gag ggg caa      2703
Ser Gln Lys Ile His Arg Ala Leu Asn Thr Gly Pro Pro Glu Gly Gln
                865                 870                 875 cag gag agg gca gag cag gag cgc agc ggc ccc aag gac gag ctg cct      2751
Gln Glu Arg Ala Glu Gln Glu Arg Ser Gly Pro Lys Asp Glu Leu Pro
                880                 885                 890 gcc acc gat ggt gca ggg cgc tgg agg cgg gtg cgc cgg gct gtg gaa      2799
Ala Thr Asp Gly Ala Gly Arg Trp Arg Arg Val Arg Arg Ala Val Glu
            895                 900                 905 cgg gag cga cgc gtg cgt ttc ctg ctg gaa cct ggg gag gct ggc gga      2847
Arg Glu Arg Arg Val Arg Phe Leu Leu Glu Pro Gly Glu Ala Gly Gly
        910                 915                 920 gac cgc ccg tgg ctc tgc tcc aac ggg ccc ggg ctg caa gcg gag ctg      2895
Asp Arg Pro Trp Leu Cys Ser Asn Gly Pro Gly Leu Gln Ala Glu Leu
925                 930                 935                 940 cgg gag ctg gag ctg cgc att gag gct gca cgg gag cgg ctg cgc agt      2943
Arg Glu Leu Glu Leu Arg Ile Glu Ala Ala Arg Glu Arg Leu Arg Ser
                945                 950                 955 gcg ctg ttg cgg cgc ggg gag ctg cgg gcc ctg ctt ggg gat ggc acc      2991
Ala Leu Leu Arg Arg Gly Glu Leu Arg Ala Leu Leu Gly Asp Gly Thr
                960                 965                 970 cgg ctc agg cca ctg cgc ctg ttg cat gcg gcg cct gct gag agc          3036
Arg Leu Arg Pro Leu Arg Leu Leu His Ala Ala Pro Ala Glu Ser
            975                 980                 985 tgaggaacca caaggccgca ctgtccacga cagtttattc tatatacaaa cacgactctg    3096
tacactgcaa ttaaatagcg tggaacgtga aaaaaa                              3133

<210> SEQ ID NO 60
<211> LENGTH: 987
<212> TYPE: PRT
<213> ORGANISM: Rattus sp.

<400> SEQUENCE: 60

Met Glu Ser Val Arg Thr Leu Trp Leu Ser Val Ala Leu Ala Leu Ala
1               5                   10                  15

Val Gly Ser Arg Val Val Arg Gly His Pro Gln Pro Cys Arg Val Pro
                20                  25                  30

Thr Arg Ala Gly Ala Ser Val Arg Leu Ala Ala Leu Leu Pro Arg Ala
            35                  40                  45
```

-continued

```
Pro Ala Ala Arg Ala Arg Val Leu Ala Ala Leu Ala Thr Pro Ala Pro
 50                  55                  60

Arg Leu Pro His Asn Leu Ser Leu Glu Leu Val Ala Val Ala Ser Pro
 65                  70                  75                  80

Thr Arg Asp Pro Ala Ser Leu Ala Arg Gly Leu Cys Gln Val Leu Ala
                 85                  90                  95

Pro Pro Gly Val Val Ala Ser Ile Ala Phe Pro Glu Ala Arg Pro Glu
            100                 105                 110

Leu Arg Leu Leu Gln Phe Leu Ala Ala Thr Glu Thr Pro Val Thr
        115                 120                 125

Pro Phe His Leu Gln Leu Asp Trp Ala Ser Pro Leu Glu Thr Ile Leu
    130                 135                 140

Asp Val Leu Val Ser Leu Val Arg Ala His Ala Trp Glu Asp Ile Ala
145                 150                 155                 160

Leu Val Leu Cys Arg Val Arg Asp Pro Gly Ser Leu Val Thr Leu Trp
                165                 170                 175

Thr Asn His Ala Ser Gln Ala Pro Lys Phe Val Leu Asp Leu Ser Arg
            180                 185                 190

Leu Asp Ser Arg Asn Asp Ser Leu Arg Ala Gly Leu Ala Leu Leu Gly
        195                 200                 205

Ala Leu Glu Gly Gly Gly Thr Pro Val Pro Ala Ala Val Leu Leu Gly
    210                 215                 220

Cys Ser Thr Ala Arg Ala His Glu Val Leu Glu Ala Ala Pro Pro Gly
225                 230                 235                 240

Pro Gln Trp Leu Leu Gly Thr Pro Leu Pro Ala Glu Ala Leu Pro Thr
                245                 250                 255

Thr Gly Leu Pro Pro Gly Val Leu Ala Leu Gly Glu Thr Glu Gln His
            260                 265                 270

Ser Leu Glu Ala Val His Asp Met Val Glu Leu Val Ala Gln Ala
        275                 280                 285

Leu Ser Ser Met Ala Leu Val His Pro Glu Arg Ala Leu Leu Pro Ala
    290                 295                 300

Val Val Asn Cys Asp Asp Leu Lys Thr Gly Gly Ser Glu Ala Thr Gly
305                 310                 315                 320

Arg Thr Leu Ala Arg Phe Leu Gly Asn Thr Ser Phe Gln Gly Arg Thr
                325                 330                 335

Gly Ala Val Trp Val Thr Gly Ser Ser Gln Val His Val Ser Arg His
            340                 345                 350

Phe Lys Val Trp Ser Leu Arg Arg Asp Pro Leu Gly Ala Pro Ala Trp
        355                 360                 365

Ala Thr Val Gly Ser Trp Gln Asp Gly Gln Leu Asp Phe Gln Pro Gly
    370                 375                 380

Ala Ala Ala Leu Arg Val Pro Ser Pro Ser Gly Thr Gln Ala Arg Pro
385                 390                 395                 400

Lys Leu Arg Val Val Thr Leu Val Glu His Pro Phe Val Phe Thr Arg
                405                 410                 415

Glu Ser Asp Glu Asp Gly Gln Cys Pro Ala Gly Gln Leu Cys Leu Asp
            420                 425                 430

Pro Gly Thr Asn Asp Ser Ala Arg Leu Asp Ala Leu Phe Ala Ala Leu
        435                 440                 445

Val Asn Gly Ser Val Pro Arg Thr Leu Arg Arg Cys Cys Tyr Gly Tyr
    450                 455                 460

Cys Ile Asp Leu Leu Glu Arg Leu Ala Glu Asp Leu Ala Phe Asp Phe
```

```
465                 470                 475                 480
Glu Leu Tyr Ile Val Gly Asp Gly Lys Tyr Gly Ala Leu Arg Asp Gly
                485                 490                 495
Arg Trp Thr Gly Leu Val Gly Asp Leu Leu Ala Gly Arg Ala His Met
                500                 505                 510
Ala Val Thr Ser Phe Ser Ile Asn Ser Ala Arg Ser Gln Val Val Asp
                515                 520                 525
Phe Thr Ser Pro Phe Phe Ser Thr Ser Leu Gly Ile Met Val Arg Thr
        530                 535                 540
Arg Asp Thr Ala Ser Pro Ile Gly Ala Phe Met Trp Pro Leu His Trp
545                 550                 555                 560
Ser Met Trp Val Gly Val Phe Ala Ala Leu His Leu Thr Ala Leu Phe
                565                 570                 575
Leu Thr Leu Tyr Glu Trp Arg Ser Pro Tyr Gly Leu Thr Pro Arg Gly
                580                 585                 590
Arg Asn Arg Gly Thr Val Phe Ser Tyr Ser Ala Leu Asn Leu Cys
                595                 600                 605
Tyr Ala Ile Leu Phe Gly Arg Thr Val Ser Ser Lys Thr Pro Lys Cys
                610                 615                 620
Pro Thr Gly Arg Phe Leu Met Asn Leu Trp Ala Ile Phe Cys Leu Leu
625                 630                 635                 640
Val Leu Ser Ser Tyr Thr Ala Asn Leu Ala Ala Val Met Val Gly Asp
                645                 650                 655
Lys Thr Phe Glu Glu Leu Ser Gly Ile His Asp Pro Lys Leu His His
                660                 665                 670
Pro Ser Gln Gly Phe Arg Phe Gly Thr Val Trp Glu Ser Ser Ala Glu
                675                 680                 685
Ala Tyr Ile Lys Ala Ser Phe Pro Glu Met His Ala His Met Arg Arg
                690                 695                 700
His Ser Ala Pro Thr Thr Pro His Gly Val Ala Met Leu Thr Ser Asp
705                 710                 715                 720
Pro Pro Lys Leu Asn Ala Phe Ile Met Asp Lys Ser Leu Leu Asp Tyr
                725                 730                 735
Glu Val Ser Ile Asp Ala Asp Cys Lys Leu Leu Thr Val Gly Lys Pro
                740                 745                 750
Phe Ala Ile Glu Gly Tyr Gly Ile Gly Leu Pro Gln Asn Ser Pro Leu
                755                 760                 765
Thr Ser Asn Leu Ser Glu Phe Ile Ser Arg Tyr Lys Ser Ser Gly Phe
        770                 775                 780
Ile Asp Leu Leu His Asp Lys Trp Tyr Lys Met Val Pro Cys Gly Lys
785                 790                 795                 800
Arg Val Phe Ala Val Thr Glu Thr Leu Gln Met Gly Val Tyr His Phe
                805                 810                 815
Ser Gly Leu Phe Val Leu Leu Cys Leu Gly Leu Gly Ser Ala Leu Leu
                820                 825                 830
Thr Ser Leu Gly Glu His Val Phe Tyr Arg Leu Val Leu Pro Arg Ile
                835                 840                 845
Arg Arg Gly Asn Lys Leu Gln Tyr Trp Leu His Thr Ser Gln Lys Ile
        850                 855                 860
His Arg Ala Leu Asn Thr Gly Pro Pro Glu Gly Gln Gln Glu Arg Ala
865                 870                 875                 880
Glu Gln Glu Arg Ser Gly Pro Lys Asp Glu Leu Pro Ala Thr Asp Gly
                885                 890                 895
```

```
Ala Gly Arg Trp Arg Arg Val Arg Arg Ala Val Glu Arg Glu Arg Arg
                900                 905                 910

Val Arg Phe Leu Leu Glu Pro Gly Glu Ala Gly Gly Asp Arg Pro Trp
            915                 920                 925

Leu Cys Ser Asn Gly Pro Gly Leu Gln Ala Glu Leu Arg Glu Leu Glu
        930                 935                 940

Leu Arg Ile Glu Ala Ala Arg Glu Arg Leu Arg Ser Ala Leu Leu Arg
945                 950                 955                 960

Arg Gly Glu Leu Arg Ala Leu Leu Gly Asp Gly Thr Arg Leu Arg Pro
                965                 970                 975

Leu Arg Leu Leu His Ala Ala Pro Ala Glu Ser
            980                 985

<210> SEQ ID NO 61
<211> LENGTH: 3097
<212> TYPE: DNA
<213> ORGANISM: Homo sapiens
<220> FEATURE:
<221> NAME/KEY: CDS
<222> LOCATION: (1)...(3024)

<400> SEQUENCE: 61
```

| | | | | | | | | | | | | | | | | |
|---|---|---|---|---|---|---|---|---|---|---|---|---|---|---|---|---|
| atg | gag | ttt | gtg | cgg | gcg | ctg | tgg | ctg | ggc | ctg | gcg | ctg | gcg | ctg | ggg | 48 |
| Met | Glu | Phe | Val | Arg | Ala | Leu | Trp | Leu | Gly | Leu | Ala | Leu | Ala | Leu | Gly | |
| 1 | | | | 5 | | | | | 10 | | | | | 15 | | |
| ccg | ggg | tcc | gcg | ggg | ggc | cac | cct | cag | ccg | tgc | ggc | gtc | ctg | gcg | cgc | 96 |
| Pro | Gly | Ser | Ala | Gly | Gly | His | Pro | Gln | Pro | Cys | Gly | Val | Leu | Ala | Arg | |
| | | | 20 | | | | | 25 | | | | | 30 | | | |
| ctc | ggg | ggc | tcc | gtg | cgc | ctg | ggc | gcc | ctc | ctg | ccc | cgc | gcg | cct | ctc | 144 |
| Leu | Gly | Gly | Ser | Val | Arg | Leu | Gly | Ala | Leu | Leu | Pro | Arg | Ala | Pro | Leu | |
| | | 35 | | | | | 40 | | | | | 45 | | | | |
| gcc | cgc | gcc | cgc | gcc | cgc | gcc | gcc | ctg | gcc | cgg | gcc | gcc | ctg | gcg | ccg | 192 |
| Ala | Arg | Ala | Arg | Ala | Arg | Ala | Ala | Leu | Ala | Arg | Ala | Ala | Leu | Ala | Pro | |
| 50 | | | | | 55 | | | | | 60 | | | | | | |
| cgg | ctg | ccg | cac | aac | ctg | agc | ttg | gag | ctg | gtg | gtc | gcc | gcg | ccc | ccc | 240 |
| Arg | Leu | Pro | His | Asn | Leu | Ser | Leu | Glu | Leu | Val | Val | Ala | Ala | Pro | Pro | |
| 65 | | | | | 70 | | | | | 75 | | | | | 80 | |
| gcc | cgc | gac | ccc | gcc | tcg | ctg | acc | cgc | ggc | ctg | tgc | cag | gcg | ctg | gtg | 288 |
| Ala | Arg | Asp | Pro | Ala | Ser | Leu | Thr | Arg | Gly | Leu | Cys | Gln | Ala | Leu | Val | |
| | | | | 85 | | | | | 90 | | | | | 95 | | |
| cct | ccg | ggc | gtg | gcg | gcc | ctg | ctc | gcc | ttt | ccc | gag | gct | cgg | ccc | gag | 336 |
| Pro | Pro | Gly | Val | Ala | Ala | Leu | Leu | Ala | Phe | Pro | Glu | Ala | Arg | Pro | Glu | |
| | | | 100 | | | | | 105 | | | | | 110 | | | |
| ctg | ctg | cag | ctg | cac | ttc | ctg | gcg | gcg | gcc | acc | gag | acc | ccc | gtg | ctc | 384 |
| Leu | Leu | Gln | Leu | His | Phe | Leu | Ala | Ala | Ala | Thr | Glu | Thr | Pro | Val | Leu | |
| | | 115 | | | | | 120 | | | | | 125 | | | | |
| agc | ctg | ctg | cgg | cgg | gag | gcg | cgc | gcg | ccc | ctc | gga | gcc | ccg | aac | cca | 432 |
| Ser | Leu | Leu | Arg | Arg | Glu | Ala | Arg | Ala | Pro | Leu | Gly | Ala | Pro | Asn | Pro | |
| | 130 | | | | | 135 | | | | | 140 | | | | | |
| ttc | cac | ctg | cag | ctg | cac | tgg | gcc | agc | ccc | ctg | gag | acg | ctg | ctg | gat | 480 |
| Phe | His | Leu | Gln | Leu | His | Trp | Ala | Ser | Pro | Leu | Glu | Thr | Leu | Leu | Asp | |
| 145 | | | | | 150 | | | | | 155 | | | | | 160 | |
| gtg | ctg | gtg | gcg | gtg | ctg | cag | gcg | cac | gcc | tgg | gaa | gac | gtc | ggc | ctg | 528 |
| Val | Leu | Val | Ala | Val | Leu | Gln | Ala | His | Ala | Trp | Glu | Asp | Val | Gly | Leu | |
| | | | | 165 | | | | | 170 | | | | | 175 | | |
| gcc | ctg | tgc | cgc | act | cag | gac | ccc | ggc | ggc | ctg | gtg | gcc | ctc | tgg | aca | 576 |
| Ala | Leu | Cys | Arg | Thr | Gln | Asp | Pro | Gly | Gly | Leu | Val | Ala | Leu | Trp | Thr | |
| | | | 180 | | | | | 185 | | | | | 190 | | | |
| agc | cgg | gct | ggc | cgg | ccc | cca | cag | ctg | gtc | ctg | gac | cta | agc | cgg | cgg | 624 |

```
                Ser Arg Ala Gly Arg Pro Pro Gln Leu Val Leu Asp Leu Ser Arg Arg
                            195                 200                 205 gac acg gga gat gca gga ctg cgg gca cgc ctg gcc ccg atg gcg gcg       672
Asp Thr Gly Asp Ala Gly Leu Arg Ala Arg Leu Ala Pro Met Ala Ala
        210                 215                 220 cca gtg ggg ggt gaa gca ccg gta ccc gcg gcg gtc ctc ctc ggc tgt       720
Pro Val Gly Gly Glu Ala Pro Val Pro Ala Ala Val Leu Leu Gly Cys
225                 230                 235                 240 gac atc gcc cgt gcc cgt cgg gtg ctg gag gcc gta cct ccc ggc ccc       768
Asp Ile Ala Arg Ala Arg Arg Val Leu Glu Ala Val Pro Pro Gly Pro
                245                 250                 255 cac tgg ctg ttg ggg aca cca ctg ccg ccc aag gcc ctg ccc acc gcg       816
His Trp Leu Leu Gly Thr Pro Leu Pro Pro Lys Ala Leu Pro Thr Ala
            260                 265                 270 ggg ctg cca cca ggg ctg ctg gcg ctg ggc gag gtg gca cga ccc ccg       864
Gly Leu Pro Pro Gly Leu Leu Ala Leu Gly Glu Val Ala Arg Pro Pro
        275                 280                 285 ctg gag gcc gcc atc cat gac att gtg caa ctg gtg gcc cgg gcg ctg       912
Leu Glu Ala Ala Ile His Asp Ile Val Gln Leu Val Ala Arg Ala Leu
    290                 295                 300 ggc agt gcg gcc cag gtg cag ccg aag cga gcc ctc ctc ccc gcc ccg       960
Gly Ser Ala Ala Gln Val Gln Pro Lys Arg Ala Leu Leu Pro Ala Pro
305                 310                 315                 320 gtc aac tgc ggg gac ctg cag ccg gcc ggg ccc gag tcc ccg ggg cgc      1008
Val Asn Cys Gly Asp Leu Gln Pro Ala Gly Pro Glu Ser Pro Gly Arg
                325                 330                 335 ttc ttg gca cgg ttc ctg gcc aac acg tcc ttc cag ggc cgc acg ggc      1056
Phe Leu Ala Arg Phe Leu Ala Asn Thr Ser Phe Gln Gly Arg Thr Gly
            340                 345                 350 ccc gtg tgg gtg aca ggc agc tcc cag gta cac atg tct cgg cac ttt      1104
Pro Val Trp Val Thr Gly Ser Ser Gln Val His Met Ser Arg His Phe
        355                 360                 365 aag gtg tgg agc ctt cgc cgg gac cca cgg ggc gcc ccg gcc tgg gcc      1152
Lys Val Trp Ser Leu Arg Arg Asp Pro Arg Gly Ala Pro Ala Trp Ala
    370                 375                 380 acg gtg ggc agc tgg cgg gac ggc cag ctg gac ttg gaa ccg gga ggt      1200
Thr Val Gly Ser Trp Arg Asp Gly Gln Leu Asp Leu Glu Pro Gly Gly
385                 390                 395                 400 gcc tct gca cgg ccc ccg ccc cca cag ggt gcc cag gtc tgg ccc aag      1248
Ala Ser Ala Arg Pro Pro Pro Pro Gln Gly Ala Gln Val Trp Pro Lys
                405                 410                 415 ctg cgt gtg gta acg ctg ttg gaa cac cca ttt gtg ttt gcc cgt gat      1296
Leu Arg Val Val Thr Leu Leu Glu His Pro Phe Val Phe Ala Arg Asp
            420                 425                 430 cca gac gaa gac ggg cag tgc cca gcg ggg cag ctg tgc ctg gac cct      1344
Pro Asp Glu Asp Gly Gln Cys Pro Ala Gly Gln Leu Cys Leu Asp Pro
        435                 440                 445 ggc acc aac gac tcg gcc acc ctg gac gca ctg ttc gcg gcg ctg gcc      1392
Gly Thr Asn Asp Ser Ala Thr Leu Asp Ala Leu Phe Ala Ala Leu Ala
    450                 455                 460 aac ggc tca gcg ccc cgt gcc ctg cgc aag tgc tgc tac ggc tac tgc      1440
Asn Gly Ser Ala Pro Arg Ala Leu Arg Lys Cys Cys Tyr Gly Tyr Cys
465                 470                 475                 480 att gac ctg ctg gag cgg ctg gcg gag gac acg ccc ttc gac ttc gag      1488
Ile Asp Leu Leu Glu Arg Leu Ala Glu Asp Thr Pro Phe Asp Phe Glu
                485                 490                 495 ctg tac ctc gtg ggt gac ggc aag tac ggc gcc ctg cgg gac ggc cgc      1536
Leu Tyr Leu Val Gly Asp Gly Lys Tyr Gly Ala Leu Arg Asp Gly Arg
            500                 505                 510
```

```
                                                     -continued tgg acc ggc ctg gtc ggg gac ctg ctg gcc ggc cgg gcc cac atg gcg    1584
Trp Thr Gly Leu Val Gly Asp Leu Leu Ala Gly Arg Ala His Met Ala
        515                 520                 525 gtc acc agc ttc agt atc aac tcc gcc cgc tca cag gtg gtg gac ttc    1632
Val Thr Ser Phe Ser Ile Asn Ser Ala Arg Ser Gln Val Val Asp Phe
    530                 535                 540 acc agc ccc ttc ttc tcc acc agc ctg ggc atc atg gtg cgg gca cgg    1680
Thr Ser Pro Phe Phe Ser Thr Ser Leu Gly Ile Met Val Arg Ala Arg
545                 550                 555                 560 gac acg gcc tca ccc atc ggt gcc ttt atg tgg ccc ctg cac tgg tcc    1728
Asp Thr Ala Ser Pro Ile Gly Ala Phe Met Trp Pro Leu His Trp Ser
                565                 570                 575 acg tgg ctg ggc gtc ttt gcg gcc ctg cac ctc acc gcg ctc ttc ctc    1776
Thr Trp Leu Gly Val Phe Ala Ala Leu His Leu Thr Ala Leu Phe Leu
            580                 585                 590 acc gtg tac gag tgg cgt agc ccc tac ggc ctc acg cca cgt ggc cgc    1824
Thr Val Tyr Glu Trp Arg Ser Pro Tyr Gly Leu Thr Pro Arg Gly Arg
        595                 600                 605 aac cgc agc acc gtc ttc tcc tac tcc tca gcc ctc aac ctg tgc tac    1872
Asn Arg Ser Thr Val Phe Ser Tyr Ser Ser Ala Leu Asn Leu Cys Tyr
    610                 615                 620 gcc atc ctc ttc aga cgc acc gtg tcc agc aag acg ccc aag tgc ccc    1920
Ala Ile Leu Phe Arg Arg Thr Val Ser Ser Lys Thr Pro Lys Cys Pro
625                 630                 635                 640 acg ggc cgc ctg ctc atg aac ctc tgg gcc atc ttc tgc ctg ctg gtg    1968
Thr Gly Arg Leu Leu Met Asn Leu Trp Ala Ile Phe Cys Leu Leu Val
                645                 650                 655 ctg tcc agc tac acg gcc aac ctg gct gcc gtc atg gtc ggg gac aag    2016
Leu Ser Ser Tyr Thr Ala Asn Leu Ala Ala Val Met Val Gly Asp Lys
            660                 665                 670 acc ttc gag gag ctg tcg ggg atc cac gac ccc aag ctg cac cac ccg    2064
Thr Phe Glu Glu Leu Ser Gly Ile His Asp Pro Lys Leu His His Pro
        675                 680                 685 gcg cag ggc ttc cgc ttc ggc acc gtg tgg gag agc agc gcc gag gcg    2112
Ala Gln Gly Phe Arg Phe Gly Thr Val Trp Glu Ser Ser Ala Glu Ala
    690                 695                 700 tac atc aag aag agc ttc ccc gac atg cac gca cac atg cgg cgc cac    2160
Tyr Ile Lys Lys Ser Phe Pro Asp Met His Ala His Met Arg Arg His
705                 710                 715                 720 agc gcg ccc acc acg ccc cgc ggc gtc gcc atg ctc acg agc gac ccc    2208
Ser Ala Pro Thr Thr Pro Arg Gly Val Ala Met Leu Thr Ser Asp Pro
                725                 730                 735 ccc aag ctc aac gcc ttc atc atg gac aag tcg ctc ctg gac tac gag    2256
Pro Lys Leu Asn Ala Phe Ile Met Asp Lys Ser Leu Leu Asp Tyr Glu
            740                 745                 750 gtc tcc atc gac gcc gac tgc aaa ctg ctg acc gtg gga aag ccc ttc    2304
Val Ser Ile Asp Ala Asp Cys Lys Leu Leu Thr Val Gly Lys Pro Phe
        755                 760                 765 gcc att gag ggc tat ggg atc gga ctg ccc cag aac tcg ccg ctc acc    2352
Ala Ile Glu Gly Tyr Gly Ile Gly Leu Pro Gln Asn Ser Pro Leu Thr
    770                 775                 780 tcc aac ctg tcc gag ttc atc agc cgc tac aag tcc tcc ggc ttc atc    2400
Ser Asn Leu Ser Glu Phe Ile Ser Arg Tyr Lys Ser Ser Gly Phe Ile
785                 790                 795                 800 gac ctg ctc cac gac aag tgg tac aag atg gtg cct tgc ggc aag cgg    2448
Asp Leu Leu His Asp Lys Trp Tyr Lys Met Val Pro Cys Gly Lys Arg
                805                 810                 815 gtc ttt gcg gtt aca gag acc ctg cag atg agc atc tac cac ttc gcg    2496
Val Phe Ala Val Thr Glu Thr Leu Gln Met Ser Ile Tyr His Phe Ala
            820                 825                 830
```

| | | |
|---|---|---|
| ggc ctc ttc gtg ttg ctg tgc ctg ggc ctg ggc agc gct ctg ctc agc<br>Gly Leu Phe Val Leu Leu Cys Leu Gly Leu Gly Ser Ala Leu Leu Ser<br>835     840     845 | | 2544 |
| tcg ctg ggc gag cac gcc ttc ttc cgc ctg gcg ctg ccg cgc atc cgc<br>Ser Leu Gly Glu His Ala Phe Phe Arg Leu Ala Leu Pro Arg Ile Arg<br> 850     855     860 | | 2592 |
| aag ggg agc agg ctg cag tac tgg ctg cac acc agc cag aaa atc cac<br>Lys Gly Ser Arg Leu Gln Tyr Trp Leu His Thr Ser Gln Lys Ile His<br>865     870     875     880 | | 2640 |
| cgc gcc ctc aac acg gag cca cca gag ggg tcg aag gag gag acg gca<br>Arg Ala Leu Asn Thr Glu Pro Pro Glu Gly Ser Lys Glu Glu Thr Ala<br>    885     890     895 | | 2688 |
| gag gcg gag ccc agg gag cag cag cag cag cag gac cag cca acg<br>Glu Ala Glu Pro Arg Glu Gln Gln Gln Gln Gln Asp Gln Pro Thr<br>900     905     910 | | 2736 |
| gct ccg gag ggc tgg aaa cgg gcg cgc cgg gcc gtg gac aag gag cgc<br>Ala Pro Glu Gly Trp Lys Arg Ala Arg Arg Ala Val Asp Lys Glu Arg<br> 915     920     925 | | 2784 |
| cgc gtg cgc ttc ctg ctg gag ccc gcc ggc tcc tac ggc cgc ccg ccc<br>Arg Val Arg Phe Leu Leu Glu Pro Ala Gly Ser Tyr Gly Arg Pro Pro<br>930     935     940 | | 2832 |
| gcc gca agg ccc acg ggg gcc ccc cag ccc ggg gag ctg cag gag ctg<br>Ala Ala Arg Pro Thr Gly Ala Pro Gln Pro Gly Glu Leu Gln Glu Leu<br>945     950     955     960 | | 2880 |
| gag cgc cgc atc gaa gtc gcg cgt gag cgg ctc cgc cag gcc ctg gtg<br>Glu Arg Arg Ile Glu Val Ala Arg Glu Arg Leu Arg Gln Ala Leu Val<br>    965     970     975 | | 2928 |
| cgg cgc ggc cag ctc ctg gca cag ctc ggg gac agc gca cgt cac cgg<br>Arg Arg Gly Gln Leu Leu Ala Gln Leu Gly Asp Ser Ala Arg His Arg<br>980     985     990 | | 2976 |
| cct cgg cgc ttg ctt cag gcc aga gcg gcc ccc gcg gag gcc cca cag<br>Pro Arg Arg Leu Leu Gln Ala Arg Ala Ala Pro Ala Glu Ala Pro Gln<br> 995     1000     1005 | | 3024 |
| tgagccgctg tcaacagaca gtttattcta tatacaaaca caattttgta cactgcaatt | | 3084 |
| aaatagaatg gaa | | 3097 |

<210> SEQ ID NO 62
<211> LENGTH: 1008
<212> TYPE: PRT
<213> ORGANISM: Homo sapiens

<400> SEQUENCE: 62

Met Glu Phe Val Arg Ala Leu Trp Leu Gly Leu Ala Leu Ala Leu Gly
1     5     10     15

Pro Gly Ser Ala Gly Gly His Pro Gln Pro Cys Gly Val Leu Ala Arg
    20     25     30

Leu Gly Gly Ser Val Arg Leu Gly Ala Leu Leu Pro Arg Ala Pro Leu
   35     40     45

Ala Arg Ala Arg Ala Arg Ala Ala Leu Ala Arg Ala Leu Ala Pro
 50     55     60

Arg Leu Pro His Asn Leu Ser Leu Glu Leu Val Ala Ala Pro Pro
65     70     75     80

Ala Arg Asp Pro Ala Ser Leu Thr Arg Gly Leu Cys Gln Ala Leu Val
    85     90     95

Pro Pro Gly Val Ala Ala Leu Leu Ala Phe Pro Glu Ala Arg Pro Glu
   100     105     110

Leu Leu Gln Leu His Phe Leu Ala Ala Ala Thr Glu Thr Pro Val Leu

-continued

```
            115                 120                 125
Ser Leu Leu Arg Arg Glu Ala Arg Ala Pro Leu Gly Ala Pro Asn Pro
    130                 135                 140
Phe His Leu Gln Leu His Trp Ala Ser Pro Leu Glu Thr Leu Leu Asp
145                 150                 155                 160
Val Leu Val Ala Val Leu Gln Ala His Ala Trp Glu Asp Val Gly Leu
                165                 170                 175
Ala Leu Cys Arg Thr Gln Asp Pro Gly Leu Val Ala Leu Trp Thr
            180                 185                 190
Ser Arg Ala Gly Arg Pro Pro Gln Leu Val Leu Asp Leu Ser Arg Arg
    195                 200                 205
Asp Thr Gly Asp Ala Gly Leu Arg Ala Arg Leu Ala Pro Met Ala Ala
    210                 215                 220
Pro Val Gly Gly Glu Ala Pro Val Pro Ala Ala Val Leu Leu Gly Cys
225                 230                 235                 240
Asp Ile Ala Arg Ala Arg Arg Val Leu Glu Ala Val Pro Pro Gly Pro
                245                 250                 255
His Trp Leu Leu Gly Thr Pro Leu Pro Pro Lys Ala Leu Pro Thr Ala
            260                 265                 270
Gly Leu Pro Pro Gly Leu Leu Ala Leu Gly Glu Val Ala Arg Pro Pro
    275                 280                 285
Leu Glu Ala Ala Ile His Asp Ile Val Gln Leu Val Ala Arg Ala Leu
    290                 295                 300
Gly Ser Ala Ala Gln Val Gln Pro Lys Arg Ala Leu Leu Pro Ala Pro
305                 310                 315                 320
Val Asn Cys Gly Asp Leu Gln Pro Ala Gly Pro Glu Ser Pro Gly Arg
                325                 330                 335
Phe Leu Ala Arg Phe Leu Ala Asn Thr Ser Phe Gln Gly Arg Thr Gly
            340                 345                 350
Pro Val Trp Val Thr Gly Ser Ser Gln Val His Met Ser Arg His Phe
        355                 360                 365
Lys Val Trp Ser Leu Arg Arg Asp Pro Arg Gly Ala Pro Ala Trp Ala
    370                 375                 380
Thr Val Gly Ser Trp Arg Asp Gly Gln Leu Asp Leu Glu Pro Gly Gly
385                 390                 395                 400
Ala Ser Ala Arg Pro Pro Pro Gln Gly Ala Gln Val Trp Pro Lys
            405                 410                 415
Leu Arg Val Val Thr Leu Leu Glu His Pro Phe Val Phe Ala Arg Asp
            420                 425                 430
Pro Asp Glu Asp Gly Gln Cys Pro Ala Gly Gln Leu Cys Leu Asp Pro
    435                 440                 445
Gly Thr Asn Asp Ser Ala Thr Leu Asp Ala Leu Phe Ala Ala Leu Ala
    450                 455                 460
Asn Gly Ser Ala Pro Arg Ala Leu Arg Lys Cys Cys Tyr Gly Tyr Cys
465                 470                 475                 480
Ile Asp Leu Leu Glu Arg Leu Ala Glu Asp Thr Pro Phe Asp Phe Glu
                485                 490                 495
Leu Tyr Leu Val Gly Asp Gly Lys Tyr Gly Ala Leu Arg Asp Gly Arg
            500                 505                 510
Trp Thr Gly Leu Val Gly Asp Leu Leu Ala Gly Arg Ala His Met Ala
        515                 520                 525
Val Thr Ser Phe Ser Ile Asn Ser Ala Arg Ser Gln Val Val Asp Phe
    530                 535                 540
```

```
Thr Ser Pro Phe Phe Ser Thr Ser Leu Gly Ile Met Val Arg Ala Arg
545                 550                 555                 560

Asp Thr Ala Ser Pro Ile Gly Ala Phe Met Trp Pro Leu His Trp Ser
                565                 570                 575

Thr Trp Leu Gly Val Phe Ala Ala Leu His Leu Thr Ala Leu Phe Leu
            580                 585                 590

Thr Val Tyr Glu Trp Arg Ser Pro Tyr Gly Leu Thr Pro Arg Gly Arg
        595                 600                 605

Asn Arg Ser Thr Val Phe Ser Tyr Ser Ser Ala Leu Asn Leu Cys Tyr
    610                 615                 620

Ala Ile Leu Phe Arg Arg Thr Val Ser Ser Lys Thr Pro Lys Cys Pro
625                 630                 635                 640

Thr Gly Arg Leu Leu Met Asn Leu Trp Ala Ile Phe Cys Leu Leu Val
                645                 650                 655

Leu Ser Ser Tyr Thr Ala Asn Leu Ala Ala Val Met Val Gly Asp Lys
                660                 665                 670

Thr Phe Glu Glu Leu Ser Gly Ile His Asp Pro Lys Leu His His Pro
            675                 680                 685

Ala Gln Gly Phe Arg Phe Gly Thr Val Trp Glu Ser Ser Ala Glu Ala
        690                 695                 700

Tyr Ile Lys Lys Ser Phe Pro Asp Met His Ala His Met Arg Arg His
705                 710                 715                 720

Ser Ala Pro Thr Thr Pro Arg Gly Val Ala Met Leu Thr Ser Asp Pro
                725                 730                 735

Pro Lys Leu Asn Ala Phe Ile Met Asp Lys Ser Leu Leu Asp Tyr Glu
                740                 745                 750

Val Ser Ile Asp Ala Asp Cys Lys Leu Leu Thr Val Gly Lys Pro Phe
            755                 760                 765

Ala Ile Glu Gly Tyr Gly Ile Gly Leu Pro Gln Asn Ser Pro Leu Thr
        770                 775                 780

Ser Asn Leu Ser Glu Phe Ile Ser Arg Tyr Lys Ser Ser Gly Phe Ile
785                 790                 795                 800

Asp Leu Leu His Asp Lys Trp Tyr Lys Met Val Pro Cys Gly Lys Arg
                805                 810                 815

Val Phe Ala Val Thr Glu Thr Leu Gln Met Ser Ile Tyr His Phe Ala
                820                 825                 830

Gly Leu Phe Val Leu Leu Cys Leu Gly Leu Gly Ser Ala Leu Leu Ser
            835                 840                 845

Ser Leu Gly Glu His Ala Phe Phe Arg Leu Ala Leu Pro Arg Ile Arg
850                 855                 860

Lys Gly Ser Arg Leu Gln Tyr Trp Leu His Thr Ser Gln Lys Ile His
865                 870                 875                 880

Arg Ala Leu Asn Thr Glu Pro Pro Glu Gly Ser Lys Glu Glu Thr Ala
                885                 890                 895

Glu Ala Glu Pro Arg Glu Gln Gln Gln Gln Asp Gln Pro Thr
            900                 905                 910

Ala Pro Glu Gly Trp Lys Arg Ala Arg Arg Ala Val Asp Lys Glu Arg
        915                 920                 925

Arg Val Arg Phe Leu Leu Glu Pro Ala Gly Ser Tyr Gly Arg Pro Pro
            930                 935                 940

Ala Ala Arg Pro Thr Gly Ala Pro Gln Pro Gly Glu Leu Gln Glu Leu
945                 950                 955                 960
```

-continued

```
Glu Arg Arg Ile Glu Val Ala Arg Glu Arg Leu Arg Gln Ala Leu Val
                965                 970                 975

Arg Arg Gly Gln Leu Leu Ala Gln Leu Gly Asp Ser Ala Arg His Arg
            980                 985                 990

Pro Arg Arg Leu Leu Gln Ala Arg Ala Ala Pro Ala Glu Ala Pro Gln
        995                 1000                1005

<210> SEQ ID NO 63
<211> LENGTH: 114
<212> TYPE: PRT
<213> ORGANISM: Artificial Sequence
<220> FEATURE:
<223> OTHER INFORMATION: Hypothetical human sequence which would be
      chemically synthesized.
<220> FEATURE:
<221> NAME/KEY: VARIANT
<222> LOCATION: (1)...(114)
<223> OTHER INFORMATION: Xaa= any amino acid

<400> SEQUENCE: 63

Xaa Xaa Xaa Xaa Xaa Xaa Xaa Xaa Xaa Xaa Xaa Xaa Xaa Trp Lys Arg
  1               5                  10                  15

Ala Arg Ala Val Asp Lys Glu Arg Val Arg Phe Leu Leu Glu
             20                  25                  30

Pro Xaa Xaa Xaa Xaa Xaa Xaa Xaa Xaa Trp Leu Cys Ser Xaa Xaa Xaa
             35                  40                  45

Xaa Xaa Xaa Xaa Glu Leu Gln Glu Leu Glu Arg Arg Ile Glu Val Ala
         50                  55                  60

Arg Glu Arg Leu Arg Gln Ala Leu Val Arg Arg Gly Gln Leu Leu Ala
 65                  70                  75                  80

Gln Leu Gly Asp Ser Ala Arg His Arg Pro Arg Arg Leu Leu Gln Ala
             85                  90                  95

Arg Ala Ala Pro Ala Glu Ala Pro Pro His Ser Gly Arg Pro Gly Ser
            100                 105                 110

Gln Glu
```